US009428783B2

(12) United States Patent
Smirnov et al.

(10) Patent No.: US 9,428,783 B2
(45) Date of Patent: Aug. 30, 2016

(54) **DNA ENCODING DIPEPTIDE-SYNTHESIZING ENZYME (VARIANTS), BACTERIUM BELONGING TO THE GENUS *ESCHERICHIA*, AND METHODS FOR PRODUCING DIPEPTIDES USING THEREOF**

(71) Applicant: Ajinomoto Co., Inc., Tokyo (JP)

(72) Inventors: Sergey Vasilievich Smirnov, Moscow (RU); Pavel Mikhailovich Sokolov, Moscow (RU); Takayuki Ito, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 14/591,387

(22) Filed: Jan. 7, 2015

(65) Prior Publication Data

US 2015/0197782 A1 Jul. 16, 2015

Related U.S. Application Data

(63) Continuation of application No. PCT/JP2013/069712, filed on Jul. 11, 2013.

(30) Foreign Application Priority Data

Jul. 11, 2012 (RU) .................................. 2012129311

(51) Int. Cl.
*C12P 21/00* (2006.01)
*C12N 9/00* (2006.01)
*C07K 5/072* (2006.01)

(52) U.S. Cl.
CPC ................. *C12P 21/00* (2013.01); *C12N 9/93* (2013.01); *C12Y 603/02028* (2013.01); *C07K 5/06104* (2013.01); *C07K 5/06113* (2013.01)

(58) Field of Classification Search
None
See application file for complete search history.

(56) References Cited

U.S. PATENT DOCUMENTS

| 4,572,894 A | 2/1986 | Imahori et al. |
| 5,652,116 A | 7/1997 | Grandi et al. |
| 5,795,738 A | 8/1998 | Grandi et al. |
| 7,037,673 B2 | 5/2006 | Nozaki et al. |
| 7,288,388 B2 | 10/2007 | Tonouchi et al. |
| 7,514,243 B2 | 4/2009 | Hashimoto et al. |
| 7,618,796 B2 | 11/2009 | Tonouchi et al. |
| 7,754,466 B2 | 7/2010 | Yokozeki et al. |
| 7,939,294 B2 | 5/2011 | Kino et al. |
| 7,939,302 B2 | 5/2011 | Hashimoto et al. |
| 8,409,653 B2 | 4/2013 | Shimono et al. |
| 2004/0137558 A1 | 7/2004 | Yokozeki et al. |
| 2006/0188976 A1 | 8/2006 | Takeshita et al. |
| 2007/0042459 A1 | 2/2007 | Nozaki et al. |
| 2007/0292916 A1 | 12/2007 | Abe et al. |
| 2009/0047706 A1 | 2/2009 | Kino et al. |

FOREIGN PATENT DOCUMENTS

| EP | 0 036 258 A2 | 9/1981 |
| EP | 0 036 258 A3 | 9/1981 |
| EP | 1 870 454 B1 | 12/2009 |
| FR | 2 662 359 A1 | 11/1991 |
| JP | 58-146539 A | 9/1983 |
| JP | 58-209992 A | 12/1983 |
| JP | 59-106298 A | 6/1984 |
| JP | 2009-209131 A | 9/2009 |
| RU | 2 279 440 C2 | 5/2005 |
| RU | 2007 127 719 A | 1/2009 |
| WO | WO 2004/076477 A1 | 9/2004 |
| WO | 2009/113563 A1 | 9/2009 |

OTHER PUBLICATIONS

"Coding: BAH46167.1", European Nucleotide Archive, Jul. 2, 2015, 2 pages.
"Coding: AD072629.1", European Nucleotide Archive, Jul. 2, 2015, 2 pages.
"Coding: EGK06810.1", European Nucleotide Archive, Jul. 2, 2015, 2 pages.
International Search Report and Written Opinion issued Dec. 13, 2013 in PCT/JP2013/069712.
Database UniProt [Online] May 2009 "SubName: Full=Putative uncharacterized protein", XP002715940, retrieved from EBI accession No. UNIPROT:C0Z5R1 Database accession No. C0Z5R1.
Database UniProt [Online] Jan. 2011 "SubName: Full=Argininosuccinate lyase 2-like protein", XP002715941, retrieved from EBI accession No. UNIPROT:E3FE26 Database accession No. E3FE26.
Database UniProt [Online] Jul. 2011 "SubName: Full=Pyridoxal-phosphate dependent enzyme", XP002715942, retrieved from EBI accession No. UNIPROT:F5SLP0 Database accession No. F5SLP0.
Makoto Yagasaki, et al., "Synthesis and application of dipeptides; current status and perspectives" Appl Microbiol Biotechnol, vol. 81, No. 1, 2008, pp. 13-22.
Akihiro Senoo, et al., "Identification of Novel $_L$-Amino Acid α-Ligases through Hidden Markov Model-Based Profile Analysis" Biosci. Biotechnol. Biochem., vol. 74, No. 2, 2010, pp. 415-418.
Sascha Doekel, et al., "Dipeptide formation on engineered hybrid peptide synthetases" Chemistry & Biology, vol. 7, No. 6, 2000, pp. 373-384.
Ralf Dieckmann, et al., "Dipeptide synthesis by an isolated adenylate-forming domain of non-ribosomal peptide synthetases (NRPS)" FEBS Letters, vol. 498, 2001, pp. 42-45.

(Continued)

*Primary Examiner* — David J Steadman
(74) *Attorney, Agent, or Firm* — Oblon, McClelland, Maier & Neustadt, L.L.P.

(57) ABSTRACT

The present invention describes novel bacterial L-amino acids α-ligases, which catalyzing reaction of dipeptide formation having an acidic L-amino acid such as L-Asp or L-Glu at the N-terminus. The method for producing dipeptides using said L-amino acids α-ligases and a bacterium of the family Enterobacteriaceae, particularly a bacterium belonging to the genus *Escherichia*, which has been modified to contain the DNA encoding said L-amino acids α-ligases, is described.

15 Claims, 61 Drawing Sheets

(56) References Cited

OTHER PUBLICATIONS

Kazuhiko Tabata, et al., "*ywfE* in *Bacillus subtilis* Codes for a Novel Enzyme, $_L$-Amino Acid Ligase" Journal of Bacteriology, vol. 187, No. 15, Aug. 2005, pp. 5195-5202.

Kuniki Kino et al., "Dipeptide synthesis by $_L$-amino acid ligase from *Ralstonia solanacearum*" Biochemical and Biophysical Research Communications, vol. 371, 2008, pp. 536-540.

Kuniki Kino, "Novel $_L$-Amino Acid Ligases Catalyzing Oligopeptide Synthesis" Yakugaku Zasshi, vol. 130, No. 11, 2010, pp. 1463-1469 (with English Abstract).

Genbank BAH46167, conserved hypothetical protein [Brevibacillus brevis NBRC 100599], May 8, 2009, https://ncbi.nlm.nih.gov/.

Genbank ADO72629, argininosuccinate lyase 2-like protein [Stigmatella aurantiaca DW4/3-1], Jan. 31, 2014, https://ncbi.nlm.nih.gov/.

Genbank EGK06810, pyridoxal-phosphate dependent enzyme [*Desmospora* sp. 8437], May 13, 2011, https://ncbi.nlm.nih.gov/.

Asp Asn Glu Gln Arg Lys  Trp Phe Tyr His Ile Leu Val  Met Cys  Ala Thr Gly Ser Pro Cnt

Asp Asn Glu Gln Arg Lys Trp Phe  Tyr His Ile Leu Val Met Cys Ala  Thr Gly Ser Pro Cnt

Asp Asn Glu  Gln Arg  Lys Trp  Phe Tyr His  Ile Leu Val Met Cys Ala Thr Gly Ser Pro Cnt

FIG. 10

```
>BBR47_51900

MNKHFLFVEANTTGTGMLAMKKARKLGFTPVFFTEKPERYHGLN---ELECHVVVTDTNS
QAELTDSVAQVSKEGREIAGIMSTSDYYLESVAKLARKFGWISNSLEAIEACRNKAIFRE
KLQRHQVSQPTFLAISSMEQLLEARSSISLPCVVKPADDSGSNNVRLCFSWDEVEHMAAE
ILAIKYNARGQETARTVLLEQYAEGPEFSVETFSWQG-QCFVIGITQKRLTGYPFFVEAG
HIFPAPLSVEEKQEIERTVERALAAVKYQFGAAHTEVKWTSAGCVVIEVNARLAGGMIPE
LVRRSTGIDLLLQQIRCAAGLEPELSQTIEEQRCAGIHFLVSESQGTFGGIKGMDTVRNL
PGIAEVAIHAKIGQNVQPPQNFSHRLGYVIVEGKHYSETAELIEQVKDSLSVQVGQQLES
GV (SEQ ID NO: 2)
*

>Staur_4851

-MNQFVFVESNTTGTGRLAVERLLAQGEQVTFITHQPEKYPFLVGNKAPGLKVLKVETND
AAAVEACVDGLVREGK-VAALLTFSTFYVPTVAAIAARHGLRYLQPRAAQACHNKHEARA
LLRAAGLPGPEFHVIASEAEAAQLAQTVRFPCVVKPPAESGSTGVRRVDTPEELLAHFRS
LHSRAANERGQSLHGEVLVESFLEGPEFSVETMTLADGTTHVLGVTQKYLSAPPYFVEMG
HDFPADLPPERRRALEEAVLAGLAAVGFDFGPAHTEIRFTPAGPVIIEINPRLAGGMIPE
LVRLSTGVDLLSAMLDQMLGRPVDLTHTR---QDVACIRFITSERPGVLARVEGQDEASRL
GTVRQVAVDKAAGTRLRPPESATDRLGYVIASGPERGQVLGDAARALSLLRVEQAAPSAP
A- (SEQ ID NO: 4)
*
```

FIG. 11-1

| N | Target | Description | E-value | Log(E-value) |
|---|---|---|---|---|
| 1 | C0Z5R1_BREBN | Putative uncharacterized protein (gene: BBR47_51900) | 1,40E-250 | 249,853872 |
| 2 | E3FE26_STIAD | Argininosuccinate lyase 2-like protein (gene: STAUR_4851) | 5,90E-234 | 233,229148 |
| 3 | F5SLP0_9BACL | Pyridoxal-phosphate dependent enzyme (gene: HMPREF9374_4022) | 4,10E-157 | 156,3872161 |
| 4 | C2PYS6_BACCE | Argininosuccinate lyase domain protein (gene: bcere0007_32210) | 6,60E-143 | 142,1804561 |
| 5 | C3BDI4_BACMY | Argininosuccinate lyase domain protein (gene: bmyco0003_56050) | 5,70E-121 | 120,2441251 |
| 6 | F1CHS8_9ACTO | DABA synthase (gene: npsI) | 1,20E-118 | 117,9208188 |
| 7 | C6WLF1_ACTMD | Cysteine synthase (gene: Amir_4500) | 1,80E-118 | 117,7447275 |
| 8 | D6APC7_STRFL | DabC (gene: SSGG_02990) | 2,90E-118 | 117,537602 |
| 9 | B0B530_STRCU | Putative pyridoxal-phosphate dependent enzyme (gene: orf_R4) | 6,50E-118 | 117,1870866 |
| 10 | F4F5X7_VERMA | Cysteine synthase (gene: VAB18032_22180) | 1,60E-117 | 116,79588 |
| 11 | E2EKQ1_9ACTO | Diaminoacid synthase/ligase fusion protein (gene: pac19) | 3,70E-117 | 116,4317983 |
| 12 | C3BTM3_9BACI | Argininosuccinate lyase domain protein (gene: bpmyx0001_50290) | 1,80E-111 | 110,7447275 |
| 13 | F0PS09_BACT0 | Putative uncharacterized protein (gene: YBT020_25570) | 1,90E-111 | 110,7212464 |
| 14 | Q63UA1_BURPS | Putative bifunctional protein (Ligase and argininosuccinate lyase) (gene: BPSL1715) | 1,40E-97 | 96,85387196 |
| 15 | C6TPZ3_BURPS | Argininosuccinate lyase (gene: BURPS1710A_2469) | 2,00E-97 | 96,69897 |
| 16 | Q3JSA0_BURP1 | Argininosuccinate lyase domain protein (gene: BURPS1710b_2158) | 2,10E-97 | 96,67778071 |
| 17 | A4LBK5_BURPS | Putative lyase (gene: BURPS305_6606) | 2,20E-97 | 96,65757732 |
| 18 | C5ZGF9_BURPS | Putative lyase (gene: BURPS1106B_A1258) | 2,20E-97 | 96,65757732 |

FIG. 11-2

| N | Target | Description | E-value | Log(E-value) |
|---|---|---|---|---|
| 19 | C0Y7H2_BURPS | Putative lyase (gene: BUH_1888) | 2,50E-97 | 96,60205999 |
| 20 | G0WV72_STRVR | Diaminobutyric acid synthase C (gene: dabC) | 5,70E-97 | 96,24412514 |
| 21 | D3Q4U1_STANL | Putative uncharacterized protein (gene: Snas_2438) | 1,10E-96 | 95,95860731 |
| 22 | F2LEB6_BURGS | Argininosuccinate lyase (gene: bgla_1g16460) | 4,70E-94 | 93,32790214 |
| 23 | G2PF82_STRVO | ATP-dependent carboxylate-amine ligase domain protein ATP-grasp (gene: Strvi_4637) | 7,60E-86 | 85,11918641 |
| 24 | Q63SV7_BURPS | Putative fusion protein (Ligase/carboxylase and argininosuccinate lyase) (gene: BPSL2214) | 1,80E-83 | 82,74472749 |
| 25 | A5TJX5_BURMA | Lyase family protein (gene: BMA721280_A1050) | 1,90E-83 | 82,7212464 |
| 26 | A3ML08_BURM7 | Argininosuccinate lyase domain protein (gene: BMA10247_1396) | 5,50E-83 | 82,25963731 |
| 27 | Q2SX49_BURTA | Argininosuccinate lyase domain protein (gene: BTH_I1971) | 6,00E-83 | 82,22184875 |
| 28 | B1HKH5_BURPS | Argininosuccinate lyase domain protein (gene: BURPSS13_P1168) | 2,00E-82 | 81,69897 |
| 29 | A4LD16_BURPS | Lyase family protein (gene: BURPS305_7168) | 3,40E-82 | 81,46852108 |
| 30 | C0YCH6_BURPS | Lyase family protein (gene: BUH_2552) | 7,30E-82 | 81,13667714 |
| 31 | C5ZJH2_BURPS | Lyase family protein (gene: BURPS1106B_A1783) | 8,20E-82 | 81,08618615 |
| 32 | G0FTB8_AMYMD | Argininosuccinate lyase (gene: RAM_24230) | 9,90E-82 | 81,00436481 |
| 33 | E2D2N4_9BACT | Diaminobutyric acid synthase C | 1,30E-81 | 80,88605665 |
| 34 | C4KPT5_BURPS | Argininosuccinate lyase 2 (Arginosuccinase 2) (Asal 2) (gene: GBP346_A2629) | 1,50E-81 | 80,82390874 |

FIG. 11-3

| N | Target | Description | E-value | Log(E-value) |
|---|---|---|---|---|
| 35 | Q3JQX0_BURP1 | Argininosuccinate lyase domain protein (gene: BURPS1710b_2646) | 4,70E-81 | 80,32790214 |
| 36 | B2H9Z1_BURPS | Argininosuccinate lyase domain protein (gene: BURPS1655_H0298) | 5,00E-81 | 80,30103 |
| 37 | A3KFG4_9ACTO | DabC (gene: dabC) | 6,40E-81 | 80,19382003 |
| 38 | A1V5D2_BURMS | Argininosuccinate lyase domain protein (gene: BMASAVP1_A2122) | 1,50E-80 | 79,82390874 |
| 39 | C5NAA5_BURMA | Lyase family protein (gene: BMAPRL20_A1664) | 1,50E-80 | 79,82390874 |
| 40 | A3NB13_BURP6 | Argininosuccinate lyase (gene: BURPS668_2507) | 1,60E-80 | 79,79588002 |
| 41 | A8KVZ6_BURPS | Argininosuccinate lyase domain protein (gene: BURPSPAST_R0310) | 1,60E-80 | 79,79588002 |
| 42 | Q62J65_BURMA | Argininosuccinate lyase domain protein (gene: BMA1620) | 4,20E-80 | 79,37675071 |
| 43 | C4AVR8_BURMA | Argininosuccinate lyase 2 (Arginosuccinase 2) (Asal 2) (gene: BMAGB8_1709) | 4,40E-80 | 79,35654732 |
| 44 | B7D052_BURPS | Lyase family protein (gene: BUC_2825) | 8,70E-80 | 79,06048075 |
| 45 | A8ECB3_BURPS | Argininosuccinate lyase domain protein (gene: BURPS406E_H0439) | 1,30E-79 | 78,88605665 |
| 46 | F1DGJ0_9ACTO | Putative uncharacterized protein | 2,30E-79 | 78,63827216 |
| 47 | A6TPU8_ALKMQ | Putative uncharacterized protein (gene: Amet_2055) | 1,40E-78 | 77,85387196 |
| 48 | Q8KJE6_RHILI | FUSION PROTEIN CONTAINS PUTATIVE LIGASE AND PROBABLE ARGINOSUCCINATE LYASE (gene:msi203) | 3,90E-78 | 77,40893539 |
| 49 | E8W7D4_STRFA | Putative uncharacterized protein (gene: Sfla_0476) | 6,40E-78 | 77,19382003 |

FIG. 13

```
>BBR47_51900

MNKHFLFVEANTTGTGMLAMKKARKLGFTPVFFTEKPERYHGLN---ELE
CHVVVTDTNSQAELTDSVAQVSKEGREIAGIMSTSDYYLESVAKLARKFG
WISNSLEAIEACRNKAIFREKLQRHQVSQPTFLAISSMEQLLEARSSISL
PCVVKPADDSGSNNVRLCFSWDEVEHMAAEILAIKYNARGQETARTVLLE
QYAEGPEFSVETFSWQ-GQCFVIGITQKRLTGYPFFVEAGHIFPAPLSVE
EKQEIERTVERALAAVKYQFGAAHTEVKWTSAGCVVIEVNARLAGGMIPE
LVRRSTGIDLLLQQIRCAAGLEPELSQTIEEQRCAGIHFLVSESQGTFGG
IKGMDTVRNLPGIAEVAIHAKIGQNVQPPQNFSHRLGYVIVEGKHYSETA
ELIEQVKDSLSVQVGQQLESGV (SEQ ID NO: 2)
*

>Staur_4851

-MNQFVFVESNTTGTGRLAVERLLAQGEQVTFITHQPEKYPFLVGNKAPG
LKVLKVETNDAAAVEACVDGLVREGK-VAALLTFSTFYVPTVAAIAARHG
LRYLQPRAAQACHNKHEARALLRAAGLPGPEFHVIASEAEAAQLAQTVRF
PCVVKPPAESGSTGVRRVDTPEELLAHFRSLHSRAANERGQSLHGEVLVE
SFLEGPEFSVETMTLADGTTHVLGVTQKYLSAPPYFVEMGHDFPADLPPE
RRRALEEAVLAGLAAVGFDFGPAHTEIRFTPAGPVIIEINPRLAGGMIPE
LVRLSTGVDLLSAMLDQMLGRPVDLTHTR--QDVACIRFITSERPGVLAR
VEGQDEASRLGTVRQVAVDKAAGTRLRPPESATDRLGYVIASGPERGQVL
GDAARALSLLRVEQAAPSAPA- (SEQ ID NO: 4)
*

>gi|333374399|ref|ZP_08466276.1_DES

MKKKLLFVEGNTTGTGILALEKARKLGYEPVFLTQEASRYDGLP---EAK
CRVHVTVTDSIHELKRCVSQE--KAEAVAGILTTSDYYLEISAKLVQELG
LTGNSPQAIHLCRNKALYREKLRSKSVPQPNFHIIRSMEDLRETRESVPL
PCLVKPADDSGSNNVRLCFSWGEVEQLTSKILKIERNARGQKTSQTVLLE
EYIEGPEYSVEMFSWQ-GKSTCIGITEKQLTGYPYFVESGHVFPAVLPTD
VQQEIEKTVKQSLEAVHFQFGASHSEVKWTPNGCVMIETNARLAGGMIPE
LVRHSTGVDLIEQQILCAAGVAPHWKQVVPTG-CSGIHFIVAAEAGRLSS
VDNLEAVRKLPGVEEMMVKAQVGQAVQPPKNFSDRLGHVIVSGKSYEEVV
ERLHKISNMISLKIS------- (SEQ ID NO: 6)
*

>gi|229168264|ref|ZP_04295989.1_BCE

----------------MLAIRKAKELGYEPIFLTQKKSLYHGLS---DLE
CRVIELDTNSVDAIKHYIIHE--KIEDIAGILTTSDYYLETVAELVQMFR
LSGNTHQAIYYCRNKAMFREKLHLEKVLQPKFHIVQSIDSLQNIYSSIQF
PCVVKPADDSGSNNVRLCSNWEEVEKIATKILANKYNARGQEKANMVLLE
EYIEGPEYSVEMFSWE-GNSICIGITEKQLTGFPYFVESGHIFPVELPKD
VQSEIEQTVKCALQAVDFRFGASHSEVKWTSNGCVVIEVNARLAGGMIPE
LVRHSTGVDLLRQQVLSSVGVAPEWKEIEYMN-YAGIHFLTAKKSGFLST
VKGIEEVRELSYIEELVVKAQVGQPVNPPENFSHRLGHVMVRGRTYEETV
LFLEEVAKKLEIQVNN------ (SEQ ID NO: 10)
*
```

FIG. 14-1

| N | Target | Description | E-value | Log(E-value) |
|---|---|---|---|---|
| 1 | C0Z5R1_BREBN | Putative uncharacterized protein (gene: BBR47_51900) | 6,10E-228 | 227,2146702 |
| 2 | F5SLP0_9BACL | Pyridoxal-phosphate dependent enzyme (gene: HMPREF9374_4022) | 1,20E-224 | 223,9208188 |
| 3 | C2PYS6_BACCE | Argininosuccinate lyase domain protein (gene: bcere0007_32210) | 5,20E-216 | 215,2839967 |
| 4 | E3FE26_STIAD | Argininosuccinate lyase 2-like protein (gene: STAUR_4851) | 3,80E-197 | 196,4202164 |
| 5 | C3BDI4_BACMY | Argininosuccinate lyase domain protein (gene: bmyco0003_56050) | 8,10E-139 | 138,091515 |
| 6 | B0B530_STRCU | Putative pyridoxal-phosphate dependent enzyme (gene: orf_R4) | 1,40E-127 | 126,853872 |
| 7 | C3BTM3_9BACI | Argininosuccinate lyase domain protein (gene: bpmyx0001_50290) | 2,20E-126 | 125,6575773 |
| 8 | F0PS09_BACTO | Putative uncharacterized protein (gene: YBT020_25570) | 2,90E-125 | 124,537602 |
| 9 | C6WLF1_ACTMD | Cysteine synthase (gene: Amir_4500) | 5,20E-125 | 124,2839967 |
| 10 | F4F5X7_VERMA | Cysteine synthase (gene: VAB18032_22180) | 7,90E-124 | 123,1023729 |
| 11 | F1CHS8_9ACTO | DABA synthase (gene: npsl) | 3,70E-122 | 121,4317983 |
| 12 | D6APC7_STRFL | DabC (gene: SSGG_02990) | 8,00E-122 | 121,09691 |
| 13 | E2EKQ1_9ACTO | Diaminoacid synthase/ligase fusion protein (gene: pac19) | 1,50E-120 | 119,8239087 |
| 14 | Q63UA1_BURPS | Putative bifunctional protein (Ligase and argininosuccinate lyase) (gene: BPSL1715)) | 6,50E-96 | 95,18708664 |
| 15 | C6TPZ3_BURPS | Argininosuccinate lyase (gene: BURPS1710A_2469) | 1,10E-95 | 94,95860731 |
| 16 | Q3JSA0_BURP1 | Argininosuccinate lyase domain protein (gene: BURPS1710b_2158) | 1,10E-95 | 94,95860731 |
| 17 | C5ZGF9_BURPS | Putative lyase (gene: BURPS1106B_A1258) | 1,20E-95 | 94,92081875 |
| 18 | A4LBK5_BURPS | Putative lyase (gene: BURPS305_6606) | 1,20E-95 | 94,92081875 |

FIG. 14-2

| N | Target | Description | E-value | Log(E-value) |
|---|---|---|---|---|
| 19 | D3Q4U1_STANL | Putative uncharacterized protein (gene: Snas_2438) | 1,30E-95 | 94,88605665 |
| 20 | C0Y7H2_BURPS | Putative lyase (gene: BUH_1888) | 1,40E-95 | 94,85387196 |
| 21 | F2LEB6_BURGS | Argininosuccinate lyase (gene: bgla_1g16460) | 4,60E-94 | 93,33724217 |
| 22 | G0WV72_STRVR | Diaminobutyric acid synthase C (gene: dabC) | 1,10E-90 | 89,95860731 |
| 23 | G2PF82_STRVO | ATP-dependent carboxylate-amine ligase domain protein ATP-grasp (Strvi_4637) | 3,00E-89 | 88,52287875 |
| 24 | Q63SV7_BURPS | Putative fusion protein (Ligase/carboxylase and argininosuccinate lyase) (gene: BPSL2214) | 3,20E-83 | 82,49485002 |
| 25 | A5TJX5_BURMA | Lyase family protein (gene: BMA721280_A1050) | 3,40E-83 | 82,46852108 |
| 26 | A3ML08_BURM7 | Argininosuccinate lyase domain protein (gene: BMA10247_1396) | 8,10E-83 | 82,09151498 |
| 27 | B7GFS1_ANOFW | Predicted carboxylase (ATP-grasp family) (gene: Aflv_0217) | 1,20E-82 | 81,92081875 |
| 28 | Q2SX49_BURTA | Argininosuccinate lyase domain protein (gene: BTH_I1971) | 2,30E-82 | 81,63827216 |
| 29 | B1HKH5_BURPS | Argininosuccinate lyase domain protein (gene: BURPSS13_P1168) | 2,70E-82 | 81,56863624 |
| 30 | C9RTG5_GEOSY | Putative uncharacterized protein (gene: GYMC61_0754) | 4,70E-82 | 81,32790214 |
| 31 | A4LD16_BURPS | Lyase family protein (gene: BURPS305_7168) | 6,50E-82 | 81,18708664 |
| 32 | D7D1Z0_GEOSC | Putative uncharacterized protein (gene: GC56T3_0730) | 7,20E-82 | 81,1426675 |
| 33 | A6TPU8_ALKMQ | Putative uncharacterized protein (gene: Amet_2055) | 7,80E-82 | 81,1079054 |
| 34 | C0YCH6_BURPS | Lyase family protein (gene: BUH_2552) | 9,80E-82 | 81,00877392 |
| 35 | C5ZJH2_BURPS | Lyase family protein (gene: BURPS1106B_A1783) | 1,30E-81 | 80,88605665 |

FIG. 14-3

| N | Target | Description | E-value | Log(E-value) |
|---|---|---|---|---|
| 36 | C4KPT5_BURPS | Argininosuccinate lyase 2 (Arginosuccinase 2) (Asal 2) (gene: GBP346_A2629) | 1,70E-81 | 80,76955108 |
| 37 | Q8KJE6_RHILI | FUSION PROTEIN CONTAINS PUTATIVE LIGASE AND PROBABLE ARGINOSUCCINATE LYASE (gene: msi203) | 1,90E-81 | 80,7212464 |
| 38 | Q5KW89_GEOKA | Hypothetical conserved protein (gene: GK2762) | 7,90E-81 | 80,10237291 |
| 39 | Q3JQX0_BURP1 | Argininosuccinate lyase domain protein (gene: BURPS1710b_2646) | 9,50E-81 | 80,02227639 |
| 40 | B2H9Z1_BURPS | Argininosuccinate lyase domain protein (gene: BURPS1655_H0298) | 1,00E-80 | 80 |
| 41 | G0FTB8_AMYMD | Argininosuccinate lyase (gene: RAM_24230) | 1,30E-80 | 79,88605665 |
| 42 | F7KHZ8_9FIRM | Putative uncharacterized protein (gene: HMPREF0994_05500) | 2,50E-80 | 79,60205999 |
| 43 | D3AGE3_9CLOT | ATP-grasp domain protein (gene: CLOSTHATH_02679) | 2,80E-80 | 79,55284197 |
| 44 | A8KVZ6_BURPS | Argininosuccinate lyase domain protein (gene: BURPSPAST_R0310) | 3,30E-80 | 79,48148606 |
| 45 | A3NB13_BURP6 | Argininosuccinate lyase (gene: BURPS668_2507) | 3,30E-80 | 79,48148606 |
| 46 | F1DGJ0_9ACTO | Putative uncharacterized protein | 5,10E-80 | 79,29242982 |
| 47 | A1V5D2_BURMS | Argininosuccinate lyase domain protein (gene: BMASAVP1_A2122) | 7,90E-80 | 79,10237291 |
| 48 | C5NAA5_BURMA | Lyase family protein (gene: BMAPRL20_A1664) | 8,30E-80 | 79,08092191 |
| 49 | B7GKI9_ANOFW | Formate-dependent phosphoribosylglycinamide formyltransferase (GAR transformylase) (gene: Aflv_1026) | 1,60E-79 | 78,79588002 |
| 50 | Q62J65_BURMA | Argininosuccinate lyase domain protein (gene: BMA1620) | 1,90E-79 | 78,7212464 |
| 51 | C4AVR8_BURMA | Argininosuccinate lyase 2 (Arginosuccinase 2) (Asal 2) (gene: BMAGB8_1709) | 2,00E-79 | 78,69897 |

FIG. 14-4

| N | Target | Description | E-value | Log(E-value) |
|---|---|---|---|---|
| 52 | B7D052_BURPS | Lyase family protein (gene: BUC_2825) | 2,60E-79 | 78,58502665 |
| 53 | A8ECB3_BURPS | Argininosuccinate lyase domain protein (gene: BURPS406E_H0439) | 2,60E-79 | 78,58502665 |
| 54 | D9WHP6_9ACTO | ATP-grasp domain protein (gene: SSOG_01010) | 2,30E-78 | 77,63827216 |
| 55 | A6TPU7_ALKMQ | Putative uncharacterized protein (gene: Amet_2054) | 3,00E-78 | 77,52287875 |
| 56 | E2D2N4_9BACT | Diaminobutyric acid synthase C | 3,90E-78 | 77,40893539 |
| 57 | C2TR35_BACCE | Phosphoribosylglycinamide synthetase, ATP-grasp (A) domain protein (gene: bcere0016_57030) | 1,00E-77 | 77 |
| 58 | B5V3S1_BACCE | Phosphoribosylglycinamide synthetase, ATP-grasp (gene: BCH308197_2192) | 1,10E-77 | 76,95860731 |
| 59 | D5TZC0_BACT1 | Phosphoribosylglycinamide synthetase ATP-grasp domain-containing protein (gene: BMB171_P0212) | 1,20E-77 | 76,92081875 |
| 60 | Q74NS4_BACC1 | Phosphoribosylglycinamide synthetase, ATP-grasp (A) domain protein (gene: BCE_A0170) | 1,20E-77 | 76,92081875 |
| 61 | E1YQG6_9BACE | L-lactate dehydrogenase (gene: HMPREF9008_01673) | 2,80E-77 | 76,55284197 |
| 62 | E8W7D4_STRFA | Putative uncharacterized protein (gene: Sfla_0476) | 3,40E-77 | 76,46852108 |
| 63 | A3KFG4_9ACTO | DabC (gene: dabC) | 3,90E-77 | 76,40893539 |
| 64 | D0TCU6_9BACE | Putative uncharacterized protein (gene: HMPREF0103_1362) | 9,90E-77 | 76,00436481 |
| 65 | A4FN76_SACEN | Putative fusion protein (Ligase/carboxylase and argininosuccinate lyase) (gene: SACE_6330) | 5,70E-76 | 75,24412514 |

FIG. 16-1

```
>Staur_4851

-MNQFVFVESNTTGTGRLAVERLLAQGEQVTFITHQPEKYPFLVGNKAPG
LKVLKVETNDAAAVEACVDGLVREG-KVAALLTFSTFYVPTVAAIAARHG
LRYLQPRAAQACHNKHEARALLRAAGLPGPEFHVIASEAEAAQLAQTVRF
PCVVKPPAESGSTGVRRVDTPEELLAHFRSLHSRAANERGQSLHGEVLVE
SFLEGPEFSVETMTLADGTTHVLGVTQKYLSAPPYFVEMGHDFPADLPPE
RRRALEEAVLAGLAAVGFDFGPAHTEIRFTPAGPVIIEINPRLAGGMIPE
LVRLSTGVDLLSAMLDQMLGRPVDLTHTR--QDVACIRFITSERPGVLAR
VEGQDEASRLGTVRQVAVDKAAGTRLRPPESATDRLGYVIASGPERGQVL
GDAARALSLLRVEQAAPSAPA- (SEQ ID NO: 4)
*

>BBR47_51900

MNKHFLFVEANTTGTGMLAMKKARKLGFTPVFFTEKPERYHGLNELECH-
---VVVTDTNSQAELTDSVAQVSKEGREIAGIMSTSDYYLESVAKLARKFG
WISNSLEAIEACRNKAIFREKLQRHQVSQPTFLAISSMEQLLEARSSISL
PCVVKPADDSGSNNVRLCFSWDEVEHMAAEILAIKYNARGQETARTVLLE
QYAEGPEFSVETFSWQ-GQCFVIGITQKRLTGYPFFVEAGHIFPAPLSVE
EKQEIERTVERALAAVKYQFGAAHTEVKWTSAGCVVIEVNARLAGGMIPE
LVRRSTGIDLLLQQIRCAAGLEPELSQTIEEQRCAGIHFLVSESQGTFGG
IKGMDTVRNLPGIAEVAIHAKIGQNVQPPQNFSHRLGYVIVEGKHYSETA
ELIEQVKDSLSVQVGQQLESGV (SEQ ID NO: 2)
*

>gi|333374399|ref|ZP_08466276.1_DES

MKKKLLFVEGNTTGTGILALEKARKLGYEPVFLTQEASRYDGLPEAKCR-
---VHVTVTDSIHELKRCVSQE---KAEAVAGILTTSDYYLEISAKLVQELG
LTGNSPQAIHLCRNKALYREKLRSKSVPQPNFHIIRSMEDLRETRESVPL
PCLVKPADDSGSNNVRLCFSWGEVEQLTSKILKIERNARGQKTSQTVLLE
EYIEGPEYSVEMFSWQ-GKSTCIGITEKQLTGYPYFVESGHVFPAVLPTD
VQQEIEKTVKQSLEAVHFQFGASHSEVKWTPNGCVMIETNARLAGGMIPE
LVRHSTGVDLIEQQILCAAGVAPHWKQVVPTG-CSGIHFIVAAEAGRLSS
VDNLEAVRKLPGVEEMMVKAQVGQAVQPPKNFSDRLGHVIVSGKSYEEVV
ERLHKISNMISLKIS------- (SEQ ID NO: 6)
*
```

FIG. 16-2

```
>gi|229168264|ref|ZP_04295989.1_BCE

------------------MLAIRKAKELGYEPIFLTQKKSLYHGLSDLECR-
---VIELDTNSVDAIKHYIIHE--KIEDIAGILTTSDYYLETVAELVQMFR
LSGNTHQAIYYCRNKAMFREKLHLEKVLQPKFHIVQSIDSLQNIYSSIQF
PCVVKPADDSGSNNVRLCSNWEEVEKIATKILANKYNARGQEKANMVLLE
EYIEGPEYSVEMFSWE-GNSICIGITEKQLTGFPYFVESGHIFPVELPKD
VQSEIEQTVKCALQAVDFRFGASHSEVKWTSNGCVVIEVNARLAGGMIPE
LVRHSTGVDLLRQQVLSSVGVAPEWKEIEYMN-YAGIHFLTAKKSGFLST
VKGIEEVRELSYIEELVVKAQVGQPVNPPENFSHRLGHVMVRGRTYEETV
LFLEEVAKKLEIQVNN------ (SEQ ID NO: 10)
*

>gi|228758608|gb|EEM07742.1|_BMY

------------------MLALNKAKLYGFSPVFITNNPDRYVGLEKAECS-
---IFICDTNNIENLYETINNN-LEVDKIQGITTTSEFYLEIVSELARKYG
LPRNSVQAIRNCRNKLETRNCLKEAKVRQPKFEEVTSISDINKSLNIIGL
PCIVKPVDDSGSNGVRFCKTVAEVKEQTLEILSWKKNSRGQSTVQTVLLE
EFIDAPEYSVEIFSFE-GKGKCVGITEKKLIGFPHFVEHQHVFPAKLPAD
VTREIQNTVEDALKAVGITNGPTHTEVKLTPQGCAIIEINARLAGGMIPK
LIQISTGIDMLEYQLLLSVGKYKAP--ILNYQRYAGIKFIVSNLDGILND
IRGVEKVRTLQGVNQVNINVNRGDKVISPKNAYDRLGYVIVEGNSYEETE
ARLNKSIEKLEILVGN------ (SEQ ID NO: 18)
*
```

FIG. 17-1

| N | Target | Description | E-value | |Log(E-value)| |
|---|---|---|---|---|
| 1 | C0Z5R1_BREBN | Putative uncharacterized protein (gene: BBR47_51900) | 4,00E-216 | 215,39794 |
| 2 | F5SLP0_9BACL | Pyridoxal-phosphate dependent enzyme (gene: HMPREF9374_4022) | 3,80E-215 | 214,4202164 |
| 3 | C2PYS6_BACCE | Argininosuccinate lyase domain protein (gene: bcere0007_32210) | 3,80E-206 | 205,4202164 |
| 4 | C3BDI4_BACMY | Argininosuccinate lyase domain protein (gene: bmyco0003_56050) | 3,70E-195 | 194,4317983 |
| 5 | E3FE26_STIAD | Argininosuccinate lyase 2-like protein (gene: STAUR_4851) | 1,30E-183 | 182,8860566 |
| 6 | C3BTM3_9BACI | Argininosuccinate lyase domain protein (gene: bpmyx0001_50290) | 8,00E-136 | 135,09691 |
| 7 | B0B530_STRCU | Putative pyridoxal-phosphate dependent enzyme (gene: orf_R4) | 2,60E-133 | 132,5850267 |
| 8 | F0PS09_BACTO | Putative uncharacterized protein (gene: YBT020_25570) | 1,30E-131 | 130,8860566 |
| 9 | F4F5X7_VERMA | Cysteine synthase (gene: VAB18032_22180) | 1,40E-128 | 127,853872 |
| 10 | C6WLF1_ACTMD | Cysteine synthase (gene: Amir_4500) | 2,30E-128 | 127,6382722 |
| 11 | E2EKQ1_9ACTO | Diaminoacid synthase/ligase fusion protein (gene: pac19) | 1,10E-125 | 124,9586073 |
| 12 | F1CHS8_9ACTO | DABA synthase (gene: npsl) | 2,30E-125 | 124,6382722 |
| 13 | D6APC7_STRFL | DabC (gene: SSGG_02990) | 3,20E-125 | 124,49485 |
| 14 | D3Q4U1_STANL | Putative uncharacterized protein (gene: Snas_2438) | 6,30E-96 | 95,20065945 |
| 15 | Q63UA1_BURPS | Putative bifunctional protein (Ligase and argininosuccinate lyase) (gene: BPSL1715) | 2,10E-94 | 93,67778071 |
| 16 | C6TPZ3_BURPS | Argininosuccinate lyase (gene: BURPS1710A_2469) | 3,10E-94 | 93,50863831 |
| 17 | Q3JSA0_BURP1 | Argininosuccinate lyase domain protein (gene: BURPS1710b_2158) | 3,20E-94 | 93,49485002 |

FIG. 17-2

| N | Target | Description | E-value | |Log(E-value)| |
|---|---|---|---|---|
| 18 | C5ZGF9_BURPS | Putative lyase (gene: BURPS1106B_A1258) | 3,60E-94 | 93,4436975 |
| 19 | A4LBK5_BURPS | Putative lyase (gene: BURPS305_6606) | 3,60E-94 | 93,4436975 |
| 20 | C0Y7H2_BURPS | Putative lyase (gene: BUH_1888) | 4,10E-94 | 93,38721614 |
| 21 | G2PF82_STRVO | ATP-dependent carboxylate-amine ligase domain protein ATP-grasp (gene: Strvi_4637) | 1,30E-93 | 92,88605665 |
| 22 | F2LEB6_BURGS | Argininosuccinate lyase (gene: bgla_1g16460) | 5,20E-93 | 92,28399666 |
| 23 | G0WV72_STRVR | Diaminobutyric acid synthase C (gene: dabC) | 6,40E-92 | 91,19382003 |
| 24 | C9RTG5_GEOSY | Putative uncharacterized protein (gene: GYMC61_0754) | 6,30E-85 | 84,20065945 |
| 25 | D7D1Z0_GEOSC | Putative uncharacterized protein (gene: GC56T3_0730) | 1,30E-84 | 83,88605665 |
| 26 | B7GFS1_ANOFW | Predicted carboxylase (ATP-grasp family) (gene: Aflv_0217) | 3,10E-84 | 83,50863831 |
| 27 | Q63SV7_BURPS | Putative fusion protein (Ligase/carboxylase and argininosuccinate lyase) (gene: BPSL2214) | 3,30E-84 | 83,48148606 |
| 28 | A5TJX5_BURMA | Lyase family protein (gene: BMA721280_A1050) | 3,50E-84 | 83,45593196 |
| 29 | Q8KJE6_RHILI | FUSION PROTEIN CONTAINS PUTATIVE LIGASE AND PROBABLE ARGINOSUCCINATE LYASE (gene: msi203) | 5,40E-84 | 83,26760624 |
| 30 | A3ML08_BURM7 | Argininosuccinate lyase domain protein (gene: BMA10247_1396) | 7,30E-84 | 83,13667714 |
| 31 | Q5KW89_GEOKA | Hypothetical conserved protein (gene: GK2762) | 1,10E-83 | 82,95860731 |
| 32 | Q2SX49_BURTA | Argininosuccinate lyase domain protein (gene: BTH_I1971) | 1,30E-83 | 82,88605665 |
| 33 | A6TPU8_ALKMQ | Putative uncharacterized protein (gene: Amet_2055) | 1,80E-83 | 82,74472749 |

FIG. 17-3

| N | Target | Description | E-value | \|Log(E-value)\| |
|---|---|---|---|---|
| 34 | F7KHZ8_9FIRM | Putative uncharacterized protein (gene: HMPREF0994_05500) | 2,10E-83 | 82,67778071 |
| 35 | D3AGE3_9CLOT | ATP-grasp domain protein (gene: CLOSTHATH_02679) | 2,30E-83 | 82,63827216 |
| 36 | B1HKH5_BURPS | Argininosuccinate lyase domain protein (gene: BURPSS13_P1168) | 2,80E-83 | 82,55284197 |
| 37 | A6TPU7_ALKMQ | Putative uncharacterized protein (gene: Amet_2054) | 3,20E-83 | 82,49485002 |
| 38 | B7GKI9_ANOFW | Formate-dependent phosphoribosylglycinamide formyltransferase (GAR transformylase) (gene: Aflv_1026) | 4,00E-83 | 82,39794001 |
| 39 | A4LD16_BURPS | Lyase family protein (gene: BURPS305_7168) | 6,00E-83 | 82,22184875 |
| 40 | C4KPT5_BURPS | Argininosuccinate lyase 2 (Arginosuccinase 2) (Asal 2) (gene: GBP346_A2629) | 9,30E-83 | 82,03151705 |
| 41 | C0YCH6_BURPS | Lyase family protein (gene: BUH_2552) | 1,00E-82 | 82 |
| 42 | C5ZJH2_BURPS | Lyase family protein (gene: BURPS1106B_A1783) | 1,30E-82 | 81,88605665 |
| 43 | Q3JQX0_BURP1 | Argininosuccinate lyase domain protein (gene: BURPS1710b_2646) | 1,00E-81 | 81 |
| 44 | B2H9Z1_BURPS | Argininosuccinate lyase domain protein (gene: BURPS1655_H0298) | 1,10E-81 | 80,95860731 |
| 45 | A8KVZ6_BURPS | Argininosuccinate lyase domain protein (gene: BURPSPAST_R0310) | 3,50E-81 | 80,45593196 |
| 46 | A3NB13_BURP6 | Argininosuccinate lyase (gene: BURPS668_2507) | 3,50E-81 | 80,45593196 |
| 47 | F1DGJ0_9ACTO | Putative uncharacterized protein | 6,10E-81 | 80,21467016 |
| 48 | A1V5D2_BURMS | Argininosuccinate lyase domain protein (gene: BMASAVP1_A2122) | 2,30E-80 | 79,63827216 |

FIG. 17-4

| N | Target | Description | E-value | |Log(E-value)| |
|---|---|---|---|---|
| 49 | C5NAA5_BURMA | Lyase family protein (gene: BMAPRL20_A1664) | 2,40E-80 | 79,61978876 |
| 50 | A8ECB3_BURPS | Argininosuccinate lyase domain protein (gene: BURPS406E_H0439) | 2,40E-80 | 79,61978876 |
| 51 | B7D052_BURPS | Lyase family protein (gene: BUC_2825) | 2,50E-80 | 79,60205999 |
| 52 | B5V3S1_BACCE | Phosphoribosylglycinamide synthetase, ATP-grasp (gene: BCH308197_2192) | 4,10E-80 | 79,38721614 |
| 53 | C2TR35_BACCE | Phosphoribosylglycinamide synthetase, ATP-grasp (A) domain protein (gene: bcere0016_57030) | 4,50E-80 | 79,34678749 |
| 54 | E1YQG6_9BACE | L-lactate dehydrogenase (gene: HMPREF9008_01673) | 4,70E-80 | 79,32790214 |
| 55 | Q62J65_BURMA | Argininosuccinate lyase domain protein (gene: BMA1620) | 4,70E-80 | 79,32790214 |
| 56 | C4AVR8_BURMA | Argininosuccinate lyase 2 (Arginosuccinase 2) (Asal 2) (gene: BMAGB8_1709) | 5,00E-80 | 79,30103 |
| 57 | D5TZC0_BACT1 | Phosphoribosylglycinamide synthetase ATP-grasp domain-containing protein (gene: BMB171_P0212) | 6,90E-80 | 79,16115091 |
| 58 | Q74NS4_BACC1 | Phosphoribosylglycinamide synthetase, ATP-grasp (A) domain protein (gene: BCE_A0170) | 6,90E-80 | 79,16115091 |
| 59 | D9WHP6_9ACTO | ATP-grasp domain protein (gene: SSOG_01010) | 7,30E-80 | 79,13667714 |
| 60 | D0TCU6_9BACE | Putative uncharacterized protein (gene: HMPREF0103_1362) | 1,10E-79 | 78,95860731 |
| 61 | G0FTB8_AMYMD | Argininosuccinate lyase (gene: RAM_24230) | 6,20E-79 | 78,20760831 |

FIG. 17-5

| N | Target | Description | E-value | |Log(E-value)| |
|---|---|---|---|---|
| 62 | D9XKV3_9ACTO | ATP-grasp domain-containing protein (gene: SSRG_01345) | 2,20E-78 | 77,65757732 |
| 63 | A4FN76_SACEN | Putative fusion protein (Ligase/carboxylase and argininosuccinate lyase) (gene: SACE_6330) | 5,00E-78 | 77,30103 |
| 64 | Q7NA29_PHOLL | Similarities with putative carboxylase (gene: plu0116) | 7,30E-78 | 77,13667714 |
| 65 | E8W7D4_STRFA | Putative uncharacterized protein (gene: Sfla_0476) | 8,20E-78 | 77,08618615 |

FIG. 18-1

```
>Staur_4851

-MNQFVFVESNTTGTGRLAVERLLAQGEQVTFITHQPEKYPFLVGNKAPG
LKVLKVETNDAAAVEACVDGLVREGK-VAALLTFSTFYVPTVAAIAARHG
LRYLQPRAAQACHNKHEARALLR-AAGLPGPEFHVIASEAEAAQLAQTVR
FPCVVKPPAESGSTGVRRVDTPEELLAHFRSLHSRAANERGQSLHGEVLV
ESFLEGPEFSVETMTLADGTTHVLGVTQKYLSAPPYFVEMGHDFPADLPP
ERRRALEEAVLAGLAAVGFDFGPAHTEIRFTPAGPVIIEINPRLAGGMIP
ELVRLSTGVDLLSAMLDQMLGRPVDLTHT--RQDVACIRFITSERPGVLA
RVEGQDEASRLGTVRQVAVDKAAGTRLRPPESATDRLGYVIASGPERGQV
LGDAARALSLLRVEQAAPSAPA---  (SEQ ID NO: 4)
*

>BBR47_51900

MNKHFLFVEANTTGTGMLAMKKARKLGFTPVFFTEKPERYHGLNELECH-
---VVVTDTNSQAELTDSVAQVSKEGREIAGIMSTSDYYLESVAKLARKFG
WISNSLEAIEACRNKAIFREKLQ-RHQVSQPTFLAISSMEQLLEARSSIS
LPCVVKPADDSGSNNVRLCFSWDEVEHMAAEILAIKYNARGQETARTVLL
EQYAEGPEFSVETFSWQ-GQCFVIGITQKRLTGYPFFVEAGHIFPAPLSV
EEKQEIERTVERALAAVKYQFGAAHTEVKWTSAGCVVIEVNARLAGGMIP
ELVRRSTGIDLLLQQIRCAAGLEPELSQTIEEQRCAGIHFLVSESQGTFG
GIKGMDTVRNLPGIAEVAIHAKIGQNVQPPQNFSHRLGYVIVEGKHYSET
AELIEQVKDSLSVQVGQQLESGV--  (SEQ ID NO: 2)
*

>gi|229168264|ref|ZP_04295989.1_BCE

------------------MLAIRKAKELGYEPIFLTQKKSLYHGLSDLECR-
---VIELDTNSVDAIKHYIIHE--KIEDIAGILTTSDYYLETVAELVQMFR
LSGNTHQAIYYCRNKAMFREKLH-LEKVLQPKFHIVQSIDSLQNIYSSIQ
FPCVVKPADDSGSNNVRLCSNWEEVEKIATKILANKYNARGQEKANMVLL
EEYIEGPEYSVEMFSWE-GNSICIGITEKQLTGFPYFVESGHIFPVELPK
DVQSEIEQTVKCALQAVDFRFGASHSEVKWTSNGCVVIEVNARLAGGMIP
ELVRHSTGVDLLRQQVLSSVGVAPEWKEIEYMN-YAGIHFLTAKKSGFLS
TVKGIEEVRELSYIEELVVKAQVGQPVNPPENFSHRLGHVMVRGRTYEET
VLFLEEVAKKLEIQVNN--------  (SEQ ID NO: 10)
*
```

FIG. 18-2

```
>P1;gi|333374399|ref|ZP_08466276.1_DES

MKKKLLFVEGNTTGTGILALEKARKLGYEPVFLTQEASRYDGLPEAKCR-
--VHVTVTDSIHELKRCVSQE--KAEAVAGILTTSDYYLEISAKLVQELG
LTGNSPQAIHLCRNKALYREKLR-SKSVPQPNFHIIRSMEDLRETRESVP
LPCLVKPADDSGSNNVRLCFSWGEVEQLTSKILKIERNARGQKTSQTVLL
EEYIEGPEYSVEMFSWQ-GKSTCIGITEKQLTGYPYFVESGHVFPAVLPT
DVQQEIEKTVKQSLEAVHFQFGASHSEVKWTPNGCVMIETNARLAGGMIP
ELVRHSTGVDLIEQQILCAAGVAPHWKQVVPTG-CSGIHFIVAAEAGRLS
SVDNLEAVRKLPGVEEMMVKAQVGQAVQPPKNFSDRLGHVIVSGKSYEEV
VERLHKISNMISLKIS--------- (SEQ ID NO: 6)
*

>gi|228758608|gb|EEM07742.1_BMY

---------------MLALNKAKLYGFSPVFITNNPDRYVGLEKAECS-
---IFICDTNNIENLYETINNN-LEVDKIQGITTTSEFYLEIVSELARKYG
LPRNSVQAIRNCRNKLETRNCLK-EAKVRQPKFEEVTSISDINKSLNIIG
LPCIVKPVDDSGSNGVRFCKTVAEVKEQTLEILSWKKNSRGQSTVQTVLL
EEFIDAPEYSVEIFSFE-GKGKCVGITEKKLIGFPHFVEHQVFPAKLPA
DVTREIQNTVEDALKAVGITNGPTHTEVKLTPQGCAIIEINARLAGGMIP
KLIQISTGIDMLEYQLLLSVGKYKAP--ILNYQRYAGIKFIVSNLDGILN
DIRGVEKVRTLQGVNQVNINVNRGDKVISPKNAYDRLGYVIVEGNSYEET
EARLNKSIEKLEILVGN-------- (SEQ ID NO: 18)
*

>BTH

-MKKLLFIESNTTGTGMLALIKARELGFTPVLLTNNPGRYIGLGETKCI-
---VLECDTNNLNCIRTIIDSEFEVG-EIKAITTTSEFYIEVVAILAKELG
LIGNPIDTVKKCRNKAEMRLLLKGIENIYEPWFYIIDSLEKLELAKDNIK
FPCVVKPVDDSGSNNVLKCYSYEEVKRHTEKILSNKYNVRSQKNAQNILV
EEYVSGQEYSVEIFTYN-GKCKIVGVTQKIVDGAPYFIECGHIFPAPVSD
DIRSVIERGVTKIIEKVNWQNGPCHLEIKIKGEKIFLVEFNGRLAGGMIP
ELIKYATGIDLLKEQLKVVTRMRPKLDQNP--TLYAGIRFIIPLRDGKIT
SIFGVNDIENTVGIKEVKLRTIVGESIRKVENAYGRIGHIIGAAENINKL
NYILDKSMDALHIEIEECEDYEDFN (SEQ ID NO: 12)
*
```

FIG. 19-1

| N | Target | Description | E-value | \|Log(E-value)\| |
|---|---|---|---|---|
| 1 | C0Z5R1_BREBN | Putative uncharacterized protein (gene: BBR47_51900) | 8,70E-211 | 210,06 |
| 2 | F5SLP0_9BACL | Pyridoxal-phosphate dependent enzyme (gene: HMPREF9374_4022) | 2,20E-207 | 206,66 |
| 3 | C2PYS6_BACCE | Argininosuccinate lyase domain protein (gene: bcere0007_32210) | 7,20E-198 | 197,14 |
| 4 | F0PS09_BACT0 | Putative uncharacterized protein (gene: YBT020_25570) | 2,10E-196 | 195,68 |
| 5 | C3BDI4_BACMY | Argininosuccinate lyase domain protein (gene: bmyco0003_56050) | 2,90E-187 | 186,54 |
| 6 | E3FE26_STIAD | Argininosuccinate lyase 2-like protein (gene: STAUR_4851) | 4,90E-176 | 175,31 |
| 8 | C3BTM3_9BACI | Argininosuccinate lyase domain protein (gene: bpmyx0001_50290) | 1,20E-137 | 136,92 |
| 9 | B0B530_STRCU | Putative pyridoxal-phosphate dependent enzyme (gene: orf_R4) | 1,50E-137 | 136,82 |
| 10 | F1CHS8_9ACTO | DABA synthase (gene: npsl) | 4,50E-132 | 131,35 |
| 11 | C6WLF1_ACTMD | Cysteine synthase (gene: Amir_4500) | 1,00E-131 | 131,00 |
| 12 | F4F5X7_VERMA | Cysteine synthase (gene: VAB18032_22180) | 4,90E-131 | 130,31 |
| 13 | E2EKQ1_9ACTO | Diaminoacid synthase/ligase fusion protein (gene: pac19) | 6,50E-131 | 130,19 |
| 14 | Q63UA1_BURPS | Putative bifunctional protein (Ligase and argininosuccinate lyase) (gene: BPSL1715) | 7,20E-97 | 96,14 |
| 15 | C5ZGF9_BURPE | Putative lyase (gene: BURPS1106B_A1258) | 1,60E-96 | 95,80 |
| 16 | A4LBK5_BURPE | Putative lyase (gene: BURPS305_6606) | 1,60E-96 | 95,80 |
| 17 | C0Y7H2_BURPE | Putative lyase (gene: BUH_1888) | 1,80E-96 | 95,74 |
| 18 | C6TPZ3_BURPE | Argininosuccinate lyase (gene: BURPS1710A_2469) | 3,00E-96 | 95,52 |

FIG. 19-2

| N | Target | Description | E-value | |Log(E-value)| |
|---|---|---|---|---|
| 19 | Q3JSA0_BURP1 | Argininosuccinate lyase domain protein (gene: BURPS1710b_2158) | 3,10E-96 | 95,51 |
| 20 | D3Q4U1_STANL | Putative uncharacterized protein (gene: Snas_2438) | 5,50E-96 | 95,26 |
| 21 | F2LEB6_BURGS | Argininosuccinate lyase (gene: bgla_1g16460) | 4,40E-95 | 94,36 |
| 22 | H2JPF8_STRHJ | Putative ligase/carboxylase (gene: SHJG_0604) | 2,10E-94 | 93,68 |
| 23 | G2PF82_STRVO | ATP-dependent carboxylate-amine ligase domain protein ATP-grasp (gene: Strvi_4637) | 4,00E-93 | 92,40 |
| 24 | G0WV72_STRVR | Diaminobutyric acid synthase C (gene: dabC) | 9,10E-93 | 92,04 |
| 25 | Q63SV7_BURPS | Putative fusion protein (Ligase/carboxylase and argininosuccinate lyase) (gene: BPSL2214) | 2,40E-88 | 87,62 |
| 26 | A5TJX5_BURMA | Lyase family protein (gene: BMA721280_A1050) | 2,50E-88 | 87,60 |
| 27 | A6TPU8_ALKMQ | Putative uncharacterized protein (gene: Amet_2055) | 4,70E-88 | 87,33 |
| 28 | A3ML08_BURM7 | Argininosuccinate lyase domain protein (gene: BMA10247_1396) | 5,50E-88 | 87,26 |
| 29 | F7KHZ8_9FIRM | Putative uncharacterized protein (gene: HMPREF0994_05500) | 9,90E-88 | 87,00 |
| 30 | D3AGE3_9CLOT | ATP-grasp domain protein (gene: CLOSTHATH_02679) | 1,10E-87 | 86,96 |
| 31 | B1HKH5_BURPE | Argininosuccinate lyase domain protein (gene: BURPSS13_P1168) | 2,00E-87 | 86,70 |
| 32 | Q2SX49_BURTA | Argininosuccinate lyase domain protein (gene: BTH_I1971) | 4,30E-87 | 86,37 |
| 33 | A4LD16_BURPE | Lyase family protein (gene: BURPS305_7168) | 5,20E-87 | 86,28 |

FIG. 19-3

| N | Target | Description | E-value | \|Log(E-value)\| |
|---|---|---|---|---|
| 34 | C4KPT5_BURPE | Argininosuccinate lyase 2 (Arginosuccinase 2) (Asal 2) (gene: GBP346_A2629) | 6,60E-87 | 86,18 |
| 35 | C0YCH6_BURPE | Lyase family protein (gene: BUH_2552) | 7,30E-87 | 86,14 |
| 36 | C5ZJH2_BURPE | Lyase family protein (gene: BURPS1106B_A1783) | 8,80E-87 | 86,06 |
| 37 | H5X7R7_9PSEU | Biotin carboxylase (gene: SacmaDRAFT_3129) | 9,80E-87 | 86,01 |
| 38 | G8N4Z9_GEOTH | Putative uncharacterized protein (gene: GTCCBUS3UF5_31070) | 1,00E-86 | 86,00 |
| 39 | Q5KW89_GEOKA | Hypothetical conserved protein (gene: GK2762) | 1,90E-86 | 85,72 |
| 40 | B7GKI9_ANOFW | Formate-dependent phosphoribosylglycinamide formyltransferase (GAR transformylase) (gene: Aflv_1026)) | 6,50E-86 | 85,19 |
| 41 | Q3JQX0_BURP1 | Argininosuccinate lyase domain protein (gene: BURPS1710b_2646) | 8,00E-86 | 85,10 |
| 42 | B2H9Z1_BURPE | Argininosuccinate lyase domain protein (gene: BURPS1655_H0298) | 8,60E-86 | 85,07 |
| 43 | A8KVZ6_BURPE | Argininosuccinate lyase domain protein (gene: BURPSPAST_R0310) | 2,70E-85 | 84,57 |
| 44 | A3NB13_BURP6 | Argininosuccinate lyase (gene: BURPS668_2507) | 2,70E-85 | 84,57 |
| 45 | B7GFS1_ANOFW | Predicted carboxylase (ATP-grasp family) (gene: Aflv_0217) | 5,00E-85 | 84,30 |
| 46 | A6TPU7_ALKMQ | Putative uncharacterized protein (gene: Amet_2054) | 8,80E-85 | 84,06 |
| 47 | A8ECB3_BURPE | Argininosuccinate lyase domain protein (gene: BURPS406E_H0439) | 1,60E-84 | 83,80 |

FIG. 19-4

| N | Target | Description | E-value | \|Log(E-value)\| |
|---|---|---|---|---|
| 48 | A1V5D2_BURMS | Argininosuccinate lyase domain protein (gene: BMASAVP1_A2122) | 1,80E-84 | 83,74 |
| 49 | C5NAA5_BURMA | Lyase family protein (gene: BMAPRL20_A1664) | 1,90E-84 | 83,72 |
| 50 | B7D052_BURPE | Lyase family protein (gene: BUC_2825) | 1,90E-84 | 83,72 |
| 51 | Q62J65_BURMA | Argininosuccinate lyase domain protein (gene: BMA1620) | 3,90E-84 | 83,41 |
| 52 | C4AVR8_BURMA | Argininosuccinate lyase 2 (Arginosuccinase 2) (Asal 2) (gene: BMAGB8_1709) | 4,10E-84 | 83,39 |
| 53 | G8SKH8_ACTS5 | Carbamoyl-phosphate synthase large chain (gene: ACPL_3592) | 3,20E-82 | 81,49 |
| 54 | G0FTB8_AMYMD | Argininosuccinate lyase (gene: RAM_24230) | 6,80E-82 | 81,17 |
| 55 | C2TR35_BACCE | Phosphoribosylglycinamide synthetase, ATP-grasp (A) domain protein (gene: bcere0016_57030) | 1,30E-81 | 80,89 |
| 56 | E1YQG6_9BACE | L-lactate dehydrogenase (gene: HMPREF9008_01673) | 1,50E-81 | 80,82 |
| 57 | G8UG75_BACCE | Putative uncharacterized protein (gene: bcf_10760) | 1,90E-81 | 80,72 |
| 58 | D5TZC0_BACT1 | Phosphoribosylglycinamide synthetase ATP-grasp domain-containing protein (gene: BMB171_P0212) | 2,30E-81 | 80,64 |
| 59 | Q74NS4_BACC1 | Phosphoribosylglycinamide synthetase, ATP-grasp (A) domain protein (gene: BCE_A0170) | 2,30E-81 | 80,64 |
| 60 | D0TCU6_9BACE | Putative uncharacterized protein (gene: HMPREF0103_1362) | 3,00E-81 | 80,52 |
| 61 | Q7NA29_PHOLL | Similarities with putative carboxylase (gene: plu0116) | 4,80E-80 | 79,32 |
| 62 | G8RVB3_MYCRN | Biotin carboxylase (gene: MycrhN_2396) | 9,30E-80 | 79,03 |

FIG. 19-5

| N | Target | Description | E-value | |Log(E-value)| |
|---|---|---|---|---|
| 63 | F1DGJ0_9ACTO | Putative uncharacterized protein | 1,00E-79 | 79,00 |
| 64 | E2D2N4_9BACT | Diaminobutyric acid synthase C | 6,00E-79 | 78,22 |
| 65 | C3GAI1_BACTU | Putative uncharacterized protein (gene: bthur0009_48460) | 8,90E-79 | 78,05 |
| 66 | E0SFE3_DICD3 | Argininosuccinate lyase (gene: Dda3937_02620) | 2,30E-78 | 77,64 |
| 67 | D9WHP6_9ACTO | ATP-grasp domain protein (gene: SSOG_01010) | 2,50E-78 | 77,60 |
| 68 | A4FN76_SACEN | Putative fusion protein (Ligase/carboxylase and argininosuccinate lyase) (gene: SACE_6330) | 3,50E-78 | 77,46 |
| 69 | C2U7K3_BACCE | Putative uncharacterized protein (gene: bcere0017_58000) | 1,30E-77 | 76,89 |
| 70 | A3KFG4_9ACTO | DabC (gene: dabC) | 2,40E-77 | 76,62 |
| 71 | B3Q278_RHIE6 | Putative carboxylase protein (gene: RHECIAT_PB0000066) | 1,20E-76 | 75,92 |
| 72 | D9XKV3_9ACTO | ATP-grasp domain-containing protein (gene: SSRG_01345) | 1,30E-76 | 75,89 |
| 73 | E8W7D4_STRFA | Putative uncharacterized protein (gene: Sfla_0476) | 4,60E-76 | 75,34 |

FIG. 20-1

```
>Staur_4851

-MNQFVFVESNTTGTGRLAVERLLAQGEQVTFITHQPEKYPFLVGNKAPG
LKVLKVETNDAAAVEACVDGLVREGKVAALLTFSTFYVPTVAAIAARHGL
RYLQPRAAQACHNKHEARALLR-AAGLPGPEFHVIASEAEAAQLAQTVRF
PCVVKPPAESGSTGVRRVDTPEELLAHFRSLHSRAANERGQSLHGEVLVE
SFLEGPEFSVETMTL-ADGTTHVLGVTQKYLSAPPYFVEMGHDFPADLPP
ERRRALEEAVLAGLAAVGFDFGPAHTEIRFTPAGPVIIEINPRLAGGMIP
ELVRLSTGVDLLSAMLDQMLGRPVDLTHT--RQDVACIRFITSERPGVLA
RVEGQDEASRLGTVRQVAVDKAAGTRLRPPESATDRLGYVIASGPE---R
GQVLGDAARALSLLRVEQAAPSAPA-------------------------
---------------------------------------------------
---------------------------------------------------
---------------------------------------------------
---------------------------------------------------
---------------------------------------------------
---------------------------------------------------
---- (SEQ ID NO: 4)
*

>BBR47_51900

MNKHFLFVEANTTGTGMLAMKKARKLGFTPVFFTEKPERYHGLN--ELEC
HVVVTDTNSQAELTDSVAQVSKEGREIAGIMSTSDYYLESVAKLARKFGW
ISNSLEAIEACRNKAIFREKLQ-RHQVSQPTFLAISSMEQLLEARSSISL
PCVVKPADDSGSNNVRLCFSWDEVEHMAAEILAIKYNARGQETARTVLLE
QYAEGPEFSVETFSWQGQC---FVIGITQKRLTGYPFFVEAGHIFPAPLSV
EEKQEIERTVERALAAVKYQFGAAHTEVKWTSAGCVVIEVNARLAGGMIP
ELVRRSTGIDLLLQQIRCAAGLEPELSQTIEEQRCAGIHFLVSESQGTFG
GIKGMDTVRNLPGIAEVAIHAKIGQNVQPPQNFSHRLGYVIVEGKHYSET
AELIEQVKDSLSVQVGQQLESGV---------------------------
---------------------------------------------------
---------------------------------------------------
---------------------------------------------------
---------------------------------------------------
---------------------------------------------------
---------------------------------------------------
---- (SEQ ID NO: 2)
*
```

FIG. 20-2

```
>gi|229168264|ref|ZP_04295989.1_BCE

------------------MLAIRKAKELGYEPIFLTQKKSLYHGLS--DLEC
RVIELDTNSVDAIKHYIIHE--KIEDIAGILTTSDYYLETVAELVQMFRL
SGNTHQAIYYCRNKAMFREKLH-LEKVLQPKFHIVQSIDSLQNIYSSIQF
PCVVKPADDSGSNNVRLCSNWEEVEKIATKILANKYNARGQEKANMVLLE
EYIEGPEYSVEMFSWEGNS--ICIGITEKQLTGFPYFVESGHIFPVELPK
DVQSEIEQTVKCALQAVDFRFGASHSEVKWTSNGCVVIEVNARLAGGMIP
ELVRHSTGVDLLRQQVLSSVGVAPEWKEIEYMN-YAGIHFLTAKKSGFLS
TVKGIEEVRELSYIEELVVKAQVGQPVNPPENFSHRLGHVMVRGRTYEET
VLFLEEVAKKLEIQVNN----------------------------------
----------------------------------------------------
----------------------------------------------------
----------------------------------------------------
----------------------------------------------------
----------------------------------------------------
----------------------------------------------------
---- (SEQ ID NO: 10)
*

>gi|333374399|ref|ZP_08466276.1_DES

MKKKLLFVEGNTTGTGILALEKARKLGYEPVFLTQEASRYDGLP--EAKC
RVHVTVTDSIHELKRCVSQE--KAEAVAGILTTSDYYLEISAKLVQELGL
TGNSPQAIHLCRNKALYREKLR-SKSVPQPNFHIIRSMEDLRETRESVPL
PCLVKPADDSGSNNVRLCFSWGEVEQLTSKILKIERNARGQKTSQTVLLE
EYIEGPEYSVEMFSWQGKS--TCIGITEKQLTGYPYFVESGHVFPAVLPT
DVQQEIEKTVKQSLEAVHFQFGASHSEVKWTPNGCVMIETNARLAGGMIP
ELVRHSTGVDLIEQQILCAAGVAPHWKQVVPTG-CSGIHFIVAAEAGRLS
SVDNLEAVRKLPGVEEMMVKAQVGQAVQPPKNFSDRLGHVIVSGKSYEEV
VERLHKISNMISLKIS-----------------------------------
----------------------------------------------------
----------------------------------------------------
----------------------------------------------------
----------------------------------------------------
----------------------------------------------------
----------------------------------------------------
---- (SEQ ID NO: 6)
*
```

FIG. 20-3

```
>gi|228758608|gb|EEM07742.1_BMY

----------------MLALNKAKLYGFSPVFITNNPDRYVGLE--KAEC
SIFICDTNNIENLYETINNN-LEVDKIQGITTTSEFYLEIVSELARKYGL
PRNSVQAIRNCRNKLETRNCLK-EAKVRQPKFEEVTSISDINKSLNIIGL
PCIVKPVDDSGSNGVRFCKTVAEVKEQTLEILSWKKNSRGQSTVQTVLLE
EFIDAPEYSVEIFSFEGKG--KCVGITEKKLIGFPHFVEHQHVFPAKLPA
DVTREIQNTVEDALKAVGITNGPTHTEVKLTPQGCAIIEINARLAGGMIP
KLIQISTGIDMLEYQLLLSVGKYKAP--ILNYQRYAGIKFIVSNLDGILN
DIRGVEKVRTLQGVNQVNINVNRGDKVISPKNAYDRLGYVIVEGNSYEET
EARLNKSIEKLEILVGN---------------------------------
--------------------------------------------------
--------------------------------------------------
--------------------------------------------------
--------------------------------------------------
--------------------------------------------------
--------------------------------------------------
--------------------------------------------------
--------------------------------------------------
--------------------------------------------------
---- (SEQ ID NO: 18)
*

>BTH

-MKKLLFIESNTTGTGMLALIKARELGFTPVLLTNNPGRYIGLG--ETKC
IVLECDTNNLNCIRTIIDSEFEVG-EIKAITTTSEFYIEVVAILAKELGL
IGNPIDTVKKCRNKAEMRLLLKGIENIYEPWFYIIDSLEKLELAKDNIKF
PCVVKPVDDSGSNNVLKCYSYEEVKRHTEKILSNKYNVRSQKNAQNILVE
EYVSGQEYSVEIFTYNGKC--KIVGVTQKIVDGAPYFIECGHIFPAPVSD
DIRSVIERGVTKIIEKVNWQNGPCHLEIKIKGEKIFLVEFNGRLAGGMIP
ELIKYATGIDLLKEQLKVVTRMRPKLDQNP--TLYAGIRFIIPLRDGKIT
SIFGVNDIENTVGIKEVKLRTIVGESIRKVENAYGRIGHIIGAAENINKL
NYILDKSMDALHIEIEECEDYEDFN-------------------------
--------------------------------------------------
--------------------------------------------------
--------------------------------------------------
--------------------------------------------------
--------------------------------------------------
--------------------------------------------------
---- (SEQ ID NO: 12)
*
```

FIG. 20-4

```
>BUR

-MKTFVFIESNTTGTGRLCLQKALLRGFDVLFVTSRPQLYPFLQ------
EEMVVPLVADTADPQRIADALAPYAGIAGIFSTSEYYIETAATVATRLGL
PAADPEAIRTCRDKGRLHRRLR-DAGVGVADTEIVSERTQLRDLAHGATY
PRVLKPAFGSGSVGVRLVRTPAEMLAHGERMLDARGNERGIALARQVLVQ
SFVDGPEFSVEVVGLGAEHGHAVLGVTGKHLGPLPHFVEAGHDFPAPIAA
AQRDAIVAETLRALDAVGHRFGPAHVECRVSGGKVVVIEINPRLAGGMIP
QAIEWATGVDVLGAMIDLHAGTPPDLGPR--RRGHAAIRFVLPARSGELR
ALSFEPDERFAGVRTRFMPLKQLGQRIEPAGDFRDRLALVIASAADPDAL
AHALEDVDRCVTVAIGDAGAAGEGAGAGRLRRTLHPEALAIVRKPAPRAE
RLAELDAFAAIDEAHLLMLVDAGICDRARAATVLAELARQRDAKFAAIAD
AIAPRGTYALYEQLLIERVGIDAGGAVHTARSRNDINACVAKLRAREWFD
TCGGKLWRVRAAIVDKAQHTLDWPLPTYSQYQAAQPGSFGYYLWSVETAL
RRDQAALERLDEELAVCPLGAGAGAGTDFPIRPGVSAALLGFARSFDSAL
DAVASRDLVLHFLAAIAIASTTLSRLAHDLQLWTMRETDFLALPDELSGG
SSLMPQKKNPYLLEIVKGKLAHVAGALNAAVFASQRTPFSNSVEIGTEML
APCADAVQAFGESCDLLRLMVSGVTGDPAKMRAAAEAGLVSATQVANALV
RETDISFHAAHRQIGALITQALDAHEDPAAALDALVRQPGASIDEAAARL
AYGGGPGAAGAGLARSRALLRQSAERLWRRRAAWHAAHARRRGCVADLLA
AAAA (SEQ ID NO: 8)
*
```

FIG. 21-1

| N | Target | Description | E-value | \|Log(E-value)\| |
|---|---|---|---|---|
| 1 | Q63UA1_BURPS | Putative bifunctional protein (Ligase and argininosuccinate lyase) (gene:BPSL1715) | 0,00E+00 | |
| 2 | A4LBK5_BURPE | Putative lyase (gene: BURPS305_6606) | 0,00E+00 | |
| 3 | C5ZGF9_BURPE | Putative lyase (gene: BURPS1106B_A1258) | 0,00E+00 | |
| 4 | C6TPZ3_BURPE | Argininosuccinate lyase (gene: BURPS1710A_2469) | 0,00E+00 | |
| 5 | Q3JSA0_BURP1 | Argininosuccinate lyase domain protein (gene: BURPS1710b_2158) | 0,00E+00 | |
| 6 | C0Y7H2_BURPE | Putative lyase (gene: BUH_1888) | 0,00E+00 | |
| 8 | F2LEB6_BURGS | Argininosuccinate lyase (gene: bgla_1g16460) | 0,00E+00 | |
| 9 | Q63SV7_BURPS | Putative fusion protein (Ligase/carboxylase and argininosuccinate lyase) (gene: BPSL2214)) | 1,00E-196 | 196 |
| 10 | A5TJX5_BURMA | Lyase family protein (gene: BMA721280_A1050) | 1,10E-196 | 195,9586073 |
| 11 | A3ML08_BURM7 | Argininosuccinate lyase domain protein (gene: BMA10247_1396) | 4,20E-196 | 195,3767507 |
| 12 | B1HKH5_BURPE | Argininosuccinate lyase domain protein (gene: BURPSS13_P1168) | 3,60E-195 | 194,4436975 |
| 13 | C4KPT5_BURPE | Argininosuccinate lyase 2 (Arginosuccinase 2) (Asal 2) (gene: GBP346_A2629) | 1,20E-194 | 193,9208188 |
| 14 | A4LD16_BURPE | Lyase family protein (gene: BURPS305_7168) | 3,30E-194 | 193,4814861 |

FIG. 21-2

| N | Target | Description | E-value | |Log(E-value)| |
|---|---|---|---|---|
| 15 | C5ZJH2_BURPE | Lyase family protein (gene: BURPS1106B_A1783) | 4,10E-194 | 193,3872161 |
| 16 | Q3JQX0_BURP1 | Argininosuccinate lyase domain protein (gene: BURPS1710b_2646) | 5,70E-194 | 193,2441251 |
| 17 | A8KVZ6_BURPE | Argininosuccinate lyase domain protein (gene: BURPSPAST_R0310) | 2,50E-193 | 192,60206 |
| 18 | C0YCH6_BURPE | Lyase family protein (gene: BUH_2552) | 2,70E-193 | 192,5686362 |
| 19 | B2H9Z1_BURPE | Argininosuccinate lyase domain protein (gene: BURPS1655_H0298) | 6,70E-193 | 192,1739252 |
| 20 | A1V5D2_BURMS | Argininosuccinate lyase domain protein (gene: BMASAVP1_A2122) | 1,30E-192 | 191,8860566 |
| 21 | C5NAA5_BURMA | Lyase family protein (gene: BMAPRL20_A1664) | 1,40E-192 | 191,853872 |
| 22 | Q2SX49_BURTA | Argininosuccinate lyase domain protein (gene: BTH_I1971) | 3,80E-192 | 191,4202164 |
| 23 | Q62J65_BURMA | Argininosuccinate lyase domain protein (gene: BMA1620) | 4,70E-192 | 191,3279021 |
| 24 | C4AVR8_BURMA | Argininosuccinate lyase 2 (Arginosuccinase 2) (Asal 2) (gene: BMAGB8_1709) | 5,20E-192 | 191,2839967 |
| 25 | B7D052_BURPE | Lyase family protein (gene: BUC_2825) | 2,80E-191 | 190,552842 |
| 26 | A8ECB3_BURPE | Argininosuccinate lyase domain protein (gene: BURPS406E_H0439) | 3,00E-191 | 190,5228787 |
| 27 | A3NB13_BURP6 | Argininosuccinate lyase (gene: BURPS668_2507) | 1,10E-190 | 189,9586073 |
| 28 | C0Z5R1_BREBN | Putative uncharacterized protein (gene: BBR47_51900) | 7,80E-186 | 185,1079054 |

FIG. 21-3

| N | Target | Description | E-value | \|Log(E-value)\| |
|---|---|---|---|---|
| 29 | F5SLP0_9BACL | Pyridoxal-phosphate dependent enzyme (gene: HMPREF9374_4022) | 7,20E-181 | 180,1426675 |
| 30 | F0PS09_BACTO | Putative uncharacterized protein (gene: YBT020_25570) | 2,50E-171 | 170,60206 |
| 31 | C2PYS6_BACCE | Argininosuccinate lyase domain protein (gene: bcere0007_32210) | 6,00E-171 | 170,2218487 |
| 32 | E3FE26_STIAD | Argininosuccinate lyase 2-like protein (gene: STAUR_4851) | 1,10E-163 | 162,9586073 |
| 33 | C3BDI4_BACMY | Argininosuccinate lyase domain protein (gene: bmyco0003_56050) | 7,80E-163 | 162,1079054 |
| 34 | Q08Q99_STIAD | Argininosuccinate lyase domain protein (gene: STIAU_0005) | 4,80E-141 | 140,3187588 |
| 35 | B0B530_STRCU | Putative pyridoxal-phosphate dependent enzyme (gene: orf_R4) | 2,80E-135 | 134,552842 |
| 36 | F0Q0P1_ACIAP | Argininosuccinate lyase (gene: Acav_2530) | 4,60E-134 | 133,3372422 |
| 37 | A4JPB5_BURVG | Argininosuccinate lyase (gene: Bcep1808_5167) | 2,20E-131 | 130,6575773 |
| 38 | C6WLF1_ACTMD | Cysteine synthase (gene: Amir_4500) | 4,20E-129 | 128,3767507 |
| 39 | C3BTM3_9BACI | Argininosuccinate lyase domain protein (gene: bpmyx0001_50290) | 9,40E-126 | 125,0268721 |
| 40 | F4F5X7_VERMA | Cysteine synthase (gene: VAB18032_22180) | 1,50E-125 | 124,8239087 |
| 41 | F1CHS8_9ACTO | DABA synthase (gene: npsl) | 3,10E-125 | 124,5086383 |
| 42 | E2EKQ1_9ACTO | Diaminoacid synthase/ligase fusion protein (gene: pac19) | 3,70E-125 | 124,4317983 |
| 43 | G0WV72_STRVR | Diaminobutyric acid synthase C (gene: dabC) | 7,30E-107 | 106,1366771 |

FIG. 21-4

| N | Target | Description | E-value | \|Log(E-value)\| |
|---|---|---|---|---|
| 44 | D3Q4U1_STANL | Putative uncharacterized protein (gene: Snas_2438) | 4,50E-104 | 103,3467875 |
| 45 | H2JPF8_STRHJ | Putative ligase/carboxylase (gene: SHJG_0604) | 1,60E-103 | 102,79588 |
| 46 | H5X7R7_9PSEU | Biotin carboxylase (gene: SacmaDRAFT_3129) | 7,10E-100 | 99,14874165 |
| 47 | E2D2N4_9BACT | Diaminobutyric acid synthase C | 2,00E-92 | 91,69897 |
| 48 | G0FTB8_AMYMD | Argininosuccinate lyase (gene: RAM_24230) | 1,70E-90 | 89,76955108 |
| 49 | A3KFG4_9ACTO | DabC (gene: dabC) | 1,90E-90 | 89,7212464 |
| 50 | G2PF82_STRVO | ATP-dependent carboxylate-amine ligase domain protein ATP-grasp (gene: Strvi_4637) | 6,30E-89 | 88,20065945 |
| 51 | A3KFG3_9ACTO | DabB (gene: dabB) | 3,60E-88 | 87,4436975 |
| 52 | G8SKH8_ACTS5 | Carbamoyl-phosphate synthase large chain (gene: ACPL_3592) | 3,70E-87 | 86,43179828 |
| 53 | E2D2N3_9BACT | Diaminobutyric acid synthase B | 7,70E-87 | 86,11350927 |
| 54 | G0WV71_STRVR | Diaminobutyric acid synthase B (gene: dabB) | 7,70E-86 | 85,11350927 |
| 55 | G0FTB9_AMYMD | Argininosuccinate lyase (gene: RAM_24235) | 1,10E-84 | 83,95860731 |
| 56 | A6TPU8_ALKMQ | Putative uncharacterized protein (gene: Amet_2055) | 4,70E-83 | 82,32790214 |
| 57 | E0SFE3_DICD3 | Argininosuccinate lyase (gene: Dda3937_02620) | 6,00E-82 | 81,22184875 |
| 58 | F7KHZ8_9FIRM | Putative uncharacterized protein (gene: HMPREF0994_05500) | 9,50E-82 | 81,02227639 |
| 59 | D3AGE3_9CLOT | ATP-grasp domain protein (gene: CLOSTHATH_02679) | 1,10E-81 | 80,95860731 |
| 60 | G8N4Z9_GEOTH | Putative uncharacterized protein (gene: GTCCBUS3UF5_31070) | 2,30E-81 | 80,63827216 |

FIG. 21-5

| N | Target | Description | E-value | |Log(E-value)| |
|---|---|---|---|---|
| 61 | B3Q278_RHIE6 | Putative carboxylase protein (gene: RHECIAT_PB0000066) | 3,40E-81 | 80,46852108 |
| 62 | Q5KW89_GEOKA | Hypothetical conserved protein (gene: GK2762) | 5,50E-81 | 80,25963731 |
| 63 | B7GKI9_ANOFW | Formate-dependent phosphoribosylglycinamide formyltransferase (GAR transformylase) (gene A | 1,50E-80 | 79,82390874 |
| 64 | B7GFS1_ANOFW | Predicted carboxylase (ATP-grasp family) (gene: Aflv_0217) | 4,40E-80 | 79,35654732 |
| 65 | A6TPU7_ALKMQ | Putative uncharacterized protein (gene: Amet_2054) | 1,10E-78 | 77,95860731 |
| 66 | C2TR35_BACCE | Phosphoribosylglycinamide synthetase, ATP-grasp (A) domain protein (gene: bcere0016_57030) | 8,20E-77 | 76,08618615 |
| 67 | D5TZC0_BACT1 | Phosphoribosylglycinamide synthetase ATP-grasp domain-containing protein (gene: BMB171_P02) | 1,30E-76 | 75,88605665 |
| 68 | Q74NS4_BACC1 | Phosphoribosylglycinamide synthetase, ATP-grasp (A) domain protein (gene: BCE_A0170) | 1,30E-76 | 75,88605665 |
| 69 | H0GBL1_RHIML | Carbamoyl-phosphate synthase L chain ATP-binding protein (gene: SM0020_34680) | 1,90E-76 | 75,7212464 |
| 70 | G8UG75_BACCE | Putative uncharacterized protein (gene: bcf_10760) | 2,10E-76 | 75,67778071 |
| 71 | F6EDQ3_SINMK | Carbamoyl-phosphate synthase L chain ATP-binding protein (gene: Sinme_6718) | 7,60E-76 | 75,11918641 |
| 72 | F1DGJ0_9ACTO | Putative uncharacterized protein | 1,60E-75 | 74,79588002 |
| 73 | E1YQG6_9BACE | L-lactate dehydrogenase (gene: HMPREF9008_01673) | 1,70E-75 | 74,76955108 |

FIG. 21-6

| N | Target | Description | E-value | \|Log(E-value)\| |
|---|---|---|---|---|
| 74 | H2JPF7_STRHJ | DabB-Fusion protein containing a ligase and an argininosuccinate lyase (gene: SHJG_0603) | 8,80E-75 | 74,05551733 |
| 75 | C2U7K3_BACCE | Putative uncharacterized protein (gene: bcere 0017_58000) | 1,60E-74 | 73,79588002 |
| 76 | G8RVB3_MYCRN | Biotin carboxylase (gene: MycrhN_2396) | 2,10E-74 | 73,67778071 |
| 77 | D9WHP6_9ACTO | ATP-grasp domain protein (gene: SSOG_01010) | 2,50E-74 | 73,60205999 |
| 78 | Q7NA29_PHOLL | Similarities with putative carboxylase (gene: plu0116) | 3,60E-74 | 73,4436975 |
| 79 | D0TCU6_9BACE | Putative uncharacterized protein (gene: HMPRE F0103_1362) | 4,60E-74 | 73,33724217 |
| 90 | D1P1Y9_9ENTR | ATP-grasp domain protein (gene: PROVRUST_06212) | 7,30E-74 | 73,13667714 |
| 91 | C3GAI1_BACTU | Putative uncharacterized protein (gene: bthur 0009_48460) | 1,30E-73 | 72,88605665 |
| 92 | H0GB56_RHIML | Carbamoyl-phosphate synthase L chain ATP-binding protein (gene: SM0020_33843) | 2,20E-73 | 72,65757732 |
| 93 | F6EDR0_SINMK | ATP-grasp fold domain protein, DUF201-type (gene: Sinme_6732) | 4,60E-73 | 72,33724217 |
| 94 | H1S861_9BURK | Argininosuccinate lyase 1 (gene: argH1) | 5,30E-73 | 72,27572413 |
| 95 | D9XKV3_9ACTO | ATP-grasp domain-containing protein (gene: SSRG_01345) | 7,20E-73 | 72,1426675 |
| 96 | Y4RH_RHISN | Uncharacterized protein y4rH (gene: NGR_a01790) | 9,90E-73 | 72,00436481 |
| 97 | G4K7A1_9RHIZ | ATP-dependent carboxylate-amine ligase domain protein ATP-grasp (gene: MesauDRAFT_5479) | 1,20E-72 | 71,92081875 |

FIG. 21-7

| N | Target | Description | E-value | |Log(E-value)| |
|---|---|---|---|---|
| 98 | E8THQ6_MESCW | Carbamoyl-phosphate synthase L chain ATP-binding protein (gene: Mesci_5771) | 1,20E-72 | 71,92081875 |
| 99 | F7Y512_MESOW | ATP-dependent carboxylate-amine ligase domain protein ATP-grasp (gene: Mesop_6349) | 1,20E-72 | 71,92081875 |
| 100 | F7XFK8_SINMM | Putative uncharacterized protein (gene: SM11_pC1255) | 2,30E-72 | 71,63827216 |
| 101 | A4FN76_SACEN | Putative fusion protein (Ligase/carboxylase and argininosuccinate lyase) (gene: SACE6330) | 3,00E-72 | 71,52287875 |
| 102 | F6EDJ3_SINMK | Carbamoyl-phosphate synthase L chain ATP-binding protein (gene: Sinme_6636) | 8,10E-72 | 71,09151498 |
| 103 | D3Q4U0_STANL | Fumarate lyase (gene: Snas_2437) | 1,00E-71 | 71 |
| 104 | E8W7D4_STRFA | Putative uncharacterized protein (gene: Sfla_0476) | 2,30E-71 | 70,63827216 |

FIG. 22-1

```
>Staur_4851

-MNQFVFVESNTTGTGRLAVERLLAQGEQVTFITHQPEKYPFLVGN-KAP
GLKVLKVETNDAAAVEACVDGLVREGKVAALLTFSTFYVPTVAAIAARHG
LRYLQPRAAQACHNKHEARALLR-AAGLPGPEFHVIASEAEAAQLAQTVR
FPCVVKPPAESGSTGVRRVDTPEELLAHFRSLHSRAANERGQSLHGEVLV
ESFLEGPEFSVETMTL-ADGTTHVLGVTQKYLSAPPYFVEMGHDFPADLP
PERRRALEEAVLAGLAAVGFDFGPAHTEIRFTPAGPVIIEINPRLAGGMI
PELVRLSTGVDLLSAMLDQMLGRPVDLTHT---RQDVACIRFITSERPGVL
ARVEGQDEASRLGTVRQVAVDKAAGTRLRPPESATDRLGYVIASGPE---
RGQVLGDAARALSLLRVEQAAPSAPA-----------------------
-----------------------------------------------
-----------------------------------------------
-----------------------------------------------
-----------------------------------------------
-----------------------------------------------
-----------------------------------------------
-----------------------------------------------
-----------------------------------------------
-----------------------------------------------
----- (SEQ ID NO: 4)
*

>BBR47_51900

MNKHFLFVEANTTGTGMLAMKKARKLGFTPVFFTEKPERYHGLN---ELE
CHVVVTDTNSQAELTDSVAQVSKEGREIAGIMSTSDYYLESVAKLARKFG
WISNSLEAIEACRNKAIFREKLQ-RHQVSQPTFLAISSMEQLLEARSSIS
LPCVVKPADDSGSNNVRLCFSWDEVEHMAAEILAIKYNARGQETARTVLL
EQYAEGPEFSVETFSWQGQC--FVIGITQKRLTGYPFFVEAGHIFPAPLS
VEEKQEIERTVERALAAVKYQFGAAHTEVKWTSAGCVVIEVNARLAGGMI
PELVRRSTGIDLLLQQIRCAAGLEPELSQTIEEQRCAGIHFLVSESQGTF
GGIKGMDTVRNLPGIAEVAIHAKIGQNVQPPQNFSHRLGYVIVEGKHYSE
TAELIEQVKDSLSVQVGQQLESGV------------------------
-----------------------------------------------
-----------------------------------------------
-----------------------------------------------
-----------------------------------------------
-----------------------------------------------
-----------------------------------------------
-----------------------------------------------
-----------------------------------------------
----- (SEQ ID NO: 2)
*
```

FIG. 22-2

```
>gi|229168264|ref|ZP_04295989.1_BCE

-------------------MLAIRKAKELGYEPIFLTQKKSLYHGLS---DLE
CRVIELDTNSVDAIKHYIIHE--KIEDIAGILTTSDYYLETVAELVQMFR
LSGNTHQAIYYCRNKAMFREKLH-LEKVLQPKFHIVQSIDSLQNIYSSIQ
FPCVVKPADDSGSNNVRLCSNWEEVEKIATKILANKYNARGQEKANMVLL
EEYIEGPEYSVEMFSWEGNS--ICIGITEKQLTGFPYFVESGHIFPVELP
KDVQSEIEQTVKCALQAVDFRFGASHSEVKWTSNGCVVIEVNARLAGGMI
PELVRHSTGVDLLRQQVLSSVGVAPEWKEIEYMN-YAGIHFLTAKKSGFL
STVKGIEEVRELSYIEELVVKAQVGQPVNPPENFSHRLGHVMVRGRTYEE
TVLFLEEVAKKLEIQVNN--------------------------------
--------------------------------------------------
--------------------------------------------------
--------------------------------------------------
--------------------------------------------------
--------------------------------------------------
--------------------------------------------------
--------------------------------------------------
------ (SEQ ID NO: 10)
*

>gi|333374399|ref|ZP_08466276.1_DES

MKKKLLFVEGNTTGTGILALEKARKLGYEPVFLTQEASRYDGLP---EAK
CRVHVTVDSIHELKRCVSQE--KAEAVAGILTTSDYYLEISAKLVQELG
LTGNSPQAIHLCRNKALYREKLR-SKSVPQPNFHIIRSMEDLRETRESVP
LPCLVKPADDSGSNNVRLCFSWGEVEQLTSKILKIERNARGQKTSQTVLL
EEYIEGPEYSVEMFSWQGKS--TCIGITEKQLTGYPYFVESGHVFPAVLP
TDVQQEIEKTVKQSLEAVHFQFGASHSEVKWTPNGCVMIETNARLAGGMI
PELVRHSTGVDLIEQQILCAAGVAPHWKQVVPTG-CSGIHFIVAAEAGRL
SSVDNLEAVRKLPGVEEMMVKAQVGQAVQPPKNFSDRLGHVIVSGKSYEE
VVERLHKISNMISLKIS---------------------------------
--------------------------------------------------
--------------------------------------------------
--------------------------------------------------
--------------------------------------------------
--------------------------------------------------
--------------------------------------------------
--------------------------------------------------
------ (SEQ ID NO: 6)
*
```

FIG. 22-3

```
>gi|228758608|gb|EEM07742.1|_BMY

-------------------MLALNKAKLYGFSPVFITNNPDRYVGLE---KAE
CSIFICDTNNIENLYETINNN-LEVDKIQGITTTSEFYLEIVSELARKYG
LPRNSVQAIRNCRNKLETRNCLK-EAKVRQPKFEEVTSISDINKSLNIIG
LPCIVKPVDDSGSNGVRFCKTVAEVKEQTLEILSWKKNSRGQSTVQTVLL
EEFIDAPEYSVEIFSFEGKG--KCVGITEKKLIGFPHFVEHQHVFPAKLP
ADVTREIQNTVEDALKAVGITNGPTHTEVKLTPQGCAIIEINARLAGGMI
PKLIQISTGIDMLEYQLLLSVGKYKAP--ILNYQRYAGIKFIVSNLDGIL
NDIRGVEKVRTLQGVNQVNINVNRGDKVISPKNAYDRLGYVIVEGNSYEE
TEARLNKSIEKLEILVGN--------------------------------
--------------------------------------------------
--------------------------------------------------
--------------------------------------------------
--------------------------------------------------
--------------------------------------------------
--------------------------------------------------
--------------------------------------------------
--------------------------------------------------
----- (SEQ ID NO: 18)
*

>BTH

-MKKLLFIESNTTGTGMLALIKARELGFTPVLLTNNPGRYIGLG---ETK
CIVLECDTNNLNCIRTIIDSEFEVG-EIKAITTTSEFYIEVVAILAKELG
LIGNPIDTVKKCRNKAEMRLLLKGIENIYEPWFYIIDSLEKLELAKDNIK
FPCVVKPVDDSGSNNVLKCYSYEEVKRHTEKILSNKYNVRSQKNAQNILV
EEYVSGQEYSVEIFTYNGKC--KIVGVTQKIVDGAPYFIECGHIFPAPVS
DDIRSVIERGVTKIIEKVNWQNGPCHLEIKIKGEKIFLVEFNGRLAGGMI
PELIKYATGIDLLKEQLKVVTRMRPKLDQNP--TLYAGIRFIIPLRDGKI
TSIFGVNDIENTVGIKEVKLRTIVGESIRKVENAYGRIGHIIGAAENINK
LNYILDKSMDALHIEIEECEDYEDFN------------------------
--------------------------------------------------
--------------------------------------------------
--------------------------------------------------
--------------------------------------------------
--------------------------------------------------
--------------------------------------------------
--------------------------------------------------
----- (SEQ ID NO: 12)
*
```

FIG. 22-4

```
>BUR

-MKTFVFIESNTTGTGRLCLQKALLRGFDVLFVTSRPQLYPFLQ------
-EEMVVPLVADTADPQRIADALAPYAGIAGIFSTSEYYIETAATVATRLG
LPAADPEAIRTCRDKGRLHRRLR-DAGVGVADTEIVSERTQLRDLAHGAT
YPRVLKPAFGSGSVGVRLVRTPAEMLAHGERMLDARGNERGIALARQVLV
QSFVDGPEFSVEVVGLGAEHGHAVLGVTGKHLGPLPHFVEAGHDFPAPIA
AAQRDAIVAETLRALDAVGHRFGPAHVECRVSGGKVVVIEINPRLAGGMI
PQAIEWATGVDVLGAMIDLHAGTPPDLGPR---RRGHAAIRFVLPARSGEL
RALSFEPDERFAGVRTRFMPLKQLGQRIEPAGDFRDRLALVIASAADPDA
LAHALEDVDRCVTVAIGDAGAAGEGAGAGRLRRTLHPEALAIVRKPAPRA
ERLAELDAFAAIDEAHLLMLVDAGICDRARAATVLAELARQRDAKFAAIA
DAIAPRGTYALYEQLLIERVGIDAGGAVHTARSRNDINACVAKLRAREWF
DTCGGKLWRVRAAIVDKAQHTLDWPLPTYSQYQAAQPGSFGYYLWSVETA
LRRDQAALERLDEELAVCPLGAGAGAGTDFPIRPGVSAALLGFARSFDSA
LDAVASRDLVLHFLAAIAIASTTLSRLAHDLQLWTMRETDFLALPDELSG
GSSLMPQKKNPYLLEIVKGKLAHVAGALNAAVFASQRTPFSNSVEIGTEM
LAPCADAVQAFGESCDLLRLMVSGVTGDPAKMRAAAEAGLVSATQVANAL
VRETDISFHAAHRQIGALITQALDAHEDPAAALDALVRQPGASIDEAAAR
LAYGGGPGAAGAGLARSRALLRQSAERLWRRRAAWHAAHARRRGCVADLL
AAAAA (SEQ ID NO: 8)
*

>AME

-MAHLLMIESFIGGNAVLLPKLLKQLGHTYTFITRSKGIFKSSFHSNEHV
VIQHADEIIEANTNDASVVLDTILGKKFDGVITTCDYYIETVVEVAKELS
IPCPFPKAVKNVRYKQKLRQTLD-AAGISNPQYGLAYNWDEVLLVAKNIG
YPVVLKPVDLSSSAYVRLIRSEEDLRDAYHQLNAFPINWRDQERDCTYLL
EKYMEGNEVSVEAVTFNGET--TIIGITQKSLMGAPYFIEDAHMFPANIS
HDMKLKISGYVVKALQAAGYDYGVSHTEVKLTDAGPRIVEINPRVAGDYI
AEIIKLVCNVDILRAFVDLSIGIEPSITKKETGISSACVRFLTPHRGGKI
VNIVGVDTLASDSHIDSFKVEDCIGKTVGDPIDNAGRIGWIITKDTEGYN
AMNYAYEAMEHIKLTFE---------------------------------
--------------------------------------------------
--------------------------------------------------
--------------------------------------------------
--------------------------------------------------
--------------------------------------------------
--------------------------------------------------
----- (SEQ ID NO: 14)
*
```

FIG. 23-1

| N | Target | Description | E-value | \|Log(E-value)\| |
|---|---|---|---|---|
| 1 | Q63UA1_BURPS | Putative bifunctional protein (Ligase and argininosuccinate lyase) (gene: BPSL1715) | 0,00E+00 | |
| 2 | A4LBK5_BURPE | Putative lyase (gene: BURPS305_6606) | 0,00E+00 | |
| 3 | C6TPZ3_BURPE | Argininosuccinate lyase (gene: BURPS1710A_2469) | 0,00E+00 | |
| 4 | Q3JSA0_BURP1 | Argininosuccinate lyase domain protein (gene: BURPS1710b_2158) | 0,00E+00 | |
| 5 | C5ZGF9_BURPE | Putative lyase (gene: BURPS1106B_A1258) | 0,00E+00 | |
| 6 | C0Y7H2_BURPE | Putative lyase (gene: BUH_1888) | 0,00E+00 | |
| 8 | F2LEB6_BURGS | Argininosuccinate lyase (gene: bgla_1g16460) | 0,00E+00 | |
| 9 | Q63SV7_BURPS | Putative fusion protein (Ligase/carboxylase and argininosuccinate lyase) (gene: BPSL2214) | 1,10E-195 | 194,9586073 |
| 10 | A5TJX5_BURMA | Lyase family protein (gene: BMA721280_A1050) | 1,20E-195 | 194,9208188 |
| 11 | A3ML08_BURM7 | Argininosuccinate lyase domain protein (gene: BMA10247_1396) | 5,00E-195 | 194,30103 |
| 12 | B1HKH5_BURPE | Argininosuccinate lyase domain protein (gene: BURPSS13_P1168) | 4,30E-194 | 193,3665315 |
| 13 | C4KPT5_BURPE | Argininosuccinate lyase 2 (Arginosuccinase 2) (Asal 2) (gene: GBP346_A2629) | 1,40E-193 | 192,853872 |
| 14 | A4LD16_BURPE | Lyase family protein (gene: BURPS305_7168) | 3,80E-193 | 192,4202164 |
| 15 | C5ZJH2_BURPE | Lyase family protein (gene: BURPS1106B_A1783) | 5,10E-193 | 192,2924298 |

FIG. 23-2

| N | Target | Description | E-value | |Log(E-value)| |
|---|---|---|---|---|
| 16 | Q3JQX0_BURP1 | Argininosuccinate lyase domain protein (gene: BURPS1710b_2646) | 6,50E-193 | 192,1870866 |
| 17 | A8KVZ6_BURPE | Argininosuccinate lyase domain protein (gene: BURPSPAST_R0310) | 2,90E-192 | 191,537602 |
| 18 | C0YCH6_BURPE | Lyase family protein (gene: BUH_2552) | 3,50E-192 | 191,455932 |
| 19 | B2H9Z1_BURPE | Argininosuccinate lyase domain protein (gene: BURPS1655_H0298) | 7,70E-192 | 191,1135093 |
| 20 | A1V5D2_BURMS | Argininosuccinate lyase domain protein (gene: BMASAVP1_A2122) | 1,50E-191 | 190,8239087 |
| 21 | C5NAA5_BURMA | Lyase family protein (gene: BMAPRL20_A1664) | 1,70E-191 | 190,7695511 |
| 22 | Q62J65_BURMA | Argininosuccinate lyase domain protein (gene: BMA1620) | 6,20E-191 | 190,2076083 |
| 23 | C4AVR8_BURMA | Argininosuccinate lyase 2 (Arginosuccinase 2) (Asal 2) (gene: BMAGB8_1709) | 6,90E-191 | 190,1611509 |
| 24 | Q2SX49_BURTA | Argininosuccinate lyase domain protein (gene: BTH_I1971) | 9,00E-191 | 190,0457575 |
| 25 | A8ECB3_BURPE | Argininosuccinate lyase domain protein (gene: BURPS406E_H0439) | 3,30E-190 | 189,4814861 |
| 26 | B7D052_BURPE | Lyase family protein (gene: BUC_2825) | 4,50E-190 | 189,3467875 |
| 27 | A3NB13_BURP6 | Argininosuccinate lyase (gene: BURPS668_2507) | 1,30E-189 | 188,8860566 |
| 28 | C0Z5R1_BREBN | Putative uncharacterized protein (gene: BBR47_51900) | 1,00E-175 | 175 |
| 29 | F5SLP0_9BACL | Pyridoxal-phosphate dependent enzyme (gene: HMPREF9374_4022) | 2,60E-169 | 168,5850267 |

FIG. 23-3

| N | Target | Description | E-value | \|Log(E-value)\| |
|---|---|---|---|---|
| 30 | C2PYS6_BACCE | Argininosuccinate lyase domain protein (gene: bcere0007_32210) | 6,50E-162 | 161,1870866 |
| 31 | F0PS09_BACT0 | Putative uncharacterized protein (gene: YBT020_25570) | 4,70E-161 | 160,3279021 |
| 32 | E3FE26_STIAD | Argininosuccinate lyase 2-like protein (gene: STAUR_4851) | 7,20E-155 | 154,1426675 |
| 33 | C3BDI4_BACMY | Argininosuccinate lyase domain protein (gene: bmyco0003_56050) | 7,60E-153 | 152,1191864 |
| 34 | A6TPU8_ALKMQ | Putative uncharacterized protein (gene: Amet_2055) | 1,50E-143 | 142,8239087 |
| 35 | Q08Q99_STIAD | Argininosuccinate lyase domain protein (gene: STIAU_0005) | 2,60E-134 | 133,5850267 |
| 36 | F0Q0P1_ACIAP | Argininosuccinate lyase (gene: Acav_2530) | 2,30E-133 | 132,6382722 |
| 37 | B0B530_STRCU | Putative pyridoxal-phosphate dependent enzyme (gene: orf_R4) | 6,30E-131 | 130,2006595 |
| 38 | A4JPB5_BURVG | Argininosuccinate lyase (gene: Bcep1808_5167) | 4,40E-129 | 128,3565473 |
| 39 | C6WLF1_ACTMD | Cysteine synthase (gene: Amir_4500) | 5,90E-124 | 123,229148 |
| 40 | F4F5X7_VERMA | Cysteine synthase (gene: VAB18032_22180) | 1,60E-122 | 121,79588 |
| 41 | C3BTM3_9BACI | Argininosuccinate lyase domain protein (gene: bpmyx0001_50290) | 4,00E-121 | 120,39794 |
| 42 | F1CHS8_9ACTO | DABA synthase (gene: npsI) | 5,20E-121 | 120,2839967 |
| 43 | E2EKQ1_9ACTO | Diaminoacid synthase/ligase fusion protein (gene: pac19) | 2,00E-120 | 119,69897 |
| 44 | F7KHZ8_9FIRM | Putative uncharacterized protein (gene: HMPREF0994_05500) | 9,80E-111 | 110,0087739 |
| 45 | D3AGE3_9CLOT | ATP-grasp domain protein (gene: CLOSTHATH_02679) | 1,10E-110 | 109,9586073 |
| 46 | G0WV72_STRVR | Diaminobutyric acid synthase C (gene: dabC) | 1,70E-103 | 102,7695511 |
| 47 | H2JPF8_STRHJ | Putative ligase/carboxylase (gene: SHJG_0604) | 3,20E-101 | 100,49485 |

FIG. 23-4

| N | Target | Description | E-value | \|Log(E-value)\| |
|---|---|---|---|---|
| 48 | A6TPU7_ALKMQ | Putative uncharacterized protein (gene: Amet_2054) | 9,30E-101 | 100,0315171 |
| 49 | D3Q4U1_STANL | Putative uncharacterized protein (gene: Snas_2438) | 6,90E-100 | 99,16115091 |
| 50 | H5X7R7_9PSEU | Biotin carboxylase (gene: SacmaDRAFT_3129) | 4,60E-98 | 97,33724217 |
| 51 | G8SKH8_ACTS5 | Carbamoyl-phosphate synthase large chain (gene: ACPL_3592) | 2,40E-92 | 91,61978876 |
| 52 | G2PF82_STRVO | ATP-dependent carboxylate-amine ligase domain protein ATP-grasp (gene: Strvi_4637) | 2,80E-92 | 91,55284197 |
| 53 | F1DGJ0_9ACTO | Putative uncharacterized protein | 2,70E-91 | 90,56863624 |
| 54 | D9WHP6_9ACTO | ATP-grasp domain protein (gene: SSOG_01010) | 4,10E-90 | 89,38721614 |
| 55 | E2D2N4_9BACT | Diaminobutyric acid synthase C | 5,70E-90 | 89,24412514 |
| 56 | A3KFG3_9ACTO | DabB (gene: dabB) | 1,50E-88 | 87,82390874 |
| 57 | A3KFG4_9ACTO | DabC (gene: dabC) | 6,00E-88 | 87,22184875 |
| 58 | E2D2N3_9BACT | Diaminobutyric acid synthase B | 3,40E-87 | 86,46852108 |
| 59 | G0FTB8_AMYMD | Argininosuccinate lyase (gene: RAM_24230) | 6,20E-87 | 86,20760831 |
| 60 | D9XKV3_9ACTO | ATP-grasp domain-containing protein (gene: SSRG_01345) | 9,60E-87 | 86,01772877 |
| 61 | G0WV71_STRVR | Diaminobutyric acid synthase B (gene: dabB) | 2,80E-86 | 85,55284197 |
| 62 | A4FN76_SACEN | Putative fusion protein (Ligase/carboxylase and argininosuccinate lyase) (gene: SACE_6330) | 5,30E-86 | 85,27572413 |
| 63 | B7GFS1_ANOFW | Predicted carboxylase (ATP-grasp family) (gene: Aflv_0217) | 1,80E-85 | 84,74472749 |
| 64 | G0FTB9_AMYMD | Argininosuccinate lyase (gene: RAM_24235) | 4,50E-85 | 84,34678749 |
| 65 | E8W7D4_STRFA | Putative uncharacterized protein (gene: Sfla_0476) | 1,30E-84 | 83,88605665 |

FIG. 24-1

```
>Staur_4851

-MNQFVFVESNTTGTGRLAVERLLAQGEQVTFITHQPEKYPFLVGN-----
-KAPGLKVLKVETNDAAAVEACVDGLVREGKVAALLTFSTFYVPTVAAIA
ARHGLRYLQPRAAQACHNKHEARALLR-AAGLPGPEFHVIASEAEAAQLA
QTVRFPCVVKPPAESGSTGVRRVDTPEELLAHFRSLHSRAANERGQSLHG
EVLVESFLEGPEFSVETMTL-ADGTTHVLGVTQKYLSAPPYFVEMGHDFP
ADLPPERRALEEAVLAGLAAVGFDFGPAHTEIRFTPAGPVIIEINPRLA
GGMIPELVRLSTGVDLLSAMLDQMLGRPVDLTHT--RQDVACIRFITSER
PGVLARVEGQDEASRLGTVRQVAVDKAAGTRLRPPESATDRLGYVIASGP
E---RGQVLGDAARALSLLRVEQAAPSAPA---------------------
----------------------------------------------------
----------------------------------------------------
----------------------------------------------------
----------------------------------------------------
----------------------------------------------------
----------------------------------------------------
----------------------------------------------------
---------- (SEQ ID NO: 4)
*

>BBR47_51900

MNKHFLFVEANTTGTGMLAMKKARKLGFTPVFFTEKPERYHGLN------
-ELECHVVVTDTNSQAELTDSVAQVSKEGREIAGIMSTSDYYLESVAKLA
RKFGWISNSLEAIEACRNKAIFREKLQ-RHQVSQPTFLAISSMEQLLEAR
SSISLPCVVKPADDSGSNNVRLCFSWDEVEHMAAEILAIKYNARGQETAR
TVLLEQYAEGPEFSVETFSWQGQC--FVIGITQKRLTGYPFFVEAGHIFP
APLSVEEKQEIERTVERALAAVKYQFGAAHTEVKWTSAGCVVIEVNARLA
GGMIPELVRRSTGIDLLLQQIRCAAGLEPELSQTIEEQRCAGIHFLVSES
QGTFGGIKGMDTVRNLPGIAEVAIHAKIGQNVQPPQNFSHRLGYVIVEGK
HYSETAELIEQVKDSLSVQVGQQLESGV------------------------
----------------------------------------------------
----------------------------------------------------
----------------------------------------------------
----------------------------------------------------
----------------------------------------------------
----------------------------------------------------
----------------------------------------------------
---------- (SEQ ID NO: 2)
*
```

FIG. 24-2

```
>gi|229168264|ref|ZP_04295989.1_BCE

------------------MLAIRKAKELGYEPIFLTQKKSLYHGLS------
-DLECRVIELDTNSVDAIKHYIIHE---KIEDIAGILTTSDYYLETVAELV
QMFRLSGNTHQAIYYCRNKAMFREKLH-LEKVLQPKFHIVQSIDSLQNIY
SSIQFPCVVKPADDSGSNNVRLCSNWEEVEKIATKILANKYNARGQEKAN
MVLLEEYIEGPEYSVEMFSWEGNS--ICIGITEKQLTGFPYFVESGHIFP
VELPKDVQSEIEQTVKCALQAVDFRFGASHSEVKWTSNGCVVIEVNARLA
GGMIPELVRHSTGVDLLRQQVLSSVGVAPEWKEIEYMN-YAGIHFLTAKK
SGFLSTVKGIEEVRELSYIEELVVKAQVGQPVNPPENFSHRLGHVMVRGR
TYEETVLFLEEVAKKLEIQVNN----------------------------
--------------------------------------------------
--------------------------------------------------
--------------------------------------------------
--------------------------------------------------
--------------------------------------------------
--------------------------------------------------
--------------------------------------------------
--------------------------------------------------
--------- (SEQ ID NO: 10)
*

>gi|333374399|ref|ZP_08466276.1_DES

MKKKLLFVEGNTTGTGILALEKARKLGYEPVFLTQEASRYDGLP-------
-EAKCRVHVTVTDSIHELKRCVSQE--KAEAVAGILTTSDYYLEISAKLV
QELGLTGNSPQAIHLCRNKALYREKLR-SKSVPQPNFHIIRSMEDLRETR
ESVPLPCLVKPADDSGSNNVRLCFSWGEVEQLTSKILKIERNARGQKTSQ
TVLLEEYIEGPEYSVEMFSWQGKS--TCIGITEKQLTGYPYFVESGHVFP
AVLPTDVQQEIEKTVKQSLEAVHFQFGASHSEVKWTPNGCVMIETNARLA
GGMIPELVRHSTGVDLIEQQILCAAGVAPHWKQVVPTG-CSGIHFIVAAE
AGRLSSVDNLEAVRKLPGVEEMMVKAQVGQAVQPPKNFSDRLGHVIVSGK
SYEEVVERLHKISNMISLKIS-----------------------------
--------------------------------------------------
--------------------------------------------------
--------------------------------------------------
--------------------------------------------------
--------------------------------------------------
--------------------------------------------------
--------------------------------------------------
--------- (SEQ ID NO: 6)
*
```

FIG. 24-3

```
>gi|228758608|gb|EEM07742.1|_BMY

------------------MLALNKAKLYGFSPVFITNNPDRYVGLE------
-KAECSIFICDTNNIENLYETINNN-LEVDKIQGITTTSEFYLEIVSELA
RKYGLPRNSVQAIRNCRNKLETRNCLK-EAKVRQPKFEEVTSISDINKSL
NIIGLPCIVKPVDDSGSNGVRFCKTVAEVKEQTLEILSWKKNSRGQSTVQ
TVLLEEFIDAPEYSVEIFSFEGKG--KCVGITEKKLIGFPHFVEHQHVFP
AKLPADVTREIQNTVEDALKAVGITNGPTHTEVKLTPQGCAIIEINARLA
GGMIPKLIQISTGIDMLEYQLLLSVGKYKAP--ILNYQRYAGIKFIVSNL
DGILNDIRGVEKVRTLQGVNQVNINVRGDKVISPKNAYDRLGYVIVEGN
SYEETEARLNKSIEKLEILVGN----------------------------
--------------------------------------------------
--------------------------------------------------
--------------------------------------------------
--------------------------------------------------
--------------------------------------------------
--------------------------------------------------
--------------------------------------------------
---------- (SEQ ID NO: 18)
*

>BTH

-MKKLLFIESNTTGTGMLALIKARELGFTPVLLTNNPGRYIGLG------
-ETKCIVLECDTNNLNCIRTIIDSEFEVG-EIKAITTTSEFYIEVVAILA
KELGLIGNPIDTVKKCRNKAEMRLLLKGIENIYEPWFYIIDSLEKLELAK
DNIKFPCVVKPVDDSGSNNVLKCYSYEEVKRHTEKILSNKYNVRSQKNAQ
NILVEEYVSGQEYSVEIFTYNGKC--KIVGVTQKIVDGAPYFIECGHIFP
APVSDDIRSVIERGVTKIIEKVNWQNGPCHLEIKIKGEKIFLVEFNGRLA
GGMIPELIKYATGIDLLKEQLKVVTRMRPKLDQNP--TLYAGIRFIIPLR
DGKITSIFGVNDIENTVGIKEVKLRTIVGESIRKVENAYGRIGHIIGAAE
NINKLNYILDKSMDALHIEIEECEDYEDFN--------------------
--------------------------------------------------
--------------------------------------------------
--------------------------------------------------
--------------------------------------------------
--------------------------------------------------
--------------------------------------------------
---------- (SEQ ID NO: 12)
*
```

FIG. 24-4

```
>BUR

-MKTFVFIESNTTGTGRLCLQKALLRGFDVLFVTSRPQLYPFLQ------
------EEMVVPLVADTADPQRIADALAPYAGIAGIFSTSEYYIETAATVA
TRLGLPAADPEAIRTCRDKGRLHRRLR-DAGVGVADTEIVSERTQLRDLA
HGATYPRVLKPAFGSGSVGVRLVRTPAEMLAHGERMLDARGNERGIALAR
QVLVQSFVDGPEFSVEVVGLAEHGHAVLGVTGKHLGPLPHFVEAGHDFP
APIAAAQRDAIVAETLRALDAVGHRFGPAHVECRVSGGKVVVIEINPRLA
GGMIPQAIEWATGVDVLGAMIDLHAGTPPDLGPR--RRGHAAIRFVLPAR
SGELRALSFEPDERFAGVRTRFMPLKQLGQRIEPAGDFRDRLALVIASAA
DPDALAHALEDVDRCVTVAIGDAGAAGEGAGAGRLRRTLHPEALAIVRKP
APRAERLAELDAFAAIDEAHLLMLVDAGICDRARAATVLAELARQRDAKF
AAIADAIAPRGTYALYEQLLIERVGIDAGGAVHTARSRNDINACVAKLRA
REWFDTCGGKLWRVRAAIVDKAQHTLDWPLPTYSQYQAAQPGSFGYYLWS
VETALRRDQAALERLDEELAVCPLGAGAGAGTDFPIRPGVSAALLGFARS
FDSALDAVASRDLVLHFLAAIAIASTTLSRLAHDLQLWTMRETDFLALPD
ELSGGSSLMPQKKNPYLLEIVKGLAHVAGALNAAVFASQRTPFSNSVEI
GTEMLAPCADAVQAFGESCDLLRLMVSGVTGDPAKMRAAAEAGLVSATQV
ANALVRETDISFHAAHRQIGALITQALDAHEDPAAALDALVRQPGASIDE
AAARLAYGGGPGAAGAGLARSRALLRQSAERLWRRRAAWHAAHARRRGCV
ADLLAAAAA (SEQ ID NO: 8)
*

>AME

-MAHLLMIESFIGGNAVLLPKLLKQLGHTYTFITRSKGIFKSSFHSNEHV
VIQHADEIIEANTNDASVVLDTIL----GKKFDGVITTCDYYIETVVEVA
KELSIPCPFPKAVKNVRYKQKLRQTLD-AAGISNPQYGLAYNWDEVLLVA
KNIGYPVVLKPVDLSSSAYVRLIRSEEDLRDAYHQLNAFPINWRDQERDC
TYLLEKYMEGNEVSVEAVTFNGET--TIIGITQKSLMGAPYFIEDAHMFP
ANISHDMKLKISGYVVKALQAAGYDYGVSHTEVKLTDAGPRIVEINPRVA
GDYIAEIIKLVCNVDILRAFVDLSIGIEPSITKKETGISSACVRFLTPHR
GGKIVNIVGVDTLASDSHIDSFKVEDCIGKTVGDPIDNAGRIGWIITKDT
EGYNAMNYAYEAMEHIKLTFE-----------------------------
--------------------------------------------------
--------------------------------------------------
--------------------------------------------------
--------------------------------------------------
--------------------------------------------------
--------------------------------------------------
--------------------------------------------------
---------- (SEQ ID NO: 14)
*
```

FIG. 24-5

```
>SFL

-MAHLLVVESWVGSMSRLLPRALGEGGHHFTFLTRDLQHYLRAAPEGTDH
PLLTARNVVTAPTNDLGALLPQVERLHEALRFDGVVTSCDYYLPTAARIA
GLLGLPGPSAEAMEKACRKDATRRVLG-AAGVPGPRFAVCADGAEAAVAA
HDLGYPLVVKPVDLCAGMFVRRVDDEDQLAEACAALAAFPYNARGQRRTP
HVLLEEYLRGPEVSVETVTCKGVA--HVVGVTDKSVGGAPAFVETGHMFP
AALSPDDLAAATGTALSAGAALGLDDVVAHTEIKLTEDGPRVVEVNPRPA
GNRITELVRHVTGIDLAAACVDVALGREPDLRPRDTGTRSAAIGFLVPGR
AGTLASVEGADRVRDADGVLEVQTAE-PGRTVEAADSNNAYLGHVMAGDA
TGLGARDRVETLLAELRPRLVRS-----------------------------
----------------------------------------------------
----------------------------------------------------
----------------------------------------------------
----------------------------------------------------
----------------------------------------------------
----------------------------------------------------
----------------------------------------------------
----------------------------------------------------
----------------------------------------------------
---------- (SEQ ID NO: 16)
*
```

FIG. 25-1

| N | Target | Description | E-value | |Log(E-value)| |
|---|---|---|---|---|
| 1 | Q63UA1_BURPS | Putative bifunctional protein (Ligase and argininosuccinate lyase) (gene: BPSL1715) | 0,00E+00 | |
| 2 | A4LBK5_BURPE | Putative lyase (gene: BURPS305_6606) | 0,00E+00 | |
| 3 | C6TPZ3_BURPE | Argininosuccinate lyase (gene: BURPS1710A_2469) | 0,00E+00 | |
| 4 | Q3JSA0_BURP1 | Argininosuccinate lyase domain protein (gene: BURPS1710b_2158) | 0,00E+00 | |
| 5 | C5ZGF9_BURPE | Putative lyase (gene: BURPS1106B_A1258) | 0,00E+00 | |
| 6 | C0Y7H2_BURPE | Putative lyase (gene: BUH_1888) | 0,00E+00 | |
| 8 | F2LEB6_BURGS | Argininosuccinate lyase (gene: bgla_1g16460) | 0,00E+00 | |
| 9 | Q63SV7_BURPS | Putative fusion protein (Ligase/carboxylase and argininosuccinate lyase) (gene: BPSL2214) | 3,60E-194 | 193,4436975 |
| 10 | A5TJX5_BURMA | Lyase family protein (gene: BMA721280_A1050) | 4,00E-194 | 193,39794 |
| 11 | A3ML08_BURM7 | Argininosuccinate lyase domain protein (gene: BMA10247_1396) | 1,60E-193 | 192,79588 |
| 12 | B1HKH5_BURPE | Argininosuccinate lyase domain protein (gene: BURPSS13_P1168) | 1,40E-192 | 191,853872 |
| 13 | C4KPT5_BURPE | Argininosuccinate lyase 2 (Arginosuccinase 2) (Asal 2) (gene: GBP346_A2629) | 4,80E-192 | 191,3187588 |
| 14 | A4LD16_BURPE | Lyase family protein (gene: BURPS305_7168) | 1,20E-191 | 190,9208188 |
| 15 | C5ZJH2_BURPE | Lyase family protein (gene: BURPS1106B_A1783) | 1,70E-191 | 190,7695511 |
| 16 | Q3JQX0_BURP1 | Argininosuccinate lyase domain protein (gene: BURPS1710b_2646) | 2,20E-191 | 190,6575773 |

FIG. 25-2

| N | Target | Description | E-value | \|Log(E-value)\| |
|---|---|---|---|---|
| 17 | A8KVZ6_BURPE | Argininosuccinate lyase domain protein (gene: BURPSPAST_R0310) | 9,70E-191 | 190,0132283 |
| 18 | C0YCH6_BURPE | Lyase family protein (gene: BUH_2552) | 1,10E-190 | 189,9586073 |
| 19 | B2H9Z1_BURPE | Argininosuccinate lyase domain protein (gene: BURPS1655_H0298) | 2,60E-190 | 189,5850267 |
| 20 | A1V5D2_BURMS | Argininosuccinate lyase domain protein (gene: BMASAVP1_A2122) | 5,10E-190 | 189,2924298 |
| 21 | C5NAA5_BURMA | Lyase family protein (gene: BMAPRL20_A1664) | 5,60E-190 | 189,251812 |
| 22 | Q2SX49_BURTA | Argininosuccinate lyase domain protein (gene: BTH_I1971) | 2,00E-189 | 188,69897 |
| 23 | Q62J65_BURMA | Argininosuccinate lyase domain protein (gene: BMA1620) | 2,10E-189 | 188,6777807 |
| 24 | C4AVR8_BURMA | Argininosuccinate lyase 2 (Arginosuccinase 2) (Asal 2) (gene: BMAGB8_1709) | 2,30E-189 | 188,6382722 |
| 25 | A8ECB3_BURPE | Argininosuccinate lyase domain protein (gene: BURPS406E_H0439) | 1,00E-188 | 188 |
| 26 | B7D052_BURPE | Lyase family protein (gene: BUC_2825) | 1,60E-188 | 187,79588 |
| 27 | A3NB13_BURP6 | Argininosuccinate lyase (gene: BURPS668_2507) | 4,50E-188 | 187,3467875 |
| 28 | C0Z5R1_BREBN | Putative uncharacterized protein (gene: BBR47_51900) | 1,50E-171 | 170,8239087 |
| 29 | F5SLP0_9BACL | Pyridoxal-phosphate dependent enzyme (gene: HMPREF9374_4022) | 3,50E-164 | 163,455932 |
| 30 | C2PYS6_BACCE | Argininosuccinate lyase domain protein (gene: bcere0007_32210) | 7,70E-158 | 157,1135093 |
| 31 | F0PS09_BACT0 | Putative uncharacterized protein (gene: YBT020_25570) | 3,10E-154 | 153,5086383 |

FIG. 25-3

| N | Target | Description | E-value | |Log(E-value)| |
|---|---|---|---|---|
| 32 | E3FE26_STIAD | Argininosuccinate lyase 2-like protein (gene: STAUR_4851) | 1,10E-150 | 149,9586073 |
| 33 | C3BDI4_BACMY | Argininosuccinate lyase domain protein (gene: bmyco0003_56050) | 2,60E-148 | 147,5850267 |
| 34 | A6TPU8_ALKMQ | Putative uncharacterized protein (gene: Amet_2055) | 2,00E-139 | 138,69897 |
| 35 | F0Q0P1_ACIAP | Argininosuccinate lyase (gene: Acav_2530) | 3,20E-133 | 132,49485 |
| 36 | B0B530_STRCU | Putative pyridoxal-phosphate dependent enzyme (gene: orf_R4) | 1,60E-132 | 131,79588 |
| 37 | Q08Q99_STIAD | Argininosuccinate lyase domain protein (gene: STIAU_0005) | 3,60E-131 | 130,4436975 |
| 38 | E8W7D4_STRFA | Putative uncharacterized protein (gene: Sfla_0476) | 3,00E-129 | 128,5228787 |

FIG. 26

| Model 1 | | Model 2 | | Model 3 | | Model 4 | | Model 5 | | Model 6 | | Model 7 | |
|---|---|---|---|---|---|---|---|---|---|---|---|---|---|
| Proteins | \|log$_{10}$(E-value)\| | Proteins | \|log$_{10}$(E-value)\| | Proteins | \|log$_{10}$(E-value)\| | Proteins | \|log$_{10}$(E-value)\| | Proteins | \|log$_{10}$(E-value)\| | Proteins | \|log$_{10}$(E-value)\| | Proteins | \|log$_{10}$(E-value)\| |
| BBR | 250 | BBR | 227 | BBR | 215 | BBR | 210 | BUR | ∞ | BUR | ∞ | BUR | ∞ |
| STA | 233 | DES | 224 | DES | 214 | DES | 206 | BBR | 185 | BBR | 175 | BBR | 171 |
| | | BCE | 215 | BCE | 205 | BCE | 197 | DES | 180 | DES | 168 | DES | 163 |
| | | STA | 196 | BMY | 194 | BTH | 196 | BTH | 171 | BCE | 161 | BCE | 157 |
| | | | | STA | 182 | BMY | 186 | BCE | 170 | BTH | 160 | BTH | 153 |
| | | | | | | STA | 175 | STA | 163 | STA | 154 | STA | 150 |
| | | | | | | | | BMY | 162 | BMY | 152 | BMY | 147 |
| | | | | | | | | | | AME | 142 | AME | 139 |
| | | | | | | | | | | | | SFL | 128 |

DNA ENCODING DIPEPTIDE-SYNTHESIZING ENZYME (VARIANTS), BACTERIUM BELONGING TO THE GENUS *ESCHERICHIA*, AND METHODS FOR PRODUCING DIPEPTIDES USING THEREOF

CROSS-REFERENCE TO RELATED APPLICATION

This application is a continuation of, and claims priority under 35 U.S.C. §120 to, International Patent Application No. PCT/JP2013/069712, filed on Jul. 11, 2013, which claims priority therethrough under 35 U.S.C. §119 to Russian Patent Application No. 2012-129311, filed on Jul. 11, 2012, which are incorporated in their entireties by reference.

TECHNICAL FIELD

The present invention relates to the biotechnology industry, and specifically to novel dipeptide-synthesizing enzymes and methods for producing dipeptides, in particular, dipeptides having an acidic L-amino acid residue at the N-terminus.

BACKGROUND ART

Dipeptides are used in the fields of pharmaceuticals, foods, and various other fields. For example, the dipeptide Asp-Glu has been used for preparation of the diuretic and natriuretic pharmaceutical composition (FR2662359 A1). A pharmaceutical composition, containing dipeptides having agonistic effects on NR1/NR2A and NR1/NR2B subtypes of NMDA receptor is known (JP 2009209131 A). Taste properties of numerous dipeptides have been studied. For example, the dipeptide Asp-Val has sourness taste (Sogame S. and Matsushita I., *New Food Ind.*, 1996, 38(12):44-49 (Japanese)). An excellent saltiness-strengthening agent is known obtained by using a dipeptide containing glutamic acid such as Glu-Ala, Glu-Asp, Glu-Glu, Glu-Ile, Asp-Glu, His-Glu, Trp-Glu, etc. (WO 2009113563 A1).

A variety of methods of producing dipeptides are known, including extraction from protein hydrolysates, chemical synthesis from protected and/or activated amino acids, and enzymatic synthesis using peptidases and protected amino acids (Akabori S. et al., *Bull. Chem. Soc. Japan*, 1961, 34:739; Monter B. et al., *Biotechnol. Appl. Biochem.*, 1991, 14(2):183-191). A cloning vehicle encoding peptide comprised by the repeating amino acid sequence (Asp-Phe)n has been reported to be useful for production of benzylated and methylated derivatives of dipeptide Asp-Phe (European Patent Application No. 0036258).

The synthesis of dipeptides using chemical and/or chemical-enzymatic approaches requires introduction and removal of protecting groups for functional groups of amino acids to be joined, and isolation of desired product from racemic mixture. The process is thus considered to be disadvantageous from the point of view cost, efficiency, and necessity to discard the concomitant chemicals such as organic solvents, salts, and the like.

Several approaches for enzymatic synthesis of dipeptides and derivatives thereof have been reported, which include a method using reverse reaction of proline iminopeptidase having ability to produce a peptide from an L-amino acid ester and an L-amino acid (Russian Patent No. 2279440), a method using non-ribosomal peptide synthetase (NRPS) (U.S. Pat. Nos. 5,795,738 and 5,652,116; Doekel S. and Marahiel M. A., *Chem. Biol.*, 2000, 7:373-384; Dieckmann R. et al., *FEBS Lett.*, 2001, 498:42-45), a method using aminoacyl-tRNA-synthetase (Japanese Patent Publication Nos.: 58-146539 (1983), 58-209992 (1983), and 59-106298 (1984)), and a method using a mutant protein having the peptide-synthesizing activity (Russian Patent Application 2007127719).

The enzymes belonging to the ATP-dependent carboxylate-amine/thiol α-ligase superfamily have been widely used for production of dipeptides having an α-peptide bond between two L-amino acids. For example, by using the homology search function of SubtiList (http(colon)//genolist (dot)pasteur(dot)fr/SubtiList/), which is a database of the genomic DNA of *Bacillus subtilis* 168, and the amino acid sequence of D-Ala-D-Ala ligase gene derived from *Bacillus subtilis* 168, the ywfE gene has been found, which encodes the enzyme capable of synthesizing dipeptides having at the N-terminus the L-amino acid such as, in particular, L-Ala, L-Gly, L-Met, L-Ser, and L-Thr (Tabata K. et al., *J. Bacteriol.*, 2005, 187(15):5195-5202; U.S. Pat. Nos. 7,514,243 and 7,939,302). Despite the YwfE protein (bacilysin synthetase, enzyme classification number (EC) 6.3.2.28) has extremely broad substrate specificity, the enzyme does not accept highly charged amino acids such as L-Lys, L-Arg, L-Glu, and L-Asp, and secondary amines such as L-Pro (Tabata K. et al., *J. Bacteriol.*, 2005, 187(15):5195-5202). Also, a protein encoded by the rhizocticin synthetase gene and having dipeptide-synthesizing activity has been described, which utilizes L-amino acids, Gly, and β-Ala as substrates (U.S. Pat. No. 7,939,294). As confirmed by the liberated phosphoric acid (Pi) as well as TOFMS and NMR analyses, the enzyme places L-Arg and L-Lys on the N-terminus of dipeptide. The Hidden Markov Model (HMM)-based profile analysis revealed five L-amino acids α-ligases (Lals) originating from *Treponema denticola* ATCC 35405, *Photorhabdus* luminescence subsp. laumondii TTO1, *Streptococcus* mutants UA159, *Streptococcus pneumoniae* TIGR4, and *Actinobacillus pleuropneumoniae* serovar 1 str. 4074, capable of forming from L-amino acids various peptidyl compounds as proved by the release of phosphoric acid (Senoo A. et al., *Biosci. Biotechnol. Biochem.*, 2010, 74(2):415-418). No dipeptide formation was confirmed in combination of L-Glu or L-Asp with other L-amino acids. A mutant protein having the peptide-synthesizing activity has been confirmed by HPLC using standard samples to form dipeptides bearing L-Met at the N-terminus (Russian Patent Application 2007127719). The in silico screening performed with the help of the NCBI's BLAST service (http(colon)//www(dot)ncbi(dot)nlm(dot)nih(dot)gov/BLAST/) and based on the amino acid sequence of Lal from *B. subtilis* (BsLal) has revealed a protein RSp1486a from *Ralstonia solanacearum*, which is capable of forming dipeptide bond as confirmed by the release of phosphoric acid (Kino K. et al., *Biochem. Biophys. Res. Comm.*, 2008, 371:536-540; European Patent Application No. 1870454). The structural analysis using NMR technique confirmed formation of dipeptides having L-Ser, L-Met, L-Gln, L-Phe, L-His, L-Ala, and L-Cys at the N-terminus. Despite the inorganic phosphate release has been confirmed in the mixture containing RSp1486a and L-Asp with L-Phe, L-His, L-Met, L-Cys or L-Ala; or RSp1486a and L-Glu with L-Phe, L-His, L-Met, L-Cys, L-Ser, or L-Ala, the structural analysis of reaction products has not been performed. No additional phosphoric acid release above background level has been observed in reaction mixture containing RSp1486a and L-Asp or L-Glu. A newly discovered L-amino acid ligase RizB from *B. subtilis* NBRC3134 has been found to synthesize various heteropeptides and homo-oligomers of branched-chain amino acids consisting of 2 to 5 amino acid residues (Kino K., *Yakugaku Zasshi*, 2010, 130(11):1463-1469). For example, formation of dimer, trimer, and tetramer of L-Val has been proven by LC-ESI-MS analysis in the mixture containing RizB, L-Val, and L-Glu or L-Asp. No heteropeptides have been revealed.

DISCLOSURE OF INVENTION

Problem to be Solved by the Invention

To date, no data has been reported demonstrating synthesis of dipeptides having an acidic L-amino acid residue such as L-Glu or L-Asp residue at the N-terminus and any other L-amino acid or a derivative thereof at the C-terminus using an L-amino acid α-ligase (Lal).

Means for Solving Problem

An aspect of the present invention is to provide a DNA encoding L-amino acid α-ligase (Lal) capable of synthesizing dipeptide(s) having an acidic L-amino acid such as L-Asp or L-Glu at the N-terminus and any other L-amino acid or a derivative thereof at the C-terminus, in a reaction mixture which contains a high-energy molecule such as adenosine 5'-triphosphate (ATP), or a salt thereof.

Another aspect of the present invention is to provide a bacterium of the genus *Escherichia*, exemplary belonging to the species *Escherichia coli*, which has been modified to contain the DNA encoding Lal as described herein.

Another aspect of the present invention is to provide methods for producing dipeptides having an acidic L-amino acid such as L-Asp or L-Glu at the N-terminus and any other L-amino acid or a derivative thereof at the C-terminus in a reaction mixture, which contains a high-energy molecule such as adenosine 5'-triphosphate, or a salt thereof, using the Lal enzyme as described herein or a bacterium of the genus *Escherichia*, which has been modified to contain the DNA encoding the Lal enzyme as described herein.

These aims were achieved by the finding novel bacterial L-amino acid α-ligases (Lals) catalyzing formation of dipeptides having an acidic L-amino acid such as L-Asp or L-Glu at the N-terminus.

An aspect of the present invention is to provide a DNA encoding a protein having dipeptide-synthesizing activity, wherein the DNA is selected from the group consisting of:

(A) a DNA having the nucleotide sequence of SEQ ID NOs: 1, 3, 5, 7, 9, 11, 13, 15 and 17;

(B) a DNA hybridizing under stringent conditions with the nucleotide sequence complementary to the sequence shown in SEQ ID NOs: 1, 3, 5, 7, 9, 11, 13, 15 and 17, wherein the stringent conditions comprise washing one time or more in a solution containing a salt concentration of 1×SSC, 0.1% SDS or 0.1×SSC, 0.1% SDS at 60° C. or 65° C.;

(C) a DNA encoding a protein having the amino acids sequence of SEQ ID NOs: 2, 4, 6, 8, 10, 12, 14, 16 and 18;

(D) a DNA encoding a variant protein having the amino acid sequence of SEQ ID NOs: 2, 4, 6, 8, 10, 12, 14, 16 and 18, but which includes substitution, deletion, insertion, or addition of one or several amino acid residues and has dipeptide-synthesizing activity according to the amino acid sequence of SEQ ID NOs: 2, 4, 6, 8, 10, 12, 14, 16 and 18;

(E) a DNA encoding a protein having homology, defined in |Log 10(E-value)|-values, of not less than 128, not less than 142, not less than 162, not less than 175, not less than 182, not less than 196, or not less than 233 to the amino acids sequence of SEQ ID NOs: 2, 4, 6, 8, 10, 12, 14, 16 and 18, and dipeptide-synthesizing activity according to the amino acid sequence of SEQ ID NOs: 2, 4, 6, 8, 10, 12, 14, 16 and 18.

It is an aspect of the present invention to provide a recombinant DNA for expression of the DNA as described above containing the DNA as described above.

It is an aspect of the present invention to provide a dipeptide-producing bacterium belonging to the genus *Escherichia* modified to contain the recombinant DNA as described above.

It is a further aspect of the present invention to provide the bacterium as described above, wherein the bacterium belongs to the species *Escherichia coli*.

It is a further aspect of the present invention to provide the bacterium as described above, wherein the bacterium is modified to have attenuated or inactivated one or more genes encoding proteins having peptidase activity.

It is a further aspect of the present invention to provide the bacterium as described above, wherein the genes encoding proteins having peptidase activity are selected from the group consisting of pepA, pepB, pepD, pepE, pepP, pepQ, pepN, pepT, iadA, iaaA(ybiK), and dapE.

It is an aspect of the present invention to provide a protein having the dipeptide-synthesizing activity, wherein the protein is selected from the group consisting of:

(F) a protein having the amino acids sequence of SEQ ID NOs: 2, 4, 6, 8, 10, 12, 14, 16 and 18;

(G) a variant protein having the amino acid sequence of SEQ ID NOs: 2, 4, 6, 8, 10, 12, 14, 16 and 18, but which includes substitution, deletion, insertion, or addition of one or several amino acid residues and has dipeptide-synthesizing activity according to the amino acid sequence of SEQ ID NOs: 2, 4, 6, 8, 10, 12, 14, 16 and 18;

(H) a protein having homology, defined in |Log 10(E-value)|-values, of not less than 128, not less than 142, not less than 162, not less than 175, not less than 182, not less than 196, or not less than 233 to the amino acids sequence of SEQ ID NOs: 2, 4, 6, 8, 10, 12, 14, 16 and 18, and dipeptide-synthesizing activity according to the amino acid sequence of SEQ ID NOs: 2, 4, 6, 8, 10, 12, 14 and 16.

It is an aspect of the present invention to provide a method for producing the protein as described above comprising:

(a) cultivating the bacterium as described above in a culture medium to produce the protein;

(b) accumulating the protein in the bacterium or culture medium, or both; and, if necessary, (c) collecting the protein from the bacterium or the culture medium.

It is an aspect of the present invention to provide a method for producing a dipeptide or a salt thereof comprising the steps of:

(a) reacting L-amino acids or L-amino acid derivatives, or salts thereof under appropriate conditions in the presence of the protein as described above;

(b) accumulating the dipeptide or a salt thereof in an appropriate solvent; and, if necessary, (c) collecting the dipeptide or a salt thereof from the appropriate solvent.

It is an aspect of the present invention to provide a method for producing a dipeptide or a salt thereof comprising the steps of:

(a) cultivating the bacterium as described above in a culture medium;

(b) accumulating the dipeptide in the bacterium or culture medium, or both; and, if necessary, (c) collecting the dipeptide from the bacterium or the culture medium.

It is a further aspect of the present invention to provide the method as described above, wherein the L-amino acids or derivatives thereof are selected from the group consisting of L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, and a lower alkyl ester of L-phenylalanine.

It is a further aspect of the present invention to provide the method as described above, wherein the dipeptide is represented by the formula:

R1-R2 wherein R1 is an acidic L-amino acid residue or a derivative of acidic L-amino acid residue, and R2 is an L-amino acid residue or a derivative of L-amino acid residue, wherein the L-amino acid residue is selected from the group consisting of L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, and a lower alkyl ester of L-phenylalanine residue.

It is a further aspect of the present invention to provide the method as described above, wherein R1 is the L-aspartic acid or L-glutamic acid residue, and R2 is the L-glutamic acid, L-isoleucine, L-phenylalanine, L-tryptophan L-valine or a lower alkyl ester of L-phenylalanine residue.

It is a further aspect of the present invention to provide the method as described above, wherein R1 is L-aspartic acid residue, and R2 is L-phenylalanine or a lower alkyl ester of L-phenylalanine residue.

It is a further aspect of the present invention to provide the method as described above, wherein the lower alkyl ester of L-phenylalanine is methyl, ethyl or propyl ester of the L-phenylalanine.

The present invention is described in details below.

BRIEF DESCRIPTION OF DRAWINGS

FIG. 10 shows the alignment of BBR47_51900 and Staur_4851 (ClustalW, outputted in PIR format).

FIG. 11-1 shows the output data obtained by the HMMsearch program using the alignment of BBR47_51900 and Staur_4851 (NOs. 1-18 of first 49 hits are presented).

FIG. 11-2 shows the output data obtained by the HMMsearch program using the alignment of BBR47_51900 and Staur_4851 (NOs. 19-34 of first 49 hits are presented).

FIG. 11-3 shows the output data obtained by the HMMsearch program using the alignment of BBR47_51900 and Staur_4851 (NOs. 35-49 of first 49 hits are presented).

FIG. 13 shows the alignment of BBR47_51900, Staur_4851, DES and BCE (ClustalW, outputted in PIR format).

FIG. 14-1 shows the output data obtained by the HMMsearch program using the alignment of BBR47_51900, Staur_4851, DES and BCE (NOs. 1-18 of first 65 hits are presented).

FIG. 14-2 shows the output data obtained by the HMMsearch program using the alignment of BBR47_51900, Staur_4851, DES and BCE (NOs. 19-35 of first 65 hits are presented).

FIG. 14-3 shows the output data obtained by the HMMsearch program using the alignment of BBR47_51900, Staur_4851, DES and BCE (NOs. 36-51 of first 65 hits are presented).

FIG. 14-4 shows the output data obtained by the HMMsearch program using the alignment of BBR47_51900, Staur_4851, DES and BCE (NOs. 52-65 of first 65 hits are presented).

FIG. 16-1 shows the aligned BBR47_51900, Staur_4851 and DES in the alignment of BBR47_51900, Staur_4851, DES, BCE and BMY (ClustalW, outputted in PIR format).

FIG. 16-2 shows the aligned BCE and BMY in the alignment of BBR47_51900, Staur_4851, DES, BCE and BMY (ClustalW, outputted in PIR format).

FIG. 17-1 shows the output data obtained by the HMMsearch program using the alignment of BBR47_51900, Staur_4851, DES, BCE and BMY (NOs. 1-17 of first 65 hits are presented).

FIG. 17-2 shows the output data obtained by the HMMsearch program using the alignment of BBR47_51900, Staur_4851, DES, BCE and BMY (NOs. 18-33 of first 65 hits are presented).

FIG. 17-3 shows the output data obtained by the HMMsearch program using the alignment of BBR47_51900, Staur_4851, DES, BCE and BMY (NOs. 34-48 of first 65 hits are presented).

FIG. 17-4 shows the output data obtained by the HMMsearch program using the alignment of BBR47_51900, Staur_4851, DES, BCE and BMY (NOs. 49-61 of first 65 hits are presented).

FIG. 17-5 shows the output data obtained by the HMMsearch program using the alignment of BBR47_51900, Staur_4851, DES, BCE and BMY (NOs. 62-65 of first 65 hits are presented).

FIG. 18-1 shows the aligned Staur_4851, BBR47_51900 and BCE in the alignment of BBR47_51900, Staur_4851, DES, BCE, BMY and BTH (ClustalW, outputted in PIR format).

FIG. 18-2 shows the aligned DES, BMY and BTH in the alignment of BBR47_51900, Staur_4851, DES, BCE, BMY and BTH (ClustalW, outputted in PIR format).

FIG. 19-1 shows the output data obtained by the HMMsearch program using the alignment of BBR47_51900, Staur_4851, DES, BCE, BMY and BTH (NOs. 1-18 of first 73 hits are presented).

FIG. 19-2 shows the output data obtained by the HMMsearch program using the alignment of BBR47_51900, Staur_4851, DES, BCE, BMY and BTH (NOs. 19-33 of first 73 hits are presented).

FIG. 19-3 shows the output data obtained by the HMMsearch program using the alignment of BBR47_51900, Staur_4851, DES, BCE, BMY and BTH (NOs. 34-47 of first 73 hits are presented).

FIG. 19-4 shows the output data obtained by the HMMsearch program using the alignment of BBR47_51900, Staur_4851, DES, BCE, BMY and BTH (NOs. 48-62 of first 73 hits are presented).

FIG. 19-5 shows the output data obtained by the HMMsearch program using the alignment of BBR47_51900, Staur_4851, DES, BCE, BMY and BTH (NOs. 63-73 of first 73 hits are presented).

FIG. 20-1 shows the aligned Staur_4851 and BBR47_51900 in the alignment of BBR47_51900, Staur_4851, DES, BCE, BMY, BTH and BUR (ClustalW, outputted in PIR format).

FIG. 20-2 shows the aligned BCE and DES in the alignment of BBR47_51900, Staur_4851, DES, BCE, BMY, BTH and BUR (ClustalW, outputted in PIR format).

FIG. 20-3 shows the aligned BMY and BTH in the alignment of BBR47_51900, Staur_4851, DES, BCE, BMY, BTH and BUR (ClustalW, outputted in PIR format).

FIG. 20-4 shows the aligned BUR in the alignment of BBR47_51900, Staur_4851, DES, BCE, BMY, BTH and BUR (ClustalW, outputted in PIR format).

FIG. 21-1 shows the output data obtained by the HMMsearch program using the alignment of BBR47_51900, Staur_4851, DES, BCE, BMY, BTH and BUR (NOs. 1-14 of first 104 hits are presented).

FIG. 21-2 shows the output data obtained by the HMMsearch program using the alignment of BBR47_51900, Staur_4851, DES, BCE, BMY, BTH and BUR (NOs. 15-28 of first 104 hits are presented).

FIG. 21-3 shows the output data obtained by the HMMsearch program using the alignment of BBR47_51900, Staur_4851, DES, BCE, BMY, BTH and BUR (NOs. 29-43 of first 104 hits are presented).

FIG. 21-4 shows the output data obtained by the HMMsearch program using the alignment of BBR47_51900, Staur_4851, DES, BCE, BMY, BTH and BUR (NOs. 44-60 of first 104 hits are presented).

FIG. 21-5 shows the output data obtained by the HMMsearch program using the alignment of BBR47_51900, Staur_4851, DES, BCE, BMY, BTH and BUR (NOs. 61-73 of first 104 hits are presented).

FIG. 21-6 shows the output data obtained by the HMMsearch program using the alignment of BBR47_51900, Staur_4851, DES, BCE, BMY, BTH and BUR (NOs. 74-97 of first 104 hits are presented).

FIG. 21-7 shows the output data obtained by the HMMsearch program using the alignment of BBR47_51900, Staur_4851, DES, BCE, BMY, BTH and BUR (NOs. 98-104 of first 104 hits are presented).

FIG. 22-1 shows the aligned Staur_4851 and BBR47_51900 in the alignment of BBR47_51900, Staur_4851, DES, BCE, BMY, BTH, BUR and AME (ClustalW, outputted in PIR format).

FIG. 22-2 shows the aligned BCE and DES in the alignment of BBR47_51900, Staur_4851, DES, BCE, BMY, BTH, BUR and AME (ClustalW, outputted in PIR format).

FIG. 22-3 shows the aligned BMY and BTH in the alignment of BBR47_51900, Staur_4851, DES, BCE, BMY, BTH, BUR and AME (ClustalW, outputted in PIR format).

FIG. 22-4 shows the aligned BUR and AME in the alignment of BBR47_51900, Staur_4851, DES, BCE, BMY, BTH, BUR and AME (ClustalW, outputted in PIR format).

FIG. 23-1 shows the output data obtained by the HMMsearch program using the alignment of BBR47_51900, Staur_4851, DES, BCE, BMY, BTH, BUR and AME (NOs. 1-15 of first 65 hits are presented).

FIG. 23-2 shows the output data obtained by the HMMsearch program using the alignment of BBR47_51900, Staur_4851, DES, BCE, BMY, BTH, BUR and AME (NOs. 16-29 of first 65 hits are presented).

FIG. 23-3 shows the output data obtained by the HMMsearch program using the alignment of BBR47_51900, Staur_4851, DES, BCE, BMY, BTH, BUR and AME (NOs. 30-47 of first 65 hits are presented).

FIG. 23-4 shows the output data obtained by the HMMsearch program using the alignment of BBR47_51900, Staur_4851, DES, BCE, BMY, BTH, BUR and AME (NOs. 48-65 of first 65 hits are presented).

FIG. 24-1 shows the aligned Staur_4851 and BBR47_51900 in the alignment of BBR47_51900, Staur_4851, DES, BCE, BMY, BTH, BUR, AME and SFL (ClustalW, outputted in PIR format).

FIG. 24-2 shows the aligned BCE and DES in the alignment of BBR47_51900, Staur_4851, DES, BCE, BMY, BTH, BUR, AME and SFL (ClustalW, outputted in PIR format).

FIG. 24-3 shows the aligned BMY and BTH in the alignment of BBR47_51900, Staur_4851, DES, BCE, BMY, BTH, BUR, AME and SFL (ClustalW, outputted in PIR format).

FIG. 24-4 shows the aligned BUR and AME in the alignment of BBR47_51900, Staur_4851, DES, BCE, BMY, BTH, BUR, AME and SFL (ClustalW, outputted in PIR format).

FIG. 24-5 shows the aligned SFL in the alignment of BBR47_51900, Staur_4851, DES, BCE, BMY, BTH, BUR, AME and SFL (ClustalW, outputted in PIR format).

FIG. 25-1 shows the output data obtained by the HMMsearch program using the alignment of BBR47_51900, Staur_4851, DES, BCE, BMY, BTH, BUR, AME and SFL (NOs. 1-16 of first 38 hits are presented).

FIG. 25-2 shows the output data obtained by the HMMsearch program using the alignment of BBR47_51900, Staur_4851, DES, BCE, BMY, BTH, BUR, AME and SFL (NOs. 17-31 of first 38 hits are presented).

FIG. 25-3 shows the output data obtained by the HMMsearch program using the alignment of BBR47_51900, Staur_4851, DES, BCE, BMY, BTH, BUR, AME and SFL (NOs. 32-38 of first 38 hits are presented).

FIG. 26 shows the analysis of isofunctional Lals using profile HMMs (Models 1 to 7). * E-value=0 (FIGS. 21, 23, and 25). BBR means BBR47_51900, and STA means Staur_4851.

BEST MODE(S) FOR CARRYING OUT THE INVENTION

1. Enzyme

Figure 1:
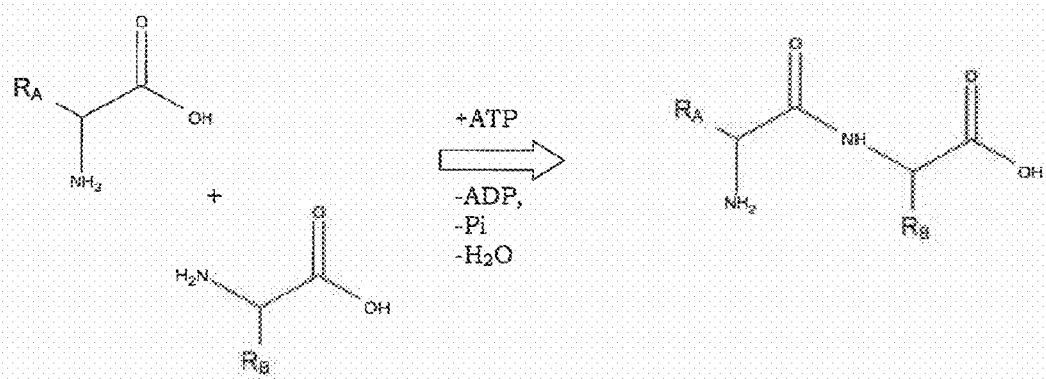
FIG. 1 shows the scheme for the ligation reaction catalyzed by L-amino acid ligases (Lals). $R_A$ and $R_B$ are side-chain groups which may be of the same or different kinds. ATP means adenosine 5'-triphosphate, ADP means adenosine 5'-diphosphate, and Pi means inorganic phosphate, phosphoric acid, or a salt thereof.

The phrase "an enzyme" can mean an L-amino acid α-ligase (Lal) having activity of joining amino acids in a high-energy molecule-dependent manner to form the peptide bond between amino acid residues.

The enzyme of the present invention can be an L-amino acid α-ligase selected from the group consisting of BBR47_51900 (a hypothetical protein), Staur_4851 (argininosuccinate lyase 2-like protein), DES (pyridoxal-phosphate dependent enzyme), BUR (putative lyase), BCE (argininosuccinate lyase domain protein), BTH (hypothetical protein YBT020_25570), AME (conserved hypothetical protein), SFL (protein of unknown function DUF201), and BMY (argininosuccinate lyase domain protein), which is not limited to the aforementioned proteins.

The nucleotide sequence of the gene (NCBI Reference Sequence: YP_002774671.1; nucleotide positions: 5464162 to 5465418, complement; Gene ID: 7721040) from $Brevibacillus$ $brevis$ NBRC 100599 (NCBI Taxonomy ID: 358681) and the amino acid sequence of BBR47_51900 encoded by the gene are shown in SEQ ID NO: 1 and SEQ ID NO: 2, respectively.

The nucleotide sequence of the gene (NCBI Reference Sequence: ADO72629.1; nucleotide positions: 5973963 to 5975216, complement; Gene ID: 9878344) from $Stigmatella$ $aurantiaca$ DW4/3-1 (NCBI Taxonomy ID: 378806) and the amino acid sequence of Staur_4851 encoded by the gene are shown in SEQ ID NO: 3 and SEQ ID NO: 4, respectively.

The nucleotide sequence of the gene (GenBank accession No. EGK06810.1, GI: 332967701) from $Desmospora$ sp. 8437 (NCBI Taxonomy ID: 997346) and the amino acid sequence of DES encoded by the gene are shown in SEQ ID NO: 5 and SEQ ID NO: 6, respectively.

The nucleotide sequence of the gene (GenBank accession No. EBA51208.1, GI: 134251129) from $Burkholderia$ $pseudomallei$ 305 (NCBI Taxonomy ID: 425067) and the amino acid sequence of BUR encoded by the gene are shown in SEQ ID NO: 7 and SEQ ID NO: 8, respectively.

The nucleotide sequence of the gene (GenBank accession No. EEK72190.1, GI: 228615090) from $Bacillus$ $cereus$ AH621 (NCBI Taxonomy ID: 526972) and the amino acid sequence of BCE encoded by the gene are shown in SEQ ID NO: 9 and SEQ ID NO: 10, respectively.

The nucleotide sequence of the gene (GenBank accession No. ADY24341.1, GI: 324329081) from $Bacillus$ $thuringiensis$ subsp. $finitimus$ (strain YBT-020) (NCBI Taxonomy ID: 930170) and the amino acid sequence of BTH encoded by the gene are shown in SEQ ID NO: 11 and SEQ ID NO: 12, respectively.

The nucleotide sequence of the gene (GenBank accession No. ABR48216.1, GI: 149949688) from $Alkaliphilus$ $metalliredigens$ QYMF (NCBI Taxonomy ID: 293826) and the amino acid sequence of AME encoded by the gene are shown in SEQ ID NO: 13 and SEQ ID NO: 14, respectively.

The nucleotide sequence of the gene (GenBank accession No. ADW01942.1, GI: 320007092) from $Streptomyces$ $flavogriseus$ ATCC 33331 (NCBI Taxonomy ID: 591167) and the amino acid sequence of SFL encoded by the gene are shown in SEQ ID NO: 15 and SEQ ID NO: 16, respectively.

The nucleotide sequence of the gene (NCBI Reference Sequence: ZP_04160564.1, GI: 229002475) from $Bacillus$ $mycoides$ Rock3-17 (NCBI Taxonomy ID: 526999) and the amino acid sequence of BMY encoded by the gene are shown in SEQ ID NO: 17 and SEQ ID NO: 18, respectively.

Since there may be some differences in DNA sequences between the genera or species and strains of said genera, the genes encoding BBR47_51900, Staur_4851, DES, BUR, BCE, BTH, AME, SFL and BMY are not limited to the genes shown in SEQ ID NOs: 1, 3, 5, 7, 9, 11, 13, 15, or 17 but may include genes which are variant nucleotide sequences of or homologous to SEQ ID NOs: 1, 3, 5, 7, 9, 11, 13, 15, or 17, and which encode variants of the BBR47_51900, Staur_4851, DES, BUR, BCE, BTH, AME, SFL and BMY proteins. Moreover, the genes encoding BBR47_51900, Staur_4851, DES, BUR, BCE, BTH, AME, SFL and BMY can be variant nucleotide sequences.

The phrase "a variant nucleotide sequence" can mean a nucleotide sequence which encodes "a variant protein".

The phrase "a variant nucleotide sequence" can mean a nucleotide sequence which encodes "a variant protein" using any synonymous amino acid codons according to the standard genetic code table (see, for example, Lewin B., $Genes$ $VIII$, 2004, Pearson Education, Inc., Upper Saddle River, N.J. 07458).

The phrase "a variant nucleotide sequence" can also mean a nucleotide sequence which hybridizes under stringent conditions with the nucleotide sequence complementary to the sequence shown in SEQ ID NOs: 1, 3, 5, 7, 9, 11, 13, 15, or 17, or a probe which can be prepared from the nucleotide sequence under stringent conditions provided that it encodes functional L-amino acid α-ligase. "Stringent conditions" include those under which a specific hybrid, for example, a hybrid having similarity of not less than 80%, not less than 90%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride) and 0.1% SDS (sodium dodecyl sulfate), or in another example, 0.1×SSC and 0.1% SDS, at 60° C. or 65° C. Duration of washing depends on the type of membrane used for blotting and, as a rule, should be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the sequences shown in SEQ ID NOs: 1, 3, 5, 7, 9, 11, 13, 15, or 17 may also be used. Such a probe can be produced by PCR using oligonucleotides as primers prepared on the basis of the sequences shown in SEQ ID NOs: 1, 3, 5, 7, 9, 11, 13, 15, or 17, and a DNA fragment containing the nucleotide sequence as a template. The length of the probe is recommended to be >50 bp; it can be suitably selected depending on the hybridization conditions, and is usually 100 bp to 1 kbp. For example, when a DNA fragment having a length of about 300 bp is used as the probe, the washing conditions after hybridization can be exemplified by 2×SSC and 0.1% SDS at 50° C., 60° C. or 65° C. Alternatively, the stringent condition may be hybridization in 6×SCC at about 45° C. followed by one or two or more washings in 0.2×SCC and 0.1% SDS at 50 to 65° C.

As the genes encoding the BBR47_51900, Staur_4851, DES, BUR, BCE, BTH, AME, SFL and BMY proteins have already been elucidated (see above), the variant nucleotide sequences encoding variant proteins of the BBR47_51900, Staur_4851, DES, BUR, BCE, BTH, AME, SFL and BMY proteins can be obtained by PCR (polymerase chain reaction; refer to White T. J. et al., *Trends Genet.*, 1989, 5:185-189) utilizing primers prepared based on the nucleotide sequence of the genes encoding BBR47_51900, Staur_4851, DES, BUR, BCE, BTH, AME, SFL and BMY. Genes encoding the BBR47_51900, Staur_4851, DES, BUR, BCE, BTH, AME, SFL and BMY proteins or their variant proteins of other microorganisms can be obtained in a similar manner.

The phrase "a variant protein" can mean a protein which has one or several changes in the sequence compared with SEQ ID NOs: 2, 4, 6, 8, 10, 12, 14, 16, and 18, whether they are substitutions, deletions, insertions, and/or additions of amino acid residues, but still maintains an activity similar to that of the BBR47_51900, Staur_4851, DES, BUR, BCE, BTH, AME, SFL and BMY proteins, respectively, or the three-dimensional structure of the BBR47_51900, Staur_4851, DES, BUR, BCE, BTH, AME, SFL and BMY proteins is not significantly changed relative to the wild-type or non-modified proteins. The number of changes in the variant protein depends on the position or the type of amino acid residues in the three dimensional structure of the protein. It can be, but is not strictly limited to, 1 to 45, or 1 to 30, or 1 to 15, or 1 to 10, or 1 to 5, in SEQ ID NOs: 2, 4, 6, 8, 10, 12, 14, 16 and 18.

The exemplary substitution, deletion, insertion, and/or addition of one or several amino acid residues can be a conservative mutation(s) so that the activity and features of the variant protein are maintained, and are similar to those of the BBR47_51900, Staur_4851, DES, BUR, BCE, BTH, AME, SFL and BMY proteins. The representative conservative mutation is a conservative substitution. The conservative substitution can be a substitution, wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His or Lys for Arg, substitution of Glu, Gln, Lys, His or Asp for Asn, substitution Asn, Glu or Gln for Asp, substitution of Ser or Ala for Cys, substitution Asn, Glu, Lys, His, Asp or Arg for Gln, substitution Asn, Gln, Lys or Asp for Glu, substitution of Pro for Gly, substitution Asn, Lys, Gln, Arg or Tyr for His, substitution of Leu, Met, Val or Phe for Ile, substitution of Ile, Met, Val or Phe for Leu, substitution Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. These changes in the variant protein can occur in regions of the protein which are not critical for the function of the protein. This is because some amino acids have high homology to one another so that the three dimensional structure or activity is not affected by such a change. Therefore, the protein variants encoded by the genes shown in SEQ ID NOs: 1, 3, 5, 7, 9, 11, 13, 15, or 17 may have a similarity or identity of not less than 40%, not less than 50%, not less than 60%, not less than 70%, not less than 80%, not less than 90%, not less than 95%, not less than 96%, not less than 97%, not less than 98%, or not less than 99% with respect to the entire amino acid sequences shown in SEQ ID NOs: 2, 4, 6, 8, 10, 12, 14, 16 and 18 as long as the functionality of the BBR47_51900, Staur_4851, DES, BUR, BCE, BTH, AME, SFL and BMY proteins, respectively, is maintained. Alternatively, the protein variants encoded by the genes shown in SEQ ID NOs: 1, 3, 5, 7, 9, 11, 13, 15, or 17 may have a homology, which can be defined using the |Log 10(E-value)|-values calculated by the HMMsearch program when the profile hidden Markov model (profile HMM) based on the aforementioned program is originated (Finn R. D. et al., HMMER web server: interactive sequence similarity searching, Nucleic Acids Res., 2011, 39 (Web Server issue):W29-37), as described below in Example 6, of not less than 128, not less than 142, not less than 162, not less than 175, not less than 182, not less than 196, or not less than 233, with respect to the entire amino acid sequences shown in SEQ ID NOs: 2, 4, 6, 8, 10, 12, 14, 16 and 18 as long as the functionality of the BBR47_51900, Staur_4851, DES, BUR, BCE, BTH, AME, SFL and BMY proteins, respectively, is maintained.

The exemplary substitution, deletion, insertion, and/or addition of one or several amino acid residues can also be a non-conservative mutation(s) provided that the mutation(s) is/are compensated for by one or more secondary mutations in the different position(s) of amino acids sequence so that the activity and features of the variant protein are maintained, and are similar to those of the BBR47_51900, Staur_4851, DES, BUR, BCE, BTH, AME, SFL and BMY proteins.

To evaluate the degree of protein or DNA homology, several calculation methods can be used, such as BLAST search, FASTA search and ClustalW method. The BLAST (Basic Local Alignment Search Tool, www(dot)ncbi(dot)nlm(dot)nih(dot)gov/BLAST/) search is the heuristic search algorithm employed by the programs blastp, blastn, blastx, megablast, tblastn, and tblastx; these programs ascribe significance to their findings using the statistical methods of Samuel K. and Altschul S. F. ("Methods for assessing the statistical significance of molecular sequence features by using general scoring schemes" *Proc. Natl. Acad. Sci. USA,* 1990, 87:2264-2268; "Applications and statistics for multiple high-scoring segments in molecular sequences". *Proc. Natl. Acad. Sci. USA,* 1993, 90:5873-5877). The computer program BLAST calculates three parameters: score, identity and similarity. The FASTA search method is described by Pearson W. R. ("Rapid and sensitive sequence comparison with FASTP and FASTA", *Methods Enzymol.,* 1990, 183: 63-98). The ClustalW method is described by Thompson J. D. et al. ("CLUSTAL W: improving the sensitivity of progressive multiple sequence alignment through sequence weighting, position-specific gap penalties and weight matrix choice", *Nucleic Acids Res.,* 1994, 22:4673-4680).

The phrase "activity of an L-amino acids α-ligase (Lal)" can mean the activity of an enzyme catalyzing reaction of joining amino acids in a high-energy molecule-dependent manner to form the peptide bond between amino acid residues. Dipeptide, tripeptide or peptide of linear or branched structure consisting of more than three amino acids residues, or derivatives thereof may be the product of the reaction catalyzed by Lal. The reaction scheme for the Lal-catalyzed reaction may be described as shown in FIG. 1 without limiting to the kind of amino acids or derivatives thereof and reaction conditions used in the following non-limiting Examples. The activity of Lal can be measured, for example, by the assay described in the Example 3 or Tabata K. et al., *J. Bacteriol.,* 2005, 187(15):5195-5202. The phrase "activity of L-amino acids α-ligase (Lal)" can be equivalent, in particular, to the phrase "dipeptide-synthesizing activity".

Furthermore, when an amino acid sequence that contains a substitution, deletion, insertion, and/or addition of one or several amino acid residues in the amino acid sequence of SEQ ID NOs: 2, 4, 6, 8, 10, 12, 14, 16 and 18., it can retain activity of L-amino acids α-ligase by 10% or more, by 30% or more, by 50% or more, by 70% or more, and by 90% or more of a protein having the amino acid sequence of SEQ ID NOs: 2, 4, 6, 8, 10, 12, 14, 16 and 18.

The phrase "an isofunctional protein" can mean the protein having the activity of an L-amino acids α-ligase (Lal) as described above. Exemplary, the isofunctional protein can synthesize dipeptide having an acidic L-amino acid residue such as L-Glu or L-Asp residue at the N-terminus and any other L-amino acid or a derivative thereof at the C-terminus.

2. Bacterium

The phrase "a dipeptide-producing bacterium" can mean a bacterium of the family Enterobacteriaceae such as a bacterium belonging to the genus *Escherichia*, which has an ability to produce and cause accumulation of a dipeptide in a culture medium when the bacterium is cultured in the medium. The dipeptide-producing ability can mean the ability of the bacterium to produce a dipeptide in a medium or the bacterial cells and cause accumulation of the dipeptide to such an extent that the dipeptide can be collected from the medium or the bacterial cells when the bacterium is cultured in the medium.

The bacterium may inherently have the dipeptide-producing ability or may be modified to have a dipeptide-producing ability by using mutation methods or DNA recombination techniques.

The bacteria belonging to the family Enterobacteriaceae can be from the genera *Enterobacter, Erwinia, Escherichia, Klebsiella, Morganella, Pantoea, Photorhabdus, Providencia, Salmonella, Yersinia*, and so forth, and can have the ability to produce a dipeptide. Specifically, those classified into the family Enterobacteriaceae according to the taxonomy used in the NCBI (National Center for Biotechnology Information) database (www(dot) ncbi(dot)nlm(dot)nih (dot)gov/Taxonomy/Browser/wwwtax(dot)cgi?id=543) can be used. Examples of strains from the family Enterobacteriaceae which can be modified include a bacterium of the genus *Escherichia, Enterobacter* or *Pantoea*.

Strains of *Escherichia* bacterium which can be modified to obtain *Escherichia* bacteria in accordance with the presently disclosed subject matter are not particularly limited, and specifically, those described in the work of Neidhardt et al. can be used (Bachmann, B. J., Derivations and genotypes of some mutant derivatives of *E. coli* K-12, p. 2460-2488. In F. C. Neidhardt et al. (ed.), *E. coli* and *Salmonella*: cellular and molecular biology, $2^{nd}$ ed. ASM Press, Washington, D.C., 1996). The species *E. coli* is a particular example. Specific examples of *E. coli* include *E. coli* W3110 (ATCC 27325), *E. coli* MG1655 (ATCC 47076), and so forth, which are derived from the prototype wild-type strain, K-12 strain. These strains are available from, for example, the American Type Culture Collection (P.O. Box 1549, Manassas, Va. 20108, United States of America). That is, registration numbers are given to each of the strains, and the strains can be ordered by using these registration numbers (refer to www(dot)atcc(dot)org). The registration numbers of the strains are listed in the catalogue of the American Type Culture Collection.

Examples of the *Enterobacter* bacteria include *Enterobacter agglomerans, Enterobacter aerogenes*, and so forth. Examples of the *Pantoea* bacteria include *Pantoea ananatis*, and so forth. Some strains of *Enterobacter agglomerans* were recently reclassified into *Pantoea agglomerans, Pantoea ananatis* or *Pantoea stewartii* on the basis of nucleotide sequence analysis of 16S rRNA, etc. A bacterium belonging to any of the genus *Enterobacter* or *Pantoea* may be used so long as it is a bacterium classified into the family Enterobacteriaceae. When a *Pantoea ananatis* strain is bred by genetic engineering techniques, *Pantoea ananatis* AJ13355 strain (FERM BP-6614), AJ13356 strain (FERM BP-6615), AJ13601 strain (FERM BP-7207) and derivatives thereof can be used. These strains were identified as *Enterobacter agglomerans* when they were isolated, and deposited as *Enterobacter agglomerans*. However, they were recently re-classified as *Pantoea ananatis* on the basis of nucleotide sequencing of 16S rRNA and so forth as described above.

The dipeptide-producing bacterium as described herein can be modified to have attenuated or inactivated one or more genes of one or more kinds encoding protein(s) having peptidase, or proteolytic activity so that the activity of peptidase(s) is decreased. For example, one or more proteases encoding genes such as pepA (KEGG, Kyoto Encyclopedia of Genes and Genomes, entry No. b4260), pepB (KEGG, entry No. b2523), pepD (KEGG, entry No. b0237), pepE (KEGG, entry No. b4021), pepP (KEGG, entry No. b2908), pepQ (KEGG, entry No. b3847), pepN (KEGG, entry No. b0932), pepT (GenBank accession No. AAC74211), iadA (KEGG, entry No. b4328), iaaA(ybiK) (KEGG, entry No. b0828), dapE (KEGG, entry No. b2472), and so forth can be attenuated and/or inactivated.

The dipeptide-producing bacterium as described herein can be also modified to have attenuated or inactivated one or more genes of one or more kinds encoding protein(s) having dipeptide permease (dpp) activity so that the activity of peptide permease(s) is decreased. For example, one or more dipeptide permeases encoding genes such as dppA (KEGG, entry No. b3544), dppB (KEGG, entry No. b3543), dppC (KEGG, entry No. b3542), dppD (KEGG, entry No. b3541), dppF (KEGG, entry No. b3540), and so forth can be attenuated and/or inactivated. Deletion of the entire dpp gene operon (dppA, dppB, dppC, dppD and dppF) may be also preferred in the dipeptide-producing bacterium.

The dipeptide-producing bacterium as described herein can be also modified to have attenuated or inactivated one or more genes of one or more kinds encoding protein(s) involved in biosynthesis of aromatic amino acids so that the activity of the protein(s) is decreased. For example, one or more proteins encoding genes such as tyrR (KEGG, entry No. b1323), tryA (KEGG, entry No. b2600), and so forth can be attenuated and/or inactivated.

The phrase "an attenuated gene encoding peptidase" or "an attenuated gene encoding protein" is equivalent to the phrase "a peptidase encoding gene with attenuated expression" or "a protein encoding gene with attenuated expression", respectively. Hereinafter, the term "peptidase" may be replaced with "protein" as recited above (e.g., protein(s) having dipeptide permease (dpp) activity, or protein(s) involved in biosynthesis of aromatic amino acids) for interpreting the phrase "an attenuated gene encoding protein" or the like. Therefore, such replaced phases may be recited as elements for specifying the present invention.

The phrase "a peptidase encoding gene with attenuated expression" can mean that an amount of a peptidase in the modified bacterium, in which expression of the peptidase encoding gene is attenuated, is reduced as compared with a non-modified bacterium, for example, a wild-type strain of the bacterium belonging to the family Enterobacteriaceae, or more specifically, genus *Escherichia* such as the *E. coli* K-12 strain.

The phrase "a peptidase encoding gene with attenuated expression" can also mean that the modified bacterium includes a modified gene, which encodes a mutant protein having decreased activity as compared with the wild-type protein, or a region operably linked to the gene, including sequences controlling gene expression such as promoters, enhancers, attenuators, ribosome-binding sites (RBS), Shine-Dalgarno (SD) sequences, etc., is modified resulting in a decrease in the expression level of the peptidase encoding gene, and other examples (see, for example, WO95/34672; Carrier T. A. and Keasling J. D., *Biotechnol. Prog.*, 1999, 15:58-64).

Expression of the peptidase encoding gene can be attenuated by replacing an expression control sequence of the gene, such as a promoter on the chromosomal DNA, with a weaker one. The strength of a promoter is defined by the frequency of initiation acts of RNA synthesis. Examples of methods for evaluating the strength of promoters and strong promoters are described in Goldstein et al., Prokaryotic promoters in biotechnology, *Biotechnol. Annu. Rev.*, 1995, 1:105-128), and so forth. Furthermore, it is also possible to introduce nucleotide substitution for several nucleotides in a promoter region of a target gene and thereby modify the promoter to be weakened as disclosed in International Patent Publication WO00/18935. Furthermore, it is known that substitution of several nucleotides in the spacer between the SD sequence and the start codon in the RBS, in particular, a sequence immediately upstream from the start codon, greatly affects the translation efficiency of mRNA. This modification of the RBS may be combined with decreasing transcription of a peptidase encoding gene.

Expression of the peptidase encoding gene can also be attenuated by insertion of a transposon or an IS factor into the coding region of the gene (U.S. Pat. No. 5,175,107) or by conventional methods, such as mutagenesis with ultraviolet irradiation (UV) irradiation or nitrosoguanidine (N-methyl-N'-nitro-N-nitrosoguanidine). Furthermore, the incorporation of a site-specific mutation by gene substitution using homologous recombination such as set forth above can also be conducted with a plasmid which is unable to replicate in the host.

The phrase "enzymatic activity is decreased" can mean that the enzymatic activity of a peptidase is lower than that in a non-modified strain, for example, a wild-type strain of the bacterium belonging to the family Enterobacteriaceae, or more specifically, genus *Escherichia*. Exemplary, the enzymatic activity of the peptidase encoding gene can be abolished by the gene inactivation.

The phrase "the activity of peptidase is decreased" can also mean that the peptide degrading activity is decreased compared with a wild-type peptidase encoded by the wild-type gene such as pepA, pepB, pepD, pepE, pepP, pepQ, pepN, pepT, iadA, iaaA(ybiK), dapE, and so forth.

In the modified bacterium, the activity of peptidase can be decreased by at least 10% or more, by at least 30% or more, by at least 50% or more, by at least 70% or more, by at least 90% or more as compared with a peptidase encoded by a wild-type gene in a non-modified bacterium belonging to the family Enterobacteriaceae, more specifically to the genus *Escherichia*.

The phrase "peptidase activity" or "proteolytic activity" can mean the activity of an enzyme catalyzing reaction of intramolecular digestion of the peptide bond (R. Beynon (ed.) and J. S. Bond (ed.), "Proteolytic Enzymes: A Practical Approach", $2^{nd}$ ed., Oxford University Press, USA (2001)).

The peptide degrading activity of a microorganism can be measured by allowing a peptide as a substrate and microorganism cells to be present in a medium, thereby performing peptide degrading reaction, and then determining the amount of the remaining peptide by a known method, for example, HPLC analysis, or as described in Kristjansson M. M., Activity measurements of proteinases using synthetic substrates (UNIT C2.1) or Akpinar O. and Penner M. H., Peptidase activity assays using protein substrates (UNIT C2.2) in Current Protocols in Food Analytical Chemistry (UNIT C2, Proteolytic Enzymes), John Wiley & Sons, Inc. (2002).

The enzymatic activity of a peptidase can be decreased by introducing a mutation into the chromosome so that intracellular activity of the peptidase is decreased as compared with a non-modified strain. Such a mutation on the gene(s) or upstream the genes in the operon structure can be the replacement of one base or more to cause an amino acid substitution in the protein encoded by the gene(s) (missense mutation), introduction of a stop codon (nonsense mutation), deletion of one or two bases to cause a frame shift, insertion of a drug-resistance gene and/or transcription termination signal, deletion of a part of the gene(s) or deletion of the entire gene(s) (Qiu Z. and Goodman M. F., *J. Biol. Chem.*, 1997, 272:8611-8617; Kwon D. H. et al., *J. Antimicrob. Chemother.*, 2000, 46:793-796).

The phrase "an inactivated gene encoding peptidase" can mean that the modified gene encodes a completely inactive or non-functional peptidase. It is also possible that the modified DNA region is unable to naturally express the gene due to deletion of a part of or the entire gene, shifting of the reading frame of the gene, introduction of missense/non-sense mutation(s), or modification of an adjacent region of the gene, including sequences controlling gene expression, such as promoter(s), enhancer(s), attenuator(s), ribosome-binding site(s), etc. Inactivation of the gene can also be performed by conventional methods such as a mutagenesis treatment using UV irradiation or nitrosoguanidine (N-methyl-N'-nitro-N-nitrosoguanidine), site-directed mutagenesis, gene disruption using homologous recombination, or/and insertion-deletion mutagenesis (Yu D. et al., *Proc. Natl. Acad. Sci. USA*, 2000, 97(12):5978-83; Datsenko K. A. and Wanner B. L., *Proc. Natl. Acad. Sci. USA*, 2000, 97(12):6640-45), also called "Red-driven integration" or "λRed-mediated integration".

The phrase "a bacterium modified to contain the recombinant DNA" can mean the bacterium modified to contain an exogenous DNA by, for example, conventional methods such as, for example, transformation, transfection, infection, conjugation, and mobilization. Transformation, transfection, infection, conjugation or mobilization of a bacterium with the DNA encoding a protein can impart the bacterium an ability to synthesize the protein encoded by the DNA. Methods of transformation, transfection, infection, conjugation and mobilization include any known methods that have been reported. For example, a method of treating recipient cells with calcium chloride so as to increase permeability of the cells of *Escherichia coli* K-12 to DNA has been reported for efficient DNA transformation and transfection (Mandel M. and Higa A., Calcium-dependent bacteriophage DNA infection, *J. Mol. Biol.*, 1970, 53:159-162). Methods of specialized and/or generalized transduction are described (Morse M. L. et al., Transduction in *Escherichia coli* K-12, Genetics, 1956, 41(1):142-156; Miller J. H., *Experiments in Molecular Genetics*. Cold Spring Harbor, N.Y.: Cold Spring Harbor La. Press, 1972). Other methods for random and/or targeted integration of DNA into the host genome can be applied, for example, "Mu-driven integration/amplification" (Akhverdyan et al., *Appl. Microbiol. Biotechnol.*, 2011, 91:857-871), "Red/ET-driven integration" or "ARed/ET-mediated integration" (Datsenko K. A. and Wanner B. L., *Proc. Natl. Acad. Sci. USA* 2000, 97(12):6640-45; Zhang Y., et al., *Nature Genet.*, 1998, 20:123-128). Moreover, for multiple insertions of desired genes in addition to Mu-driven replicative transposition (Akhverdyan et al., *Appl. Microbiol. Biotechnol.*, 2011, 91:857-871) and chemically inducible chromosomal evolution based on recA-dependent homologous recombination resulted in an amplification of desired genes (Tyo K. E. J. et al., *Nature Biotechnol.*, 2009, 27:760-765), another methods can be used, which utilize different combinations of transposition, site-specific and/or homologous Red/ET-mediated recombinations, and/or P1-mediated generalized transduction (see, for example, Minaeva et al., *BMC Biotechnology*, 2008, 8:63; Koma D. et al., *Appl. Microbiol. Biotechnol.*, 2012, 93(2):815-829).

The bacterium of the present invention can be modified further in such a way that expression level of a gene encoding L-amino acid α-ligase (Lal) or one or more genes encoding one or more proteins involved in biosynthesis of phenylalanine are enhanced. Examples of such a protein include pheA, aroG4 and aroL encoding chorismate mutase-prephenate dehydratase (CM-PD), 3-deoxy-D-arabinoheptulosonate-7-phosphate synthetase (DAHP synthetase) and shikimate kinase (SK), respectively (see, e.g., Japanese Patent No. 3225597). Hereinafter, the term "Lal" may be replaced with the protein involved in biosynthesis of phenylalanine, for interpreting the phrase "a gene encoding proteins involved in biosynthesis of phenylalanine" or the like. Therefore, such replaced phases may be recited as elements for specifying the present invention.

The phrase "enhanced expression of a gene encoding Lal" can mean that the number of the molecules encoded by the Lal-encoding gene per cell is increased, or the activity per molecule (may be referred to as a specific activity) of the protein encoded by these gene improved, as compared with a non-modified strain such as a wild-type or a parent strain. Examples of a non-modified strain serving as a reference for the above comparison include a wild-type strain of a microorganism belonging to the family Enterobacteriaceae such as the *E. coli* MG1655 strain (ATCC 47076), W3110 strain (ATCC 27325), *Pantoea ananatis* AJ13335 strain (FERN BP-6614), and so forth.

The phrase "enhanced expression of a gene encoding Lal" can also mean that the expression level of the Lal-encoding gene is higher than that level in a non-modified strain, for example, a wild-type or parent strain.

Methods which can be used to enhance expression of the Lal-encoding gene include, but are not limited to, increasing the Lal-encoding gene copy number in bacterial genome (in the chromosome and/or in the autonomously replicated plasmid) and/or introducing the Lal-encoding gene into a vector that is able to increase the copy number and/or the expression level of the Lal-encoding gene in a bacterium of the genus *Escherichia* according to genetic engineering methods known to the one skilled in the art.

Examples of the vectors include, but are not limited to broad-host-range vectors such as pCM110, pRK310, pVK101, pBBR122, pBHR1, and the like. Multiple copies of the Lal-encoding gene can also be introduced into the chromosomal DNA of a bacterium by, for example, homologous recombination, Mu-driven integration, or the like. Homologous recombination can be carried out using a sequence multiple copies in the chromosomal DNA. Sequences with multiple copies in the chromosomal DNA include, but are not limited to repetitive DNA or inverted repeats present at the end of a transposable element. In addition, it is possible to incorporate the Lal-encoding gene into a transposon and allow it to be transferred to introduce multiple copies of the Lal-encoding gene into the chromosomal DNA. By using Mu-driven integration, more than 3 copies of the gene can be introduced into the chromosomal DNA during a single act (Akhverdyan V. Z. et al., *Biotechnol. (Russian)*, 2007, 3:3-20).

Enhancing of the Lal-encoding gene expression can also be achieved by increasing the expression level of the Lal-encoding gene by modification of adjacent regulatory regions of the Lal-encoding gene or introducing native and/or modified foreign regulatory regions. Regulatory regions or sequences can be exemplified by promoters, enhancers, attenuators and transcription termination signals, anti-termination signals, ribosome-binding sites (RBS) and other expression control elements (e.g., regions to which repressors or inducers bind and/or binding sites for transcriptional and translational regulatory proteins, for example, in the transcribed mRNA). Such regulatory sequences are described, for example, in Sambrook J., Fritsch E. F. and Maniatis T., "Molecular Cloning: A Laboratory Manual", 2$^{nd}$ ed., Cold Spring Harbor Laboratory Press (1989). Modifications of regions controlling gene(s) expression can be combined with increasing the copy number of the modified gene(s) in bacterial genome using the known methods (see, for example, Akhverdyan V. Z. et al., *Appl. Microbial. Biotechnol.*, 2011, 91:857-871; Tyo K. E. J. et al., *Nature Biotechnol.*, 2009, 27:760-765).

The exemplary promoters enhancing the Lal-encoding gene expression can be the potent promoters. For example, the lac promoter, the trp promoter, the trc promoter, the tac promoter, the $P_R$ or the $P_L$ promoters of lambda phage are all known to be potent promoters. Potent promoters providing a high level of gene expression in a bacterium belonging to the family Enterobacteriaceae can be used. Alternatively, the effect of a promoter can be enhanced by, for example, introducing a mutation into the promoter region of the Lal-encoding gene to obtain a stronger promoter function, thus resulting in the increased transcription level of the Lal-encoding gene located downstream of the promoter. Furthermore, it is known that substitution of several nucleotides in the ribosome binding site (RBS), especially the sequences immediately upstream of the start codon, profoundly affect the mRNA translatability. For example, a 20-fold range in the expression levels was found, depending on the nature of the three nucleotides preceding the start codon (Gold L. et al., *Annu. Rev. Microbiol.*, 1981: 35, 365-403; Hui A. et al., *EMBO J.*, 1984: 3, 623-629).

Enhancing of the Lal-encoding gene heterologous expression in host microorganisms can also be achieved by substituting rare and/or low-usage codons for synonymous middle- or high-usage codons, where codon usage can be defined as the number of times (frequency) a codon is translated per unit time in the cell of an organism or an average codon frequency of the sequenced protein-coding reading frames of an organism (Zhang S. P. et al., *Gene*, 1991, 105(1):61-72). The codon usage per organism can be found in the Codon Usage Database, which is an extended web-version of the CUTG (Codon Usage Tabulated from GenBank) (http(colon)//www(dot)kazusa(dot)or(dot)jp/codon/; Nakamura Y. et al., Codon usage tabulated from the international DNA sequence databases: status for the year 2000, *Nucl. Acids Res.*, 2000, 28(1):292). In *E. coli* such mutations can include, without limiting, the substitution of rare Arg codons AGA, AGG, CGG, CGA for CGT or CGC; rare Ile codon ATA for ATC or ATT; rare Leu codon CTA for CTG, CTC, CTT, TTA or TTG; rare Pro codon CCC for CCG or CCA; rare Ser codon TCG for TCT, TCA, TCC, AGC or AGT; rare Gly codons GGA, GGG for GGT or GGC; and so forth. The substitution of low-usage codons for synonymous high-usage codons can be preferable. The substituting rare and/or low-usage codons for synonymous middle- or high-usage codons may be combined with co-expression of the genes which encode rare tRNAs recognizing rare codons.

The copy number, presence or absence of the gene and/or operon genes can be measured, for example, by restricting the chromosomal DNA followed by Southern blotting using a probe based on the gene sequence, fluorescence in situ hybridization (FISH), and the like. The level of the gene and/or operon gene's expression can be measured by various known methods including Northern blotting, quantitative RT-PCR, and the like. In addition, the level of gene expression can be determined by measuring the amount of mRNA transcribed from the gene using various well-known methods, including Northern blotting, quantitative RT-PCR, and the like. The amount of the protein coded by the gene can be measured by known methods including SDS-PAGE followed by immunoblotting assay (Western blotting analysis), or mass spectrometry analysis of the protein samples, and the like.

Methods for preparation of plasmid DNA, digestion, ligation and transformation of DNA, selection of an oligonucleotide as a primer, and the like may be ordinary methods well-known to the one skilled in the art. These methods are described, for instance, in Sambrook J., Fritsch E. F. and Maniatis T., "Molecular Cloning: A Laboratory Manual", $2^{nd}$ ed., Cold Spring Harbor Laboratory Press (1989) or Green M. R. and Sambrook J. R., "Molecular Cloning: A Laboratory Manual", $4^{th}$ ed., Cold Spring Harbor Laboratory Press (2012). Methods for molecular cloning and heterologous gene expression are described in Bernard R. Glick, Jack J. Pasternak and Cheryl L. Patten, "Molecular Biotechnology: principles and applications of recombinant DNA", $4^{th}$ ed., Washington, D.C: ASM Press (2009); Evans Jr., T. C. and Xu M.-Q., "Heterologous gene expression in *E. coli*", $1^{st}$ ed., Humana Press (2011).

The phrase "operably linked to a gene" can mean that the regulatory sequence(s) is linked to the nucleotide sequence of the nucleic acid molecule or gene of interest in a manner which allows for expression (e.g., enhanced, increased, constitutive, basal, attenuated, decreased or repressed expression) of the nucleotide sequence, preferably expression of a gene product encoded by the nucleotide sequence.

The bacterium as described herein can be obtained by imparting the required properties to a bacterium inherently having the ability to produce a dipeptide. Alternatively, the bacterium can be obtained by imparting the ability to produce a dipeptide to a bacterium which already has the required properties.

The bacterium can have, in addition to the properties already mentioned, other specific properties such as various nutrient requirements, drug resistance, drug sensitivity, and drug dependence, without departing from the scope of the present invention.

3. Methods for Producing Dipeptides

The methods of the present invention can be the methods for producing a dipeptide, more specifically a dipeptide having an acidic L-amino acid at the N-terminus, using an L-amino acid α-ligase (Lal) or a bacterium belonging to the family Enterobacteriaceae modified to contain said Lal, therefore, referred to as a enzymatic method and a fermentative method, respectively.

The phrase "an amino acid" can mean an ordinal amino acid known to the one skilled in the art, a derivative of amino acid, or salts thereof. The exemplary amino acids can be α-amino acids and β-amino acids having $C^\alpha$ or $C^\beta$ chiral carbon atom respectively, to which the amino group, carboxy group, and side-chain group are attached. The β-amino acids can be exemplified by βAla. The α-amino acids can be exemplified by proteinogenic and non-proteinogenic amino acids. Proteinogenic amino acids can be exemplified by L-amino acids such as L-alanine, L-arginine, L-asparagine, L-aspartic acid, L-cysteine, glycine, L-glutamic acid, L-glutamine, L-histidine, L-isoleucine, L-leucine, L-lysine, L-methionine, L-phenylalanine, L-proline, L-serine, L-threonine, L-tryptophan, L-tyrosine, and L-valine, or salts thereof, having $C^\alpha$ chiral carbon atom. The amino acids can be used in unprotected or protected form. The protected form of amino acid can mean, contrary to the unprotected form, an amino acid having one or more substituents attached to amino group, carboxy group, and/or side-chain group. The amino acid having substituents(s) attached can be referred to as an amino acid derivative. The amino acid derivative can be exemplified by a lower alkyl ester of amino acid such as a lower alkyl ester of L-phenylalanine. As lower alkyl ester, methyl ester, ethyl ester, and propyl ester, or the like can be mentioned.

The phrase "an amino acid" can be equivalent to the phrase "a substrate of the Lal-catalyzed reaction" or "a substrate" for the reasons of simplicity.

The phrase "an acidic L-amino acid" can mean the aspartic acid (Asp) and glutamic acid (Glu) of L-form, or salts thereof.

The phrase "a dipeptide" can mean an organic molecule or a salt thereof consisting of two amino acid residues or derivatives of two amino acid residues, or a combination thereof, joined via peptide bond. The dipeptide can be consisted of amino acids or derivatives thereof, which are specified above. For example, the phrase "a dipeptide" can mean a dipeptide formed by two proteinogenic L-amino acid residues in such a way that an acidic L-amino acid residue such as L-Asp or L-Glu is located at the N-terminus of the dipeptide and another L-amino acid residue of the same kind or different kind is located at the C-terminus of the dipeptide. It is also accepted that a derivative of an amino acid, for example, a lower alkyl ester of an L-amino acid such as the methyl ester of L-Phe can be located at the C-terminus of the dipeptide.

The dipeptide as described herein is not limited to the dipeptide having an acidic amino acid residue at the N-terminus. The dipeptide can be represented by the formula R1-R2, where R1 and R2 can mean amino acid residues or derivatives thereof located at the N- and C-terminus of the dipeptide respectively and joined via peptide bond. R1 and R2 can be exemplified by L-amino acids such as L-Ala, L-Arg, L-Asp, L-Asn, L-Cys, Gly, L-Glu, L-Gln, L-His, L-Ile, L-Leu, L-Lys, L-Met, L-Phe, L-Pro, L-Ser, L-Thr, L-Trp, L-Tyr, and L-Val, or derivatives thereof such as L-PheOMe, or salts thereof. R1 and R2 may be of the same kind or different kinds.

The phrase "peptide bond" can mean a covalent chemical bond —C(O)NH— formed between two molecules when the carboxy part of one molecule, referred to as a carboxy component, reacts with the amino part of another molecule, referred to as an amino component, causing the release of a molecule. For example, amino acids can form the peptide bond upon joining with the release of a molecule of water.

Any carboxy component may be used as far as it can form a peptide by condensation with the other substrate in the form of the amine component. Examples of carboxy component include L-amino acid esters, D-amino acid esters, L-amino acid amides, and D-amino acid amides as well as organic acid esters not having unprotected an amino group. In addition, examples of amino acid esters include not only amino acid esters corresponding to naturally-occurring amino acids, but also amino acid esters corresponding to non-naturally-occurring amino acids or their derivatives. In addition, examples of amino acid esters include α-amino acid esters as well as β-, γ- and ω-amino acid esters and the like having different amino group bonding sites. Typical examples of amino acid esters include methyl esters, ethyl esters, n-propyl esters, iso-propyl esters, n-butyl esters, iso-butyl esters, and tert-butyl esters of amino acids. Also, the carboxy part of carboxy component can be exemplified by the carboxyl group COOH or a derivative thereof COR, where R can mean a substituted phenyl group or a halogenyl group such as chloro group.

Any amine component may be used as far as it can form a peptide by condensation with the other substrate in the form of the carboxy component. Examples of the amine component include L-amino acids, C-protected L-amino acids, D-amino acids, C-protected D-amino acids, and amines. In addition, examples of the amines include not only naturally-occurring amines, but also non-naturally-occurring amines or their derivatives. In addition, examples of the amino acids include not only naturally-occurring amino acids, but also non-naturally-occurring amino acids or their derivatives. These include α-amino acids as well as β-, γ- or ω-amino acids and the like having different carboxy group bonding sites.

3.1. Enzymatic Method

The enzymatic method can include at least the step of allowing the L-amino acids α-ligase or Lal-containing substance to contact with one or more amino acid(s) of the same kind or different kinds, or derivatives thereof, or salts thereof, under appropriate conditions to obtain the reaction product in accordance with the activity of Lal as described above.

The method of allowing the Lal or Lal-containing substance used in the present invention to act on a carboxy component and an amino component may be mixing the Lal or Lal-containing substance, the molecule with carboxy part, and the molecule with amino part with each other. More specifically, a method of adding the Lal or Lal-containing substance to a solution containing carboxy and amino components to form a dipeptide and allowing them to react may be used. Alternatively, in the case of using a bacterium that produces the Lal, a method may be used that includes culturing the bacterium that forms the Lal, producing, and accumulating the Lal in the bacterium or cultivation medium, and then adding the molecule with carboxy component and the molecule with amine component to the medium. The produced dipeptide can then be collected by established methods and purified as necessary.

The phrase "Lal-containing substance" can mean any substance so far as it contains the Lal, and examples of specific forms thereof include a culture of bacteria that produce the Lal, bacterial cells isolated from the culture, and a product obtained by treating the bacterial cells (also referred to as "treated bacterial cell product"). A culture of bacteria can mean what is obtained by culturing a bacterium, and more specifically, a mixture of bacterial cells, the medium used for culturing the bacterium, and substances produced by the cultured bacterium, and so forth. In addition, the bacterial cells may be washed and used in the form of washed bacterial cells. In addition, the treated bacterial cell product includes the products of disrupted, lysed or freeze-dried bacterial cells, and the like, and also includes a crude enzyme recovered by treating bacterial cells, and so forth, as well as a purified enzyme obtained by purification of the crude enzyme, and so forth. A partially purified enzyme obtained by various types of purification methods may be used for the purified enzyme, or immobilized enzymes may be used that have been immobilized by a covalent bonding method, an adsorption method, an entrapment method, or the like. In addition, since some bacteria are partially lysed during culturing depending on the microbes used, the culture supernatant may also be used as the enzyme-containing substance in such cases.

In addition, wild-type strains may be used as bacteria that contain the Lal, or gene recombinant strains that express the Lal may also be used as described above. The bacteria are not limited to intact bacterial cells, but rather acetone-treated bacterial cells, freeze-dried bacterial cells or other treated bacterial cells may also be used. Immobilized bacterial cells and an immobilized treated bacterial cell product obtained by immobilizing the bacterial cells or treated bacterial cell product by covalent bonding, adsorption, entrapment or other methods, as well as treated immobilized bacterial cells, may also be used.

Furthermore, when using cultures, cultured bacterial cells, washed bacterial cells or a treated bacterial cell product that has been obtained by disrupting or lysing bacterial cells, it is often the case that an enzyme exists therein that decomposes the formed peptides without being involved in peptide formation. In this situation, it may be rather preferable in some cases to add a metal protease inhibitor like ethylene diamine tetraacetic acid (EDTA). The addition amount can be within the range of 0.1 mM to 300 mM, and preferably within the range of 1 mM to 100 mM.

An exemplary mode of the enzymatic method of the present invention is a method in which the transformed cells described herein are cultured in a medium, and a peptide-forming enzyme (Lal) is allowed to accumulate in the medium and/or transformed cells. Since the peptide-forming enzyme can be easily produced in large volumes by using a transformant, dipeptides can be produced in large amounts and rapidly.

The amount of Lal or Lal-containing substance used may be enough if it is an amount at which the target effect is demonstrated (effective amount), and this effective amount can be easily determined through simple, preliminary experimentation by a person with ordinary skill in the art. In the case of using the Lal, for example, the amount used can be about 0.1 g/L to 10 g/L (see, for example, Example 3), while in the case of using washed bacterial cells, the amount used can be higher that depends on the amount of Lal in a bacterial cell.

The phase "appropriate conditions" can mean the conditions under which the Lal-catalyzed reaction can proceed; i.e. a reaction product, for example, a dipeptide can be formed from a carboxy component and an amino component. The phrase "appropriate conditions" can include without limiting the phrases "an enzyme", "an amino acid", "a substrate", "an appropriate solvent", "a high-energy molecule", "appropriate temperature conditions", and so forth.

The phrase "a high-energy molecule" can mean any organic or inorganic molecule required for the Lal-catalyzed reaction to proceed under appropriate conditions. Conventionally, cofactors may be exemplified as the high-energy molecule. More specifically, the high-energy molecule can be exemplified by the adenosine 5'-triphosphate (ATP) or a salt thereof. Sodium, potassium, ammonium salts, or the like in any combinations thereof can be used.

The phrase "an appropriate solvent" can mean any solvent, in which the Lal-catalyzed reaction can proceed, that is a reaction product, for example, a dipeptide can be formed. Organic and aqueous solvents, or mixtures thereof in various proportions may be an appropriate solvent. An appropriate solvent may contain the Lal enzyme of the present invention; cofactors such as ATP, and the like; metal ions such as sodium, potassium, ammonium, calcium, magnesium ions, and the like; anions such as sulfate, chloride, phosphate ions, and the like; other inorganic and/or organic molecules required for the activity of L-amino acids α-ligase. Tris(hydroxymethyl)aminomethane (Tris), N-tris(hydroxymethyl)methylglycine (Tricine) or N,N-bis(2-hydroxyethyl)glycine (Bicine), or the like as described in Carmody W. R. *J. Chem. Educ.*, 1961, 38(11):559-560 can be added into a reaction mixture as a buffering agent. The acidity (pH) of a reaction mixture may be maintained between 6.5 and 10.5, or between 7.0 and 10.0, or between 7.5 and 9.5, or between 8 and 9. The appropriate solvent may be subjected to appropriate temperature conditions.

The phrase "appropriate temperature conditions" can mean temperature conditions in which the Lal-catalyzed reaction can proceed, that is a reaction product, for example, a dipeptide can be formed. The appropriate temperature conditions may be between 0 and 60° C., or 20 and 40° C., or between 25 and 37° C., or between 28 and 35° C.

The concentrations of the carboxy component and amine component serving as starting materials can be 1 mM to 10 M, and preferably 50 mM to 2 M, respectively; however, there are cases where it is preferable to add amine component in an amount equimolar or excess molar with respect to the carboxy component. In addition, in cases where high concentrations of substrates inhibit the reaction, these can be added stepwise during the reaction after they are adjusted to concentrations that do not cause inhibition.

After the dipeptide is produced and accumulated in an appropriate solvent in a required amount, solids such as cells, cell debris and denaturated proteins can be removed from a medium by centrifugation or membrane filtration, and then the target dipeptide can be recovered from the appropriate solvent by any combination of conventional techniques such as concentration, ion-exchange chromatography, high-performance liquid chromatography (HPLC), crystallization, and so forth.

Collecting and Purification of Enzyme

The L-amino acids α-ligase can be purified from the bacterium belonging to the genus *Escherichia*, for example, the species *E. coli*. A method for accumulating, collecting, and purifying the Lal from the bacterium can be an ordinary method known to the one skilled in the art.

The bacterium is grown in a culture medium as described hereinafter to produce Lal. A bacterial cell extract can be prepared from the cells by disrupting the cells using a physical method such as ultrasonic disruption or an enzymatic method using a cell wall-dissolving enzyme and removing the insoluble fraction by centrifugation and so forth. The peptide-forming enzyme can then be purified by fractionating the bacterial cell extract solution obtained in the above manner by combining ordinary protein purification methods such as anion exchange chromatography, cation exchange chromatography or gel filtration chromatography.

The examples of the carriers for use in anion exchange chromatography can be Q-Sepharose HP or DEAE (diethylaminoethyl) agarose (GE Healthcare), and so forth. The enzyme can be recovered in the non-adsorbed fraction under conditions of neutral pH such as between 7 and 8 when the cell extract containing the enzyme is allowed to pass through a column packed with the carrier. Various eluents can be used depending on the carrier. For example, when the cation exchange chromatography is performed using the MonoS HR (GE Healthcare), the cell extract containing the enzyme is allowed to pass through a column packed with the carrier. To elute the enzyme, the column can be washed with a buffer solution having a high salt concentration. At that time, the salt concentration may be sequentially increased or a concentration gradient may be applied. As a saline solution, NaCl of about 0 to about 0.5 M can be applied. If required, the enzyme can be purified by gel filtration chromatography. The examples of the carrier for use in gel filtration chromatography can be Superdex 200 HR or Sephadex 200 (GE Healthcare).

In the aforementioned purification procedure, the fraction containing the enzyme can be verified by assaying the Lal activity of each fraction according to the method indicated in the examples to be described later.

3.2. Fermentative Method

The method of the present invention can also be a method for producing a dipeptide, more specifically a dipeptide having an acidic L-amino acid at the N-terminus, by cultivating the bacterium of the present invention in a culture medium to allow the dipeptide to be produced, excreted, and accumulated in the culture medium, and collecting the dipeptide from the culture medium.

The cultivation of a bacterium of the invention, collection, and the purification of a dipeptide from the medium and the like may be performed in a manner similar to conventional fermentation methods, wherein a dipeptide or an amino acid is produced using a microorganism. The culture medium for a dipeptide production may be a typical medium that contains a carbon source, a nitrogen source, inorganic ions, and other organic components as required. As the carbon source, saccharides such as glucose, lactose, galactose, fructose, arabinose, maltose, xylose, trehalose, ribose, and hydrolyzates of starches; alcohols such as glycerol, mannitol, and sorbitol; organic acids such as gluconic acid, fumaric acid, citric acid, malic acid, and succinic acid; and the like can be used. As the nitrogen source, inorganic ammonium salts such as ammonium sulfate, ammonium chloride, and ammonium phosphate; organic nitrogen such as of soy bean hydrolyzates; ammonia gas; aqueous ammonia; and the like can be used. Vitamins such as vitamin B1, required substances, for example, organic nutrients such as nucleic acids such as adenine and RNA, or yeast extract, and the like may be present in appropriate, even if trace, amounts. Other than these, small amounts of calcium phosphate, magnesium sulfate, iron ions, manganese ions, and the like may be added, if necessary.

To increase the dipeptide-producing ability of a bacterium of the present invention, the culture medium can be additionally supplemented with amino acids or amino acid derivatives, cofactors, and other (bio)chemicals. For example, to increase the ability of a bacterium to produce the Asp-Phe dipeptide, the culture medium may be supplemented with additional quantities of L-Phe and L-Asp.

Cultivation can be performed under aerobic conditions for 16 to 72 hours, the culture temperature during cultivation can be controlled within 15 to 45° C., or within 28 to 37° C. The acidity (pH) can be adjusted between 5 and 8, or between 6.5 and 7.2 by using an inorganic or organic acidic or alkaline substance, as well as ammonia gas.

After cultivation, solids such as cells and cell debris can be removed from the liquid medium by centrifugation or membrane filtration, and then the target dipeptide can be recovered from the fermentation liquor by any combination of conventional techniques such as concentration, ion-exchange chromatography, high-performance liquid chromatography (HPLC), crystallization, and so forth.

EXAMPLES

The present invention is more precisely explained below with reference to the following non-limiting Examples.

Example 1

Cloning of BBR47_51900 from *Brevibacillus brevis* NBRC 100599 and Staur_4851 from *Stigmatella aurantiaca* DW4/3-1

The primary structure of the genes encoding the hypothetical proteins BBR47_51900 and Staur_4851 was optimized for expression in *E. coli* The genes encoding BBR47_51900 from *Brevibacillus brevis* NBRC 100599 and Staur_4851 from *Stigmatella aurantiaca* DW4/3-1 were synthesized by the SlonoGene™ gene synthesis service (http://www.sloning.com/) and delivered as a set of pSlo.X plasmids harboring the synthesized XbaI-EcoRI fragment which included the target genes having optimized sequences. The XbaI-EcoRI fragments harboring genes with optimized sequences encoding the BBR47_51900 and Staur_4851 proteins are shown in SEQ ID NOs: 19 and 20, respectively.

To construct the pET-HT-BBR and pET-HT-STA plasmids, the corresponding XbaI-EcoRI fragments of the pSlo.X plasmids were excised by digestion with XbaI and EcoRI and then ligated with the pET15(b+) vector (Novagen, USA) digested by the same restrictases.

Example 2

Expression and Purification of His6-Tagged BBR47_51900 and Staur_4851

Plasmids pET-HT-BBR and pET-HT-STA were introduced into BL21 (DE3) strain (Novagen, USA) by $Ca^{2+}$-dependent transformation to construct the BL21 (DE3) [pET-HT-BBR] and BL21 (DE3) [pET-HT-STA] strains. The electrotransformation was done using "Bio-Rad" electroporator (USA) (No. 165-2098, version 2-89) according to the manufacturer's instructions. Cells of the BL21 (DE3) [pET-HT-BBR] and BL21 (DE3) [pET-HT-STA] strains were each grown in LB broth (also referred to as lysogenic broth as described in Sambrook, J. and Russell, D. W. (2001) Molecular Cloning: A Laboratory Manual ($3^{rd}$ ed.). Cold Spring Harbor Laboratory Press) at 37° C. up to $OD_{540}$ ~1 and 150 rpm. Isopropyl-β-D-thio-galactoside (IPTG) was added to a final concentration of 1 mM, and the cell culture was incubated for 2 hours at 37° C. and 150 rpm. Induced cells were harvested from 1 L of cultivation broth, resuspended in 60-80 mL of HT-I-buffer (20 mM $NaH_2PO_4$, 0.5 M NaCl, 20 mM imidazole, pH 7.4, adjusted with NaOH), and disrupted under 2000 Psi (~140 bar) using French-press (Thermo Spectronic). The debris was removed by centrifugation for two times at 4° C. and 13000 rpm followed by filtration through 0.45 μm filter (CHROMAFIL Xtra CA-45/25, MACHEREY-NAGEL GmbH). A solution of crude proteins was loaded onto HiTrap Chelating column (GE Healthcare) pre-packed with immobilized metal affinity chromatography (IMAC) sorbent of 1 ml total volume and equilibrated with the HT-I-buffer. The IMAC was performed in accordance with the manufacturer's recommendations. The active fractions were collected, combined, and desalted using PD10 columns (GE Healthcare) equilibrated with SB-buffer (20 mM Tris-HCl, 120 mM NaCl, 1 mM β-mercaptoethanol, 15% glycerol, pH 7.5). The protein preparations were divided into aliquots of volume (200 μL) and stored at −70° C. The protein concentration was determined using BIO-RAD PROTEIN ASSAY (BIO-RAD, USA).

Example 3

Preliminary Analysis of Substrate Specificity of BBR47_51900 and Staur_4851

The substrate specificity of BBR47_51900 and Staur_4851 was studied in the reaction mixture containing the enzyme and canonical L-amino acids such as L-alanine, L-arginine, L-asparagine, L-aspartic acid, L-cysteine, glycine, L-glutamic acid, L-glutamine, L-histidine, L-isoleucine, L-leucine, L-lysine, L-methionine, L-phenylalanine, L-proline, L-serine, L-threonine, L-tryptophan, L-tyrosine, and L-valine, or salts thereof, of the same or two different kinds. The composition of the reaction mixture of total volume of 50 μL was as follows unless otherwise noted:

| | |
|---|---|
| BBR47_51900 or Staur_4851 | 4 μg |
| Tris-HCl, pH 8.0 | 50 mM |
| First L-amino acid | 10 mM |
| Second L-amino acid | 10 mM |
| Adenosine 5'-triphosphate (ATP) | 10 mM |
| MgSO$_4$×7H$_2$O | 10 mM |
| H$_2$O | to 50 μL |

Figure 2:
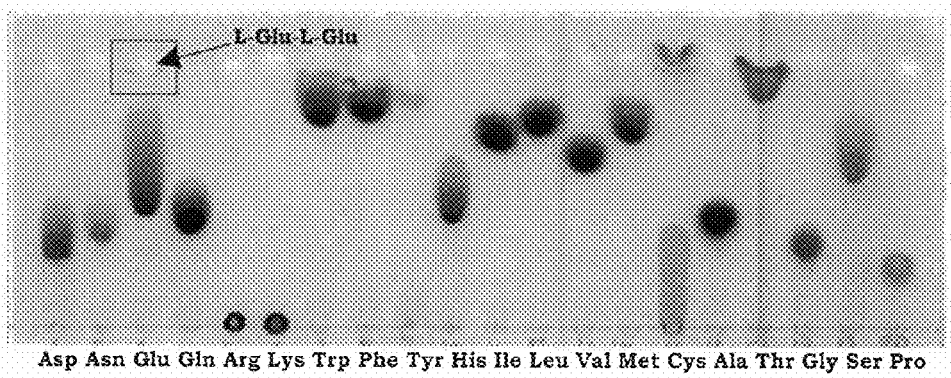
FIG. 2 shows the activity of BBR47_51900 in ligation of canonical L-amino acids of the same kind.
Figure 3:
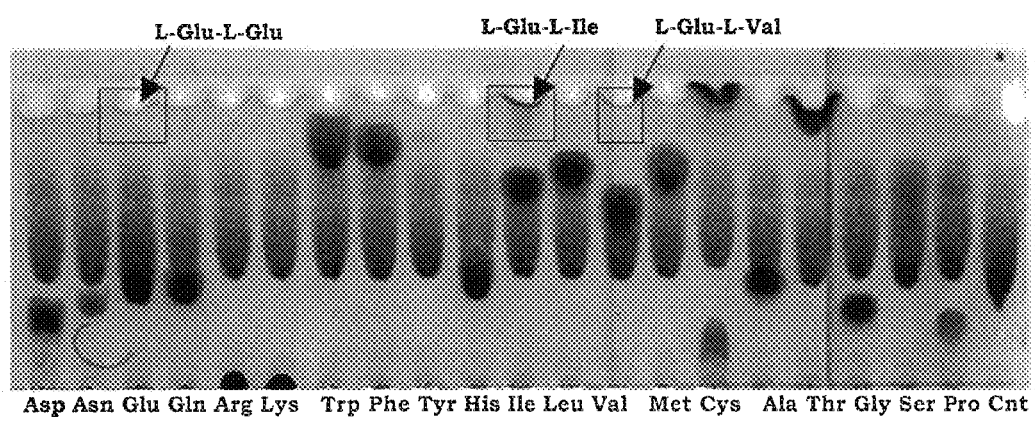
FIG. 3 shows the activity of BBR47_51900 in ligation of canonical L-amino acids of two different kinds, wherein one kind is L-Glu. Cnt: control (L-Asp).
Figure 4:
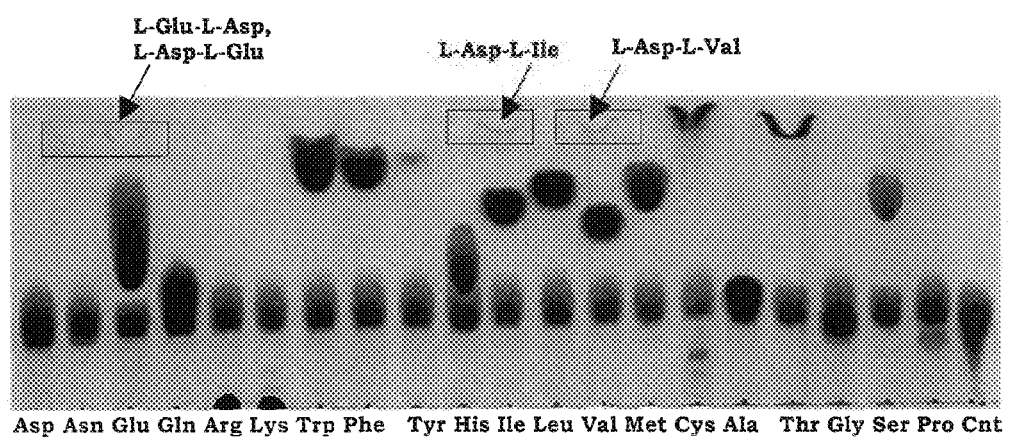
FIG. 4 shows the activity of BBR47_51900 in ligation of canonical L-amino acids of two different kinds, wherein one kind is L-Asp. Cnt: control (L-Asp).
Figure 5:
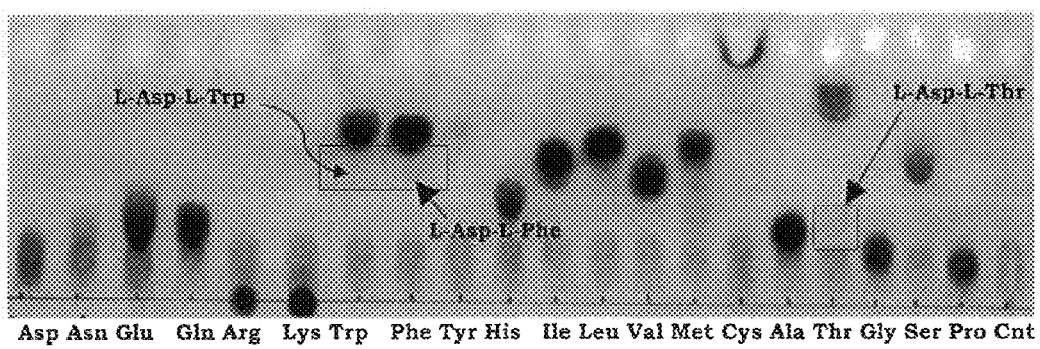
FIG. 5 shows the activity of Staur_4851 in ligation of canonical L-amino acids of two different kinds, wherein one kind is L-Asp.
Figure 6:
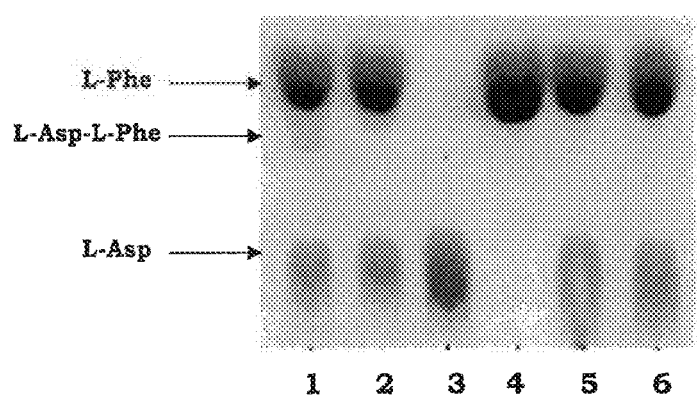
FIG. 6 shows the activity of Staur_4851 in ligation of L-Asp and L-Phe determined by TLC analysis. 1—(Tris-HCl pH 9.0 50 mM, MgCl$_2$ 10 mM, L-Asp 10 mM, L-Phe 10 mM, ATP 10 mM, Staur_4851 2 μg); 2—(Tris-HCl pH 8.0 50 mM, MgCl$_2$ 10 mM, L-Asp 10 mM, L-Phe 10 mM, ATP 10 mM, Staur_4851 2 μg); 3—(Tris-HCl pH 8.0 50 mM, MgCl$_2$ 10 mM, L-Asp 20 mM, L-Phe 0 mM, ATP 10 mM, Staur_4851 2 μg); 4—(Tris-HCl pH 8.0 50 mM, MgCl$_2$ 10 mM, L-Asp 0 mM, L-Phe 20 mM, ATP 10 mM, Staur_4851 2 μg); 5—(Tris-HCl pH 8.0 50 mM, MgCl$_2$ 10 mM, L-Asp 10 mM, L-Phe 10 mM, ATP 0 mM, Staur_4851 2 μg); 6—(Tris-HCl pH 8.0 50 mM, MgCl$_2$ 10 mM, L-Asp 10 mM, L-Phe 10 mM, ATP 10 mM, Staur_4851 0 μg).

Reactions were carried out at 32° C. for 15 hours. 1-2 μL of reaction mixture was subjected to thin layer chromatography (TLC) analysis using as mobile phase the mixture of 2-propanol:acetone:250 mM ammonia:H$_2$O as 100:100:12:28. A solution (0.3%, w/v) of ninhydrin in acetone was used as a visualizing reagent. Detection was performed at 540 nm. The new spots on TLC-plates were detected after developing the reaction mixtures, which contained:

1) BBR47_51900 and L-Glu/L-Glu, or L-Glu/L-Asp, or L-Glu/L-Val, or L-Glu/L-Ile, or L-Asp/L-Ile, or L-Asp/L-Val (FIGS. 2-4);

2) Staur_4851 and L-Asp/L-Phe, or L-Asp/L-Trp, or L-Asp/L-Thr) (FIGS. 5 and 6).

The obtained results indicate that BBR47_51900 and Staur_4851 can catalyze ligation of an acidic L-amino acid such as L-Glu and L-Asp with other L-amino acids.

Example 4

Determination by HPLC Analysis of Dipeptides Synthesized by BBR47_51900 and Staur_4851

Dipeptides synthesized by BBR47_51900 and Staur_4851 were determined using HPLC analysis of reaction mixtures of total volume of 400 μL, which contained:

| | |
|---|---|
| BBR47_51900 or Staur_4851 | 160 μg |
| Tris-HCl, pH 9.0 | 50 mM |
| L-Asp or L-Glu | 10 mM |
| L-Phe or L-PheOMe, L-Val, L-Trp | 10 mM |
| Adenosine 5'-triphosphate (ATP) | 10 mM |
| MgSO$_4$×7H$_2$O | 10 mM, | where Me denote methyl group.

Reactions were carried out at 32° C. for 15 hours. Then 0.5 mL of reaction mixture was filtered through the Amicon Ultra-0.5 mL, 3K Centrifugal Filters (Millipore, #UFC500396) and subjected to HPLC analysis.

The conditions were as follows:
Equipment: HITACHI L-2000 series.
Column: Inertsil ODS-3 4.6×250 mm, 5 mm (GL Sciences Inc.).
Temperature: 40° C.
Buffers:
A (for mixture L-Asp/L-Val and L-Glu/L-Val): 0.1 M KH$_2$PO$_4$ (pH 2.2)+5 mM octanesulfonate, sodium salt: CH$_3$CN as 4:1 (v/v),
B (for mixture L-Asp/L-Phe): 0.1 M KH$_2$PO$_4$ (pH 2.2)+5 mM octanesulfonate, sodium salt: CH$_3$CN as 7:3 (v/v),
C (for mixture L-Asp/L-PheOMe, L-Asp/L-Trp, and L-Val/L-Val): 0.1 M KH$_2$PO$_4$ (pH 2.2)+5 mM octanesulfonate, sodium salt:CH$_3$CN as 3:2 (v/v),
D (for mixture L-Phe/L-Phe): 0.1 M KH$_2$PO$_4$ (pH 2.2)+5 mM octanesulfonate, sodium salt: CH$_3$CN as 1:1 (v/v).
Gradient profile: isocratic.
Flow rate: 1.5 mL/min.
Injection volume: 10 μL.
Detection: UV 210 nm.

Chemicals used for HPLC analysis were as follows:
L-Asp (L-Aspartic acid, sodium salt): Nacalai Tesque, Inc. #03504-75
L-Phe (L-Phenylalanine): Nacalai Tesque, Inc. #26901-35
L-Val (L-Valine): Ajinomoto Co., Inc. #317LG13
L-Trp (L-Tryptophan): Ajinomoto Co., Inc. #0000002205
L-PheOMe (L-Phenylalanine methyl ester hydrochloride): Tokyo Chemical Industry Co., Ltd. #P1278
ATP: Oriental yeast Co., Ltd. #45142000
MgSO$_4$×7H$_2$O: Junsei Chemical Co., Ltd. #83580-0301
αAsp-Phe (H-Asp-Phe-OH): Bachem G-1620
βAsp-Phe (H-Asp(Phe-OH)—OH): Bachem G-4750
αAsp-Asp (H-Asp-Asp-OH): Bachem G-1565
Phe-Asp (H-Phe-Asp-OH): Bachem G-2870
Phe-Phe (H-Phe-Phe-OH): Bachem G-2925
αAsp-Val (H-Asp-Val-OH): Bachem G-1635
Val-Asp (H-Val-Asp-OH): Bachem G-3510
Val-Val (H-Val-Val-OH): Bachem G-3595
αGlu-Val (H-Glu-Val-OH): Bachem G-2010
γGlu-Val (H-Glu(Val-OH)—OH): Bachem G-2015
Val-Glu (H-Val-Glu-OH): Bachem G-3520
αGlu-Glu (H-Glu-Glu-OH): Bachem G-1915
αAspartame (H-Asp-Phe-OMe): Bachem G-1545
βAspartame: (H-Asp(Phe-OMe)-OH): Bachem G-3725
Asp-Trp (H-Asp-Trp-OH): Bachem G-3705

Solution of αGlu-Val, γGlu-Val, αAsp-Val (10 mM each) and αAsp-Phe, βAsp-Phe (5 mM each) were prepared for HPLC analysis. The concentration of a dipeptide formed was determined using corresponding calibration curves. Each solution with standard sample was diluted to 50-folds or 100-folds for LC-QTOF/MS/MS analysis (Example 5).

The results of HPLC analysis of reaction mixtures are shown in Table 1. As it can be seen from the Table 1, BBR47_51900 and Staur_4851 catalyze formation of dipeptide having an acidic L-amino acid such as L-Asp and L-Glu at the N-terminus.

Example 5

Determination by LC-QTOF/MS/MS Analysis of Dipeptides Synthesized by BBR47_51900

Samples of reaction mixtures and standard solutions obtained as described in Example 4 were subjected to LC-QTOF/MS/MS analysis.
The conditions were as follows:
Equipment: LC (Agilent1200SL), MS (Micromass Q-TOF Premier)
LC Conditions:
Column: Develosil C30 2.0×250 mm, 3 μm (Nomura Chemical).
Temperature: 20° C.
Buffers:
A: H$_2$O (0.025% Formic acid),
B: CH$_3$CN (0.025% Formic acid).
Gradient Profile:

| Time (min) | B (%) |
|---|---|
| 0 | 0 |
| 20 | 22.5 |
| 20.1 | 100 |
| 25 | 100 |

Flow rate: 0.3 mL/min.
Injection volume: 2-5 μL.
MS Conditions:
Capillary voltage: 3.0 kV.

Cone voltage: 20 V.
Collision voltage: 4 V (MS/MS 12 V).
Source temperature: 80° C.
Desolvation temperature: 120° C.
Cone gas flow rate: 50 L/hr.
Desolvation gas flow rate: 700 L/hr.

Figure 7:
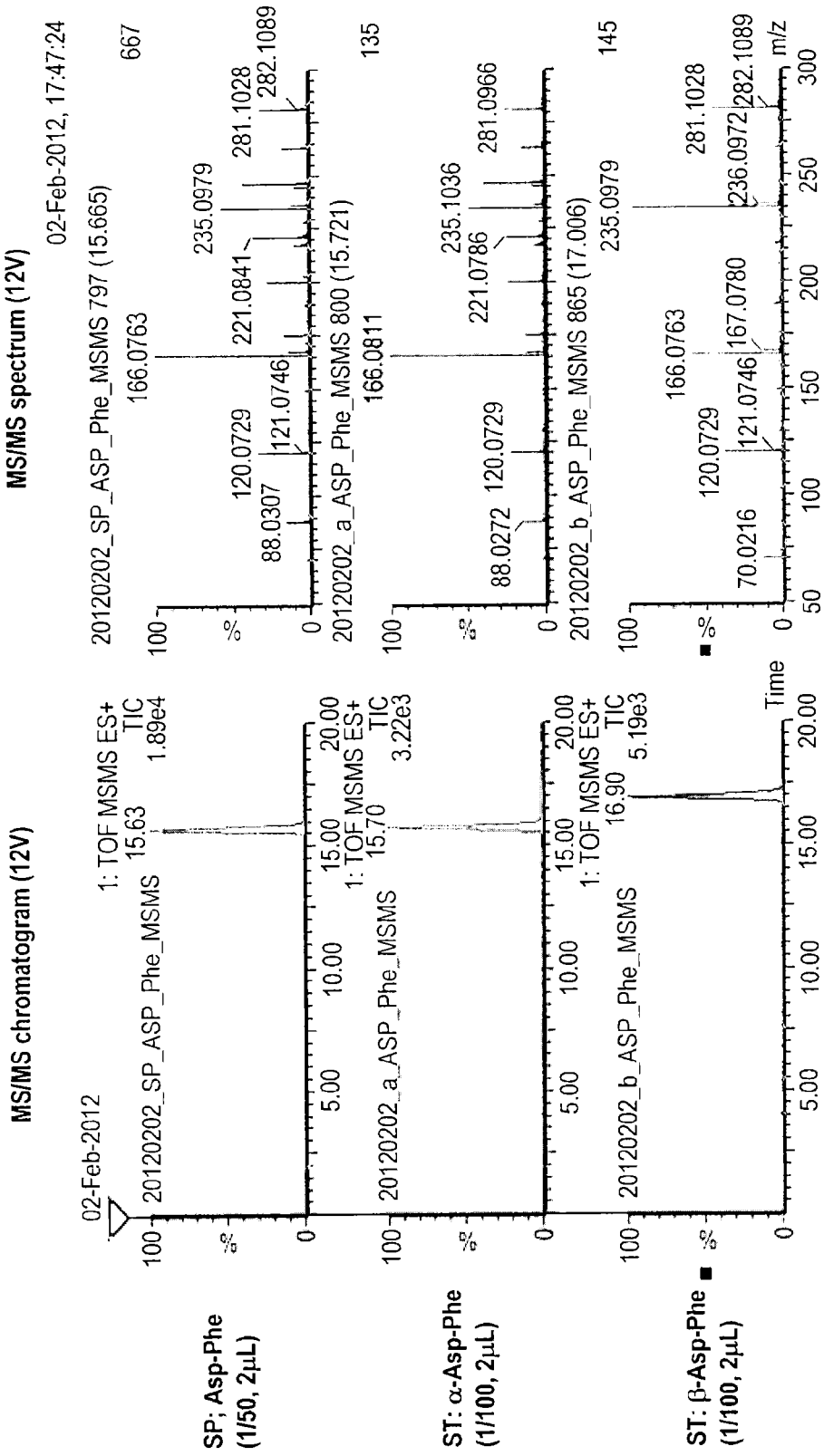
FIG. 7 shows the activity of BBR47_51900 in ligation of L-Asp and L-Phe determined by LC-QTOF/MS/MS analysis. SP: sample; ST: standard (αAsp-Phe and βAsp-Phe).
Figure 8:
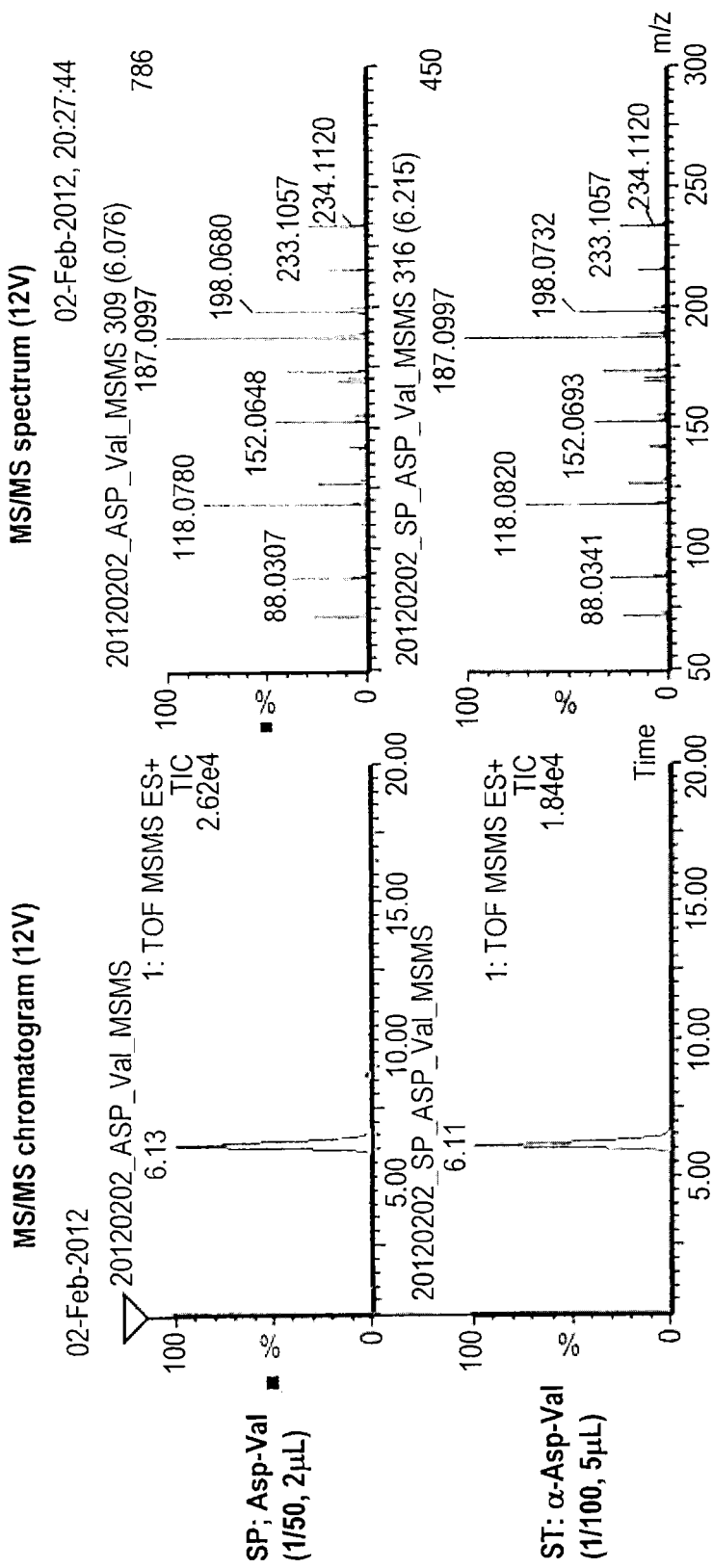
FIG. 8 shows the activity of BBR47_51900 in ligation of L-Asp and L-Val determined by LC-QTOF/MS/MS analysis. SP: sample; ST: standard (αAsp-Val).
Figure 9:
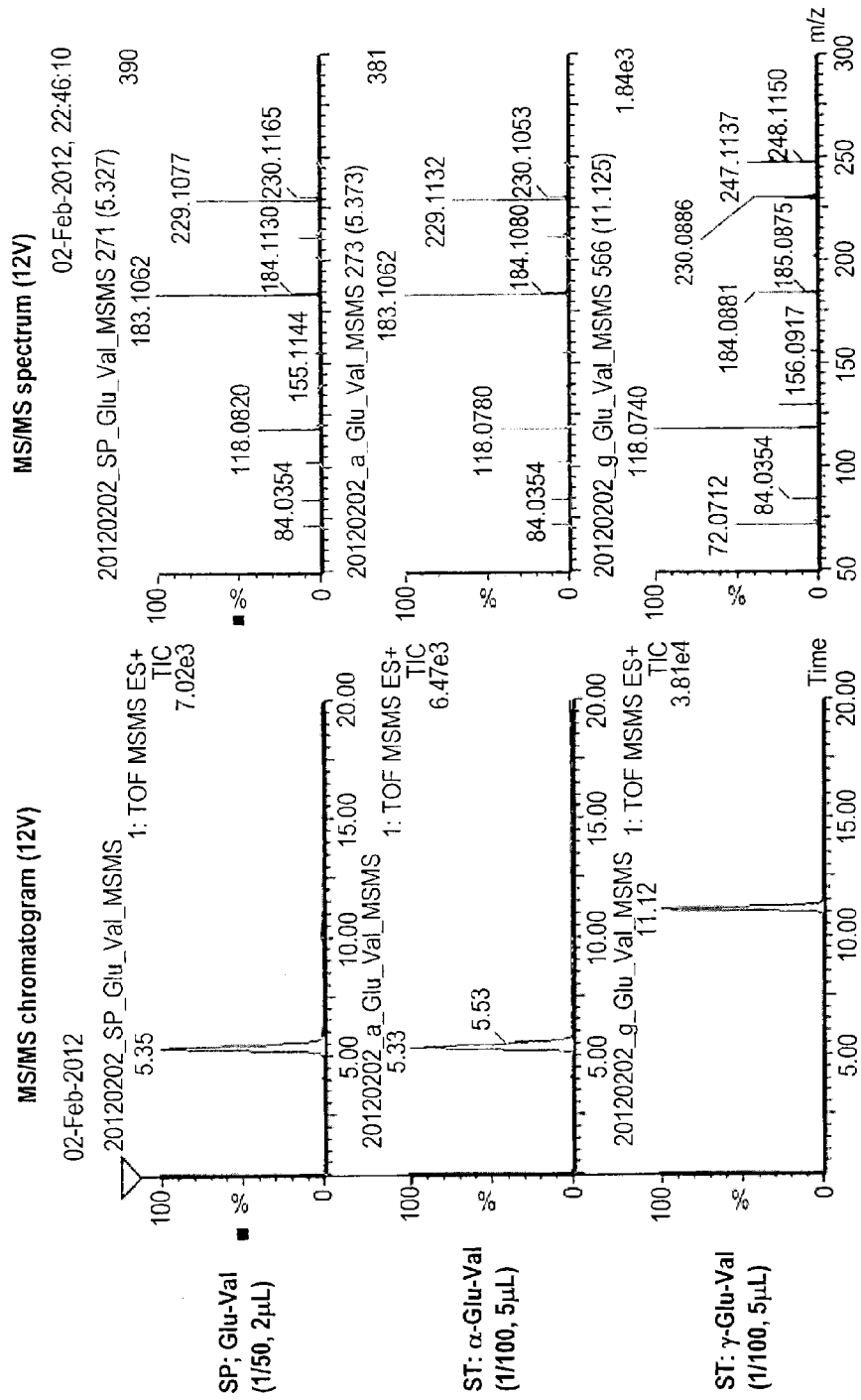
FIG. 9 shows the activity of BBR47_51900 in ligation of L-Glu and L-Val determined by LC-QTOF/MS/MS analysis. SP: sample; ST: standard (αGlu-Val and γGlu-Val).

The results of LC-QTOF/MS/MS analysis of reaction mixtures are shown in FIGS. 7-9. As it can be seen from the FIGS. 7-9, BBR47_51900 catalyze formation of αAsp-Phe, αAsp-Val, and αGlu-Val dipeptides.

Example 6

Searching for Enzymes which are Isofunctional to BBR47_51900 and Staur_4851

The HMMER method was used for searching in the sequence databases for homologues of protein sequences, and for making protein sequence alignments. The method uses a probabilistic model referred to as the profile hidden Markov model (profile HMM) (Finn R. D. et al., HMMER web server: interactive sequence similarity searching, *Nucleic Acids Res.*, 2011, 39(Web Server issue):W29-37).

Compared to BLAST, FASTA, and other sequence alignment and database search tools based on older scoring methodology, HMMER aims to be significantly more accurate and more reliable to detect remote homologues such as isofunctional proteins because of the strength of its underlying mathematical models. In the past, this strength came at significant computational expense, but in the new HMMER3 project, HMMER has become essentially as fast as BLAST (Finn R. D. et al., HMMER web server: interactive sequence similarity searching, *Nucleic Acids Res.*, 2011, 39(Web Server issue):W29-37).

Figure 12:
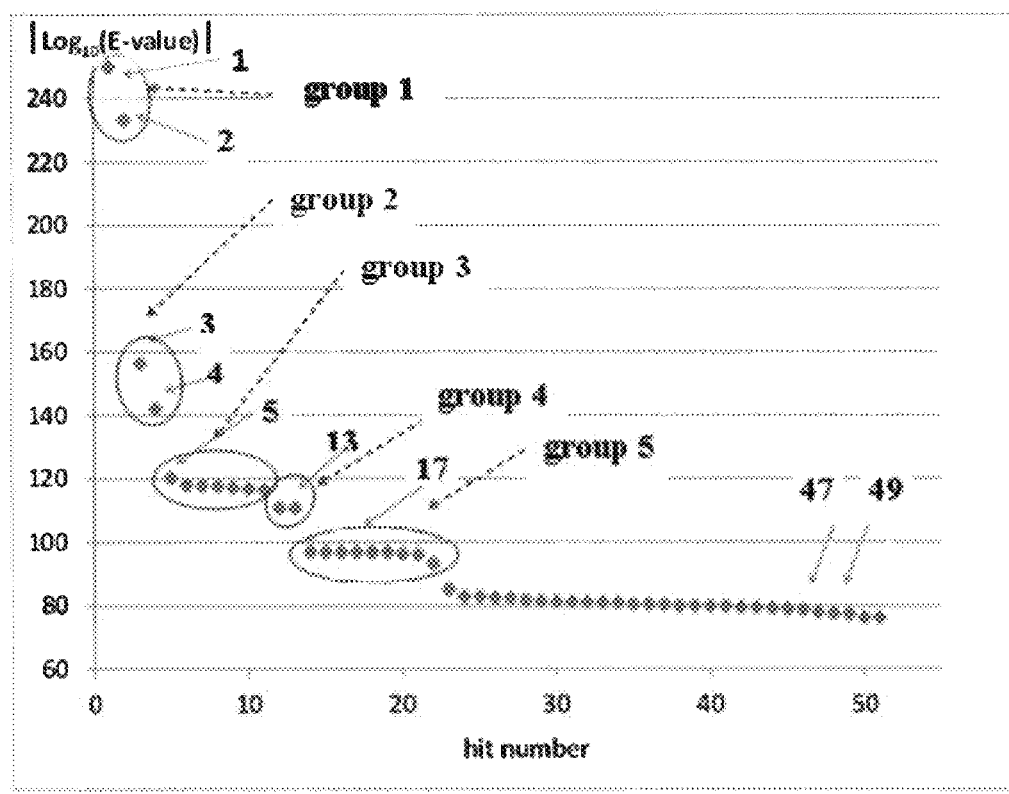
FIG. 12 shows the distribution diagram of |Log 10(E-value)|-values obtained by the HMMsearch program using the alignment of BBR47_51900 and Staur_4851 (see FIG. 10). The following hits are marked with solid arrows: 1—BBR47_51900, 2—Staur_4851, 3—DES, 4—BCE, 5—BMY, 13—BTH, 17—BUR, 47—AME, 49—SFL.

To search enzymes which are isofunctional to BBR47_51900 and Staur_4851, the alignment of BBR47_51900 and Staur_4851 (FIG. 10) was subjected to the HMMsearch program from HMMER3 suite that allows searching for one or more profiles against a protein sequence database (http(colon)//hmmer(dot)janelia(dot)org/). Based on the sequences alignment for BBR47_51900 and Staur_4851, the profile HMM had been originated (Model 1), which was used for homologues search. The list of the nearest isofunctional proteins found (hits) is shown on FIG. 11). Analysis of the distribution diagram of |Log(E-value)|-values revealed five groups of proteins sharing the |Log(E-value)|-values between the members of a group lower than that values between groups (FIG. 12). The first group comprises BBR47_51900 and Staur_4851, the second group comprises DES and BCE, the third group comprises BMY, the fourth group comprises BTH, and the fifth group comprises BUR. The rest proteins are a number of ungrouped homologues having stochastic |Log(E-value)|-values. The AME and SFL proteins were selected from such ungrouped homologues as the negative control.

Figure 15:
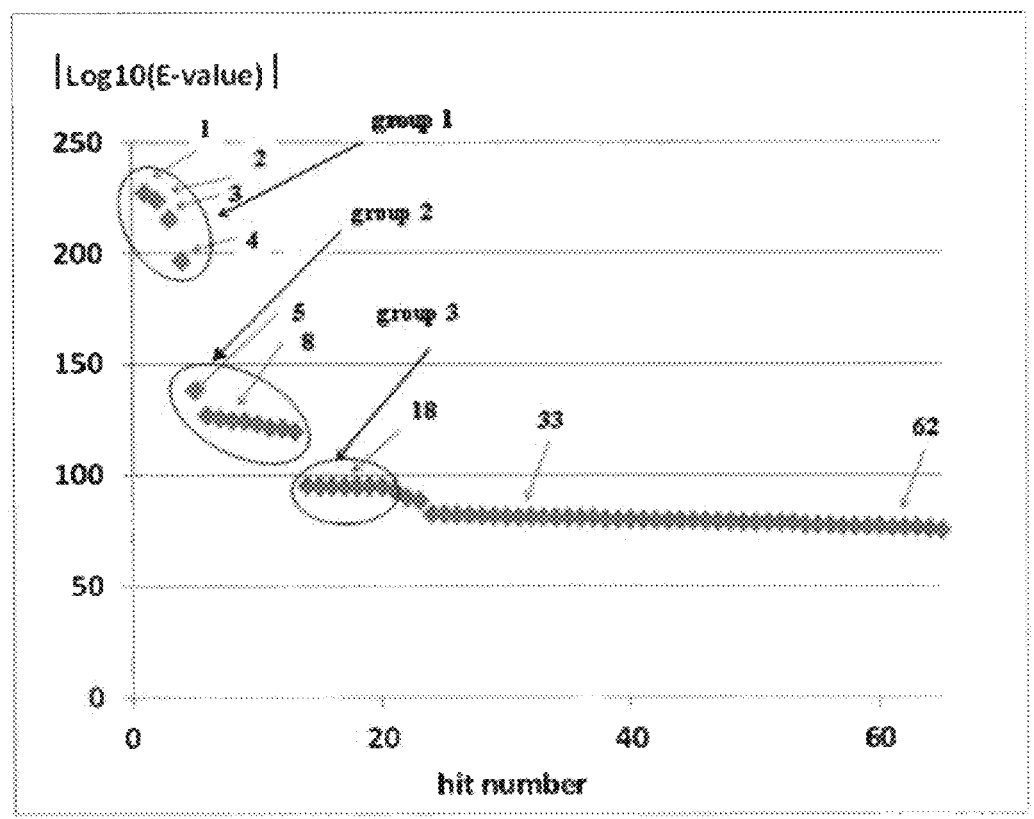
FIG. 15 shows the distribution diagram of |Log 10(E-value)|-values obtained by the HMMsearch program using the alignment of BBR47_51900, Staur_4851, DES and BCE (see FIG. 13). The following hits are marked with solid arrows: 1—BBR47_51900, 2—DES, 3—BCE, 4—Staur_4851, 5—BMY, 8—BTH, 18—BUR, 33—AME, 62—SFL.

Given the proteins from the first (BBR47_51900, Staur_4851) and second (DES and BCE) groups are isofunctional, the new profile HMM (Model 2) based on alignment of BBR47_51900, Staur_4851, DES and BCE (FIG. 13) can be originated, which can be used for the isofunctional proteins search using the HMMsearch program as described above. Thus, a new list of isofunctional proteins can be originated (FIG. 14), which is described by a distribution diagram of |Log 10(E-value)|-values, which is different from the initial diagram (FIG. 15). The new list of isofunctional proteins can comprise three groups such as the first group comprising BBR47_51900, Staur_4851, DES and BCE; the second group comprising BMY and BTH; and the third group comprising BUR, wherein AME is closer to the first group (the position change from No. 47 (FIG. 12) to No. 33 (FIG. 15)) and SFL is more distant from the first group (the position change from No. 49 (FIG. 12) to No. 62 (FIG. 15)).

Given the proteins from the first (BBR47_51900, Staur_4851, DES and BCE) and second (such as BMY) groups are isofunctional, the new profile HMM (Model 3) based on alignment of BBR4751900, Staur_4851, DES, BCE and BMY (FIG. 16) can be originated, which can be used for the isofunctional proteins search using the HMMsearch program as described above. Thus, a new list of isofunctional proteins can be originated (FIG. 17). The new list of isofunctional proteins can comprise three groups such as the first group comprising BBR47_51900, Staur_4851, DES, BCE and BMY; the second group comprising BTH; the third group comprising BUR, wherein AME is at the position No. 37 and SFL is at the position No. 65 (FIG. 17).

Given the proteins from the first (BBR47_51900, Staur_4851, DES, BCE and BMY) and second (BTH) groups are isofunctional, the new profile HMM (Model 4) based on alignment of BBR47_51900, Staur_4851, DES, BCE, BMY and BTH (FIG. 18) can be originated, which can be used for the isofunctional proteins search using the HMMsearch program as described above. Thus, a new list of isofunctional proteins can be originated (FIG. 19). The new list of isofunctional proteins can comprise three groups such as the first group comprising BBR47_51900, Staur_4851, DES, BCE, BMY and BTH; the second group comprising BUR; the third group comprising AME, wherein SFL is at the position No. 73 (FIG. 19).

Given the proteins from the first (BBR47_51900, Staur_4851, DES, BCE, BMY and BTH) and second (BUR) groups are isofunctional, the new profile HMM (Model 5) based on alignment of BBR47_51900, Staur_4851, DES, BCE, BMY, BTH and BUR (FIG. 20) can be originated, which can be used for the isofunctional proteins search using the HMMsearch program as described above. Thus, a new list of isofunctional proteins can be originated (FIG. 21). The new list of isofunctional proteins can comprise three groups such as the first group comprising BUR; the second group comprising BBR47_51900, Staur_4851, DES, BCE, BMY and BTH; the third group comprising AME, wherein SFL is at the position No. 104 (FIG. 21).

Given the proteins from the first (BUR), second (BBR47_51900, Staur_4851, DES, BCE, BMY and BTH) and third (AME) groups are isofunctional, the new profile HMM (Model 6) based on alignment of BBR47_51900, Staur_4851, DES, BCE, BMY, BTH, BUR and AME (FIG. 22) can be originated, which can be used for the isofunctional proteins search using the HMMsearch program as described above. Thus, a new list of isofunctional proteins can be originated (FIG. 23). The new list of isofunctional proteins can comprise two groups such as the first group comprising BUR; the second group comprising BBR47_51900, Staur_4851, DES, BCE, BMY, BTH and AME, wherein SFL is at the position No. 65 (FIG. 23).

Given the proteins from the first (BUR) and second (BBR47_51900, Staur_4851, DES, BCE, BMY, BTH and AME) groups, and the SFL protein are isofunctional, the new profile HMM (Model 7) based on alignment of BBR47_51900, Staur_4851, DES, BCE, BMY, BTH, BUR, AME and SFL (FIG. 24) can be originated, which can be used for the isofunctional proteins search using the HMMsearch program as described above. Thus, a new list of isofunctional proteins can be originated (FIG. 25). The new list of isofunctional proteins can comprise three groups such as the first group comprising BUR; the second group comprising BBR47_ 51900, Staur_4851, DES, BCE, BMY, BTH and AME; and the third group comprising SFL is at the position No. 38 (FIG. 25).

In the similar manner new lists of isofunctional L-amino acids α-ligases, capable of synthesizing a dipeptide having an acidic L-amino acid such as L-Asp or L-Glu at the N-terminus and any other L-amino acid or a derivative thereof at the C-terminus, can be originated. If the BBR47_51900 and Staur_4851 proteins are used to originate the profile HMM (Model 1), the |Log 10(E-value)|≥233 can be used for the new isofunctional Lals search; if the BBR47_51900, Staur_4851, DES and BCE proteins are used to originate the HMM profile (Model 2), the |Log 10(E-value)|≥196 can be used for the new isofunctional Lals search; if the BBR47_51900, Staur_4851, DES, BCE and BMY proteins are used to originate the HMM profile (Model 3), the |Log 10(E-value)|≥182 can be used for the new isofunctional Lals search; if the BBR47_51900, Staur_4851, DES, BCE, BMY and BTH proteins are used to originate the HMM profile (Model 4), the |Log 10(E-value)|≥175 can be used for the new isofunctional Lals search; if the BBR47_51900, Staur_4851, DES, BCE, BMY, BTH and BUR proteins are used to originate the HMM profile (Model 5), the |Log 10(E-value)|≥162 can be used for the new isofunctional Lals search; if the BBR47_51900, Staur_4851, DES, BCE, BMY, BTH, BUR and AME proteins are used to originate the HMM profile (Model 6), the |Log 10(E-value)|≥142 can be used for the new isofunctional Lals search; and if the BBR47_51900, Staur_4851, DES, BCE, BMY, BTH, BUR, AME and SFL proteins are used to originate the HMM profile (Model 7), the |Log 10(E-value)|≥128 can be used for the new isofunctional Lals search (FIG. 26), wherein the E-value is a parameter of the HMMsearch program (Finn R. D. et al., HMMER web server: interactive sequence similarity searching, *Nucleic Acids Res.*, 2011, 39(Web Server issue):W29-37).

Example 7

Cloning, Expression, and Purification of the DES, BUR, BCE, BTH, AME, SFL and BMY Enzymes The primary structure of the genes encoding the DES, BUR, BCE, BTH, AME, SFL and BMY proteins was optimized for expression in *E. coli* using "Back translation" function of Gene Designer program (Villalobos A. et al., Gene Designer: a synthetic biology tool for constructing artificial DNA segments, *BMC Bioinformatics*, 2006, 7:285). All constructs were synthesized by the SlonoGene™ gene synthesis service (http(colon)//www(dot)sloning(dot)com/) and delivered as a set of pSlo.X plasmids harboring the synthesized XbaI-EcoRI fragment, which included the target genes having optimized sequences. The XbaI-EcoRI fragments harboring genes with optimized sequences encoding the DES, BUR, BCE, BTH, AME, SFL and BMY proteins are shown in SEQ ID NOs: 21, 22, 23, 24, 25, 26 and 27, respectively.

The DES, BUR, BCE, BTH, AME, SFL and BMY proteins can be expressed in *E. coli*, purified, and their activities can be investigated as described for BBR47_51900 and Staur_4851 in Examples 1-5.

Example 8

Construction of the *E. coli* Peptidase-Deficient 1-6Δ Strains 8.1. Construction of the *E. coli* Peptidase-Deficient 1-5Δ Strains.

The iadA gene was deleted in the *E. coli* BW25113 strain (KEIO collection, strain No. ME9062) having the ΔpepB mutation (KEIO collection, strain No. JW2507; The *E. coli* Genetic Stock Center, Yale University, New Haven, USA, the accession No. CGSC9995) (*E. coli* 1Δstrain). For this purpose, the DNA fragment bearing the λattL-cat-λattR cassette was PCR (polymerase chain reaction) amplified using the primers P1 (SEQ ID NO: 28) and P2 (SEQ ID NO: 29), and the pMW118-λattR-cat-λattL plasmid as the template (Kataskhina Zh. I. et al., *Mol. Biol. (Mosk.)*, 2005, 39(5):823-831). The resulting DNA fragment was introduced into the *E. coli* BW25113(ΔpepB)/pKD46 strain by electrotransformation using "Bio-Rad" electroporator (USA) (No. 165-2098, version 2-89) according to the manufacturer's instructions. The recombinant plasmid pKD46 (Datsenko K. A. and Wanner B. L., *Proc. Natl. Acad. Sci. USA*, 2000, 97:6640-6645) with the temperature-sensitive replicon was used as the donor of the phage λ-derived genes responsible for the λRed-mediated recombination system. The pKD46 plasmid can be integrated into *E. coli* BW25113 (ΔpepB) by the described method (Datsenko K. A. and Wanner B. L., *Proc. Natl. Acad. Sci. USA*, 2000, 97:6640-6645) to obtain the *E. coli* BW25113(ΔpepB)/pKD46 strain. Alternatively, the *E. coli* BW25113(ΔpepB) strain containing the recombinant plasmid pKD46 can be obtained from the *E. coli* Genetic Stock Center, Yale University, New Haven, USA, the accession number is CGSC7739.

The *E. coli* BW25113 (ΔpepB, iadA::λattR-cat-λattL) transformant is resistant to chloramphenicol (Cm) encoded by the cat gene and harbors in chromosome the "excisable" chloramphenicol-resistance marker ($Cm^R$-marker) instead of iadA. The $Cm^R$-marker was excised as described in (Kataskhina Zh. I. et al., *Mol. Biol. (Mosk.)*, 2005, 39(5):823-831) to construct the *E. coli* BW25113 (ΔpepB, iadA::λattB) strain (*E. coli* 2Δ strain).

The pepE gene was deleted in the *E. coli* BW25113 (ΔpepB, iadA::λattB) strain. A DNA fragment bearing the λattL-cat-λattR cassette was PCR amplified using the primers P3 (SEQ ID NO: 30) and P4 (SEQ ID NO: 31), and the pMW118-λattR-cat-λattL plasmid as the template. The resulting DNA fragment was introduced into the *E. coli* BW25113(ΔpepB, iadA::λattB)/pKD46 strain by electrotransformation as described above. The $Cm^R$-marker was excised from the *E. coli* BW25113(ΔpepB, iadA::λattB, pepE::λattR-cat-λattL) transformant to construct the *E. coli* BW25113(ΔpepB, iadA::λattB, pepE::λattB) strain (*E. coli* 3Δ strain).

The ybiK gene was deleted in the *E. coli* BW25113 (ΔpepB, iadA::λattB, pepE::λattB) strain. A DNA fragment bearing the λattL-cat-λattR cassette was PCR amplified using the primers P5 (SEQ ID NO: 32) and P6 (SEQ ID NO: 33), and the pMW118-λattR-cat-λattL plasmid as the template. The resulting DNA fragment was introduced into the *E. coli* BW25113(ΔpepB, iadA::λattB, pepE::λattB)/pKD46 strain by electrotransformation as described above. The $Cm^R$-marker was excised from the *E. coli* BW25113(ΔpepB, iadA::λattB, pepE::λattB, ybiK::λattR-cat-λattL) transformant to construct the *E. coli* BW25113(ΔpepB, iadA::λattB, pepE::λattB, ybiK::λattB) strain (*E. coli* 4Δ strain).

The dapE gene was deleted in the *E. coli* BW25113 (ΔpepB, iadA::λattB, pepE::λattB, ybiK::λattB) strain. A DNA fragment bearing the λattL-cat-λattR cassette was PCR amplified using the primers P7 (SEQ ID NO: 34) and P8 (SEQ ID NO: 35), and the pMW118-λattR-cat-λattL plasmid as the template. The resulting DNA fragment was introduced into the *E. coli* BW25113(ΔpepB, iadA::λattB, pepE::λattB, ybiK::λattB)/pKD46 strain by electrotransformation as described above. The $Cm^R$-marker was excised from the *E. coli* BW25113(ΔpepB, iadA::λattB, pepE::λattB, ybiK::λattB, dapE::λattR-cat-λattL) transformant to construct the *E. coli* BW25113(ΔpepB, iadA::λattB, pepE::λattB, ybiK::λattB, dapE::λattB) strain (*E. coli* 5Δ strain).

Thus the *E. coli* strains having one to five deleted the peptidases encoding genes (the *E. coli* 1-5Δ strains) were constructed.

8.2. Analysis of the Specific Aspartic Peptide-Hydrolyzing Activity in the *E. coli* 5Δ Strain.

To analyze the specific aspartic peptide-hydrolyzing activity, the artificial dipeptide DP3 (L-Asp-L-5-Fluorotryptophan) was synthesized (the Branch of the Institute for Bioorganic Chemistry (BIBCh) of the Russian Academy of Sciences, Pushchino, Russian Federation). The peptide hydrolyzing activity was investigated in vitro and in vivo.

For in vitro studies, cells of *E. coli* BW25113 and *E. coli* 5Δ strain were grown on LB and M9-salts+Glucose (0.2%, w/v) media (Sambrook, J. and Russell, D. W. (2001) Molecular Cloning: A Laboratory Manual (3$^{rd}$ ed.). Cold Spring Harbor Laboratory Press) at 37° C. to cells density of $OD_{595nm}$~1. Grown cells were harvested by centrifugation (4° C., 10000 rpm), re-suspended in buffer E (50 mM Tris-HCl pH 8.0, 20 mM NaCl), disrupted by sonication followed by centrifugation (14000 g, 4° C., 20 min) to remove cell debris. The crude protein concentration can be determined using the Bradford protein assay (Bradford M. M., *Anal. Biochem.*, 1976, 72:248-254) using bovine serum albumin as a standard. The obtained crude proteins preparations were used to investigate DP3-hydrolyzing activity.

The reaction mixture contained:
50 mM Tris-HCl pH 8.0,
20 mM NaCl,
5 mM DP3 dipeptide,
1 mM $ZnSO_4$ or $MnCl_2$,
24 μg of crude proteins preparation,
$H_2O$ to a total volume of 10 μL.

Figure 27:
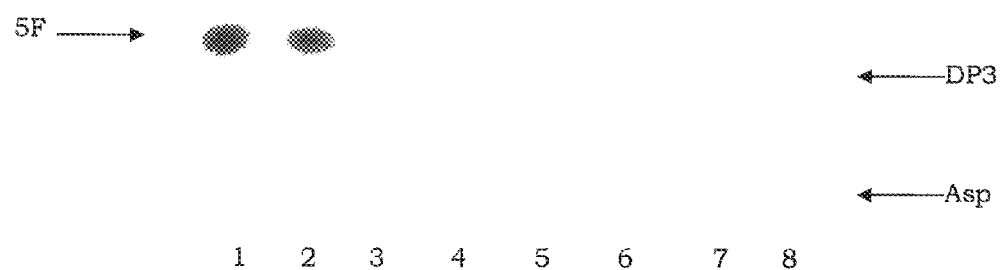
FIG. 27 shows the TLC-analysis of the specific aspartic peptide-hydrolyzing (DP3-hydrolyzing) activity in the $E.$ $coli$ 4-5Δ strains. A solution (1 μL) of the 5-fluorotryptophan (standard) was used for calibration: (1) 3 mM, (2) 2 mM, (3) 1 mM, and (4) 0.5 mM. An aliquot (1 μL) of reaction mixture containing $Mn^{2+}$ (5, 6) or $Zn^{2+}$ (7, 8) was loaded onto TLC-plate. Abbreviations: 5FT—5-fluorotryptophan, DP3—L-Asp-L-5-fluorotryptophane dipeptide, Asp—L-Aspartate.

Reaction mixtures were incubated at 37° C. for different time. The DP3-hydrolyzing activity was measured by quantitative TLC analysis of the 5-fluorotryptophan released (FIG. 27, Table 4). As a mobile phase, the mixture of 2-propanol:acetone:$H_2O$ as 25:25:4 was used. A solution (0.3%, w/v) of ninhydrin in acetone was used as a visualizing reagent. The obtained results indicate that aspartic peptide-hydrolyzing activity can be determined in 5Δ strain suggesting that there are unknown peptidases having DP3-hydrolyzing activity in the *E. coli* 5Δ strain.

Figure 28:
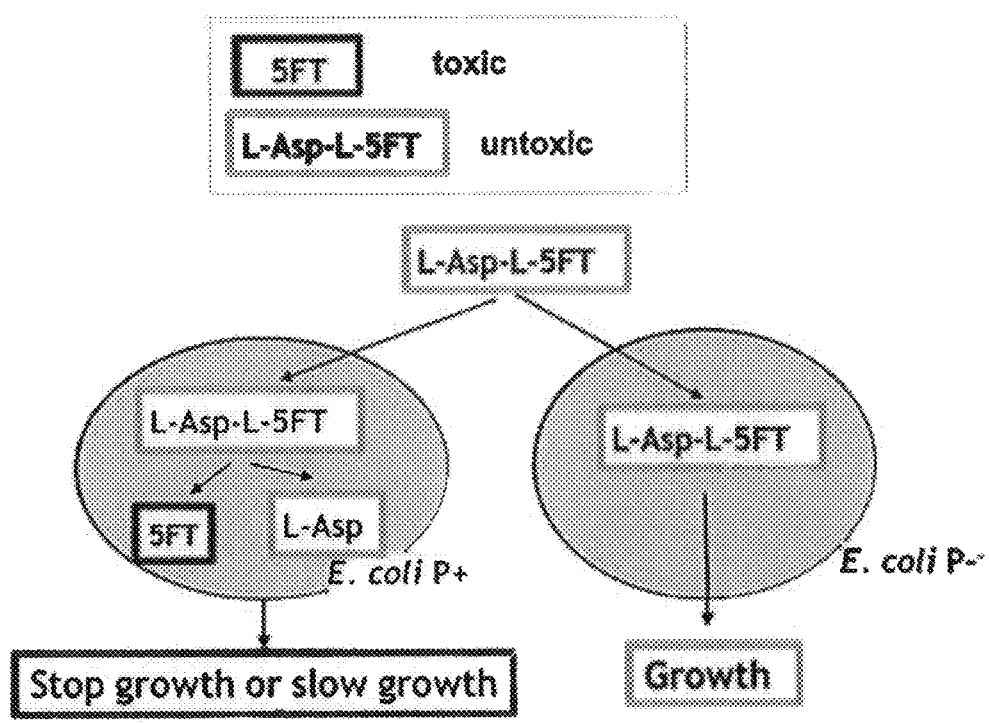
FIG. 28 shows the scheme for investigation of the DP3 toxicity due to the specific aspartic peptide-hydrolyzing activity in the $E.$ $coli$ 1-5Δ strains. The $E.$ $coli$ strain is grown in the presence of DP3 dipeptide. Being accepted by the peptidase plus strain ($E.$ $coli$ $P^+$), DP3 is hydrolyzed resulting in formation of L-aspartate and 5-fluorotryptophane (5FT). The 5FT is toxic for cell thus resulting in growth arrest. The DP3 dipeptide is stable and does not affect cell growth in a peptidase-deficient strain or in the strain with low peptidase activity ($E.$ $coli$ $P^-$)

For in vivo studies, toxicity of DP3 dipeptide for constructed peptidase-deficient *E. coli* 5Δ strain was investigated (FIG. 28). Cells of *E. coli* BW25113 and *E. coli* 5Δ strains were grown on M9-salts medium supplemented with D-glucose or glycerol (0.4%, w/v) to cells density of $OD_{555nm}$~2. The cells biomass was diluted and about 106 cells were plated onto M9-salts agar supplemented with D-glucose or glycerol (0.4%, w/v), and DP3 dipeptide. Plates were incubated at 37° C. for 48 hours (for D-glucose) or 72 hours (for glycerol) (Table 5). Visual analysis showed that deletion of five known aspartic peptide-hydrolyzing enzymes encoded by the pepB, iadA, pepE, ybiK and dapE genes decreases DP3 toxicity for *E. coli* 5Δ strain (from 6 μM for BW25113 to 30 μM for 5Δ strain grown on M9-salts+D-glucose medium). Increasing DP3 concentration up to 50 μM resulted in growth arrest of the *E. coli* 5Δ strain suggesting the residual intracellular DP3 peptidase activity.

8.3. Identification of Residual Peptidases in the *E. coli* 5Δ Strain Having Specific Aspartic Peptide-Hydrolyzing Activity.

To identify the residual intracellular peptidases having specific aspartic peptide-hydrolyzing activity, the following procedure was used. Cells of the *E. coli* 5Δ strain were grown at 37° C. overnight in 4 L of M9-salts media supplemented with D-glucose (0.4%, w/v). Grown cells were harvested by centrifugation (4° C., 10000 rpm) and re-suspended in 100 mL of buffer F (20 mM Tris-HCl pH 7.5, 20 mM NaCl).

Purification protocol was as follows:

Step 1. Cells were disrupted by 2 passages through French-press (Thermo Spectronic) followed by centrifugation (14000 g, 4° C., 20 min) to remove cell debris. The obtained crude proteins preparation was loaded onto DEAE FF 16/10 column (20 mL) (GE Healthcare) equilibrated with buffer F (20 mM Tris-HCl pH 7.5, 20 mM NaCl). The elution was carried out at flow rate of 1 mL/min by applying the liner gradient of NaCl (from 20 to 600 mM in 20 column volumes) in buffer F. Fractions (10 mL each) were collected and analyzed as described in Example 8.2. Active fractions 16-21 were found.

Step 2. Proteins from collected fractions 16-21 were precipitated by saturated (60%) $(NH_4)_2SO_4$, re-suspended in 2 mL of buffer F and loaded onto standard Superdex 200 HR 10/30A column (GE Healthcare) equilibrated with buffer G (20 mM Tris-HCl pH 7). Isocratic elution was carried out at flow rate of 0.5 mL/min by applying buffer G. 0.5 ml Fractions (0.5 mL each) were collected and analyzed as described in Example 8.2. Active fractions (12-13) were found.

Step 3. Proteins from collected fractions 12-13 (Step 2) were loaded onto Sourse15Q column (1.6 mL) (GE Healthcare) equilibrated with buffer G (20 mM Tris-HCl pH 7). The elution was carried out at flow rate of 0.5 mL/min by applying the liner gradient of NaCl (from 0 to 400 mM in 20 column volumes) in buffer G. Fractions (0.5 mL each) were collected and analyzed as described in Example 8.2. Active fractions (15-17) were found. Purification data are summarized in Table 6.

Step 4. To identify the peptidases having specific aspartic peptide-hydrolyzing activity the proteins from several fractions (15-17) were subjected to SDS-PAGE (Laemmli U. K., Cleavage of structural proteins during the assembly of the head of bacteriophage T4, *Nature*, 1970, 227:680-685). The profile of activity elution was compared with that of proteins elution. Only one protein was found, for which activity and elution profiles were identical.

The purified protein was extracted from SDS-gel and digested with trypsin (Govorun V. M. et al., *Biochemistry (Mosc.)*, 2003, 68(1):42-49). The digestion mixture was mass-analyzed using MALDI-TOF as described in (Govorun V. M. et al., *Biochemistry (Mosc.)*, 2003, 68(1):42-49). The resulted mass-spectrum of the isolated protein matched with that obtained for aminopeptidase A/I (PepA) of *E. coli*. Thus the sixth peptidase was found in *E. coli* 5Δ strain.

8.4. Construction of the *E. coli* Peptidase-Deficient Strain.

The pepA gene was deleted in the *E. coli* BW25113 (ΔpepB, iadA::λattB, pepE::λattB, ybiK::λattB, dapE::λattB) strain as described in Example 8.1. A DNA fragment bearing the λattL-cat-λattR cassette was PCR amplified using the primers P9 (SEQ ID NO: 36) and P10 (SEQ ID NO: 37), and the pMW118-λattR-cat-λattL plasmid as the template. The resulting DNA fragment was introduced into the *E. coli* BW25113(ΔpepB, iadA::λattB, pepE::λattB, ybiK::λattB, dapE::λattB)/pKD46 strain by electrotransformation as described above to construct the *E. coli* BW25113 (ΔpepB, iadA::λattB, pepE::λattB, ybiK::λattB, dapE::λattB, pepA::λattL-cat-λattR) strain (*E. coli* 6Δ strain).

8.5. Analysis of the Specific Aspartic Peptide-Hydrolyzing Activity in the *E. coli* 6Δ Strain.

The specific aspartic peptide-hydrolyzing activity was analyzed in vitro as described in Example 8.2. The obtained results (Table 4) indicate that aspartic peptide-hydrolyzing activity can be determined in 6Δ strain, which is lower as compared with 4-5Δ strains.

Example 9

Fermentative Production of Dipeptides Having an Acidic L-Amino Acid Such as L-Asp or L-Glu at the N-Terminus Using the Modified E. coli 5Δ and 6Δ Strains Having Lal Activity The dipeptides having an acidic L-amino acid such as L-Asp or L-Glu at the N-terminus is produced using a bacterium of the family Enterobacteriaceae, more specifically a bacterium belonging to the genus *Escherichia* such as E. coli having dipeptide-producing ability, in a medium supplemented with or devoid of, for example, but not limited to required amino acids. A dipeptide-producing bacterium is the E. coli 5Δ or 6Δ strain as described above deficient of peptidase activity, further modified to have L-amino acid α-ligase activity. The dipeptide-producing strain is further The gene(s) encoding Lal(s) selected from the group consisting of BBR47_51900, Staur_4851, DES, BUR, BCE, BTH, AME, SFL and BMY is(are) introduced into chromosome of the E. coli or introduced into the bacterial cell on a plasmid having the gene encoding the Lal. The gene(s) encoding Lal(s) is(are) placed under a promoter.

The modified E. coli 5Δ or 6Δ harboring gene(s) encoding Lal(s) and the control 5Δ or 6Δ strains are each cultivated at 28-37° C. for 18-72 hours in Luria-Bertani broth (also referred to as lysogenic broth as described in Sambrook, J. and Russell, D. W. (2001) Molecular Cloning: A Laboratory Manual ($3^{rd}$ ed.). Cold Spring Harbor Laboratory Press). The E. coli 5Δ or 6Δ strain harboring gene(s) encoding Lal(s) is inoculated into 2 mL of a fermentation medium in 20×200 mm test-tubes and cultivated at 28-37° C. for 18-72 hours on a rotary shaker at 250 rpm.

The composition of the fermentation medium is (g/L):

| | |
|---|---|
| Glucose | 5-40 |
| NaCl | 0.8 |
| $(NH_4)_2SO_4$ | 22 |
| $K_2HPO_4$ | 2.0 |

-continued

| | |
|---|---|
| $MgSO_4×7H_2O$ | 0.8 |
| $MnSO_4×5H_2O$ | 0.02 |
| $FeSO_4×7H_2O$ | 0.02 |
| Thiamine hydrochloride | 0.002 |
| Yeast extract | 1.0-2.0 |
| $CaCO_3$ | 30 |
| L-Phe | 0-100 (mM) |
| L-Asp | 0-100 (mM) |

The fermentation medium is sterilized at 116° C. for 30 min, except that glucose and $CaCO_3$ are sterilized separately and as follows: glucose at 110° C. for 30 min, $CaCO_3$ at 116° C. for 30 min. The pH is adjusted to 5-8 by KOH solution.

After cultivation, accumulated dipeptide is measured using thin-layer chromatography (TLC). TLC plates (10×20 cm) are coated with 0.11 mm layers of Sorbfil silica gel containing non-fluorescent indicator (Sorbpolymer, Krasnodar, Russian Federation). The TLC plates are developed with a mobile phase consisting of 2-propanol:acetone:250 mM ammonia:$H_2O$ as 100:100:12:28. A solution (0.3%, w/v) of ninhydrin in acetone is used as a visualizing reagent. Detection is performed at 540 nm.

Auxiliary Example 1

The multiple alignments of the BBR47_51900 and Staur_4851 proteins with known L-amino acid α-ligases (Lals) are shown in Table 2 (identity) and Table 3 (similarity). As it can be seen from the Tables 2 and 3, the BBR47_51900 and Staur_4851 proteins have the identity value of not higher than 25% (Table 2) and the similarity value of not higher than 43% (Table 3) with known Lals.

Auxiliary Example 2

The pair-wise alignment data for the BBR47_51900, Staur_4851, DES, BUR, BCE, BTH, AME, SFL and BMY proteins are shown in Table 7 (identity) and Table 8 (similarity). As it can be seen from the Tables 7 and 8, the BBR47_51900, Staur_4851, DES, BUR, BCE, BTH, AME, SFL and BMY proteins have the identity value of not higher than 25% (Table 7) and the similarity value of not higher than 44% (Table 8).

TABLE 1

Dipeptides synthesized by BBR47_51900 and Staur_4851.

| | Dipeptides (mM) | | | | |
|---|---|---|---|---|---|
| Enzyme | Asp-Phe | Asp-PheOMe | Asp-Trp | Asp-Val | Glu-Val |
| BBR47_51900 | 1.22 | 0.03 | 0.13 | 3.9 | 1.48 |
| Staur_4851 | 2.54 | 0.02 | 1.48 | 4.4 | 0.40 |

TABLE 2

Multiple alignment (identity, in %) of BBR47_51900 and Staur_4851 with known Lals.

| | Lals with known substrate specificity | | | | | | | | | | | | | | | | | | |
|---|---|---|---|---|---|---|---|---|---|---|---|---|---|---|---|---|---|---|---|
| Enzyme | 1 | 2 | 3 | 4 | 5 | 6 | 7 | 8 | 9 | 10 | 11 | 12 | 13 | 14 | 15 | 16 | 17 | 18 | 19 |
| BBR47_51900 | 100 | 38 | 23 | 25 | 20 | 17 | 19 | 15 | 12 | 13 | 15 | 15 | 15 | 16 | 12 | 13 | 18 | 10 | 13 |
| Staur_4851 | 38 | 100 | 25 | 23 | 17 | 16 | 21 | 17 | 13 | 13 | 13 | 16 | 16 | 17 | 14 | 14 | 14 | 9 | 13 |

Identity can be defined as percentage of identical amino acids residues among all ungapped positions between the pairs.

Protein abbreviation:
1—BBR47_51900 (NCBI Reference Sequence: YP_002774671.1);
2—Staur_4851 (NCBI Reference Sequence: AD072629.1);
3—TDE2209 (NCBI Reference Sequence: NP 972809.1);
4—BL00235 (NCBI Reference Sequence: YP_081312.1);
5—plu1218 (NCBI Reference Sequence: NP 928530.1);
6—YwfE (UniProtKB/Swiss-Prot: P39641.1);
7—Rsp1486 (NCBI Reference Sequence: NP 523045.1);
8—NP_900476 (NCBI Reference Sequence: NP 900476.1);
9—Aple02000835 (NCBI Reference Sequence: ZP_00134462.2);

10—SMU1321c (NCBI Reference Sequence: NP_721690.1);
11—YP 816266 (NCBI Reference Sequence: YP 816266.1);
12—YP_001544794 (NCBI Reference Sequence: YP 001544794.1);
13—YP_077482 (NCBI Reference Sequence: YP 077482.1);
14—BAH56723 (GenBank: BAH56723.1);
15—NP 358563 (NCBI Reference Sequence: NP 358563.1);
16—YP_910063 (NCBI Reference Sequence: YP_910063.1);
17—BAG72134 (GenBank: BAG72134.1);
18—plu1440 (NCBI Reference Sequence: NP 928738.1);
19—AAZ37741 (GenBank: AAZ37741.1).

Abbreviations:

WT—BW25113;

4Δ—BW25113(ΔpepB, iadA::λattB, pepE::λattB, ybiK::λattB);

5Δ—BW25113(ΔpepB, iadA::λattB, pepE::λattB, ybiK::λattB, dapE::λattB;

6Δ—BW25113(ΔpepB, iadA::λattB, pepE::λattB, ybiK::λattB, dapE::λattB, pepA::λattL-cat-λattR).

TABLE 3

Multiple alignment (similarity, in %) of BBR47_51900 and Staur_4851 with known Lals.

| | Lals with known substrate specificity | | | | | | | | | | | | | | | | | | |
|---|---|---|---|---|---|---|---|---|---|---|---|---|---|---|---|---|---|---|---|
| Enzyme | 1 | 2 | 3 | 4 | 5 | 6 | 7 | 8 | 9 | 10 | 11 | 12 | 13 | 14 | 15 | 16 | 17 | 18 | 19 |
| BBR47_51900 | 100 | 57 | 42 | 43 | 37 | 33 | 39 | 33 | 30 | 30 | 31 | 32 | 34 | 36 | 34 | 32 | 37 | 26 | 29 |
| Staur_4851 | 57 | 100 | 43 | 42 | 36 | 32 | 38 | 31 | 32 | 32 | 30 | 32 | 33 | 35 | 29 | 34 | 34 | 20 | 30 |

Similarity can be defined as percentage of identical plus similar amino acid residues Protein Abbreviation:
1—BBR47_51900 (NCBI Reference Sequence: YP_002774671.1);
2—Staur_4851 (NCBI Reference Sequence: AD072629.1);
3—TDE2209 (NCBI Reference Sequence: NP_972809.1);
4—BL00235 (NCBI Reference Sequence: YP_081312.1);
5—plu1218 (NCBI Reference Sequence: NP_928530.1);
6—YwfE (UniProtKB/Swiss-Prot: P39641.1);
7—Rsp1486 (NCBI Reference Sequence: NP_523045.1);
8—NP 900476 (NCBI Reference Sequence: NP_900476.1);
9—Ap1e02000835 (NCBI Reference Sequence: ZP_00134462.2);
10—SMU1321c (NCBI Reference Sequence: NP_721690.1);
11—YP 816266 (NCBI Reference Sequence: YP_816266.1);
12—YP_001544794 (NCBI Reference Sequence: YP_001544794.1);
13—YP 077482 (NCBI Reference Sequence: YP_077482.1);
14—BAH56723 (GenBank: BAH56723.1);
15—NP 358563 (NCBI Reference Sequence: NP_358563.1);
16—YP 910063 (NCBI Reference Sequence: YP_910063.1);
17—BAG72134 (GenBank: BAG72134.1);
18—plu1440 (NCBI Reference Sequence: NP_928738.1);
19—AAZ37741 (GenBank: AAZ37741.1)

TABLE 4

The specific aspartic peptide-hydrolyzing activity (A, in nmoles/mg min) in the E. coli 4-6Δ strains.

| | Strain | | | |
|---|---|---|---|---|
| Cofactors | WT | 4Δ | 5Δ | 6Δ |
| — | 110.48 | 6.98 | 7.41 | 6.07 |
| $Zn^{2+}$ | 123.03 | 6.38 | 5.63 | 4.69 |
| $Mn^{2+}$ | 282.34 | 13.26 | 14.14 | 6.86 |

Standard Deviation: <5%.

TABLE 5

Investigation of the DP3 toxicity due to the specific aspartic peptide-hydrolyzing activity in the E. coli 5Δ strain.

| DP3 | | Cultivation medium | |
|---|---|---|---|
| conc. (mM) | strains | M9-salt/Glucose (0.4%, W/V) | M9-salt/Glycerol (0.4%, W/V) |
| 0 | WT | ++ | ++ |
| | 5Δ | ++ | ++ |
| 2 | WT | ++ | ++ |
| | 5Δ | ++ | ++ |
| 4 | WT | + | + |
| | 5Δ | ++ | ++ |
| 6 | WT | +− | +− |
| | 5Δ | ++ | ++ |
| 10 | WT | − | − |
| | 5Δ | ++ | + |
| 15 | WT | − | − |
| | 5Δ | ++ | + |
| 20 | WT | − | − |
| | 5Δ | ++ | +− |
| 30 | WT | − | − |
| | 5Δ | +− | − |
| 50 | WT | − | − |
| | 5Δ | − | − |

++: the level of growth is equal to that of the wild-type strain observed at 0 mM DP3
+: the level of growth is lower compared to that of the wild-type strain observed at 0 mM DP3
+−: the level of growth could be observed but is very low compared to that of the wild-type strain observed at 0 mM DP3
−: growth could not be observed

TABLE 6

Purification of peptidases having specific aspartic peptide-hydrolyzing (DP3-hydrolyzing) activity.

| Fraction | V (mL) | Conc. (mg/mL) | Protein (mg) | Activity (nmoles/ mg min) | Total activity (nmoles/ min) |
|---|---|---|---|---|---|
| Lysate | 30.0 | 4.550 | 136.5 | 14.7 | 2006.6 |
| Unbound | 30.0 | 1.080 | 32.4 | 1.4 | 45.4 |
| DEAE (16-21) | 60.0 | 1.100 | 66.0 | 22.4 | 1477.8 |
| Superdex (12-13) | 2.0 | 0.520 | 1.04 | 69.8 | 72.5 |

TABLE 6-continued

Purification of peptidases having specific aspartic peptide-hydrolyzing (DP3-hydrolyzing) activity.

| Fraction | V (mL) | Conc. (mg/mL) | Protein (mg) | Activity (nmoles/ mg min) | Total activity (nmoles/ min) |
|---|---|---|---|---|---|
| Source 15Q (15) | 0.5 | 0.050 | 0.025 | 116.6 | 2.9 |
| Source 15Q (16) | 0.5 | 0.050 | 0.025 | 382.8 | 9.6 |
| Source 15Q (17) | 0.5 | 0.050 | 0.025 | 155.7 | 3.9 |

TABLE 7

Pair-wise alignment (identity, in %) of Lals.

| Enzyme | AME | SFL | BBR | BCE | DES | BMY | BTH | BUR | STA |
|---|---|---|---|---|---|---|---|---|---|
| AME | 100 | 36 | 29 | 29 | 25 | 27 | 31 | 25 | 29 |
| SFL |  | 100 | 32 | 30 | 30 | 28 | 26 | 28 | 36 |
| BBR |  |  | 100 | 55 | 57 | 46 | 40 | 35 | 36 |
| BCE |  |  |  | 100 | 61 | 47 | 38 | 30 | 33 |
| DES |  |  |  |  | 100 | 47 | 40 | 32 | 36 |
| BMY |  |  |  |  |  | 100 | 41 | 30 | 34 |
| BTH |  |  |  |  |  |  | 100 | 30 | 32 |
| BUR |  |  |  |  |  |  |  | 100 | 38 |
| STA |  |  |  |  |  |  |  |  | 100 |

Identity can be defined as percentage of identical amino acids residues among all ungapped positions between the pairs. BBR means BBR47_51900, and STA means Staur_4851.

TABLE 8

Pair-wise alignment (similarity, in %) of Lals.

| Enzyme | AME | SFL | BBR | BCE | DES | BMY | BTH | BUR | STA |
|---|---|---|---|---|---|---|---|---|---|
| AME | 100 | 58 | 51 | 52 | 51 | 50 | 51 | 45 | 50 |
| SFL |  | 100 | 47 | 48 | 49 | 46 | 45 | 44 | 50 |
| BBR |  |  | 100 | 74 | 76 | 65 | 64 | 54 | 55 |
| BCE |  |  |  | 100 | 79 | 65 | 64 | 49 | 54 |
| DES |  |  |  |  | 100 | 67 | 66 | 53 | 56 |
| BMY |  |  |  |  |  | 100 | 61 | 48 | 53 |
| BTH |  |  |  |  |  |  | 100 | 50 | 51 |
| BUR |  |  |  |  |  |  |  | 100 | 55 |
| STA |  |  |  |  |  |  |  |  | 100 |

Similarity can be defined as percentage of identical plus similar amino acid residues among all ungapped positions between the pairs. BBR means BBR47_51900, and STA means Staur_4851.

Example 10

Enzymatic Production of Asp-Phe with BBR47_51900 and Staur_4851 Using ATP Regeneration System The product yield of Asp-Phe was studied in the reaction mixture of BBR47_51900 and Staur_4851 containing phosphoenolpyruvate and pyruvate kinase for regeneration of ATP in order to prevent highly concentrated ATP from inhibiting the enzyme reaction. The composition of the reaction mixture of total volume of 1 ml was as follows.

| | |
|---|---|
| BBR47_51900 or Staur_4851 | 0.15 U |
| Tris-HCl pH 9.0 | 50 mM |
| L-AspNa | 100 mM |
| L-Phe | 100 mM |
| ATP | 10 mM |
| Phosphoenolpyruvate | 100 mM |
| MgSO$_4$×7H$_2$O | 10 mM |
| Pyruvate kinase | 25 U |

H$_2$O to a total volume of 1 mL

Reactions were carried out at 37° C. for 1-48 hours. 100 µL out of the 1 mL reaction mixture was sampled at each reaction time. Each reaction mixture, into which 10 µL of 1 M EDTA (pH9.0) was added to stop the reaction, was subjected to HPLC analysis. The condition was as described in Example 4. As a result, BBR47_51900 and Staur_4851 could produce Asp-Phe in the ATP regeneration system (Table 9).

TABLE 9

| | Asp-Phe (mM) | | | | | |
|---|---|---|---|---|---|---|
| | 1 hr | 2 hr | 4 hr | 8 hr | 24 hr | 48 hr |
| BBR47_51900 | 7 | 13 | 24 | 40 | 68 | 74 |
| Staur_5841 | 10 | 20 | 33 | 49 | 56 | 56 |

Example 11

Analysis of the Specific Asp-Phe Hydrolyzing Activity in the E. coli 7Δ Strain 11.1. Construction of the E. coli Asp-Phe Hydrolysing Peptidase-Deficient 7Δ Strains The pepD gene was deleted in the E. coli JM109 strain. A DNA fragment bearing the ΔattL-cat-ΔattR cassette was PCR amplified using the primers P11 (SEQ ID NO:38) and P12 (SEQ ID NO:39), and the pMW118-ΔattL-cat-ΔattR plasmid as the template. The resulting DNA fragment was introduced into the E. coli JM109/pKD46 strain as described above. The Cm$^R$-marker was excised from the E. coli JM109 (pepD:: ΔattR-cat-ΔattL) transformant to construct the E. coli JM109 (pepD:: ΔattB) strain.

The pepE gene was deleted in the E. coli JM109 (pepD:: ΔattB) strain. A DNA fragment bearing the ΔattL-cat-ΔattR cassette was PCR amplified using the primers P13 (SEQ ID NO: 40) and P14 (SEQ ID NO: 41), and the pMW118-ΔattL-cat-ΔattR plasmid as the template. The resulting DNA fragment was introduced into the E. coli JM109 (pepB:: ΔattB)/pKD46 strain as described above. The Cm$^R$-marker was excised from the E. coli JM109 (pepD:: ΔattB, pepE:: ΔattR-cat-ΔattL) transformant to construct the E. coli JM109 (pepD:: ΔattB, pepE:: ΔattB) strain.

The iadA gene was deleted in the E. coli JM109 (pepD:: ΔattB, pepE:: ΔattB) strain. A DNA fragment bearing the ΔattL-cat-ΔattR cassette was PCR amplified using the primers P15 (SEQ ID NO: 42) and P16 (SEQ ID NO: 43), and the pMW118-ΔattL-cat-ΔattR plasmid as the template. The resulting DNA fragment was introduced into the E. coli JM109 (pepD:: ΔattB, pepE:: ΔattB)/pKD46 strain as described above. The Cm$^R$-marker was excised from the E. coli JM109 (pepD:: ΔattB, pepE:: ΔattB, iadA:: ΔattR-cat-ΔattL) transformant to construct the E. coli JM109 (pepD:: ΔattB, pepE:: ΔattB, iadA:: ΔattB) strain.

The pepA gene was deleted in the E. coli JM109 (pepD:: ΔattB, pepE:: ΔattB, iadA:: ΔattB) strain. A DNA fragment bearing the ΔattL-cat-ΔattR cassette was PCR amplified using the primers P17 (SEQ ID NO: 44) and P18 (SEQ ID NO: 45), and the pMW118-ΔattL-cat-ΔattR plasmid as the template. The resulting DNA fragment was introduced into the E. coli JM109 (pepD:: ΔattB, pepE:: ΔattB, iadA:: ΔattB)/pKD46 strain as described above. The Cm$^R$-marker was excised from the E. coli JM109 (pepD:: ΔattB, pepE:: ΔattB, iadA:: ΔattB, pepA:: ΔattR-cat-ΔattL) transformant to construct the E. coli JM109 (pepD:: ΔattB, pepE:: ΔattB, iadA:: ΔattB, pepA:: ΔattB) strain.

The pepB gene was deleted in the E. coli JM109 (pepD:: ΔattB, pepE:: ΔattB, iadA:: ΔattB, pepA:: ΔattB) strain. A DNA fragment bearing the ΔattL-cat-ΔattR cassette was PCR amplified using the primers P19 (SEQ ID NO: 46) and P20 (SEQ ID NO: 47), and the pMW118-ΔattL-cat-ΔattR plasmid as the template. The resulting DNA fragment was introduced into the E. coli JM109 (pepD:: ΔattB, pepE:: ΔattB, iadA:: ΔattB, pepA:: ΔattB)/pKD46 strain as described above. The Cm$^R$-marker was excised from the E. coli JM109 (pepD:: ΔattB, pepE:: ΔattB, iadA:: ΔattB, pepA:: ΔattB, pepB:: ΔattR-cat-ΔattL) transformant to construct the E. coli JM109 (pepD:: ΔattB, pepE:: ΔattB, iadA:: ΔattB, pepA:: ΔattB, pepB:: ΔattB) strain.

The iaaA gene was deleted in the E. coli JM109 (pepD:: ΔattB, pepE:: ΔattB, iadA:: ΔattB, pepA:: ΔattB, pepB:: ΔattB) strain. A DNA fragment bearing the ΔattL-cat-ΔattR cassette was PCR amplified using the primers P21 (SEQ ID NO: 48) and P22 (SEQ ID NO: 49), and the pMW118-ΔattL-cat-ΔattR plasmid as the template. The resulting DNA fragment was introduced into the E. coli JM109 (pepD:: ΔattB, pepE:: ΔattB, iadA:: ΔattB, pepA:: ΔattB, pepB:: ΔattB)/pKD46 strain as described above. The Cm$^R$-marker was excised from the E. coli JM109 (pepD:: ΔattB, pepE:: ΔattB, iadA:: ΔattB, pepA:: ΔattB, pepB:: ΔattB, iaaA:: ΔattR-cat-ΔattL) transformant to construct the E. coli JM109 (pepD:: ΔattB, pepE:: ΔattB, iadA:: ΔattB, pepA:: ΔattB, pepB:: ΔattB, iaaA:: ΔattB) strain.

The dpp gene operon (dppA, dppB, dppC, dppD, dppF) was deleted in the E. coli JM109 (pepD:: ΔattB, pepE:: ΔattB, iadA:: ΔattB, pepA:: ΔattB, pepB:: ΔattB, iaaA:: ΔattB) strain. A DNA fragment bearing the ΔattL-cat-ΔattR cassette was PCR amplified using the primers P23 (SEQ ID NO: 50) and P24 (SEQ ID NO: 51), and the pMW118-ΔattL-cat-ΔattR plasmid as the template. The resulting DNA fragment was introduced into the E. coli JM109 (pepD:: ΔattB, pepE:: ΔattB, iadA:: ΔattB, pepA:: ΔattB, pepB:: ΔattB, iaaA:: ΔattB)/pKD46 strain as described above. The Cm$^R$-marker was excised from the E. coli JM109 (pepD:: ΔattB, pepE:: ΔattB, iadA:: ΔattB, pepA:: ΔattB, pepB:: ΔattB, iaaA:: ΔattB, dpp:: ΔattR-cat-ΔattL) transformant to construct the E. coli JM109 (pepD:: ΔattB, pepE:: λattB, iadA:: λattB, pepA:: λattB, pepB:: λattB, iaaA:: λattB, dpp:: λattB) strain.

11.2. Analysis of the Specific Asp-Phe Hydrolyzing Activity in the E. coli 7ΔStrain Cells of E. coli JM109 and E. coli 7Δ strain were grown on LB agar medium at 37° C. for 16 hours. Grown cells were inoculated into 20 mL of MS medium and grown at 37° C. to cells density of OD$_{610nm}$~20. And then, the authentic Asp-Phe was added into the culture (final concentration of 2 mM), further 32 hours cultivation was carried out. The resulting culture at each cultivation time was centrifuged to obtain a culture supernatant. The residual Asp-Phe in the culture supernatant was analyzed by HPLC. The results are shown in Table 10. Asp-Phe hydrolyzing activity in the culture of E. coli 7Δ strain was much lower as compared with that of E. coli JM109.

The composition of the MS medium is (g/L)

| Glucose | 20 |
| (NH$_4$)$_2$SO$_4$ | 8 |
| KH$_2$PO$_4$ | 0.5 |
| FeSO$_4$×7H$_2$O | 0.005 |
| MnSO$_4$×7H$_2$O | 0.005 |
| Yeast extract | 1 |
| L-Tyr | 0.05 |
| MgSO$_4$×7H$_2$O | 0.5 |
| CaCO$_3$ | 30 |

The fermentation medium is sterilized at 121° C. for 20 minutes, except that glucose, MgSO$_4$7H$_2$O and CaCO$_3$ are sterilized separately and as follows: glucose and MgSO$_4$7H$_2$O at 121° C. for 20 min, CaCO$_3$ at 180° C. for 2 hours. The pH is adjusted to 7 by KOH solution. As a result, the specific Asp-Phe hydrolyzing activity was lowered in the E. coli strain compared with that in the E. coli JM109(Table 10).

TABLE 10

|  | 0 hr | 2 hr | 4 hr | 6 hr | 8 hr | 24 hr | 32 hr |
| --- | --- | --- | --- | --- | --- | --- | --- |
| JM109 | 100 | 0 | 0 | 0 | 0 | 0 | 0 |
| 7Δ strain | 100 | 97 | 96 | 96 | 95 | 91 | 87 |

Example 12

Evaluation of Productivity of Asp-Phe by E. coli 7Δ Strain Overexpressing a Lal Gene The primary structure of the genes encoding BBR47_51900 and Staur_4851 was further optimized for expression in E. coli. The genes encoding BBR47_51900 from Brevibacillus brevis NBRC 100599 and Staur_4851 from Stigmatella aurantiaca DW4/3-1 were synthesized by the GenScript and delivered as a set of pUC57 plasmids (pUC57-cBBR and pUC57-cSTA). The nucleotide sequences of the prepared cBBR and cSTA are represented by SEQ ID NO: 68 and SEQ ID NO: 69, respectively.

12.1. Construction of pSF12-cBBR and pSF12-cSTA

A DNA fragment bearing BBR47_51900 was PCR amplified using the primers P25 (SEQ ID NO:52) and P26 (SEQ ID NO:53), and the pUC57-cBBR plasmid as the template. The PCR was carried out using the following step program: 98° C., 30 seconds; (98° C., 15 seconds; 58° C., 10 seconds; 72° C., 1 minute)×30 cycles; 72° C., 5 minutes with 50 μL of a reaction mixture comprising 0.04 μg of the plasmid DNA, 0.2 μmol/L each of the primers, 1.0 unit of Phusion High-Fidelity DNA Polymerase (New England Labs), 10 μL of 5× Phusion HF buffer and 0.2 mmol/L each dNTPs. The amplified DNA fragment was purified by MinElute PCR Purification Kit (Qiagen).

A DNA fragment bearing Staur_4851 was PCR amplified using the primers P27 (SEQ ID NO:54) and P28 (SEQ ID NO:55), and the pUC57-cSTA plasmid as the template. The PCR condition and purification method was as described above.

The thus obtained solutions were subjected to reaction to cleave the amplified DNA with restriction enzyme Nde I and Pst I, and then each 1.3 kb fragments was purified with MinElute Reaction Cleanup Kit (Qiagen).

pSF12-ggt vector was constructed from pUC18 vector and harbours the rpoH promoter and ggt gene encoding gamma-glutamyltranspeptidase from E. coli W3110 strain (WO02013051685A1). The pSF12-ggt vector was cleaved with Nde I and Pst I. DNA fragments were separated by agarose gel electrophoresis, and a 3.0 kb DNA fragment was recovered by QIAquick Gel Extraction Kit (Qiagen).

The 1.3 kb DNA fragment containing BBR47_51900 gene or Staur_4851 and the 3.0 kb DNA fragment obtained above were subjected to ligation reaction using TaKaRa Ligation Kit Ver.2.1 (TaKaRa) at 16° C. for 30 minutes. *E. coli* JM109 competent cell (TaKaRa) was transformed by a heat shock method using the ligation reaction mixture, spread on LB agar medium containing 100 μg/mL ampicillin, and cultured overnight at 30° C. A plasmid was extracted from a colony of the transformant that grew on the medium according to a known method, whereby pSF12-cBBR and pSF12-cSTA were obtained. The DNA sequence of the vectors was confirmed using 3130 Genetic Analyzer (Applied Biosystems).

12.2. Fermentative Production of Asp-Phe Using the Modified *E. coli* 7Δ Strains Having Lal Activity A dipeptide-producing bacterium is the *E. coli* 7Δ strain as described above deficient of peptidase and dipeptide permease activity, further modified to have L-amino acid α-ligase activity. The dipeptide-producing strains harbour the gene encoding BBR47_51900 or Staur_4851 introduced into the bacterial cell on a plasmid, pSF12-cBBR or pSF12-cSTA, respectively. Each genes encoding Lals is placed under the rpoH promoter. The modified *E. coli* 7Δ strains harboring the gene encoding Lal and the control 7Δ strain were each cultivated at 25° C. for 24 hours on LB agar medium (containing 100 μg/ml ampicillin for the modified *E. coli* 7Δ strains harboring the gene encoding Lal). The *E. coli* 7Δ strains harboring gene encoding Lal and the control 7Δ strain were inoculated into 20 mL of a MS medium supplemented with 100 mM L-Asp and 100 mM L-Phe in 500 mL Sakaguchi flask and cultivated at 25° C. for 32 hours on a reciprocal shaker at 120 rpm. The resulting culture was centrifuged to obtain a culture supernatant. Accumulated Asp-Phe in the culture supernatant was analyzed by HPLC. The results are shown in Table 11.

TABLE 11

| *E. coli* strain | Asp-Phe (mM) |
|---|---|
| 7Δ strain | 0 |
| 7Δ strain/pSF12-cBBR | 0.20 |
| 7Δ strain/pSF12-cSTA | 0.24 |

As it can be seen from Table 11, Asp-Phe was not produced by use of the 7Δ strain, whereas Asp-Phe was produced by use of 7Δ strains harbouring gene encoding Lal.

Example 13

Evaluation of Asp-Phe productivity by *E. coli* 9Δ/pMGAL1/pHSG-cLal 13.1. Construction of Both tyrR and tyrA-Deficient *E. coli* 7Δ Strain First, to derepress the synthesis of enzymes involved in the biosynthesis of aromatic amino acids, the tyrR gene was deleted in the *E. coli* JM109 (pepD:: λattB, pepE:: λattB, iadA:: λattB, pepA:: λattB, pepB:: λattB, iaaA:: λattB, dpp:: λattB) strain. A DNA fragment bearing the ΔattL-cat-ΔattR cassette was PCR amplified using the primers P29 (SEQ ID NO: 56) and P30 (SEQ ID NO: 57), and the pMW118-ΔattL-cat-ΔattR plasmid as the template. The resulting DNA fragment was introduced into the *E. coli* JM109 (pepD:: λattB, pepE:: λattB, iadA:: λattB, pepA:: λattB, pepB:: λattB, iaaA:: λattB, dpp:: λattB)/pKD46 strain as described in Example 11.1. The Ce-marker was excised from the *E. coli* JM109 (pepD:: λattB, pepE:: λattB, iadA:: ΔattB, pepA:: λattB, pepB:: λattB, iaaA:: λattB, dpp:: λattB, tyrR:: ΔattR-cat-ΔattL) transformant to construct the *E. coli* JM109 (pepD:: λattB, pepE:: λattB, iadA:: λattB, pepA:: λattB, pepB:: λattB, iaaA:: λattB, dpp:: λattB, tyrR:: λattB) strain.

Next, the tyrA gene was deleted in the *E. coli* JM109 (pepD:: λattB, pepE:: λattB, iadA:: λattB, pepA:: λattB, pepB:: λattB, iaaA:: λattB, dpp:: λattB, tyrR:: λattB) strain so that a prephenate, the common intermediate in the biosynthesis of Phe and Tyr, wouldn't be utilized for Tyr biosynthesis. A DNA fragment bearing the ΔattL-cat-ΔattR cassette was PCR amplified using the primers P31 (SEQ ID NO: 58) and P32 (SEQ ID NO: 59), and the pMW118-ΔattL-cat-ΔattR plasmid as the template. The resulting DNA fragment was introduced into the *E. coli* JM109 (pepD:: λattB, pepE:: λattB, iadA:: λattB, pepA:: λattB, pepB:: λattB, iaaA:: λattB, dpp:: λattB, tyrR:: λattB)/pKD46 strain as described above. The Cm$^R$-marker was excised from the *E. coli* JM109 (pepD:: λattB, pepE:: λattB, iadA:: λattB, pepA:: λattB, pepB:: λattB, iaaA:: λattB, dpp:: λattB, tyrR:: λattB, tyrA:: ΔattR-cat-ΔattL) transformant to construct the *E. coli* JM109 (pepD:: λattB, pepE:: λattB, iadA:: λattB, pepA:: λattB, pepB:: λattB, iaaA:: λattB, dpp:: λattB, tyrR:: λattB, tyrA:: λattB) strain.

13.2. Construction of pHSG-cBBR and pHSG-cSTA

To construct the pHSG-cBBR plasmid, the corresponding EcoRI—SphI fragment containing of the rpoH promoter and BBR47_51900 gene of the pSF12-cBBR plasmid were excised by digestion with EcoRI and SphI and then ligated with the pHSG396 vector (TaKaRa) digested by the same restrictases.

To construct the pHSG-cSTA, a DNA fragment bearing Staur_4851 under the rpoH promoter was PCR amplified using the primers P33 (SEQ ID NO:60) and P34 (SEQ ID NO:61), and the pSF12-cSTA plasmid as the template. The PCR was carried out using the following step program: 98° C., 30 seconds; (98° C., 15 seconds; 58° C., 10 seconds; 72° C., 1 minute)×30 cycles; 72° C., 5 minutes with 50 μL of a reaction mixture comprising 0.04 μg of the plasmid DNA, 0.2 μmol/L each of the primers, 1.0 unit of Phusion High-Fidelity DNA Polymerase (New England Labs), 10 μL of 5× Phusion HF buffer and 0.2 mmol/L each dNTPs. Then 1.5 kb fragment digested by BamHI and XhoI was ligated with pHSG396 vector digested by the same restrictases.

13.3. Transformation of pMGAL1 and pHSG-cLal vectors into *E. coli* 9Δ Strain pMGAL1 vector was constructed from pMW19 (Wako) and harbours three genes involved in Phe biosynthesis in *E. coli*; pheA, aroG4 and aroL encoding chorismate mutase-prephenate dehydratase (CM-PD), 3-deoxy-D-arabinoheptulosonate-7-phosphate synthetase (DAHP synthetase) and shikimate kinase (SK), respectively (JP3225597). Each of pheA and aroG4 genes was mutated from the corresponding original genes to avoid negative feedback by Phe biosynthesized.

pMGAL1 and pHSG-cLal vector was simultaneously introduced into *E. coli* 9Δ strain by electroporation method using LB agar medium containing 100 μg/mL ampicillin and 25 μg/mL chloramphenicol. Thus obtained strain was named *E. coli* 9Δ/pMGAL1/pHSG-cLal.

13.4. Fermentative Production of Asp-Phe by *E. coli* 9Δ/pMGAL1/pHSG-cLal

The modified *E. coli* 9Δ/pMGAL1/pHSG-cLal and the control 9Δ strain/pMGAL1 were each cultivated at 25° C. for 24 hours on LB agar medium (containing 100 μg/ml ampicillin and 25 μg/ml chloramphenicol for the *E. coli* 9Δ/pMGAL1/pHSG-cLal). The *E. coli* 9Δ/pMGAL1/pHSGcLal and the control 9Δ/pMGAL1 strain were inoculated into 20 mL of a MS medium supplemented with 100 mM L-Asp in 500 mL Sakaguchi flask and cultivated at 25° C. for 72 hours on a reciprocal shaker at 120 rpm. The resulting culture was centrifuged to obtain a culture supernatant. Accumulated Phe and Asp-Phe in the culture supernatant was analyzed by HPLC. The results are shown in Table 12.

TABLE 12

| E. coli strain | Phe (mM) | Asp-Phe (mM) |
|---|---|---|
| 9D/pMGAL1 | 24.4 | n.d. |
| 9D/pMGAL1/pHSG2-cBBR | 21.4 | 0.003 |
| 9D/pMGAL1/pHSG2-cSTA | 25.5 | 0.0006 |

As it can be seen from Table 12, Asp-Phe was not produced by use of the 9Δ/pMGAL1 strain, whereas Asp-Phe was produced by use of 9Δ/pMGAL1 strains harboring gene encoding Lal.

Example 14

Analysis of Substrate Specificity of DES 14.1. Construction of the pELAC-MBP-DES-HT Plasmid
14.1.1. Construction of the Ancillary Plasmid pELAC The <PlacUV5> DNA-fragment was PCR-amplified using oligoprimers P35 (SEQ ID NO:62), P36 (SEQ ID NO:63), and DNA of pUC18 plasmid (GenBank: L08752.1) as a template.

Resulting DNA fragment was digested by BglII and XbaI and cloned into pET22(b+) plasmid (Novagen, Cat. No. 69744-3) digested by the same endonucleases thus constructing the pELAC plasmid.

14.1.2. Construction of the Ancillary Plasmid pELAC-MBP-HT

The malE gene (without signal peptide sequence) was PCR-amplified using oligoprimers P37 (SEQ ID NO:64), P38 (SEQ ID NO:65), and E. coli MG1655 chromosome as a template. Obtained DNA-fragment was digested by XbaI and BamHI and cloned into pELAC-/XbaI-BamRI vector thus constructing pELAC-MBP-HT plasmid.

14.1.3. Construction of the pELAC-MBP-DES-HT Plasmid

To construct the pELAC-MBP-DES-HT plasmid, we amplified DNA fragment containing DES gene by using oligoprimers P39 (SEQ ID NO:66), P40 (SEQ ID NO:67), and DNA of pUC57-DES (described in dipeptide patent application) as a template. Obtained DNA fragment was digested with BamHI and NotI and ligated with pELAC-MBP-HT/BamHI-NotI vector thus constructing the pELAC-MBP-DES-HT plasmid.

14.2. Expression and Purification of MBP Fusion his$_6$-Tagged DES

Cells of E. coli 7Δ harboring pELAC-MBP-DES-HT was grown in LB medium containing 100 μg/mL ampicillin in a test tube at 37° C. up to $OD_{610nm}$~2. 2 mL of the resulting culture was inoculated into 100 mL of LB medium supplemented with IPTG (final concentration of 0.1 mmol/L) in a 500 ml Sakaguchi flask at 30° C., for 8 hours. Induced cells were harvested from 1.6 L of cultivation broth, re-suspended in 200-240 mL of HT-II buffer (50 mM Tris-HCL, pH 8.0, 0.3 M NaCl, 10 mM imidazole, 15% glycerol), and sonicated using sonicator (INSONATOR 201M, KUBOTA). The debris was removed by centrifugation at 4° C. and 14,000 rpm for 15 minutes followed by filtration through 0.45 mm filter (Millipore). A solution of crude proteins was loaded onto HisTALON Superflow cartridge, 5 ml (Clontech) using AKTA avant 25 (GE Healthcare) in accordance with the manufacturer's recommendations. Fractions containing MBP fused His6-tagged DES were combined, and desalted using PD-10 columns (GE Healthcare) equilibrated with SC-buffer (50 mM Tris-HCl, pH8.0, 0.3 M NaCl, 15% glycerol).

14.3. Analysis of Asp-Phe Synthesizing Activity of MBP Fused His6-Tagged DES

Dipeptides synthesized by MBP fused His$_6$-tagged DES were determined using HPLC analysis of reaction mixture of total volume of 400 μL, which contained:

| | |
|---|---|
| DES | 160 μg |
| Tris-HCl, pH 9.0 | 50 mM |
| L-Asp | 100 mM |
| L-Phe | 100 mM |
| Adenosine 5'-triphosphate (ATP) | 10 mM |
| MgSO$_4$×7H$_2$O | 10 mM, | where Me denote methyl group.

Reactions were carried out at 37° C. for 15 hours. Then the reaction mixture, into which 10 μl of 1 M EDTA, pH9.0 was added to stop the enzymatic reaction, was subjected to HPLC analysis. The conditions were as described in Example 4. As a result, DES catalyzes formation of 0.30 mM Asp-Phe.

While the invention has been described in detail with reference to preferred embodiments thereof, it will be apparent to the one skilled in the art that various changes can be made, and equivalents employed, without departing from the scope of the invention. All the cited references herein are incorporated as a part of this application by reference.

Where a numerical limit or range is stated herein, the endpoints are included. Also, all values and subranges within a numerical limit or range are specifically included as if explicitly written out.

As used herein the words "a" and "an" and the like carry the meaning of "one or more."

DESCRIPTION OF SEQUENCES

SEQ ID NO:1 shows the BBR47_51900 gene
SEQ ID NO:2 shows the BBR47_51900 protein
SEQ ID NO:3 shows the Staur_4851 gene
SEQ ID NO:4 shows the Staur_4851 protein
SEQ ID NO:5 shows the DES gene
SEQ ID NO:6 shows the DES protein
SEQ ID NO:7 shows the BUR gene
SEQ ID NO:8 shows the BUR protein
SEQ ID NO:9 shows the BCE gene
SEQ ID NO:10 shows the BCE protein
SEQ ID NO:11 shows the BTH gene
SEQ ID NO:12 shows the BTH protein
SEQ ID NO:13 shows the AME gene
SEQ ID NO:14 shows the AME protein
SEQ ID NO:15 shows the SFL gene
SEQ ID NO:16 shows the SFL protein
SEQ ID NO:17 shows the BMY gene
SEQ ID NO:18 shows the BMY protein
SEQ ID NO:19 shows the XbaI-EcoRI fragment harboring BBR47_51900
SEQ ID NO:20 shows the XbaI-EcoRI fragment harboring Staur_4851
SEQ ID NO:21 shows the XbaI-EcoRI fragment harboring DES SEQ ID NO:22 shows the XbaI-EcoRI fragment harboring BUR
SEQ ID NO:23 shows the XbaI-EcoRI fragment harboring BCE
SEQ ID NO:24 shows the XbaI-EcoRI fragment harboring BTH
SEQ ID NO:25 shows the XbaI-EcoRI fragment harboring AME
SEQ ID NO:26 shows the XbaI-EcoRI fragment harboring SFL
SEQ ID NO:27 shows the XbaI-EcoRI fragment harboring BMY
SEQ ID NO:28 shows the Primer P1
SEQ ID NO:29 shows the Primer P2
SEQ ID NO:30 shows the Primer P3
SEQ ID NO:31 shows the Primer P4
SEQ ID NO:32 shows the Primer P5
SEQ ID NO:33 shows the Primer P6
SEQ ID NO:34 shows the Primer P7
SEQ ID NO:35 shows the Primer P8
SEQ ID NO:36 shows the Primer P9
SEQ ID NO:37 shows the Primer P10
SEQ ID NO:38 shows the Primer P11
SEQ ID NO:39 shows the Primer P12
SEQ ID NO:40 shows the Primer P13
SEQ ID NO:41 shows the Primer P14
SEQ ID NO:42 shows the Primer P15
SEQ ID NO:43 shows the Primer P16
SEQ ID NO:44 shows the Primer P17
SEQ ID NO:45 shows the Primer P18
SEQ ID NO:46 shows the Primer P19
SEQ ID NO:47 shows the Primer P20
SEQ ID NO:48 shows the Primer P21
SEQ ID NO:49 shows the Primer P22
SEQ ID NO:50 shows the Primer P23
SEQ ID NO:51 shows the Primer P24
SEQ ID NO:52 shows the Primer P25
SEQ ID NO:53 shows the Primer P26
SEQ ID NO:54 shows the Primer P27
SEQ ID NO:55 shows the Primer P28
SEQ ID NO:56 shows the Primer P29
SEQ ID NO:57 shows the Primer P30
SEQ ID NO:58 shows the Primer P31
SEQ ID NO:59 shows the Primer P32
SEQ ID NO:60 shows the Primer P33
SEQ ID NO:61 shows the Primer P34
SEQ ID NO:62 shows the Primer P35
SEQ ID NO:63 shows the Primer P36
SEQ ID NO:64 shows the Primer P37
SEQ ID NO:65 shows the Primer P38
SEQ ID NO:66 shows the Primer P39
SEQ ID NO:67 shows the Primer P40
SEQ ID NO:68 shows the optimized gene encoding BBR47_51900 from *Brevibacillus brevis* NBRC 100599
SEQ ID NO:69 shows the optimized gene encoding Staur_4851 from *Stigmatella aurantiaca*

The invention claimed is:

1. A method for producing a dipeptide or a salt thereof, comprising:
   (a) reacting L-amino acids, L-amino acid derivatives, or salts thereof under appropriate conditions in the presence of a protein having dipeptide-synthesizing activity such that a dipeptide or a salt thereof is produced;
   (b) accumulating the dipeptide or a salt thereof in an appropriate solvent; and
   (c) collecting the dipeptide or a salt thereof from the appropriate solvent,
   wherein the protein is selected from the group consisting of:
   a protein having the amino acid sequence of SEQ ID NO: 2, 4, or 6;
   a variant of a protein having the amino acid sequence of SEQ ID NO: 2, 4, or 6 in which no more than fifteen amino acid residues of the amino acid sequence of SEQ ID NO: 2, 4, or 6 are changed by substitution, deletion, insertion, or addition, and wherein the variant protein has the dipeptide-synthesizing activity; and
   a protein having an amino acid sequence having not less than 95% sequence identity to the amino acid sequence of SEQ ID NO: 2, 4, or 6 and wherein the protein has the dipeptide-synthesizing activity,
   wherein the dipeptide comprises two L-amino acids, two L-amino acid derivatives, or an L-amino acid and an L-amino acid derivative, and
   wherein the L-amino acids or the L-amino acid derivatives are selected from the group consisting of L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, and a lower alkyl ester of L-phenylalanine, wherein the lower alkyl ester of L-phenylalanine is methyl, ethyl or propyl ester of the L-phenylalanine.

2. A method for producing a dipeptide or a salt thereof, comprising:
   (a) cultivating a bacterium in a culture medium comprising an L-amino acid or an L-amino acid derivative;
   (b) accumulating the dipeptide in the bacterium, the culture medium, or both; and
   (c) collecting the dipeptide from the bacterium, the culture medium, or both,
   wherein the bacterium is a dipeptide-producing bacterium belonging to the genus *Escherichia* transformed with a recombinant DNA comprising a DNA encoding a protein having dipeptide-synthesizing activity, wherein the DNA encoding the protein having a dipeptide-synthesizing activity is selected from the group consisting of:
a DNA having the nucleotide sequence of SEQ ID NO: 1, 3, or 5;
a DNA encoding a protein having the amino acid sequence of SEQ ID NO: 2, 4, or 6;
a DNA encoding a variant of a protein having the amino acid sequence of SEQ ID NO: 2, 4, or 6 in which no more than fifteen amino acid residues of the amino acid sequence of SEQ ID NO: 2, 4, or 6 are changed by substitution, deletion, insertion, or addition, and wherein the variant protein has the dipeptide-synthesizing activity; and
a DNA encoding a protein having an amino acid sequence having not less than 95% sequence identity to the amino acid sequence of SEQ ID NO: 2, 4, or 6 and wherein the protein has the dipeptide-synthesizing activity,
wherein the dipeptide comprises two L-amino acids, two L-amino acid derivatives, or an L-amino acid and an L-amino acid derivative, and
wherein the L-amino acids or the L-amino acid derivatives are selected from the group consisting of L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, and a lower alkyl ester of L-phenylalanine, wherein the lower alkyl ester of L-phenylalanine is methyl, ethyl or propyl ester of the L-phenylalanine.

3. The method according to claim 1,
wherein the dipeptide is represented by the formula:

R1-R2 wherein R1 is an acidic L-amino acid residue,
wherein R2 is an L-amino acid or a derivative of the L-amino acid, and
wherein the L-amino acid or the derivative of the L-amino acid is selected from the group consisting of L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, and a lower alkyl ester of L-phenylalanine, wherein the lower alkyl ester of L-phenylalanine is methyl, ethyl or propyl ester of the L-phenylalanine.

4. The method according to claim 3,
wherein R1 is L-aspartic acid or L-glutamic acid, and
wherein R2 is L-glutamic acid, L-isoleucine, L-phenylalanine, L-tryptophan, L-valine or a lower alkyl ester of L-phenylalanine, and wherein the lower alkyl ester of L-phenylalanine is methyl, ethyl or propyl ester of the L-phenylalanine.

5. The method according to claim 3,
wherein R1 is L-aspartic acid, and
wherein R2 is L-phenylalanine or a lower alkyl ester of L-phenylalanine, and wherein the lower alkyl ester of L-phenylalanine is methyl, ethyl or propyl ester of the L-phenylalanine.

6. The method according to claim 2, wherein the bacterium is the species *Escherichia coli*.

7. The method according to claim 2,
wherein a chromosomal gene encoding a protein having peptidase activity is attenuated or inactivated in the bacterium.

8. The method according to claim 7,
wherein the gene encoding a protein having peptidase activity is selected from the group consisting of pepA, pepB, pepD, pepE, pepP, pepQ, pepN, pepT, iadA, iaaA (ybiK), and dapE.

9. The method according to claim 1,
wherein the protein having dipeptide-synthesizing activity is at least one of:
a protein having the amino acid sequence of SEQ ID NO: 2, 4, or 6, and
a protein having an amino acid sequence having not less than 95% sequence identity to the amino acid sequence of SEQ ID NO: 2, 4, or 6 and wherein the protein has the dipeptide-synthesizing activity.

10. The method according to claim 9,
wherein the dipeptide is represented by the formula:

R1-R2 wherein R1 is L-aspartic acid or L-glutamic acid, and
wherein R2 is L-glutamic acid, L-isoleucine, L-phenylalanine, L-tryptophan, L-valine or a lower alkyl ester of L-phenylalanine, and wherein the lower alkyl ester of L-phenylalanine is methyl, ethyl or propyl ester of the L-phenylalanine.

11. The method according to claim 9,
wherein the dipeptide is represented by the formula:

R1-R2 wherein R1 is L-aspartic acid, and
wherein R2 is L-phenylalanine or a lower alkyl ester of L-phenylalanine, and wherein the lower alkyl ester of L-phenylalanine is methyl, ethyl or propyl ester of the L-phenylalanine.

12. The method according to claim 2,
wherein the DNA encoding the protein having dipeptide-synthesizing activity is at least one of:
a DNA having the nucleotide sequence of SEQ ID NO: 1, 3, or 5;
a DNA encoding a protein having the amino acid sequence of SEQ ID NO: 2, 4, or 6; and
a DNA encoding a protein having an amino acid sequence having not less than 95% sequence identity to the amino acid sequence of SEQ ID NO: 2, 4, or 6 and wherein the protein has the dipeptide-synthesizing activity.

13. The method according to claim 12,
wherein the dipeptide is represented by the formula:

R1-R2 wherein R1 is L-aspartic acid or L-glutamic acid, and
wherein R2 is L-glutamic acid, L-isoleucine, L- phenylalanine, L-tryptophan, L-valine or a lower alkyl ester of L-phenylalanine, and wherein the lower alkyl ester of L-phenylalanine is methyl, ethyl or propyl ester of the L-phenylalanine.

14. The method according to claim 12,
wherein the dipeptide is represented by the formula:

R1-R2 wherein R1 is L-aspartic acid, and
wherein R2 is L-phenylalanine or a lower alkyl ester of L-phenylalanine, and wherein the lower alkyl ester of L-phenylalanine is methyl, ethyl or propyl ester of the L-phenylalanine.

15. The method according to claim 1,
wherein the collecting of (c) comprises centrifuging the appropriate solvent or filtrating the appropriate solvent through a membrane.

* * * * *

```
                           SEQUENCE LISTING

<160> NUMBER OF SEQ ID NOS: 69

<210> SEQ ID NO 1
<211> LENGTH: 1257
<212> TYPE: DNA
<213> ORGANISM: Brevibacillus brevis NBRC 100599

<400> SEQUENCE: 1
atgaacaaac actttctgtt cgttgaagcg aatacgacgg ggacaggtat gctcgctatg      60
aaaaaggcgc gtaaattggg gtttacaccc gtattttca cagagaagcc tgaacgttac     120
cacggtttga atgagttgga atgtcatgta gtcgtgacag acacgaattc ccaggcagag     180
ctgactgaca gtgtagcaca agtgagtaag gaaggcagag agatagccgg aatcatgtcg     240
acaagcgact attacctcga atcggttgcc aagctggccc ggaaattcgg ttggataagc     300
aattcgctgg aggcaattga ggcctgccgc aataaagcga tatttcgcga gaagcttcag     360
aggcatcaag tgtctcagcc tacattttg gcaataagct ctatggagca attgctggaa     420
gcgcgctctt ccatttctct gccctgcgtg gtgaagcccg ctgacgatag cgggtccaat     480
aacgtgcggc tgtgctttag ctgggatgaa gtggagcata tggcagcgga aatccttgcc     540
atcaagtaca atgcgcgcgg tcaggaaaca gctcggacag ttcttctcga gcagtatgcc     600
gagggccctg aatttagcgt ggagacgttt tcatggcaag gcaatgctt tgttatcggc     660 attacccaga aacggttaac gggatatcca ttttcgtgg aagcagggca tattttccct     720
gcaccgttgt ccgtagaaga gaaacaggag atcgagcgaa cagtggaaag ggcattagcg     780
gcggtgaagt accagttcgg tgctgcccat acggaagtga agtggacatc agcaggttgt     840
gttgtcatcg aagtcaacgc aaggcttgcc ggaggaatga ttccagagct ggttcgccga     900
tccacgggga ttgatctgct tttgcaacag attcggtgtg cggctggact tgagccagaa     960
ttgtctcaaa ccatcgaaga gcaacgctgt gcaggcattc attttctcgt gtctgagagt    1020
```

```
cagggcacct tggcgggat aaagggaatg ataccgttc gcaacctgcc ggggattgct      1080
gaagtggcga ttcatgcgaa atcggacaa acgtccagc ctccgcaaaa tttttcgcat      1140
cgtctcggct atgtcatcgt ggaaggcaag cattacagtg agaccgctga gttgatcgag     1200
caggtgaaag acagcctgag tgtacaagta ggtcaacaat tggagagtgg ggtatga       1257
```

```
<210> SEQ ID NO 2
<211> LENGTH: 418
<212> TYPE: PRT
<213> ORGANISM: Brevibacillus brevis NBRC 100599

<400> SEQUENCE: 2

Met Asn Lys His Phe Leu Phe Val Glu Ala Asn Thr Thr Gly Thr Gly
1               5                   10                  15

Met Leu Ala Met Lys Lys Ala Arg Lys Leu Gly Phe Thr Pro Val Phe
            20                  25                  30

Phe Thr Glu Lys Pro Glu Arg Tyr His Gly Leu Asn Glu Leu Glu Cys
        35                  40                  45

His Val Val Thr Asp Thr Asn Ser Gln Ala Glu Leu Thr Asp Ser
    50                  55                  60

Val Ala Gln Val Ser Lys Glu Gly Arg Glu Ile Ala Gly Ile Met Ser
65                  70                  75                  80

Thr Ser Asp Tyr Tyr Leu Glu Ser Val Ala Lys Leu Ala Arg Lys Phe
                85                  90                  95

Gly Trp Ile Ser Asn Ser Leu Glu Ala Ile Glu Ala Cys Arg Asn Lys
            100                 105                 110

Ala Ile Phe Arg Glu Lys Leu Gln Arg His Gln Val Ser Gln Pro Thr
        115                 120                 125

Phe Leu Ala Ile Ser Ser Met Glu Gln Leu Leu Glu Ala Arg Ser Ser
    130                 135                 140

Ile Ser Leu Pro Cys Val Val Lys Pro Ala Asp Asp Ser Gly Ser Asn
145                 150                 155                 160

Asn Val Arg Leu Cys Phe Ser Trp Asp Glu Val His Met Ala Ala
                165                 170                 175

Glu Ile Leu Ala Ile Lys Tyr Asn Ala Arg Gly Gln Glu Thr Ala Arg
            180                 185                 190

Thr Val Leu Leu Glu Gln Tyr Ala Glu Gly Pro Glu Phe Ser Val Glu
        195                 200                 205

Thr Phe Ser Trp Gln Gly Gln Cys Phe Val Ile Gly Ile Thr Gln Lys
    210                 215                 220

Arg Leu Thr Gly Tyr Pro Phe Val Glu Ala Gly His Ile Phe Pro
225                 230                 235                 240

Ala Pro Leu Ser Val Glu Glu Lys Gln Glu Ile Glu Arg Thr Val Glu
                245                 250                 255

Arg Ala Leu Ala Ala Val Lys Tyr Gln Phe Gly Ala Ala His Thr Glu
            260                 265                 270

Val Lys Trp Thr Ser Ala Gly Cys Val Val Ile Glu Val Asn Ala Arg
        275                 280                 285

Leu Ala Gly Gly Met Ile Pro Glu Leu Val Arg Arg Ser Thr Gly Ile
    290                 295                 300

Asp Leu Leu Leu Gln Gln Ile Arg Cys Ala Ala Gly Leu Glu Pro Glu
305                 310                 315                 320

Leu Ser Gln Thr Ile Glu Glu Gln Arg Cys Ala Gly Ile His Phe Leu
                325                 330                 335
```

```
Val Ser Glu Ser Gln Gly Thr Phe Gly Gly Ile Lys Gly Met Asp Thr
            340                 345                 350

Val Arg Asn Leu Pro Gly Ile Ala Glu Val Ala Ile His Ala Lys Ile
        355                 360                 365

Gly Gln Asn Val Gln Pro Pro Gln Asn Phe Ser His Arg Leu Gly Tyr
    370                 375                 380

Val Ile Val Glu Gly Lys His Tyr Ser Glu Thr Ala Glu Leu Ile Glu
385                 390                 395                 400

Gln Val Lys Asp Ser Leu Ser Val Gln Val Gly Gln Gln Leu Glu Ser
                405                 410                 415

Gly Val

<210> SEQ ID NO 3
<211> LENGTH: 1254
<212> TYPE: DNA
<213> ORGANISM: Stigmatella aurantiaca DW4/3-1

<400> SEQUENCE: 3
gtgaatcaat tcgttttcgt cgagagcaac accacgggga cgggccggct ggccgtggag      60
cggctgctgg cccagggcga gcaggtgacg ttcatcaccc accagccaga gaagtacccc     120
ttcctggtgg gcaacaaggc cccggggctg aaggtgttga aggtggagac caacgacgcg     180
gcggccgtgg aggcctgtgt cgatgggctg gtgcggagg ggaaggtggc ggcgctgctc      240
accttctcca ccttctatgt gcccacggtg gcggccatcg cggcgcggca cggcctgcgc     300
tacctccagc ctcgcgcggc ccaggcttgc acaacaagc acgaggcgcg ggccctgctg      360
cgcgcggcgg ggctgcccgg gcctgagttc cacgtcatcg cctccgaggc cgaggcggcg     420
cagctcgccc agacggtgcg ctttccgtgt gtggtgaagc ctcccgccga gagcggcagc     480 acggggtgc ggcgggtgga cacccgagg gagctgctcg cgcacttccg ctccctgcac       540
tcccgcgccg ccaacgagcg cggccagtcc ttgcacgggg aagtgctcgt ggagtcattc     600
ctggaggggc cggagttcag cgtggagacg atgacgctgg ccgatggcac cacgcacgtg     660
ctcggggtga cccagaagta cctctccgcg ccgccgtact tcgtggagat ggggcatgac     720
ttcccggcgg acctgccgcc cgagcggcgg cgggcgctgg aggaggccgt gctcgcgggg     780
ctcgcggcgg tgggctttga cttcggcccg gcccacacgg agatccgctt cacgcccgcg     840
gggccggtca tcatcgagat caaccccggg ctggcgggag gatgattcc ggagctggtg      900 cggctgtcca ccggcgtgga tctgctctcg gcgatgctgg atcaaatgct ggggcggccc     960
gtggacctga cgcacacgcg ccaggatgtg gcctgtatcc gcttcatcac ctcggagcgt    1020
cccggcgtgc tggcgcgcgt ggagggccag gacgaggcct cccggctggg caccgtccgg    1080
caggtggccg tggacaaggc ggcgggggacc cggctgcgcc cgcccgagag cgcgacggac    1140
cggctgggct atgtcatcgc cagcgggccc gagcgcggac aggtgcttgg cgacgcggcg    1200
agggcgctgt cgctgctccg ggtcgagcaa gccgcgccct cggccccggc gtga          1254

<210> SEQ ID NO 4
<211> LENGTH: 417
<212> TYPE: PRT
<213> ORGANISM: Stigmatella aurantiaca DW4/3-1

<400> SEQUENCE: 4

Met Asn Gln Phe Val Phe Val Glu Ser Asn Thr Thr Gly Thr Gly Arg
1               5                   10                  15

Leu Ala Val Glu Arg Leu Leu Ala Gln Gly Glu Gln Val Thr Phe Ile
```

```
            20                  25                  30
Thr His Gln Pro Glu Lys Tyr Pro Phe Leu Val Gly Asn Lys Ala Pro
            35                  40                  45
Gly Leu Lys Val Leu Lys Val Glu Thr Asn Asp Ala Ala Val Glu
50                  55                  60
Ala Cys Val Asp Gly Leu Val Arg Glu Gly Lys Val Ala Ala Leu Leu
65                  70                  75                  80
Thr Phe Ser Thr Phe Tyr Val Pro Thr Val Ala Ile Ala Ala Arg
                    85                  90                  95
His Gly Leu Arg Tyr Leu Gln Pro Arg Ala Ala Gln Ala Cys His Asn
                100                 105                 110
Lys His Glu Ala Arg Ala Leu Leu Arg Ala Ala Gly Leu Pro Gly Pro
            115                 120                 125
Glu Phe His Val Ile Ala Ser Glu Ala Glu Ala Ala Gln Leu Ala Gln
            130                 135                 140
Thr Val Arg Phe Pro Cys Val Val Lys Pro Pro Ala Glu Ser Gly Ser
145                 150                 155                 160
Thr Gly Val Arg Arg Val Asp Thr Pro Glu Glu Leu Leu Ala His Phe
                165                 170                 175
Arg Ser Leu His Ser Arg Ala Ala Asn Glu Arg Gly Gln Ser Leu His
                180                 185                 190
Gly Glu Val Leu Val Glu Ser Phe Leu Glu Gly Pro Glu Phe Ser Val
            195                 200                 205
Glu Thr Met Thr Leu Ala Asp Gly Thr Thr His Val Leu Gly Val Thr
            210                 215                 220
Gln Lys Tyr Leu Ser Ala Pro Pro Tyr Phe Val Glu Met Gly His Asp
225                 230                 235                 240
Phe Pro Ala Asp Leu Pro Pro Glu Arg Arg Ala Leu Glu Glu Ala
                245                 250                 255
Val Leu Ala Gly Leu Ala Ala Val Gly Phe Asp Phe Gly Pro Ala His
                260                 265                 270
Thr Glu Ile Arg Phe Thr Pro Ala Gly Pro Val Ile Ile Glu Ile Asn
            275                 280                 285
Pro Arg Leu Ala Gly Gly Met Ile Pro Glu Leu Val Arg Leu Ser Thr
            290                 295                 300
Gly Val Asp Leu Leu Ser Ala Met Leu Asp Gln Met Leu Gly Arg Pro
305                 310                 315                 320
Val Asp Leu Thr His Thr Arg Gln Asp Val Ala Cys Ile Arg Phe Ile
                325                 330                 335
Thr Ser Glu Arg Pro Gly Val Leu Ala Arg Val Glu Gly Gln Asp Glu
                340                 345                 350
Ala Ser Arg Leu Gly Thr Val Arg Gln Val Ala Val Asp Lys Ala Ala
            355                 360                 365
Gly Thr Arg Leu Arg Pro Pro Glu Ser Ala Thr Asp Arg Leu Gly Tyr
            370                 375                 380
Val Ile Ala Ser Gly Pro Glu Arg Gly Gln Val Leu Gly Asp Ala Ala
385                 390                 395                 400
Arg Ala Leu Ser Leu Leu Arg Val Glu Gln Ala Ala Pro Ser Ala Pro
                405                 410                 415
Ala

<210> SEQ ID NO 5
<211> LENGTH: 1227
```

```
<212> TYPE: DNA
<213> ORGANISM: Desmospora sp. 8437

<400> SEQUENCE: 5
ttgaagaaaa aactgctatt cgttgaagga acaccacgg  gaacggggat attggcccttt     60
gaaaaggcga gaaagctcgg ttatgagccg gtattcctga cgcaagaggc gagtcgttat    120
gatggacttc cggaggcgaa gtgccgtgtc catgtgactg ttacggattc gatccatgaa    180
ctgaaacgtt gtgtatcgca ggaaaaggcg gaagcggtcg ccgggatttt aacgacaagt    240
gattattatc tggagatctc cgcaaagctg gtacaggaat tggggctgac aggcaactcg    300
ccgcaggcga tccatttgtg ccggaacaaa gcactgtatc gtgaaaaact ccgctccaaa    360
agtgtgccgc agcccaactt ccatatcatt cgctccatgg aggatctgcg ggaaactcgt    420
gagtctgttc cactcccttg tttggtgaag ccagctgacg acagtggctc aaacaacgtt    480
cgcctatgtt tcagttgggg agaagtggaa caactgacat ccaaaattct taaaattgaa    540
cgcaatgcgc gtgggcagaa gacatcgcaa accgtattgc tggaagagta tattgaaggc    600
ccggaataca gcgtggagat gttttcatgg caagggaagt caacctgcat cggaattact    660
gaaaaacagc tgaccggata tccctatttt gtcgaatccg gacatgtttt tccggcagtg    720
cttcccactg acgtacagca ggaaatcgaa aagacagtga acagtcact  ggaggcagtc    780
cattttcagt ttggggcatc gcattcagaa gtgaagtgga caccgaatgg gtgtgtcatg    840
atcgaaacca acgcccggct cgcaggggga atgataccgg aattggtacg ccattcaacc    900
ggggtggatc tgattgagca acagatcctc tgcgccgcag gggtggctcc ccactggaag    960
caggttgtgc aacaggctg  ttccggcatt cattttatcg ttgcagcgga ggcaggtcgc   1020
ctatcctccg tggacaacct ggaagcggtg cgaaaacttc cgggtgtgga agaaatgatg   1080
gtcaaagcgc aggtcggaca ggctgtacag ccaccaaaaa attttttcgga tcgtctcggg   1140
catgtgattg tcagcggcaa gtcctatgaa gaggtggttg aacgcttaca caagatatcc   1200
aacatgattt ctttaaagat atcgtaa                                        1227

<210> SEQ ID NO 6
<211> LENGTH: 408
<212> TYPE: PRT
<213> ORGANISM: Desmospora sp. 8437

<400> SEQUENCE: 6

Met Lys Lys Lys Leu Leu Phe Val Glu Gly Asn Thr Thr Gly Thr Gly
  1               5                  10                  15

Ile Leu Ala Leu Glu Lys Ala Arg Lys Leu Gly Tyr Glu Pro Val Phe
             20                  25                  30

Leu Thr Gln Glu Ala Ser Arg Tyr Asp Gly Leu Pro Glu Ala Lys Cys
         35                  40                  45

Arg Val His Val Thr Val Thr Asp Ser Ile His Glu Leu Lys Arg Cys
     50                  55                  60

Val Ser Gln Glu Lys Ala Glu Ala Val Ala Gly Ile Leu Thr Thr Ser
 65                  70                  75                  80

Asp Tyr Tyr Leu Glu Ile Ser Ala Lys Leu Val Gln Glu Leu Gly Leu
                 85                  90                  95

Thr Gly Asn Ser Pro Gln Ala Ile His Leu Cys Arg Asn Lys Ala Leu
            100                 105                 110

Tyr Arg Glu Lys Leu Arg Ser Lys Ser Val Pro Gln Pro Asn Phe His
        115                 120                 125
```

```
Ile Ile Arg Ser Met Glu Asp Leu Arg Glu Thr Arg Glu Ser Val Pro
        130                 135                 140

Leu Pro Cys Leu Val Lys Pro Ala Asp Asp Ser Gly Ser Asn Asn Val
145                 150                 155                 160

Arg Leu Cys Phe Ser Trp Gly Val Glu Gln Leu Thr Ser Lys Ile
                165                 170                 175

Leu Lys Ile Glu Arg Asn Ala Arg Gly Gln Lys Thr Ser Gln Thr Val
                180                 185                 190

Leu Leu Glu Glu Tyr Ile Glu Gly Pro Glu Tyr Ser Val Glu Met Phe
            195                 200                 205

Ser Trp Gln Gly Lys Ser Thr Cys Ile Gly Ile Thr Glu Lys Gln Leu
210                 215                 220

Thr Gly Tyr Pro Tyr Phe Val Glu Ser Gly His Val Phe Pro Ala Val
225                 230                 235                 240

Leu Pro Thr Asp Val Gln Gln Glu Ile Glu Lys Thr Val Lys Gln Ser
                245                 250                 255

Leu Glu Ala Val His Phe Gln Phe Gly Ala Ser His Ser Glu Val Lys
            260                 265                 270

Trp Thr Pro Asn Gly Cys Val Met Ile Glu Thr Asn Ala Arg Leu Ala
        275                 280                 285

Gly Gly Met Ile Pro Glu Leu Val Arg His Ser Thr Gly Val Asp Leu
    290                 295                 300

Ile Glu Gln Gln Ile Leu Cys Ala Ala Gly Val Ala Pro His Trp Lys
305                 310                 315                 320

Gln Val Val Pro Thr Gly Cys Ser Gly Ile His Phe Ile Val Ala Ala
                325                 330                 335

Glu Ala Gly Arg Leu Ser Ser Val Asp Asn Leu Glu Ala Val Arg Lys
            340                 345                 350

Leu Pro Gly Val Glu Glu Met Met Val Lys Ala Gln Val Gly Gln Ala
        355                 360                 365

Val Gln Pro Pro Lys Asn Phe Ser Asp Arg Leu Gly His Val Ile Val
    370                 375                 380

Ser Gly Lys Ser Tyr Glu Glu Val Val Glu Arg Leu His Lys Ile Ser
385                 390                 395                 400

Asn Met Ile Ser Leu Lys Ile Ser
                405

<210> SEQ ID NO 7
<211> LENGTH: 2685
<212> TYPE: DNA
<213> ORGANISM: Burkholderia pseudomallei 305

<400> SEQUENCE: 7
atgaagacct tcgtattcat cgaaagcaac accaccggca ccggccggct ctgtctgcaa        60
aaagcgctgc tgcgcggctt cgacgtgctg ttcgtcacga gccggccgca gctctatccg       120
ttcctgcagg aagagatggt cgtgccgctc gtcgccgaca cggccgatcc gcagcggatc       180
gccgatgcac ttgcgccgta tgcgggcatc gccgggatct tctcgacgtc gagtactac        240 atcgaaaccg ccgcgacggt ggccacgcgc ctgggcttgc ccgcggcgga tccggaggcg       300
atccgcacct gccgcgacaa gggccggctg caccgccgcc tgcgcgacgc gggcgtcggc       360
gtggccgaca ctgagatcgt gtccgagcgc acgcaactgc gcgacctggc gcacggcgcc       420
acgtatccgc gcgtgctgaa gccggcgttc ggctccggca cgtcggcgt gcggctcgtg        480 cggacgccgg ccgaaatgct cgcgcacggc gagcgcatgc tcgacgcgcg cggcaacgag       540
```

```
cgcggcatcg cgctcgcgcg gcaggtgctc gtgcaatcgt tcgtcgacgg gccggaattt      600
tcggtcgaag tcgtcgggct cggcgcggag cacggccatg cggtgctcgg cgtgacgggc      660
aagcacctcg ggccgctgcc gcacttcgtc gaagccggcc acgattttcc ggcgccgatc      720
gcggccgcgc agcgcgatgc gatcgtggcc gagacgctgc gtgcgctcga cgcggtgggc      780
caccgcttcg ggcccgccca tgtcgaatgc cgcgtgagcg cggcaaggt cgtcgtgatc       840 gagatcaatc cgcgtctcgc gggcggcatg atcccgcagg cgatcgaatg ggcgacgggc      900
gtcgacgtgc tcggcgcgat gatcgacctg cacgcgggca cgccgcctga cctgggcccg      960
cgccgccgcg gccacgcggc gatccgcttc gtgctgcccg cgcgcagcgg cgagctgagg     1020
gcgctgtcgt tcgagcccga cgagcgcttt gcggggtgc gcacgcgctt catgccgctc      1080
aagcagcttg gccagcgcat cgagccggcc ggcgacttcc gcgaccgtct cgcgctcgtc     1140
atcgcgtccg cggccgatcc ggacgcgctc gcgcacgcgc tcgaggacgt cgatcgctgc     1200
gtgacggttg cgatcggcga cgccggcgcg cggggcgagg gcgcaggcgc cggccggctg     1260
cgccgcacgc tgcatccgga ggcgctcgcg atcgtgcgca agccggcgcc gcgcgccgag     1320
cggctcgccg aactcgacgc gttcgcggcg atcgacgagg cgcacctgct gatgctcgtc     1380
gacgcgggaa tctgcgaccg ggcgcgggcc gcgacggtgc tcgcggaact cgcgcggcag     1440
cgcgacgcga aattcgccgc gatcgccgac gcgatcgcgc cgcgcggcac ctacgcactg     1500
tacgagcaac tgctcatcga gcgggtcggg atcgacgcgg gggcgcggt gcatacggcg      1560 cgctcgcgca acgacatcaa cgcgtgcgtc gcgaagctgc gcgcacgcga gtggttcgac     1620
acgtgcggcg gcaagctgtg gcgcgtgcgc gcggcgatcg tcgacaaggc gcagcacacg     1680
ctcgactggc cgttgcccac gtacagccag taccaggcgg cgcagccgg cagcttcggc      1740 tattacctgt ggtcggtcga gaccgcgctg cggcgcgacc aggcggcgct cgaacggctc     1800
gacgaggagc tcgccgtctg tccgctcggc gcgggcgcgg gcgcgggcac cgatttcccg     1860
atccgcccgg gcgtgagcgc ggcgctgctc ggcttcgcgc gcagcttcga cagcgcgctc     1920
gacgcggtcg cgagccgcga tctcgtgctg catttcctgg ccgcgatcgc gatcgcatcg     1980
acgacgctca gccggctcgc gcacgacctg cagctctgga cgatgcgcga gaccgacttc     2040
ctcgcgctgc cggacgaact gagcggcggc tcgtcgctga tgccgcagaa gaagaaccca     2100
tacctgctgg agatcgtcaa aggcaagctc gcgcacgtcg cgggcgcgct gaacgcggcg     2160
gtgttcgcgt cgcagcgcac gccgttcagc aattcggtcg agatcggcac cgagatgctc     2220
gcgccgtgcg cggacgccgt gcaggcgttc ggcgaaagct gcgatctgct gcggctgatg     2280
gtgagcggcg tgacgggtga tccggcgaag atgcgcgcgg cggccgaggc ggggctcgtg     2340
agcgcgacgc aggtcgccaa cgcgctggtg cgggaaacgg acatcagctt tcacgccgcg     2400
catcggcaga tcggcgcgct gatcacgcag gcgctcgacg cgcacgagga cccggccgcg     2460
gcgctcgacg cgctcgtgcg gcagccgggc gcatcgatcg acgaagcggc cgcgcggctc     2520
gcctacggcg gcgggccggg cgcggcgggc gcggggctcg cgcgctcgcg cgcgctgctg     2580
cggcagtcgg ccgaacgcct gtggcggcgc cgcgccgcgt ggcacgcggc gcacgcgcgg     2640
cggcgcgggt gcgtcgccga tctgctcgcg gcggcggcgg cctga                    2685
```

<210> SEQ ID NO 8
<211> LENGTH: 894
<212> TYPE: PRT
<213> ORGANISM: Burkholderia pseudomallei 305

<400> SEQUENCE: 8

```
Met Lys Thr Phe Val Phe Ile Glu Ser Asn Thr Thr Gly Thr Gly Arg
1               5                   10                  15

Leu Cys Leu Gln Lys Ala Leu Leu Arg Gly Phe Asp Val Leu Phe Val
                20                  25                  30

Thr Ser Arg Pro Gln Leu Tyr Pro Phe Leu Gln Glu Glu Met Val Val
            35                  40                  45

Pro Leu Val Ala Asp Thr Ala Asp Pro Gln Arg Ile Ala Asp Ala Leu
50                  55                  60

Ala Pro Tyr Ala Gly Ile Ala Gly Ile Phe Ser Thr Ser Glu Tyr Tyr
65                  70                  75                  80

Ile Glu Thr Ala Ala Thr Val Ala Thr Arg Leu Gly Leu Pro Ala Ala
                85                  90                  95

Asp Pro Glu Ala Ile Arg Thr Cys Arg Asp Lys Gly Arg Leu His Arg
            100                 105                 110

Arg Leu Arg Asp Ala Gly Val Gly Val Ala Asp Thr Glu Ile Val Ser
        115                 120                 125

Glu Arg Thr Gln Leu Arg Asp Leu Ala His Gly Ala Thr Tyr Pro Arg
130                 135                 140

Val Leu Lys Pro Ala Phe Gly Ser Gly Ser Val Gly Val Arg Leu Val
145                 150                 155                 160

Arg Thr Pro Ala Glu Met Leu Ala His Gly Glu Arg Met Leu Asp Ala
                165                 170                 175

Arg Gly Asn Glu Arg Gly Ile Ala Leu Ala Arg Gln Val Leu Val Gln
            180                 185                 190

Ser Phe Val Asp Gly Pro Glu Phe Ser Val Glu Val Val Gly Leu Gly
        195                 200                 205

Ala Glu His Gly His Ala Val Leu Gly Val Thr Gly Lys His Leu Gly
210                 215                 220

Pro Leu Pro His Phe Val Glu Ala Gly His Asp Phe Pro Ala Pro Ile
225                 230                 235                 240

Ala Ala Ala Gln Arg Asp Ala Ile Val Ala Glu Thr Leu Arg Ala Leu
                245                 250                 255

Asp Ala Val Gly His Arg Phe Gly Pro Ala His Val Glu Cys Arg Val
            260                 265                 270

Ser Gly Gly Lys Val Val Ile Glu Ile Asn Pro Arg Leu Ala Gly
        275                 280                 285

Gly Met Ile Pro Gln Ala Ile Glu Trp Ala Thr Gly Val Asp Val Leu
290                 295                 300

Gly Ala Met Ile Asp Leu His Ala Gly Thr Pro Pro Asp Leu Gly Pro
305                 310                 315                 320

Arg Arg Arg Gly His Ala Ala Ile Arg Phe Val Leu Pro Ala Arg Ser
                325                 330                 335

Gly Glu Leu Arg Ala Leu Ser Phe Glu Pro Asp Glu Arg Phe Ala Gly
            340                 345                 350

Val Arg Thr Arg Phe Met Pro Leu Lys Gln Leu Gly Gln Arg Ile Glu
        355                 360                 365

Pro Ala Gly Asp Phe Arg Asp Arg Leu Ala Leu Val Ile Ala Ser Ala
370                 375                 380

Ala Asp Pro Asp Ala Leu Ala His Ala Leu Glu Asp Val Asp Arg Cys
385                 390                 395                 400

Val Thr Val Ala Ile Gly Asp Ala Gly Ala Ala Gly Glu Gly Ala Gly
                405                 410                 415
```

```
Ala Gly Arg Leu Arg Arg Thr Leu His Pro Glu Ala Leu Ala Ile Val
            420                 425                 430

Arg Lys Pro Ala Pro Arg Ala Glu Arg Leu Ala Glu Leu Asp Ala Phe
        435                 440                 445

Ala Ala Ile Asp Glu Ala His Leu Leu Met Leu Val Asp Ala Gly Ile
    450                 455                 460

Cys Asp Arg Ala Arg Ala Ala Thr Val Leu Ala Glu Leu Ala Arg Gln
465                 470                 475                 480

Arg Asp Ala Lys Phe Ala Ala Ile Ala Asp Ala Ile Ala Pro Arg Gly
                485                 490                 495

Thr Tyr Ala Leu Tyr Glu Gln Leu Leu Ile Glu Arg Val Gly Ile Asp
            500                 505                 510

Ala Gly Gly Ala Val His Thr Ala Arg Ser Arg Asn Asp Ile Asn Ala
        515                 520                 525

Cys Val Ala Lys Leu Arg Ala Arg Glu Trp Phe Asp Thr Cys Gly Gly
    530                 535                 540

Lys Leu Trp Arg Val Arg Ala Ala Ile Val Asp Lys Ala Gln His Thr
545                 550                 555                 560

Leu Asp Trp Pro Leu Pro Thr Tyr Ser Gln Tyr Gln Ala Ala Gln Pro
                565                 570                 575

Gly Ser Phe Gly Tyr Tyr Leu Trp Ser Val Glu Thr Ala Leu Arg Arg
            580                 585                 590

Asp Gln Ala Ala Leu Glu Arg Leu Asp Glu Glu Leu Ala Val Cys Pro
        595                 600                 605

Leu Gly Ala Gly Ala Gly Ala Gly Thr Asp Phe Pro Ile Arg Pro Gly
    610                 615                 620

Val Ser Ala Ala Leu Leu Gly Phe Ala Arg Ser Phe Asp Ser Ala Leu
625                 630                 635                 640

Asp Ala Val Ala Ser Arg Asp Leu Val Leu His Phe Leu Ala Ala Ile
                645                 650                 655

Ala Ile Ala Ser Thr Thr Leu Ser Arg Leu Ala His Asp Leu Gln Leu
            660                 665                 670

Trp Thr Met Arg Glu Thr Asp Phe Leu Ala Leu Pro Asp Glu Leu Ser
        675                 680                 685

Gly Gly Ser Ser Leu Met Pro Gln Lys Lys Asn Pro Tyr Leu Leu Glu
    690                 695                 700

Ile Val Lys Gly Lys Leu Ala His Val Ala Gly Ala Leu Asn Ala Ala
705                 710                 715                 720

Val Phe Ala Ser Gln Arg Thr Pro Phe Ser Asn Ser Val Glu Ile Gly
                725                 730                 735

Thr Glu Met Leu Ala Pro Cys Ala Asp Ala Val Gln Ala Phe Gly Glu
            740                 745                 750

Ser Cys Asp Leu Leu Arg Leu Met Val Ser Gly Val Thr Gly Asp Pro
        755                 760                 765

Ala Lys Met Arg Ala Ala Ala Glu Ala Gly Leu Val Ser Ala Thr Gln
    770                 775                 780

Val Ala Asn Ala Leu Val Arg Glu Thr Asp Ile Ser Phe His Ala Ala
785                 790                 795                 800

His Arg Gln Ile Gly Ala Leu Ile Thr Gln Ala Leu Asp Ala His Glu
                805                 810                 815

Asp Pro Ala Ala Ala Leu Asp Ala Leu Val Arg Gln Pro Gly Ala Ser
            820                 825                 830
```

-continued

```
Ile Asp Glu Ala Ala Ala Arg Leu Ala Tyr Gly Gly Gly Pro Gly Ala
        835                 840                 845

Ala Gly Ala Gly Leu Ala Arg Ser Arg Ala Leu Leu Arg Gln Ser Ala
    850                 855                 860

Glu Arg Leu Trp Arg Arg Arg Ala Ala Trp His Ala Ala His Ala Arg
865                 870                 875                 880

Arg Arg Gly Cys Val Ala Asp Leu Leu Ala Ala Ala Ala Ala
                885                 890

<210> SEQ ID NO 9
<211> LENGTH: 1227
<212> TYPE: DNA
<213> ORGANISM: Bacillus cereus AH621

<400> SEQUENCE: 9
ttgaagaaaa aactgctatt cgttgaagga aacaccacgg gaacggggat attggccctt      60
gaaaaggcga gaaagctcgg ttatgagccg gtattcctga cgcaagaggc gagtcgttat     120
gatggacttc cggaggcgaa gtgccgtgtc catgtgactg ttacggattc gatccatgaa     180
ctgaaacgtt gtgtatcgca ggaaaaggcg gaagcggtcg ccgggatttt aacgacaagt     240
gattattatc tggagatctc cgcaaagctg gtacaggaat tggggctgac aggcaactcg     300
ccgcaggcga tccatttgtg ccggaacaaa gcactgtatc gtgaaaaact ccgctccaaa     360
agtgtgccgc agcccaactt ccatatcatt cgctccatgg aggatctgcg ggaaactcgt     420
gagtctgttc cactcccttg tttggtgaag ccagctgacg acagtggctc aaacaacgtt     480
cgcctatgtt tcagttgggg agaagtggaa caactgacat ccaaaattct taaaattgaa     540
cgcaatgcgc gtgggcagaa gacatcgcaa accgtattgc tggaagagta tattgaaggc     600
ccggaataca gcgtggagat gttttcatgg caagggaagt caacctgcat cggaattact     660
gaaaaacagc tgaccggata tccctatttt gtcgaatccg gacatgtttt tccggcagtg     720
cttcccactg acgtacagca ggaaatcgaa aagacagtga aacagtcact ggaggcagtc     780
cattttcagt ttggggcatc gcattcagaa gtgaagtgga caccgaatgg gtgtgtcatg     840
atcgaaacca acgcccggct cgcaggggga atgataccgg aattggtacg ccattcaacc     900
ggggtggatc tgattgagca acagatcctc tgcgccgcag ggtggctccc ccactggaag     960
caggttgtgc caacaggctg ttccggcatt cattttatcg ttgcagcgga ggcaggtcgc    1020
ctatcctccg tggacaacct ggaagcggtg cgaaaacttc cgggtgtgga agaaatgatg    1080
gtcaaagcgc aggtcggaca ggctgtacag ccaccaaaaa atttttcgga tcgtctcggg    1140
catgtgattg tcagcggcaa gtcctatgaa gaggtggttg aacgcttaca caagatatcc    1200
aacatgattt ctttaaagat atcgtaa                                        1227

<210> SEQ ID NO 10
<211> LENGTH: 393
<212> TYPE: PRT
<213> ORGANISM: Bacillus cereus AH621

<400> SEQUENCE: 10

Met Leu Ala Ile Arg Lys Ala Lys Glu Leu Gly Tyr Glu Pro Ile Phe
1               5                   10                  15

Leu Thr Gln Lys Lys Ser Leu Tyr His Gly Leu Ser Asp Leu Glu Cys
            20                  25                  30

Arg Val Ile Glu Leu Asp Thr Asn Ser Val Asp Ala Ile Lys His Tyr
        35                  40                  45
```

```
Ile Ile His Glu Lys Ile Glu Asp Ile Ala Gly Ile Leu Thr Thr Ser
 50                  55                  60

Asp Tyr Tyr Leu Glu Thr Val Ala Glu Leu Val Gln Met Phe Arg Leu
 65                  70                  75                  80

Ser Gly Asn Thr His Gln Ala Ile Tyr Tyr Cys Arg Asn Lys Ala Met
                 85                  90                  95

Phe Arg Glu Lys Leu His Leu Glu Lys Val Leu Gln Pro Lys Phe His
            100                 105                 110

Ile Val Gln Ser Ile Asp Ser Leu Gln Asn Ile Tyr Ser Ser Ile Gln
            115                 120                 125

Phe Pro Cys Val Val Lys Pro Ala Asp Asp Ser Gly Ser Asn Asn Val
130                 135                 140

Arg Leu Cys Ser Asn Trp Glu Glu Val Glu Lys Ile Ala Thr Lys Ile
145                 150                 155                 160

Leu Ala Asn Lys Tyr Asn Ala Arg Gly Gln Glu Lys Ala Asn Met Val
                165                 170                 175

Leu Leu Glu Glu Tyr Ile Glu Gly Pro Glu Tyr Ser Val Glu Met Phe
            180                 185                 190

Ser Trp Glu Gly Asn Ser Ile Cys Ile Gly Ile Thr Glu Lys Gln Leu
            195                 200                 205

Thr Gly Phe Pro Tyr Phe Val Glu Ser Gly His Ile Phe Pro Val Glu
210                 215                 220

Leu Pro Lys Asp Val Gln Ser Glu Ile Glu Gln Thr Val Lys Cys Ala
225                 230                 235                 240

Leu Gln Ala Val Asp Phe Arg Phe Gly Ala Ser His Ser Glu Val Lys
                245                 250                 255

Trp Thr Ser Asn Gly Cys Val Val Ile Glu Val Asn Ala Arg Leu Ala
            260                 265                 270

Gly Gly Met Ile Pro Glu Leu Val Arg His Ser Thr Gly Val Asp Leu
            275                 280                 285

Leu Arg Gln Gln Val Leu Ser Ser Val Gly Val Ala Pro Glu Trp Lys
290                 295                 300

Glu Ile Glu Tyr Met Asn Tyr Ala Gly Ile His Phe Leu Thr Ala Lys
305                 310                 315                 320

Lys Ser Gly Phe Leu Ser Thr Val Lys Gly Ile Glu Glu Val Arg Glu
                325                 330                 335

Leu Ser Tyr Ile Glu Glu Leu Val Val Lys Ala Gln Val Gly Gln Pro
            340                 345                 350

Val Asn Pro Pro Glu Asn Phe Ser His Arg Leu Gly His Val Met Val
            355                 360                 365

Arg Gly Arg Thr Tyr Glu Glu Thr Val Leu Phe Leu Glu Glu Val Ala
370                 375                 380

Lys Lys Leu Glu Ile Gln Val Asn Asn
385                 390

<210> SEQ ID NO 11
<211> LENGTH: 1254
<212> TYPE: DNA
<213> ORGANISM: Bacillus thuringiensis subsp. finitimus (strain YBT-020)

<400> SEQUENCE: 11
atgaagaaac tattatttat tgaatcaaac acaacgggaa ctggaatgct agccttaata    60
aaagctagag agctaggttt tacaccagta ttgcttacga ataatcccgg gcgatatata   120
ggtttaggag agacaaaatg tatagtttta gaatgcgata cgaacaactt aaattgtatt   180
```

-continued

```
agaacaataa ttgattcaga attcgaagta ggtgaaataa aagctatcac aacaaccagt    240 gaatttata ttgaagtggt agctatttta gcaaaagagt taggcctgat tggtaatcct     300
atagatactg ttaaaaaatg tagaaataaa gcagaaatgc gtctgttact aaaagggata    360
gagaatattt atgaaccatg gttttatatt attgattctc ttgaaaagtt agagttggct    420
aaggataata taaaatttcc atgtgttgtt aaaccggttg atgatagtgg ctctaataac    480
gtattgaagt gttattcata tgaagaagta aaaaggcata ctgaaaaaat tttgagcaat    540
aagtataatg tgaggtctca aaaaaatgct cagaatatat tggtggaaga gtatgtatct    600
gggcaagaat atagtgtgga aatttttact tacaatggta agtgtaaaat tgttggagtg    660
actcagaaga ttgtagatgg agctccatat tttattgaat gtggtcacat atttccggca    720
ccagtctctg atgataaag atcagttatt gaaagaggag taacaaaaat tatagaaaaa      780
gttaattggc aaaacggtcc ttgtcattta gaaattaaga taagggaga aaaaatattt      840 ttagtagagt ttaatggcag gcttgctggg gggatgatac cagaattaat taagtatgct    900
accggaatag atttgcttaa agagcaatta aaagtcgtaa ctaggatgag gccaaaacta    960
gatcagaatc ctactttata tgcagggata cgatttatta taccacttag agatgggaaa    1020
ataacaagta ttttggagt aaatgatata gaaaacactg tagggattaa agaggtaaaa     1080
cttcgtacaa ttgtgggaga atctatccgg aaggttgaaa atgcgtatgg acggataggg    1140
catataattg gagcggctga aaatatcaat aagctaaatt atattttaga taaaagtatg    1200
gatgctttac atatagaaat agaggagtgt gaagactatg aagactttaa ttaa           1254
```

<210> SEQ ID NO 12
<211> LENGTH: 417
<212> TYPE: PRT
<213> ORGANISM: Bacillus thuringiensis subsp. finitimus (strain YBT-020)

<400> SEQUENCE: 12

```
Met Lys Lys Leu Leu Phe Ile Glu Ser Asn Thr Thr Gly Thr Gly Met
1               5                   10                  15

Leu Ala Leu Ile Lys Ala Arg Glu Leu Gly Phe Thr Pro Val Leu Leu
            20                  25                  30

Thr Asn Asn Pro Gly Arg Tyr Ile Gly Leu Gly Glu Thr Lys Cys Ile
        35                  40                  45

Val Leu Glu Cys Asp Thr Asn Asn Leu Asn Cys Ile Arg Thr Ile Ile
    50                  55                  60

Asp Ser Glu Phe Glu Val Gly Glu Ile Lys Ala Ile Thr Thr Thr Ser
65                  70                  75                  80

Glu Phe Tyr Ile Glu Val Val Ala Ile Leu Ala Lys Glu Leu Gly Leu
                85                  90                  95

Ile Gly Asn Pro Ile Asp Thr Val Lys Lys Cys Arg Asn Lys Ala Glu
            100                 105                 110

Met Arg Leu Leu Leu Lys Gly Ile Glu Asn Ile Tyr Glu Pro Trp Phe
        115                 120                 125

Tyr Ile Ile Asp Ser Leu Glu Lys Leu Glu Leu Ala Lys Asp Asn Ile
    130                 135                 140

Lys Phe Pro Cys Val Val Lys Pro Val Asp Asp Ser Gly Ser Asn Asn
145                 150                 155                 160

Val Leu Lys Cys Tyr Ser Tyr Glu Glu Val Lys Arg His Thr Glu Lys
                165                 170                 175

Ile Leu Ser Asn Lys Tyr Asn Val Arg Ser Gln Lys Asn Ala Gln Asn
```

|  |  | 180 |  |  | 185 |  |  | 190 |  |  |  |
|---|---|---|---|---|---|---|---|---|---|---|---|

Ile Leu Val Glu Glu Tyr Val Ser Gly Gln Glu Tyr Ser Val Glu Ile
           195                   200               205

Phe Thr Tyr Asn Gly Lys Cys Lys Ile Val Gly Val Thr Gln Lys Ile
210                   215                   220

Val Asp Gly Ala Pro Tyr Phe Ile Glu Cys His Ile Phe Pro Ala
225            230                235           240

Pro Val Ser Asp Asp Ile Arg Ser Val Ile Glu Arg Gly Val Thr Lys
                 245                 250              255

Ile Ile Glu Lys Val Asn Trp Gln Asn Gly Pro Cys His Leu Glu Ile
           260                   265              270

Lys Ile Lys Gly Glu Lys Ile Phe Leu Val Glu Phe Asn Gly Arg Leu
        275                   280              285

Ala Gly Gly Met Ile Pro Glu Leu Ile Lys Tyr Ala Thr Gly Ile Asp
     290               295                 300

Leu Leu Lys Glu Gln Leu Lys Val Val Thr Arg Met Arg Pro Lys Leu
305                   310                 315           320

Asp Gln Asn Pro Thr Leu Tyr Ala Gly Ile Arg Phe Ile Ile Pro Leu
           325                   330              335

Arg Asp Gly Lys Ile Thr Ser Ile Phe Gly Val Asn Asp Ile Glu Asn
               340                 345              350

Thr Val Gly Ile Lys Glu Val Lys Leu Arg Thr Ile Val Gly Glu Ser
        355                   360              365

Ile Arg Lys Val Glu Asn Ala Tyr Gly Arg Ile Gly His Ile Ile Gly
     370               375                 380

Ala Ala Glu Asn Ile Asn Lys Leu Asn Tyr Ile Leu Asp Lys Ser Met
385                   390                 395           400

Asp Ala Leu His Ile Glu Ile Glu Glu Cys Glu Asp Tyr Glu Asp Phe
           405                   410              415

Asn

<210> SEQ ID NO 13
<211> LENGTH: 1242
<212> TYPE: DNA
<213> ORGANISM: Alkaliphilus metalliredigens QYMF

<400> SEQUENCE: 13

| | | |
|---|---|---|
| atggcacatt tattgatgat tgaaagtttt ataggtggta atgcagtatt acttcctaag | 60 |
| ttactcaaac agttggggca tacttacaca tttattactc gaagcaaagg gattttcaag | 120 |
| agttcttttc actctaatga acatgtggta attcaacatg cagatgaaat aattgaggcc | 180 |
| aatactaatg acgcttcagt ggtgttggat accattttag gtaagaaatt tgatggtgtc | 240 |
| attacaacat gcgattatta tattgaaaca gtggtggaag ttgccaagga attgagtatt | 300 |
| ccgtgcccat ttcccaaggc tgtcaagaac gtaaggtaca acaaaaatt acgacagaca | 360 |
| ttggatgcag ccggtatttc taatccacag tatggtttag cctataattg ggatgaggta | 420 |
| ttattggtgg caaaaaatat cggatatccg ttgtattga agccggtgga tctttcttct | 480 |
| agtgcctacg ttcgactaat tagaagcgaa gaggatttac gagatgctta tcatcagctt | 540 |
| aatgctttcc caataaattg gagagatcaa gaacgagatt gtacgtatct tttggaaaaa | 600 |
| tacatggaag caacgaagt gagcgtagaa gccgtaacat taatggaga acaacgattt | 660 |
| attgaatta cacagaaatc cttaatggga gcgcctatt ttatagagga tgcccacatg | 720 |
| tttccagcaa atatatcaca tgatatgaag ttgaaaatct caggttatgt ggtaaaggca | 780 |

-continued

```
ttacaagctg cgggatatga ttatggagtg agtcacactg aagtaaagct tacagatgca    840
ggtcctagaa ttgtcgaaat taatccaaga gttgctggtg attatattgc agaaataatc    900
aaattagtat gcaacgttga tatattgcgt gcttttgtgg atctttctat tggaatagaa    960
ccaagtatta ctaagaaaga aactggtatt tctagtgctt gcgttaggtt tttaactcca   1020
catcgcggtg gaaaaatagt gaatattgta ggtgttgaca ctttagcatc ggattcacat   1080
attgattcct ttaaagtgga ggattgtatt ggcaaaactg ttggtgatcc tattgataat   1140
gcagggagaa tcgggtggat cattacgaaa gatacagaag gatataatgc gatgaattat   1200
gcatatgaag cgatggagca cattaagctg acttttgaat aa                      1242
```

<210> SEQ ID NO 14
<211> LENGTH: 413
<212> TYPE: PRT
<213> ORGANISM: Alkaliphilus metalliredigens QYMF

<400> SEQUENCE: 14

```
Met Ala His Leu Leu Met Ile Glu Ser Phe Ile Gly Gly Asn Ala Val
1               5                  10                  15

Leu Leu Pro Lys Leu Leu Lys Gln Leu Gly His Thr Tyr Thr Phe Ile
            20                  25                  30

Thr Arg Ser Lys Gly Ile Phe Lys Ser Phe His Ser Asn Glu His
        35                  40                  45

Val Val Ile Gln His Ala Asp Glu Ile Ile Glu Ala Asn Thr Asn Asp
    50                  55                  60

Ala Ser Val Val Leu Asp Thr Ile Leu Gly Lys Lys Phe Asp Gly Val
65                  70                  75                  80

Ile Thr Thr Cys Asp Tyr Tyr Ile Glu Thr Val Val Glu Val Ala Lys
                85                  90                  95

Glu Leu Ser Ile Pro Cys Pro Phe Pro Lys Ala Val Lys Asn Val Arg
            100                 105                 110

Tyr Lys Gln Lys Leu Arg Gln Thr Leu Asp Ala Ala Gly Ile Ser Asn
        115                 120                 125

Pro Gln Tyr Gly Leu Ala Tyr Asn Trp Asp Glu Val Leu Leu Val Ala
    130                 135                 140

Lys Asn Ile Gly Tyr Pro Val Val Leu Lys Pro Val Asp Leu Ser Ser
145                 150                 155                 160

Ser Ala Tyr Val Arg Leu Ile Arg Ser Glu Glu Asp Leu Arg Asp Ala
                165                 170                 175

Tyr His Gln Leu Asn Ala Phe Pro Ile Asn Trp Arg Asp Gln Glu Arg
            180                 185                 190

Asp Cys Thr Tyr Leu Leu Glu Lys Tyr Met Glu Gly Asn Glu Val Ser
        195                 200                 205

Val Glu Ala Val Thr Phe Asn Gly Glu Thr Thr Ile Ile Gly Ile Thr
    210                 215                 220

Gln Lys Ser Leu Met Gly Ala Pro Tyr Phe Ile Glu Asp Ala His Met
225                 230                 235                 240

Phe Pro Ala Asn Ile Ser His Asp Met Lys Leu Lys Ile Ser Gly Tyr
                245                 250                 255

Val Val Lys Ala Leu Gln Ala Ala Gly Tyr Asp Tyr Gly Val Ser His
            260                 265                 270

Thr Glu Val Lys Leu Thr Asp Ala Gly Pro Arg Ile Val Glu Ile Asn
        275                 280                 285
```

```
Pro Arg Val Ala Gly Asp Tyr Ile Ala Glu Ile Ile Lys Leu Val Cys
        290                 295                 300

Asn Val Asp Ile Leu Arg Ala Phe Val Asp Leu Ser Ile Gly Ile Glu
305                 310                 315                 320

Pro Ser Ile Thr Lys Lys Glu Thr Gly Ile Ser Ser Ala Cys Val Arg
                325                 330                 335

Phe Leu Thr Pro His Arg Gly Gly Lys Ile Val Asn Ile Val Gly Val
                340                 345                 350

Asp Thr Leu Ala Ser Asp Ser His Ile Asp Ser Phe Lys Val Glu Asp
                355                 360                 365

Cys Ile Gly Lys Thr Val Gly Asp Pro Ile Asp Asn Ala Gly Arg Ile
        370                 375                 380

Gly Trp Ile Ile Thr Lys Asp Thr Glu Gly Tyr Asn Ala Met Asn Tyr
385                 390                 395                 400

Ala Tyr Glu Ala Met Glu His Ile Lys Leu Thr Phe Glu
                405                 410

<210> SEQ ID NO 15
<211> LENGTH: 1257
<212> TYPE: DNA
<213> ORGANISM: Streptomyces flavogriseus ATCC 33331

<400> SEQUENCE: 15
atggctcatc tgttggtggt cgagagctgg gtcggatcga tgagcagact gctgccgcgg    60
gccctggggg agggaggaca ccacttcacc ttcctcaccc gcgatctgca gcactacctc   120
cgggcggcgc cggagggcac ggaccatccg ctgctcaccg cccgtaacgt cgtcacggcg   180
cccaccaacg acctcggcgc actgcttccg caggtcgagc ggctgcacga ggccctgcgc   240
ttcgacgggg tggtcaccct ctgtgactac tacctgccga ccgccgctcg gatcgcgggc   300
ctgttgggcc tgcccgggcc gtcggccgaa gccatggaga aagcctgccg caaggacgcc   360
acccggcgcg tcctcggcgc cgccggcgtg cccggacccc gcttcgccgt ctgcgcggac   420
ggggcggagg cggccgtggc cgcccacgac ctcggctatc ccctggtcgt caagccggtg   480
gacctctgcg cgggcatgtt cgtgcgccgg tcgacgacg aggaccagct ggccgaggcg   540
tgcgcggctc tcgccgcctt cccgtacaac gccagggac agcggcgtac gccccacgtc   600
ctgctggaga gtaccctccg aggccccgag gtgagcgtcg agaccgtgac ctgcaagggc   660
gtcgcccacg tcgtcggagt caccgacaag agcgtcggcg gggctccggc cttcgtcgag   720
accggtcaca tgttcccggc cgccctctct ccggacgatc tcgccgcagc caccggcacc   780
gcgctgagcg ccggcgcggc gctcggtctc gacgacgtcg tggcgcacac cgagatcaaa   840
ctgaccgagg acggcccag gtggtggag gtcaatcccc gtcccgcggg caatcgcatc   900
accgagctgg tccgccacgt caccgggatc gacctcgccg ccgcctgcgt cgacgtggca   960
ctcggccggg aacccgacct cgcccccgc gacaccggta cgcggagcgc ggccatcgga  1020
ttcctcgtgc ccgccgcgc gggaaccctc gcgtccgtcg agggcgccga ccgtgtccgc  1080
gacgccgacg gtgtgctgga ggtccagacc gcggaaccgg ggcgcacggt cgaggcggcg  1140
gacagcaaca acgcctacct cggccacgtc atggccggcg acgccaccgg actcggcgcg  1200
cgggaccgcg tggagacact gctcgcggaa ctgcgccctc ggctggtgcg ctcatga     1257

<210> SEQ ID NO 16
<211> LENGTH: 418
<212> TYPE: PRT
<213> ORGANISM: Streptomyces flavogriseus ATCC 33331
```

<400> SEQUENCE: 16

```
Met Ala His Leu Leu Val Val Glu Ser Trp Val Gly Ser Met Ser Arg
1               5                   10                  15

Leu Leu Pro Arg Ala Leu Gly Glu Gly Gly His His Phe Thr Phe Leu
            20                  25                  30

Thr Arg Asp Leu Gln His Tyr Leu Arg Ala Ala Pro Glu Gly Thr Asp
        35                  40                  45

His Pro Leu Leu Thr Ala Arg Asn Val Val Thr Ala Pro Thr Asn Asp
    50                  55                  60

Leu Gly Ala Leu Leu Pro Gln Val Glu Arg Leu His Glu Ala Leu Arg
65                  70                  75                  80

Phe Asp Gly Val Val Thr Ser Cys Asp Tyr Tyr Leu Pro Thr Ala Ala
                85                  90                  95

Arg Ile Ala Gly Leu Leu Gly Leu Pro Gly Pro Ser Ala Glu Ala Met
            100                 105                 110

Glu Lys Ala Cys Arg Lys Asp Ala Thr Arg Arg Val Leu Gly Ala Ala
        115                 120                 125

Gly Val Pro Gly Pro Arg Phe Ala Val Cys Ala Asp Gly Ala Glu Ala
    130                 135                 140

Ala Val Ala Ala His Asp Leu Gly Tyr Pro Leu Val Val Lys Pro Val
145                 150                 155                 160

Asp Leu Cys Ala Gly Met Phe Val Arg Arg Val Asp Asp Glu Asp Gln
                165                 170                 175

Leu Ala Glu Ala Cys Ala Ala Leu Ala Ala Phe Pro Tyr Asn Ala Arg
            180                 185                 190

Gly Gln Arg Arg Thr Pro His Val Leu Leu Glu Glu Tyr Leu Arg Gly
        195                 200                 205

Pro Glu Val Ser Val Glu Thr Val Thr Cys Lys Gly Val Ala His Val
    210                 215                 220

Val Gly Val Thr Asp Lys Ser Val Gly Gly Ala Pro Ala Phe Val Glu
225                 230                 235                 240

Thr Gly His Met Phe Pro Ala Ala Leu Ser Pro Asp Asp Leu Ala Ala
                245                 250                 255

Ala Thr Gly Thr Ala Leu Ser Ala Gly Ala Ala Leu Gly Leu Asp Asp
            260                 265                 270

Val Val Ala His Thr Glu Ile Lys Leu Thr Glu Asp Gly Pro Arg Val
        275                 280                 285

Val Glu Val Asn Pro Arg Pro Ala Gly Asn Arg Ile Thr Glu Leu Val
    290                 295                 300

Arg His Val Thr Gly Ile Asp Leu Ala Ala Ala Cys Val Asp Val Ala
305                 310                 315                 320

Leu Gly Arg Glu Pro Asp Leu Arg Pro Arg Asp Thr Gly Thr Arg Ser
                325                 330                 335

Ala Ala Ile Gly Phe Leu Val Pro Gly Arg Ala Gly Thr Leu Ala Ser
            340                 345                 350

Val Glu Gly Ala Asp Arg Val Arg Asp Ala Asp Gly Val Leu Glu Val
        355                 360                 365

Gln Thr Ala Glu Pro Gly Arg Thr Val Glu Ala Ala Asp Ser Asn Asn
    370                 375                 380

Ala Tyr Leu Gly His Val Met Ala Gly Asp Ala Thr Gly Leu Gly Ala
385                 390                 395                 400

Arg Asp Arg Val Glu Thr Leu Leu Ala Glu Leu Arg Pro Arg Leu Val
```

Arg Ser

<210> SEQ ID NO 17
<211> LENGTH: 1182
<212> TYPE: DNA
<213> ORGANISM: Bacillus mycoides Rock3-17

<400> SEQUENCE: 17

```
atgttagctt taaataaagc taaattatat ggttttttcac ctgtttttat tactaataat    60
ccagatcgat atgttggtct ggaaaaggca gaatgttcaa tattcatctg tgatacgaat   120
aacattgaaa atttatacga aactataaat aataatttag aagtagataa aattcaaggt   180
attactacca ctagtgaatt ttatttagaa attgtatctg aattagcgcg taaatatggt   240
ctacctagga attctgtaca agcgatacgt aactgtcgaa ataagctaga aacaagaaat   300
tgtttaaaag aggctaaagt tagacaacca aagtttgaag aagttacttc tatttcagat   360
ataaataaat ctcttaatat tattggtctt ccttgtattg taaagccagt tgatgatagt   420
ggttcaaatg gagtgcgatt ttgtaaaact gttgcagagg ttaaagagca aactttagaa   480
atttatcat ggaaaaagaa ttcccgtgga caatcaacag tacagacagt ccttttagaa   540
gaatttattg atgctccaga gtatagtgtt gaaatatttt cttttgaggg aaagggaaaa   600
tgtgttggta ttactgaaaa aaaattgata ggatttccac actttgtgga gcatcaacat   660
gtatttccag caaaattacc agctgatgtt actcgggaaa ttcaaaacac tgtagaagat   720
gcacttaaag cagtagggat aactaatgga ccgactcata cagaggttaa gcttactcct   780
cagggttgcg ctattataga aattaatgca aggcttgctg gaggaatgat acccaaactt   840
attcaaattt ctacaggaat tgatatgtta gaatatcaac tcctattgtc agtagggaaa   900
tataaagcac aatattaaa ttatcagaga tatgctggaa ttaaatttat agtttctaat   960
ttagatggaa tattgaatga cattagaggt gttgaaaaag ttagaacact tcaaggtgtc  1020
aaccaagtca atattaatgt taatcgaggg gataaggtta tctcaccaaa aaatgcttat  1080
gatcgactag gctatgtaat tgttgaagga aattcgtatg aagaaacgga agcacgactt  1140
aataaatcta tagaaaaact agaaatattg gtgggaaatt aa                     1182
```

<210> SEQ ID NO 18
<211> LENGTH: 393
<212> TYPE: PRT
<213> ORGANISM: Bacillus mycoides Rock3-17

<400> SEQUENCE: 18

```
Met Leu Ala Leu Asn Lys Ala Lys Leu Tyr Gly Phe Ser Pro Val Phe
1               5                   10                  15

Ile Thr Asn Asn Pro Asp Arg Tyr Val Gly Leu Glu Lys Ala Glu Cys
                20                  25                  30

Ser Ile Phe Ile Cys Asp Thr Asn Asn Ile Glu Asn Leu Tyr Glu Thr
            35                  40                  45

Ile Asn Asn Asn Leu Glu Val Asp Lys Ile Gln Gly Ile Thr Thr Thr
        50                  55                  60

Ser Glu Phe Tyr Leu Glu Ile Val Ser Glu Leu Ala Arg Lys Tyr Gly
65                  70                  75                  80

Leu Pro Arg Asn Ser Val Gln Ala Ile Arg Asn Cys Arg Asn Lys Leu
                85                  90                  95

Glu Thr Arg Asn Cys Leu Lys Glu Ala Lys Val Arg Gln Pro Lys Phe
```

100                 105                 110
Glu Glu Val Thr Ser Ile Ser Asp Ile Asn Lys Ser Leu Asn Ile Ile
                115                 120                 125
Gly Leu Pro Cys Ile Val Lys Pro Val Asp Asp Ser Gly Ser Asn Gly
            130                 135                 140
Val Arg Phe Cys Lys Thr Val Ala Glu Val Lys Glu Gln Thr Leu Glu
145                 150                 155                 160
Ile Leu Ser Trp Lys Lys Asn Ser Arg Gly Gln Ser Thr Val Gln Thr
                165                 170                 175
Val Leu Leu Glu Glu Phe Ile Asp Ala Pro Glu Tyr Ser Val Glu Ile
            180                 185                 190
Phe Ser Phe Glu Gly Lys Gly Lys Cys Val Gly Ile Thr Glu Lys Lys
                195                 200                 205
Leu Ile Gly Phe Pro His Phe Val Glu His Gln His Val Phe Pro Ala
            210                 215                 220
Lys Leu Pro Ala Asp Val Thr Arg Glu Ile Gln Asn Thr Val Glu Asp
225                 230                 235                 240
Ala Leu Lys Ala Val Gly Ile Thr Asn Gly Pro Thr His Thr Glu Val
                245                 250                 255
Lys Leu Thr Pro Gln Gly Cys Ala Ile Ile Glu Ile Asn Ala Arg Leu
                260                 265                 270
Ala Gly Gly Met Ile Pro Lys Leu Ile Gln Ile Ser Thr Gly Ile Asp
                275                 280                 285
Met Leu Glu Tyr Gln Leu Leu Leu Ser Val Gly Lys Tyr Lys Ala Pro
            290                 295                 300
Ile Leu Asn Tyr Gln Arg Tyr Ala Gly Ile Lys Phe Ile Val Ser Asn
305                 310                 315                 320
Leu Asp Gly Ile Leu Asn Asp Ile Arg Gly Val Glu Lys Val Arg Thr
                325                 330                 335
Leu Gln Gly Val Asn Gln Val Asn Ile Asn Val Asn Arg Gly Asp Lys
            340                 345                 350
Val Ile Ser Pro Lys Asn Ala Tyr Asp Arg Leu Gly Tyr Val Ile Val
                355                 360                 365
Glu Gly Asn Ser Tyr Glu Glu Thr Glu Ala Arg Leu Asn Lys Ser Ile
            370                 375                 380
Glu Lys Leu Glu Ile Leu Val Gly Asn
385                 390

<210> SEQ ID NO 19
<211> LENGTH: 1344
<212> TYPE: DNA
<213> ORGANISM: Artificial Sequence
<220> FEATURE:
<223> OTHER INFORMATION: XbaI-EcoRI fragment harboring BBR47_51900

<400> SEQUENCE: 19
tctagaaata attttgttta actttaagaa ggagatatac catgggcagc agccatcatc      60
atcatcatca cagcagcggc catatgaaca aacactttct gttcgttgaa gcgaatacga     120
cggggacagg tatgctcgct atgaaaaagg cgcgtaaatt ggggtttaca cccgtatttt     180
tcacagagaa gcctgaacgt taccacggtt tgaatgagtt ggaatgtcat gtagtcgtga     240
cagacacgaa ctcccaggca gagctgactg acagtgtagc acaagtgagt aaggaaggca     300
gagagatagc cggaatcatg tcgacaagcg actattacct cgaatcggtt gccaagctgg     360
cccggaaatt cggttggata agcaattcgc tggaggcaat tgaggcctgc cgcaataaag     420

| cgatatttcg cgagaagctt cagcgccatc aagtgtctca gcctacattt ttggcaataa | 480 |
| gctctatgga gcaattgctg gaagcgcgct cttccatttc tctgccctgc gtggtgaagc | 540 |
| ccgctgacga tagcgggtcc aataacgtgc ggctgtgctt tagctgggat gaagtggagc | 600 |
| acatggcagc ggaaatcctt gccatcaagt acaatgcgcg cggtcaggaa acagctcgga | 660 |
| cagttcttct cgagcagtat gccgagggcc ctgaatttag cgtggagacg ttttcatggc | 720 |
| aagggcaatg ctttgttatc ggcattaccc agaaacggtt aacggatat ccattttcg | 780 |
| tggaagcagg gcatattttc cctgcaccgt tgtccgtaga agagaaacag gagatcgagc | 840 |
| gaacagtgga acgcgcatta gcggcggtga agtaccagtt cggtgctgcc catacggaag | 900 |
| tgaagtggac atcagcaggt tgtgttgtca tcgaagtcaa cgcacgcctt gccggaggaa | 960 |
| tgattccaga gctggttcgc cgatccacgg ggattgatct gcttttgcaa cagattcggt | 1020 |
| gtgcggctgg acttgagcca gaattgtctc aaaccatcga agagcaacgc tgtgcaggca | 1080 |
| ttcattttct cgtgtctgag agtcagggca cctttggcgg gataaaggga atggataccg | 1140 |
| ttcgcaacct gccggggatt gctgaagtgg cgattcatgc gaaaatcgga caaaacgtcc | 1200 |
| agcctccgca aaattttccg catcgtctcg gctatgtcat cgtggaaggc aagcattaca | 1260 |
| gtgagaccgc tgagttgatc gagcaggtga agacagcct gagtgtacaa gtaggtcaac | 1320 |
| aattggagag tggggtatga attc | 1344 |

<210> SEQ ID NO 20
<211> LENGTH: 1341
<212> TYPE: DNA
<213> ORGANISM: Artificial Sequence
<220> FEATURE:
<223> OTHER INFORMATION: XbaI-EcoRI fragment harboring Staur_4851

<400> SEQUENCE: 20

| tctagaaata attttgttta actttaagaa ggagatatac catgggcagc agccatcatc | 60 |
| atcatcatca cagcagcggc catatgaatc aattcgtttt cgtcgagagc aacaccacgg | 120 |
| ggacgggccg gctggccgtg gagcggctgc tgggcccaggg cgagcaggtg acgttcatca | 180 |
| cccaccagcc agagaagtac cccttcctgg tgggcaacaa ggccccgggg ctgaaggtgt | 240 |
| tgaaggtgga gaccaacgac gcggcggccg tggaggcctg tgtcgatggg ctggtgcggg | 300 |
| aggggaaggt ggcggcgctg ctcaccttct ccaccttcta tgtgcccacg gtggcggcca | 360 |
| tcgcggcgcg gcacggcctg cgctacctcc agcctcgcgc ggcccaggct tgccacaaca | 420 |
| agcacgaggc gcgggccctg ctgcgcgcgg cggggctgcc cgggcctgag ttccacgtca | 480 |
| tcgcctccga ggccgaggcg gcgcagctcg cccagacggt gcgctttccg tgtgtggtga | 540 |
| agcctcccgc cgagagcggc agcacggggg tgcggcgggt ggacacaccc gaggagctgc | 600 |
| tcgcgcactt ccgctcccctg cactcccgcg ccgccaacga gcgcggccag tccttgcacg | 660 |
| gggaagtgct cgtggagtca ttcctggagg ggccggagtt cagcgtggag acgatgacgc | 720 |
| tggccgatgg caccacgcac gtgctcgggg tgacccagaa gtacctctcc gcgccgccgt | 780 |
| acttcgtgga gatggggcat gacttcccgg cggacctgcc gcccgagcgg cggcgggcgc | 840 |
| tggaggaggc cgtgctcgcg gggctcgcgg cggtgggctt tgacttcggc ccggcccaca | 900 |
| cggagatccg cttcacgccc gcggggccgg tcatcatcga gatcaacccc cggctggcgg | 960 |
| gagggatgat tccggagctg gtgcggctgt ccaccgcgt ggatctgctc tcggcgatgc | 1020 |
| tggatcaaat gctggggcgg cccgtggacc tgacgcacac gcgccaggat gtggcctgta | 1080 |

| | |
|---|---:|
| tccgcttcat cacctcggag cgtcccggcg tgctggcgcg cgtggagggc caggacgagg | 1140 |
| cctcccggct gggcaccgtc cggcaggtgg ccgtggacaa ggcggcgggg acccggctgc | 1200 |
| gcccgcccga gagcgcgacg gaccggctgg gctatgtcat cgccagcggg cccgagcgcg | 1260 |
| gacaggtgct tggcgacgcg gcgcgcgcgc tgtcgctgct ccgggtcgag caagccgcgc | 1320 |
| cctcggcccc ggcgtgaatt c | 1341 |

<210> SEQ ID NO 21
<211> LENGTH: 1311
<212> TYPE: DNA
<213> ORGANISM: Artificial Sequence
<220> FEATURE:
<223> OTHER INFORMATION: XbaI-EcoRI fragment harboring DES

<400> SEQUENCE: 21

| | |
|---|---:|
| tctagaaata attttgttta actttaagaa ggagatatac catgggcagc agccatcatc | 60 |
| atcatcatca gcagcggc catatgaaaa agctgttatt cgtggaaggt aataccaccg | 120 |
| gcaccggcat tttagcactg gaaaaagcgc gcaaactggg ttatgaaccg gttttttctga | 180 |
| cccaagaagc gtcccgctac gacggtttac cggaggccaa atgtcgtgtc catgtgaccg | 240 |
| tgactgatag catccatgag ctgaaacgct gcgtttcaca ggaaaaagcg gaagccgtcg | 300 |
| cgggcattct gaccacctcg gattactatc tggaaatcag cgcaaagctg gtacaggaac | 360 |
| tgggtctgac gggcaattcc ccgcaggcca ttcatctgtg ccgtaacaaa gcgctgtatc | 420 |
| gcgaaaaatt acgtagcaaa tccgttccgc agccgaactt ccacatcatt cgttcaatgg | 480 |
| aagacctgcg cgagacccgt gagagcgttc ctctgccgtg tctggtgaaa ccggcggatg | 540 |
| attcaggttc caataatgtg cgcttatgct tttcctgggg tgaagtcgaa caactgacct | 600 |
| cgaaaatttt aaagattgaa cgcaacgcgc gcggccagaa aacgagccaa acggtattat | 660 |
| tagaagagta tattgaaggc cctgaatatt ccgtcgaaat gttcagctgg cagggtaaga | 720 |
| gcacctgcat tggcattacc gaaaagcagc tgaccggtta cccttacttc gtggagagcg | 780 |
| gccatgtatt tccggcggtt ttaccgaccg acgtacaaca ggagatcgaa aagaccgtta | 840 |
| aacagtcact ggaagcggtt catttccagt ttggcgcaag tcattcagag gtcaaatgga | 900 |
| cgcctaacgg ttgcgttatg atcgaaacga atgcgcgtct ggcaggcggc atgattccgg | 960 |
| agttagtacg ccattcaacc ggcgttgatc tgattgagca gcagattta tgcgcggcag | 1020 |
| gtgtggcgcc gcattggaag caagtggtcc cgacgggctg ctcaggcatc cactttatcg | 1080 |
| tagccgcgga ggcgggccgc ttatcctcgg tggataactt agaagccgtc cgtaaactgc | 1140 |
| cgggtgttga agaaatgatg gtgaaagcgc aagttggtca ggcggtccaa ccgcctaaga | 1200 |
| atttcagcga ccgcctgggt cacgttattg tgagcggcaa aagttacgaa gaagtcgttg | 1260 |
| aacgtttaca caaaattagt aatatgatca gtttaaaaat ttcttgaatt c | 1311 |

<210> SEQ ID NO 22
<211> LENGTH: 2772
<212> TYPE: DNA
<213> ORGANISM: Artificial Sequence
<220> FEATURE:
<223> OTHER INFORMATION: XbaI-EcoRI fragment harboring BUR

<400> SEQUENCE: 22

| | |
|---|---:|
| tctagaaata attttgttta actttaagaa ggagatatac catgggcagc agccatcatc | 60 |
| atcatcatca gcagcggc catatgaaga cctttgtttt tatcgagagc aacacgactg | 120 |
| gcaccggtcg cttatgtctg caaaaggcac tgttacgtgg ttttgatgtg ttattcgtga | 180 |

```
cgtctcgccc tcagctgtac ccgtttctgc aggaagaaat ggtggtgccg ctggttgccg    240
ataccgccga tccgcagcgc attgcggatg cactggcacc gtacgccggc attgcgggta    300
tcttttccac ttcagaatat tatatcgaaa cggcggccac ggtagcgacc cgcctgggtt    360
taccggccgc ggacccggaa gcaatccgca cctgccgcga taaaggccgt ctgcaccgcc    420
gcctgcgcga tgcaggtgtc ggtgtggcag atacggaaat tgtgagcgaa cgcacccagc    480
tgcgcgacct ggcgcacggc gcaacctatc cgcgcgtcct gaaaccggcc ttcggcagcg    540
gcagtgtggg cgtacgtctg gtccgcaccc cggcggaaat gttagcgcat ggtgaacgca    600
tgttagacgc ccgtggcaac gagcgtggta ttgcgttagc acgccaggtc ctggtccaaa    660
gttttgttga cggcccggag ttttccgtgg aagtagttgg cctgggcgcc gagcatggtc    720
atgcagttct gggtgttacg ggtaaacact taggcccgtt accgcatttc gtcgaagccg    780
gtcatgactt cccggccccg attgcagcgg cccagcgcga cgcgattgta gcggagacgt    840
tacgtgcgtt agatgcggta ggtcatcgct tcggcccggc gcacgtcgag tgccgtgtat    900
caggtggtaa agttgtagtg attgaaatta accctcgcct ggccggcggc atgatccctc    960
aggccattga atgggcgacc ggcgtcgatg tgctgggcgc aatgattgat ctgcatgcag   1020
gcactccgcc ggacctgggt cctcgtcgtc gcggtcatgc ggcgattcgc ttcgttctgc   1080
cggcgcgtag cggcgaatta cgtgcactgt catttgagcc ggatgaacgt ttcgcgggcg   1140
tgcgtactcg cttcatgccg ctgaaacaac tgggtcagcg tatcgaaccg gcgggcgact   1200
tccgcgatcg tctggccctg gttattgcaa gcgcggccga cccggatgcc ttagcccacg   1260
ccttagaaga tgtcgaccgt tgtgttaccg tagccattgg cgacgcgggc gcggccggtg   1320
aaggcgcggg cgcaggccgc ctgcgccgca ctctgcatcc ggaagccctg gcgattgtcc   1380
gcaaacctgc gccgcgcgcg gaacgcttag cggaactgga tgcctttgcg gcgatcgacg   1440
aagcacacct gctgatgctg gtggacgcag gcatctgcga tcgcgcccgt gcggcgactg   1500
tgctggcaga attagcccgc caacgtgatg cgaagttcgc agcgattgca gacgccattg   1560
cgcctcgtgg tacctacgcc ctgtacgaac agttattaat cgagcgcgta ggcattgatg   1620
caggtggcgc agtgcatacc gcgcgttcgc gtaacgatat taatgcgtgc gtggcgaagc   1680
tgcgcgcccg tgagtggttt gatacctgcg gtggcaagct gtggcgtgta cgcgcagcaa   1740
ttgttgacaa agcgcagcac acgctggact ggccgctgcc gacctatagt cagtaccagg   1800
cggcccaacc tggcagcttc ggctactact tatggtcggt ggaaactgca ttacgccgtg   1860
atcaagcggc gctggagcgt ctggacgaag aattagccgt ttgtccgctg ggtgccggcg   1920
cgggcgcggg taccgatttc cctattcgcc ctggcgtaag cgccgcgtta ttaggctttg   1980
cacgctcctt tgatagcgcg ttagacgccg tggcctcacg cgatctggtc ctgcacttcc   2040
tggcggcgat cgccattgcc agcactactc tgagccgtct ggcccatgac ctgcaactgt   2100
ggactatgcg cgagactgat ttttagcgc tgccggacga gctgtctggc ggctcttcgc   2160
tgatgccgca gaaaaaaaac ccttacctgc tggaaattgt caaaggcaaa ctggcccatg   2220
ttgcaggtgc actgaatgcc gccgtcttcg cgagccagcg cacgccgttt tctaacagcg   2280
tagaaattgg caccgaaatg ctggcgcctt gcgccgatcg cgttcaggcg tttggcgagt   2340
cttgcgatct gctgcgtctg atggtgagcg tgtcaccgg cgatcctgcg aagatgcgtg   2400
cagccgcgga agcggtctg gtgagcgcca ctcaggttgc gaatgcgtta gttcgtgaaa   2460
cggatatttc gtttcacgcc gcgcatcgtc agatcggtgc gctgattacc caagccttag   2520
```

| | |
|---|---|
| atgcccatga ggacccggcg gcagccttag acgcgttagt tcgccagccg ggcgcctcaa | 2580 |
| ttgatgaagc ggcggcgcgt ctggcctatg gcggtggtcc tggtgccgcg ggcgccggcc | 2640 |
| tggcccgcag ccgcgccctg ctgcgtcaga gcgcagaacg cctgtggcgt cgtcgtgcgg | 2700 |
| catggcacgc cgcacacgca cgccgtcgtg gctgcgtggc agatctgctg gcggcagccg | 2760 |
| cggcctgaat tc | 2772 |

<210> SEQ ID NO 23
<211> LENGTH: 1269
<212> TYPE: DNA
<213> ORGANISM: Artificial Sequence
<220> FEATURE:
<223> OTHER INFORMATION: XbaI-EcoRI fragment harboring BCE

<400> SEQUENCE: 23

| | |
|---|---|
| tctagaaata attttgttta actttaagaa ggagatatac catgggcagc agccatcatc | 60 |
| atcatcatca cagcagcggc catatgctgg ccatccgtaa agcgaaagaa ctgggttacg | 120 |
| agccgatctt tttaacgcag aagaaatctc tgtatcacgg cttatccgat ctggagtgtc | 180 |
| gtgtaattga gttagatact aactccgtgg atgccattaa gcattacatt attcacgaaa | 240 |
| aaattgaaga cattgcaggc attctgacca ccagcgatta ttatctggaa accgtggcgg | 300 |
| agctggtgca gatgtttcgt ctgagcggca tacccacca ggccatctat tactgtcgta | 360 |
| ataaagccat gttccgcgaa aaattacacc tggaaaaagt actgcagccg aagttccata | 420 |
| ttgtccaaag cattgattcg ctgcagaata tctatagttc tatccagttt ccgtgcgtgg | 480 |
| ttaagccggc ggatgactca ggttcaaaca acgtgcgtct gtgctcgaat gggaagaag | 540 |
| tggaaaaaat cgccaccaaa attctggcaa acaagtataa tgcgcgcggt caagagaaag | 600 |
| ccaacatggt gctgctggaa gaatatatcg aaggtccgga atatagtgtg agatgtttta | 660 |
| gttgggaagg caattcaatc tgcatcggca ttaccgaaaa acagctgacc ggctttccgt | 720 |
| actttgtgga aagcggccat attttccegg tggaactgcc gaaggacgtc cagagcgaga | 780 |
| ttgagcagac ggtgaaatgc gcgctgcagg cggtggattt tcgtttcggt gcaagccatt | 840 |
| cagaagtgaa atggacctcg aacggttgtg tggtcattga agtcaatgcg cgcctggccg | 900 |
| gcggcatgat tccggaactg gtgcgccatt cgacgggcgt agacctgctg cgccagcagg | 960 |
| tgttatcctc tgtgggcgtg gcacctgaat ggaaagagat tgaatatatg aactacgcag | 1020 |
| gcatccattt tctgaccgcg aaaaaaagcg gcttcttatc aaccgtgaaa ggtatcgaag | 1080 |
| aagtccgcga actgtcgtat attgaagaac tggtggtcaa ggcccaggtc ggccagccgg | 1140 |
| ttaatccgcc ggaaaacttt agccatcgcc tgggtcatgt gatggtgcgc ggccgtacgt | 1200 |
| atgaagaaac cgtgctgttc ctggaggaag tcgcgaaaaa actggaaatc caggtaaaca | 1260 |
| actgaattc | 1269 |

<210> SEQ ID NO 24
<211> LENGTH: 1341
<212> TYPE: DNA
<213> ORGANISM: Artificial Sequence
<220> FEATURE:
<223> OTHER INFORMATION: XbaI-EcoRI fragment harboring BTH

<400> SEQUENCE: 24

| | |
|---|---|
| tctagaaata attttgttta actttaagaa ggagatatac catgggcagc agccatcatc | 60 |
| atcatcatca cagcagcggc catatgaaaa aactgctgtt tattgaaagc aataccactg | 120 |
| gtactggcat gctggcatta attaaagccc gcgagctggg cttcacgccg gtcctgctga | 180 |

```
ccaataatcc gggccgttat attggtttag gcgaaaccaa atgcattgtt ctggagtgcg      240
ataccaacaa cttaaactgt atccgcacta tcatcgatag tgagttcgaa gtgggcgaga      300
tcaaggccat cacgactacc tccgaattt acattgaggt ggtggccatc ctggcaaagg      360
aactgggctt aatcggcaat ccgattgata ccgtgaagaa atgtcgtaac aaagcggaaa      420
tgcgtctgct gctgaagggc atcgagaaca tctacgagcc gtggttctat attatcgatt      480
cactggagaa gttagaatta gcgaaagaca acatcaaatt tccgtgtgtg gttaagccgg      540
tggatgattc cggttcaaat aacgtgctga atgttactc ttacgaagaa gtcaaacgtc      600
acaccgagaa gatcctgagc aataagtata acgtccgcag ccagaaaaat gcgcagaaca      660
ttttagtaga agaatacgtg tcaggtcagg aatactcggt tgaaatcttt acgtataatg      720
gcaaatgcaa aatcgtgggt gtaacccaga aaatcgtgga tggcgccccg tacttcattg      780
aatgtggcca tattttcccg gccccggtta gcgacgatat ccgtagcgtg attgaacgcg      840
gcgtgacgaa aattattgaa aaagtcaatt ggcagaacgg cccgtgccac ctggaaatta      900
aaattaaggg cgaaaaaatt tttctggtag agtttaatgg tcgcctggcg ggcggtatga      960
ttccggaatt aatcaaatat gcaaccggta tcgatctgtt aaaagagcag ttaaaagttg     1020
tgacccgtat gcgtccgaag ctggatcaaa acccgaccct gtacgcgggc attcgcttta     1080
ttatcccgct gcgtgatggc aaaatcacgt ctattttttgg tgtcaacgac attgaaaata     1140
ctgtgggtat taagaggta aaactgcgca cgatcgttgg cgaatctatt cgtaaagttg     1200
aaaacgccta tggtcgcatt ggtcatatca ttggcgcagc cgaaaatatc aacaaactga     1260
actatatttt agataagagc atggacgccc tgcacattga aattgaagaa tgcgaggatt     1320
atgaggactt taattgaatt c                                                1341
```

<210> SEQ ID NO 25
<211> LENGTH: 1329
<212> TYPE: DNA
<213> ORGANISM: Artificial Sequence
<220> FEATURE:
<223> OTHER INFORMATION: XbaI-EcoRI fragment harboring AME

<400> SEQUENCE: 25

```
tctagaaata atttgtttta actttaagaa ggagatatac catgggcagc agccatcatc       60
atcatcatca cagcagcggc catatggccc acctgctgat gatcgaaagc ttcattggcg      120
gtaatgccgt attactgcct aagctgttaa aacagctggg ccatacgtac acctttatca      180
cccgttcaaa aggcattttc aaatcctcat ttcatagcaa cgaacacgta gtaattcagc      240
atgcggatga aatcattgaa gcgaacacga atgacgcaag tgttgttctg acaccatttt      300
taggcaaaaa gtttgacggc gttattacca cctgcgatta ttacattgaa acggtggtgg      360
aagttgcaaa agaactgagt atcccgtgtc cgttcccgaa ggcggttaag aatgtacgtt      420
ataaacaaaa actgcgtcag acgctggatg cagcgggtat ctctaacccg cagtatggtc      480
tggcgtataa ttgggatgaa gtcctgctgg ttgcgaaaaa tatcggctat ccggttgtgc      540
tgaagccggt ggacttaagc agcagtgcct acgtgcgctt aattcgcagt gaggaagacc      600
tgcgcgacgc gtaccaccag ttaaacgcct tcccgattaa ttggcgcgat caggaacgtg      660
attgcacgta cttattagag aaatacatgg agggcaacga ggtttcggtg aagcggtta      720 cgtttaacgg cgaaacgacc attattgca tcacccaaaa gtcgctgatg ggcgccccgt      780 atttttattga agacgcgcac atgttcccgg caaatattag ccatgatatg aaattaagga     840
```

```
tctcgggtta tgtggtcaaa gccctgcagg ccgcgggcta cgattacggc gtctcgcata    900
ccgaagttaa actgaccgat gcgggtccgc gcatcgtgga aatcaaccct cgcgtagcgg    960
gtgattacat tgcggaaatt atcaagttag tgtgtaatgt agatattctg cgtgcgtttg   1020
tagatctgtc gatcggtatc gagccgagta tcacgaaaaa ggaaaccggt atcagcagcg   1080
catgtgttcg ttttctgacc ccgcatcgtg gtggtaaaat tgtgaacatc gtaggcgttg   1140
atactttagc gagtgactcc catatcgata gcttcaaagt ggaggattgc attggcaaga   1200
cggtgggtga tcctattgac aacgccggtc gtattggctg gattattacg aaagatactg   1260
aaggttacaa cgcgatgaat tacgcgtatg aagcaatgga acacattaag ctgacgtttg   1320
aatgaattc                                                           1329
```

<210> SEQ ID NO 26
<211> LENGTH: 1302
<212> TYPE: DNA
<213> ORGANISM: Artificial Sequence
<220> FEATURE:
<223> OTHER INFORMATION: XbaI-EcoRI fragment harboring SFL

<400> SEQUENCE: 26

```
tctagaaata attttgttta actttaagaa ggagatatac catggcacac ctgctggtag     60
tagaatcatg ggtaggtagc atgtcgcgcc tgttaccgcg tgccctgggc gagggcggcc    120
atcacttcac ctttctgacg cgcgatctgc agcactatct gcgtgcgcg ccggaaggca    180 cggaccaccc tctgctgact gcacgcaacg ttgttactgc gccgactaat gatctgggcg    240
cgctgctgcc gcaggtggaa cgtctgcacg aggcgttacg ttttgacggc gtagttacgt    300
cgtgcgacta ttacctgccg accgccgcgc gcattgcagg cctgctgggc ctgccgggcc    360
ctagtgcgga agcgatggaa aaagcgtgcc gcaaagacgc aacccgccgc gttctgggtg    420
cagccggtgt tccgggtccg cgcttcgccg tttgcgccga cggtgccgaa gcggcggtgg    480
cggcgcacga tctgggctac ccgctggtgg tgaaaccggt tgatctgtgc gcgggcatgt    540
tcgtgcgtcg cgtggatgat gaagaccagc tggccgaagc atgcgcggcg ctggcggcgt    600
tcccgtataa tgcccgcggt cagcgccgca cgccgcacgt gttactggaa gaatatctgc    660
gcggccctga agtttctgta gaaacggtta cttgtaaagg tgtggcccat gtagtgggtg    720
tgaccgataa aagcgtgggc ggcgcaccgg cctttgtgga aacgggccac atgtttccgg    780
ccgcactgtc cccggatgac ctggcggccg caaccggcac ggcgttatct gccggcgccg    840
cgctgggtct ggacgacgta gtagcgcaca ccgaaattaa gctgactgaa gatgcccgc    900 gcgttgtgga agtgaacccg cgtccggcag gtaatcgtat taccgaactg gtgcgccacg    960
ttacgggtat cgacctggcg gcggcctgtg tcgacgtggc actgggccgt gaacctgact   1020
tacgcccgcg tgacaccggc acgcgctcgg cggcgattgg ttttctggtc ccgggccgcg   1080
ccggcacttt agcgagtgtg gaaggcgcgg accgcgtccg cgacgccgat ggcgtgttag   1140
aagtgcaaac cgcggaaccg ggtcgcaccg tggaagcggc ggatagcaac aatgcgtacc   1200
tgggccatgt tatggcaggt gacgccacgg gcctgggcgc acgcgaccgc gtagagaccc   1260
tgctggccga actgcgtccg cgcctggttc gcagttgaat tc                     1302
```

<210> SEQ ID NO 27
<211> LENGTH: 1269
<212> TYPE: DNA
<213> ORGANISM: Artificial Sequence
<220> FEATURE:
<223> OTHER INFORMATION: XbaI-EcoRI fragment harboring BMY

<400> SEQUENCE: 27

```
tctagaaata attttgttta actttaagaa ggagatatac catgggcagc agccatcatc    60
atcatcatca cagcagcggc catatgttag cttttaaataa agctaaatta tatggttttt   120
cacctgtttt tattactaat aatccagatc gatatgttgg tctggaaaag gcagaatgtt   180
caatattcat ctgtgatacg aataacattg aaaatttata cgaaactata aataataatt   240
tagaagtaga taaaattcaa ggtattacta ccactagtga atttatttta gaaattgtat   300
ctgaattagc gcgtaaatat ggtctacctc gcaattctgt acaagcgata cgtaactgtc   360
gaaataagct agaaacacgc aattgtttaa aagaggctaa agttcgccaa ccaaagtttg   420
aagaagttac ttctatttca gatataaata aatctcttaa tattattggt cttccttgta   480
ttgtaaagcc agttgatgat agtggttcaa atggagtgcg attttgtaaa actgttgcag   540
aggttaaaga gcaaacttta gaaattttat catggaaaaa gaactcccgt ggacaatcaa   600
cagtacagac agtcctttta gaagaattta ttgatgctcc agagtatagt gttgaaatat   660
tttcttttga gggaaaggga aaatgtgttg gtattactga aaaaaaattg ataggatttc   720
cacactttgt ggagcatcaa catgtatttc cagcaaaatt accagctgat gttactcggg   780
aaattcaaaa cactgtagaa gatgcactta aagcagtagg gataactaat ggaccgactc   840
atacagaggt taagcttact cctcagggtt gcgctattat agaaattaat gcacgccttg   900
ctggaggaat gatacccaaa cttattcaaa tttctacagg aattgatatg ttagaatatc   960
aactcctatt gtcagtaggg aaatataaag caccaatatt aaattatcag cgctatgctg  1020
gaattaaatt tatagtttct aatttagatg gaatattgaa tgacattcgc ggtgttgaaa  1080
aagttcgcac acttcaaggt gtcaaccaag tcaatattaa tgttaatcga ggggataagg  1140
ttatctcacc aaaaaatgct tatgatcgac taggctatgt aattgttgaa ggaaattcgt  1200
atgaagaaac ggaagcacga cttaataaat ctatagaaaa actagaaata ttggtgggaa  1260
attgaattc                                                          1269
```

<210> SEQ ID NO 28
<211> LENGTH: 72
<212> TYPE: DNA
<213> ORGANISM: Artificial Sequence
<220> FEATURE:
<223> OTHER INFORMATION: Synthetic Primer P1

<400> SEQUENCE: 28

```
ttcccggtca ggttaaggaa accggctacg ctactggtga gcggcgctca agttagtata    60
aaaaagctga ac                                                        72
```

<210> SEQ ID NO 29
<211> LENGTH: 72
<212> TYPE: DNA
<213> ORGANISM: Artificial Sequence
<220> FEATURE:
<223> OTHER INFORMATION: Synthetic Primer P2

<400> SEQUENCE: 29

```
cgttgccagc aatatccctt ctgacattgt accgaactgc acggtgaagc ctgctttttt    60
atactaagtt gg                                                        72
```

<210> SEQ ID NO 30
<211> LENGTH: 72
<212> TYPE: DNA

```
<213> ORGANISM: Artificial Sequence
<220> FEATURE:
<223> OTHER INFORMATION: Synthetic Primer P3

<400> SEQUENCE: 30
gcactgccgc taattgctga acagttgcag ggtcgccgct cagctgaagc ctgctttttt      60
atactaagtt gg                                                          72

<210> SEQ ID NO 31
<211> LENGTH: 72
<212> TYPE: DNA
<213> ORGANISM: Artificial Sequence
<220> FEATURE:
<223> OTHER INFORMATION: Synthetic Primer P4

<400> SEQUENCE: 31
taagtggtgt tcgggccacc cagcgtagcg tgacctttac tcaccgctca agttagtata      60
aaaaagctga ac                                                          72

<210> SEQ ID NO 32
<211> LENGTH: 72
<212> TYPE: DNA
<213> ORGANISM: Artificial Sequence
<220> FEATURE:
<223> OTHER INFORMATION: Synthetic Primer P5

<400> SEQUENCE: 32
ggtcgatagc gattaagcca ccgctaccgc caagcgcagg gagtcgctca agttagtata      60
aaaaagctga ac                                                          72

<210> SEQ ID NO 33
<211> LENGTH: 72
<212> TYPE: DNA
<213> ORGANISM: Artificial Sequence
<220> FEATURE:
<223> OTHER INFORMATION: Synthetic Primer P6

<400> SEQUENCE: 33
aattacgcta catcgaggcg ttgtctgcca ttgttgaaac cgggtgaagc ctgctttttt      60
atactaagtt gg                                                          72

<210> SEQ ID NO 34
<211> LENGTH: 72
<212> TYPE: DNA
<213> ORGANISM: Artificial Sequence
<220> FEATURE:
<223> OTHER INFORMATION: Synthetic Primer P7

<400> SEQUENCE: 34
ggatgccagg ctttgttgat tgaacgtttg caggcgatcg gttttgaagc ctgctttttt      60
atactaagtt gg                                                          72

<210> SEQ ID NO 35
<211> LENGTH: 72
<212> TYPE: DNA
<213> ORGANISM: Artificial Sequence
<220> FEATURE:
<223> OTHER INFORMATION: Synthetic Primer P8

<400> SEQUENCE: 35
gcgttcacac attcattaat tttatgaata gtggcattga ccggcgctca agttagtata      60
aaaaagctga ac                                                          72
```

<210> SEQ ID NO 36
<211> LENGTH: 72
<212> TYPE: DNA
<213> ORGANISM: Artificial Sequence
<220> FEATURE:
<223> OTHER INFORMATION: Synthetic Primer P9

<400> SEQUENCE: 36
cagcggagtg cctgcatcgt cgtgggcgtc ttcgaaccac gtcgtgaagc ctgcttttt    60 atactaagtt gg                                                       72

<210> SEQ ID NO 37
<211> LENGTH: 72
<212> TYPE: DNA
<213> ORGANISM: Artificial Sequence
<220> FEATURE:
<223> OTHER INFORMATION: Synthetic Primer P10

<400> SEQUENCE: 37
aggaactgtg ccagcaacgc taccggacga ccggtggcgc ctttcgctca agttagtata    60
aaaaagctga ac                                                       72

<210> SEQ ID NO 38
<211> LENGTH: 54
<212> TYPE: DNA
<213> ORGANISM: Artificial Sequence
<220> FEATURE:
<223> OTHER INFORMATION: Synthetic Primer P11

<400> SEQUENCE: 38
gtgtctgaac tgtctcaatt atctccacag ccgctgtgaa gcctgctttt ttat          54

<210> SEQ ID NO 39
<211> LENGTH: 58
<212> TYPE: DNA
<213> ORGANISM: Artificial Sequence
<220> FEATURE:
<223> OTHER INFORMATION: Synthetic Primer P12

<400> SEQUENCE: 39
cttcgccgga atttctttca gcagttcagt cagcagcagc gctcaagtta cttataaa      58

<210> SEQ ID NO 40
<211> LENGTH: 54
<212> TYPE: DNA
<213> ORGANISM: Artificial Sequence
<220> FEATURE:
<223> OTHER INFORMATION: Synthetic Primer P13

<400> SEQUENCE: 40
atggaactgc ttttattgag taactcgacg ctgccgtgaa gcctgctttt ttat          54

<210> SEQ ID NO 41
<211> LENGTH: 54
<212> TYPE: DNA
<213> ORGANISM: Artificial Sequence
<220> FEATURE:
<223> OTHER INFORMATION: Synthetic Primer P14

<400> SEQUENCE: 41
ggtgaccagc ttccagcgga accgcttctt caccagcgct caagttagta taaa          54

<210> SEQ ID NO 42

```
<211> LENGTH: 58
<212> TYPE: DNA
<213> ORGANISM: Artificial Sequence
<220> FEATURE:
<223> OTHER INFORMATION: Synthetic Primer P15

<400> SEQUENCE: 42
gatctgggtt atgcagctta ttgtttaaca aggagttacc ttgaagcctt ttttatac        58

<210> SEQ ID NO 43
<211> LENGTH: 60
<212> TYPE: DNA
<213> ORGANISM: Artificial Sequence
<220> FEATURE:
<223> OTHER INFORMATION: Synthetic Primer P16

<400> SEQUENCE: 43
ttgcgggcat tctacgtcca ttcggccggc tgacaaccgt ccctcaagtt agtataaaaa      60

<210> SEQ ID NO 44
<211> LENGTH: 67
<212> TYPE: DNA
<213> ORGANISM: Artificial Sequence
<220> FEATURE:
<223> OTHER INFORMATION: Synthetic Primer P17

<400> SEQUENCE: 44
atggagttta gtgtaaaaag cggtagcccg gagaaacagc ggagtgcctg tgaagcctgc      60
tttttat                                                                67

<210> SEQ ID NO 45
<211> LENGTH: 68
<212> TYPE: DNA
<213> ORGANISM: Artificial Sequence
<220> FEATURE:
<223> OTHER INFORMATION: Synthetic Primer P18

<400> SEQUENCE: 45
ttactcttcg ccgttaaacc cagcgcggtt taacaggaac tgtgccagca cgctcaagtt      60
agtataaa                                                               68

<210> SEQ ID NO 46
<211> LENGTH: 68
<212> TYPE: DNA
<213> ORGANISM: Artificial Sequence
<220> FEATURE:
<223> OTHER INFORMATION: Synthetic Primer P19

<400> SEQUENCE: 46
atgacagaag cgatgaagat taccctctct accaacctgc cgacgcgcgg tgaagcctgc      60
tttttttat                                                              68

<210> SEQ ID NO 47
<211> LENGTH: 68
<212> TYPE: DNA
<213> ORGANISM: Artificial Sequence
<220> FEATURE:
<223> OTHER INFORMATION: Synthetic Primer P20

<400> SEQUENCE: 47
ttacgccgtt aacagattag ctatcgtgcg cacaccaagt cccgtagcgc cgctcaagtt      60
agtataaa                                                               68
```

<210> SEQ ID NO 48
<211> LENGTH: 69
<212> TYPE: DNA
<213> ORGANISM: Artificial Sequence
<220> FEATURE:
<223> OTHER INFORMATION: Synthetic Primer P21

<400> SEQUENCE: 48
atgggcaaag cagtcattgc aattcatggt ggcgcaggtg caattagccg gtgaagcctg     60
cttttttat                                                            69

<210> SEQ ID NO 49
<211> LENGTH: 68
<212> TYPE: DNA
<213> ORGANISM: Artificial Sequence
<220> FEATURE:
<223> OTHER INFORMATION: Synthetic Primer P22

<400> SEQUENCE: 49
tcactgtgtg gcaacggtgt cccctttttc acggtagata ccggtggttg cgctcaagtt     60
agtataaa                                                             68

<210> SEQ ID NO 50
<211> LENGTH: 69
<212> TYPE: DNA
<213> ORGANISM: Artificial Sequence
<220> FEATURE:
<223> OTHER INFORMATION: Synthetic Primer P23

<400> SEQUENCE: 50
ctgtacggca ttttgctatg cttgtcgcca ctgttgaagc tgattgagta gtgaagcctg     60
cttttttat                                                            69

<210> SEQ ID NO 51
<211> LENGTH: 68
<212> TYPE: DNA
<213> ORGANISM: Artificial Sequence
<220> FEATURE:
<223> OTHER INFORMATION: Synthetic Primer P24

<400> SEQUENCE: 51
gcatccccac ctcataacgt tgacccgacc gggcaaaaaa caaaaaaggt cgctcaagtt     60
agtataaa                                                             68

<210> SEQ ID NO 52
<211> LENGTH: 39
<212> TYPE: DNA
<213> ORGANISM: Artificial Sequence
<220> FEATURE:
<223> OTHER INFORMATION: Synthetic Primer P25

<400> SEQUENCE: 52
ctgagatcat atgaataagc actttctgtt tgttgaagc                            39

<210> SEQ ID NO 53
<211> LENGTH: 36
<212> TYPE: DNA
<213> ORGANISM: Artificial Sequence
<220> FEATURE:
<223> OTHER INFORMATION: Synthetic Primer P26

<400> SEQUENCE: 53
aaggttccct gcagttagac gcccgattcc agttgc                              36

<210> SEQ ID NO 54
<211> LENGTH: 37
<212> TYPE: DNA
<213> ORGANISM: Artificial Sequence
<220> FEATURE:
<223> OTHER INFORMATION: Synthetic Primer P27

<400> SEQUENCE: 54
ctgagatcat atgaatcagt ttgtctttgt cgaatcc                      37

<210> SEQ ID NO 55
<211> LENGTH: 34
<212> TYPE: DNA
<213> ORGANISM: Artificial Sequence
<220> FEATURE:
<223> OTHER INFORMATION: Synthetic Primer P28

<400> SEQUENCE: 55
aaggttccct gcagtcacgc cggagcagac ggag                         34

<210> SEQ ID NO 56
<211> LENGTH: 69
<212> TYPE: DNA
<213> ORGANISM: Artificial Sequence
<220> FEATURE:
<223> OTHER INFORMATION: Synthetic Primer P29

<400> SEQUENCE: 56
atgcgtctgg aagtcttttg tgaagaccga ctcggtctga cccgcgaatt gtgaagcctg    60
cttttttat                                                          69

<210> SEQ ID NO 57
<211> LENGTH: 68
<212> TYPE: DNA
<213> ORGANISM: Artificial Sequence
<220> FEATURE:
<223> OTHER INFORMATION: Synthetic Primer P30

<400> SEQUENCE: 57
ttactcttcg ttcttcttct gactcagacc atattcccgc aacttattgg cgctcaagtt    60
agtataaa                                                          68

<210> SEQ ID NO 58
<211> LENGTH: 69
<212> TYPE: DNA
<213> ORGANISM: Artificial Sequence
<220> FEATURE:
<223> OTHER INFORMATION: Synthetic Primer P31

<400> SEQUENCE: 58
atggttgctg aattgaccgc attacgcgat caaattgatg aagtcgataa gtgaagcctg    60
cttttttat                                                          69

<210> SEQ ID NO 59
<211> LENGTH: 68
<212> TYPE: DNA
<213> ORGANISM: Artificial Sequence
<220> FEATURE:
<223> OTHER INFORMATION: Synthetic Primer P32

<400> SEQUENCE: 59
ttactggcga ttgtcattcg cctgacgcaa taacacgcgg ctttcactct cgctcaagtt    60
agtataaa                                                          68

<210> SEQ ID NO 60
<211> LENGTH: 20
<212> TYPE: DNA
<213> ORGANISM: Artificial Sequence
<220> FEATURE:
<223> OTHER INFORMATION: Synthetic Primer P33

<400> SEQUENCE: 60
ggtacccggg gatcctctag                                              20

<210> SEQ ID NO 61
<211> LENGTH: 35
<212> TYPE: DNA
<213> ORGANISM: Artificial Sequence
<220> FEATURE:
<223> OTHER INFORMATION: Synthetic Primer P34

<400> SEQUENCE: 61
caagcttgct cgagtgcagt cacgccggag cagac                             35

<210> SEQ ID NO 62
<211> LENGTH: 31
<212> TYPE: DNA
<213> ORGANISM: Artificial Sequence
<220> FEATURE:
<223> OTHER INFORMATION: Synthetic Primer P35

<400> SEQUENCE: 62
gctacagatc tgcgggcagt gagcgcaacg c                                 31

<210> SEQ ID NO 63
<211> LENGTH: 75
<212> TYPE: DNA
<213> ORGANISM: Artificial Sequence
<220> FEATURE:
<223> OTHER INFORMATION: Synthetic Primer P36

<400> SEQUENCE: 63
cggactctag atcctgtgtg aaattgttat ccgctcacaa ttccacacat tatacgagcc  60
ggaagcataa agtgt                                                   75

<210> SEQ ID NO 64
<211> LENGTH: 70
<212> TYPE: DNA
<213> ORGANISM: Artificial Sequence
<220> FEATURE:
<223> OTHER INFORMATION: Synthetic Primer P37

<400> SEQUENCE: 64
caggatctag atttaagaag gagatataca tatggccgaa gaaggtaaac tggtaatctg  60
gattaacggc                                                         70

<210> SEQ ID NO 65
<211> LENGTH: 44
<212> TYPE: DNA
<213> ORGANISM: Artificial Sequence
<220> FEATURE:
<223> OTHER INFORMATION: Synthetic Primer P38

<400> SEQUENCE: 65
gaattcggat ccttagtctg cgcgtctttc agggcttcat cgac                   44

<210> SEQ ID NO 66

```
<211> LENGTH: 41
<212> TYPE: DNA
<213> ORGANISM: Artificial Sequence
<220> FEATURE:
<223> OTHER INFORMATION: Synthetic Primer P39

<400> SEQUENCE: 66
caagtaggat ccgaaaaagc tgttattcgt ggaaggtaat a                      41

<210> SEQ ID NO 67
<211> LENGTH: 50
<212> TYPE: DNA
<213> ORGANISM: Artificial Sequence
<220> FEATURE:
<223> OTHER INFORMATION: Synthetic Primer P40

<400> SEQUENCE: 67
ctattagcgg ccgcagaaat ttttaaactg atcatattac taattttgtg            50

<210> SEQ ID NO 68
<211> LENGTH: 1257
<212> TYPE: DNA
<213> ORGANISM: Artificial Sequence
<220> FEATURE:
<223> OTHER INFORMATION: Optimized gene encoding BBR47_51900 from
      Brevibacillus brevis NBRC 100599

<400> SEQUENCE: 68
atgaataagc actttctgtt tgttgaagcg aatacgacgg gcacgggtat gctggcgatg    60
aagaaggcac gcaagctggg ttttacgccg gtgtttttca ccgaaaaacc ggaacgttat   120
catggcctga cgaactgga atgccacgtg ttgtcaccg atacgaatag ccaggccgaa    180
ctgaccgaca gcgtggcaca agtttctaaa gaaggccgcg aaattgcagg tatcatgtca   240
acgtcggatt attacctgga aagcgtcgcg aaactggccc gtaagtttgg ttggattagc   300
aactctctgg aagcaatcga agcttgtcgc aataaagcga ttttcgtga aaagctgcaa   360 cgccatcaag tgagccagcc gaccttcctg gccattagct ctatgaaaca gctgctggaa   420
gcacgtagtt ccatctctct gccgtgcgtg gttaaaccgg cggatgacag tggctccaac   480
aatgttcgcc tgtgtttcag ttgggatgaa gtcgaacaca tggcggccga aattctggcc   540
atcaagtata acgacgtgg ccaggaaacc gctcgcacgg ttctgctgga caatacgcg    600 gaaggtccgg aatttagtgt cgaaaccttc tcctggcagg gccaatgctt tgtgattggt   660
atcacccaga acgtctgac gggctatccg ttttttcgttg aagctggtca tatttcccg   720 gcgccgctgt ctgtcgaaga aaagcaggaa atcgaacgta cggtcgaacg cgctctggca   780
gctgtgaaat accagtttgg cgcggcccac accgaagtga agtggacgag cgccggttgt   840
gtcgtgattg aagttaacgc acgtctgccc ggcggtatga tcccggaact ggtgcgtcgc   900
tccaccggca ttgatctgct gctgcaacaa atccgttgcg cagctggtct ggaaccggaa   960
ctgagtcaga cgattgaaga caacgctgt gccggtatcc attttctggt ttcagaatcg  1020
cagggcacct tcggcggtat taagggtatg gacacggtgc gtaatctgcc gggcatcgca  1080
gaagttgcta ttcacgcgaa gatcggtcaa aacgtgcagc cgccgcaaaa ttttttcacat  1140 cgcctgggct atgttattgt cgaaggtaaa cactactcgg aaaccgcgga actgatcgaa  1200
caagtcaaag atagcctgtc cgtgcaagtc ggtcagcaac tggaatcggg cgtctaa     1257

<210> SEQ ID NO 69
<211> LENGTH: 1254
<212> TYPE: DNA
```

<213> ORGANISM: Artificial Sequence
<220> FEATURE:
<223> OTHER INFORMATION: Optimized gene encoding Staur_4851 from Stigmatella aurantiaca DW4/3-1

<400> SEQUENCE: 69

```
atgaatcagt ttgtctttgt cgaatccaat accacgggca cgggtcgtct ggcggttgaa      60
cgtctgctgg cgcaaggtga acaggtgacc tttattacgc atcagccgga aaaatatccg     120
ttcctggttg gtaacaaggc gccgggcctg aaagtgctga aggttgaaac caatgatgcg     180
gccgcagtcg aagcatgcgt ggacggtctg gttcgcgaag gcaaagtggc tgcgctgctg     240
accttttcaa cgttctatgt cccgaccgtg gccgcaattg ctgcgcgtca tggcctgcgt     300
tacctgcaac cgcgtgccgc acaagcctgc cataacaagc acgaagcccg cgcactgctg     360
cgtgctgcgg gcctgccggg tccggaattt cacgttatcg cttccgaagc ggaagccgca     420
cagctggctc aaaccgtgcg cttcccgtgt gtggttaaac cgccggcgga aagcggctct     480
accggtgttc gtcgcgtcga tacgccggaa gaactgctgg cgcatttttcg cagtctgcac     540
tcccgtgctg cgaatgaacg cggtcagagc ctgcacggcg aagtcctggt ggaaagcttt     600
ctggaaggtc cggaattctc tgttgaaacc atgacgctgg ccgatggtac cacgcatgtg     660
ctgggcgtta cccaaaagta tctgtctgca ccgccgtact ttgtggaaat gggtcacgat     720
ttccggccg acctgccgcc ggaacgtcgc cgtgcactgg aagaagccgt gctggcaggt     780
ctggccgcag ttggttttga tttcggtccg gctcataccg aaattcgttt tacgccggcg     840
ggtccggtga ttatcgaaat taacccgcgt ctggcaggcg gtatgatccc ggaactggtt     900
cgtctgtcaa ccggtgtcga tctgctgtcg gcaatgctgg accagatgct gggtcgtccg     960
gtcgatctga cccacacgcg tcaagacgtg gcctgtattc gtttcatcac ctcagaacgt    1020
ccgggtgtcc tggctcgtgt ggagggtcag gatgaagcgt cgcgtctggg tacggtgcgc    1080
caagttgcag tcgacaaagc tgcgggcacc cgtctgcgtc cgccggaaag tgcaacggat    1140
cgtctgggtt acgttatcgc atccggcccg gaacgtggtc aggtcctggg cgacgctgcc    1200
cgtgctctgt ccctgctgcg tgtggaacaa gcggctccgt ctgctccggc gtga           1254
```